(12) United States Patent
O'Neill et al.

(10) Patent No.: US 11,858,922 B2
(45) Date of Patent: Jan. 2, 2024

(54) SULFONYLUREAS AND RELATED COMPOUNDS AND USE OF SAME

(71) Applicants: The University of Queensland, Queensland (AU); THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH NEAR DUBLIN, Dublin (IE)

(72) Inventors: Luke O'Neill, Dublin (IE); Rebecca Coll, West End (AU); Matthew Cooper, Chapel Hill (AU); Avril Robertson, Kenmore (AU); Kate Schroder, Fairfield (AU); Angus Murray Macleod, Cambridge (GB); David John Miller, Cambridge (GB)

(73) Assignees: THE UNIVERSITY OF QUEENSLAND, Queensland (AU); THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH NEAR DUBLIN, Dublin (IE)

( * ) Notice: Subject to any disclaimer, the term of this patent is extended or adjusted under 35 U.S.C. 154(b) by 112 days.

(21) Appl. No.: 15/999,424

(22) PCT Filed: Feb. 16, 2017

(86) PCT No.: PCT/EP2017/053498
§ 371 (c)(1),
(2) Date: Aug. 17, 2018

(87) PCT Pub. No.: WO2017/140778
PCT Pub. Date: Aug. 24, 2017

(65) Prior Publication Data
US 2020/0299284 A1 Sep. 24, 2020

(30) Foreign Application Priority Data
Feb. 16, 2016 (AU) .................. 2016900535

(51) Int. Cl.
*C07D 413/12* (2006.01)
*A61K 49/00* (2006.01)
(Continued)

(52) U.S. Cl.
CPC ........ *C07D 413/12* (2013.01); *A61K 49/0004* (2013.01); *C07C 311/47* (2013.01);
(Continued)

(58) Field of Classification Search
CPC .... C07C 311/47; C07D 209/08; C07D 213/42
See application file for complete search history.

(56) References Cited

U.S. PATENT DOCUMENTS 3,242,174 A 3/1966 McManus et al.
3,856,786 A 12/1974 Huber
(Continued)

FOREIGN PATENT DOCUMENTS

AU 2015900507 2/2015
CH 490350 A 5/1970
(Continued)

OTHER PUBLICATIONS

Belai, Responses of Different Fungal and Plant Species to Acetolactate Synthase Inhibitors & Their Derivatives, 1996, J. Environ. Sci. Health, Part B, p. 615-620 (Year: 1996).*
Wu et al., CAPLUS abstract of Doc. No. 88:74272, 1977, p. 1 (Year: 1977).*
Kelley et al. "The NLRP3 Inflammasome: An Overview of Mechanisms of Activation and Regulation" International Journal of Molecular Sciences, 2019, vol. 20, Article 3328, pp. 1-24.*
CAS RN 1136411-26-1; STN Entry Date: Apr. 19, 2009; 1-Piperidinesulfonamide, 2,6-dimethyl-N-[(2-pyridinylamino)carbonyl]-.
CAS RN 1137082-14-4; STN Entry Date: Apr. 20, 2009; 1 -Piperidinesulfonamide, N-[(2-pyridinylamino)carbonyl]-.
(Continued)

*Primary Examiner* — Joseph R Kosack
(74) *Attorney, Agent, or Firm* — Alston & Bird LLP

(57) ABSTRACT

The present invention relates to compounds of formula (I), and pharmaceutically acceptable salts, solvates and prodrugs thereof:

Formula (I)

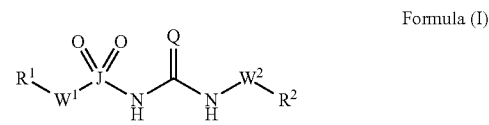

wherein Q is selected from O, S and Se; J is S or Se; $W^1$ and $W^2$, when present, are independently selected from N and C; $R^1$ and $R^2$ are independently selected from the group consisting of hydrogen, $C_1$-$C_{12}$ alkyl, $C_2$-$C_{12}$ alkenyl, $C_2$-$C_{12}$ alkynyl, aryl, heterocyclyl, heteroaryl, cycloalkyl, cycloalkenyl, amino, amido, alkylthio, acyl, arylalkyl and acylamido, all of which may be optionally substituted; and wherein at least one of $W^1$ and $W^2$ is present and is a nitrogen atom and when $R^1$ or $R^2$ are cyclic then the respective $W^1$ or $W^2$ may form part of the ring structure. The present invention also relates to pharmaceutical compositions including such compounds, to methods of treatment using such compounds, in particular in relation to NLRP3 inflammasome mediated disorders, and to associated diagnostic uses.

36 Claims, 1 Drawing Sheet

(51) Int. Cl.
| | | |
|---|---|---|
| *C07C 311/47* | (2006.01) | |
| *C07D 209/08* | (2006.01) | |
| *C07D 209/14* | (2006.01) | |
| *C07D 213/42* | (2006.01) | |
| *C07D 233/64* | (2006.01) | |
| *C07D 235/26* | (2006.01) | |
| *C07D 241/04* | (2006.01) | |
| *C07D 271/06* | (2006.01) | |
| *C07D 277/28* | (2006.01) | |
| *C07D 295/26* | (2006.01) | |
| *C07D 307/52* | (2006.01) | |
| *C07D 311/20* | (2006.01) | |
| *C07D 317/66* | (2006.01) | |
| *C07D 403/12* | (2006.01) | |
| *C07D 413/04* | (2006.01) | |

(52) U.S. Cl.
CPC ......... *C07D 209/08* (2013.01); *C07D 209/14* (2013.01); *C07D 213/42* (2013.01); *C07D 233/64* (2013.01); *C07D 235/26* (2013.01); *C07D 241/04* (2013.01); *C07D 271/06* (2013.01); *C07D 277/28* (2013.01); *C07D 295/26* (2013.01); *C07D 307/52* (2013.01); *C07D 311/20* (2013.01); *C07D 317/66* (2013.01); *C07D 403/12* (2013.01); *C07D 413/04* (2013.01)

(56) References Cited

U.S. PATENT DOCUMENTS

| | | | | |
|---|---|---|---|---|
| 4,401,816 | A * | 8/1983 | Levitt | C07D 521/00 504/212 |
| 4,515,620 | A * | 5/1985 | Bohner | A01N 47/34 504/178 |
| 5,185,330 | A | 2/1993 | Ochiai et al. | |
| 5,214,206 | A * | 5/1993 | Picard | A61P 43/00 564/40 |
| 5,300,497 | A | 4/1994 | Ochiai et al. | |
| 5,486,618 | A | 1/1996 | Hagen et al. | |
| 6,346,359 | B1 | 2/2002 | Yamada et al. | |
| 10,538,487 | B2 | 1/2020 | O'Neill et al. | |
| 2003/0134898 | A1 | 7/2003 | Homan | |
| 2018/0044287 | A1 * | 2/2018 | O'Neill | C07D 405/12 |
| 2022/0194923 | A1 * | 6/2022 | Cooper | C07D 205/04 |

FOREIGN PATENT DOCUMENTS

| | | |
|---|---|---|
| CN | 103159651 A | 6/2013 |
| CN | 107428696 A | 12/2017 |
| DE | 1064284 B | 8/1959 |
| EP | 0556322 A1 | 8/1993 |
| EP | 1236478 * | 4/2002 |
| EP | 1236468 A1 | 9/2002 |
| EP | 1236478 A1 | 9/2002 |
| EP | 1281399 A2 | 2/2003 |
| EP | 1354871 A1 | 10/2003 |
| GB | 1031361 A | 6/1966 |
| GB | 1155936 A | 6/1969 |
| GB | 2110689 A | 6/1983 |
| GG | 968805 A | 9/1964 |
| JP | 2001-071647 A | 3/2001 |
| KR | 20090121832 A | 11/2009 |
| WO | WO 1992/08694 A1 | 5/1992 |
| WO | WO 1992/10480 A1 | 6/1992 |
| WO | WO 1998/032733 A1 | 7/1998 |
| WO | WO 2001/019390 A1 | 3/2001 |
| WO | WO 2001/096298 A2 | 12/2001 |
| WO | WO 2013/086980 A1 | 6/2013 |
| WO | WO 2016/131098 A1 | 8/2016 |
| WO | WO 2016/150428 A1 | 9/2016 |
| WO | WO 2017/129897 A1 | 8/2017 |
| WO | WO 2017/140778 A1 | 8/2017 |
| WO | WO 2017/189651 A1 | 11/2017 |
| WO | WO 2017/189652 A1 | 11/2017 |
| WO | WO 2017/189663 A1 | 11/2017 |
| WO | WO 2017/201150 A1 | 11/2017 |
| WO | WO 2017/201152 A1 | 11/2017 |
| WO | WO 2018/015445 A1 | 1/2018 |
| WO | WO 2018/215818 A1 | 11/2018 |
| WO | WO 2019/034686 A1 | 2/2019 |
| WO | WO 2019/034688 A1 | 2/2019 |
| WO | WO 2019/034692 A1 | 2/2019 |
| WO | WO 2019/034693 A1 | 2/2019 |
| WO | WO 2019/092171 A1 | 5/2019 |
| WO | WO 2019/092172 A1 | 5/2019 |
| WO | WO 2019/166619 A1 | 9/2019 |
| WO | WO 2019/166629 A1 | 9/2019 |
| WO | WO 2019/166633 A1 | 9/2019 |
| WO | WO 2020/035464 A1 | 2/2020 |
| WO | WO 2020/035465 A1 | 2/2020 |
| WO | WO 2020/035466 A1 | 2/2020 |

OTHER PUBLICATIONS

CAS RN 252654-28-7; STN Entry Date: Jan. 11, 2000; Urea, N-[[bis(1-methylethyl)annino]sulfonyl]-N'-2-pyridinyl-.
CAS RN 253864-92-5; STN Entry Date: Jan. 31, 2000; Thieno[3,2-c]pyridine-5(4H)-sulfonamide, 6,7-dihydro-N-[[(6-methyl-2-pyridinyl)amino]carbonyl]-4-propyl-.
CAS RN 400840-16-6; STN Entry Date: Mar. 14, 2002; 4-Morpholinesulfonamide, N-[[(5-methyl-2-pyrimidinyl)amino]carbonyl]-.
CAS RN 400840-17-7; STN Entry Date: Mar. 14, 2002; Urea, N-[(diethylamino)sulfonyl]-N'-(4,6-dimethyl-2-pyrimidinyl)-.
CAS RN 400840-33-7; STN Entry Date: Mar. 14, 2002; 1-Piperidinesulfonamide, N-[[(4,6-dimethyl-2-pyrimidinyl)amino]carbonyl]-.
CAS RN 400841-40-9; STN Entry Date: Mar. 14, 2002; 1-Piperidinesulfonamide, N-[[[4-(1,1-dimethylethyl)-6-(trifluoromethyl)-2-pyrimidinyl]amino]carbonyl]-.
CAS RN 864174-60-7; STN Entry Date: Sep. 29, 2005; 4-Morpholinesulfonamide, N-[[(4,6-dimethyl-2-pyrimidinyl)amino]carbonyl]-.
CAS RN 864389-24-2; STN Entry Date: Oct. 3, 2005; 4-Morpholinesulfonamide, N-[[[4-(1,1-dimethylethyl)-6-(trifluoromethyl)-2-pyrimidinyl]amino]carbonyl]-.
CAS RN 864424-64-6; STN Entry Date: Oct. 4, 2005; 4-Morpholinesulfonamide, N-[[(4,6-dimethoxy-2-pyrimidinyl)amino]carbonyl]-.
CAS RN 865074-37-9; STN Entry Date: Oct. 12, 2005; 1-Piperidinesulfonamide, N-[[(5-methyl-2-pyridinyl)amino]carbonyl]-.
CAS RN 956262-42-3; STN Entry Date Nov. 29, 2007; Urea, N-(4-cyano-1-phenyl-1H-pyrazol-5-yl)-N'-[(diethylamino) sulfonyl]-.
CAS RN 959321-29-0; STN Entry Date: Dec. 21, 2007; Benzo[b]thiophene-3-carboxylic acid, 2-[[[[(3,4-dihydro-2(1H)-isoquinolinyl)sulfonyl]amino]carbonyl]amino]-4,5,6,7-tetrahydro-, ethyl ester.
CAS RN 959361-83-2; STN Entry Date: Dec. 21, 2007; Benzo[b]thiophene-3-carboxylic acid, 4,5,6,7-tetrahydro-2-[[[(1-pyrrolidinylsulfonyl)amino]carbonyl]amino]-, ethyl ester.
CAS RN 959378-15-5; STN Entry Date: Dec. 21, 2007; Benzo[b]thiophene-3-carboxylic acid, 4,5,6,7-tetrahydro-6,6-dimethyl-2-[[[[(2-methyl-1H-imidazol-1-yl)sulfonyl]amino]carbonyl] amino]-, ethyl ester.
CAS RN 959378-16-6; STN Entry Date: Dec. 21, 2007; Benzo[b]thiophene-3-carboxylic acid, 4,5,6,7-tetrahydro-2-[[[(4-morpholinylsulfonyl)amino]carbonyl]amino]-, ethyl ester.
CAS RN 959378-20-2; STN Entry Date: Dec. 21, 2007; Benzo[b]thiophene-3-carboxylic acid, 4,5,6,7-tetrahydro-2-[[[(1-piperidinylsulfonyl)amino]carbonyl]amino]-, ethyl ester.
CAS RN 959663-63-9; STN Entry Date: Dec. 28, 2007; Benzo[b]thiophene-3-carboxylic acid, 4,5,6,7-tetrahydro-2-[[[[(4-methyl-1-piperazinyl)sulfonyl]amino]carbonyl]amino]-, ethyl ester.

(56) References Cited

OTHER PUBLICATIONS

CAS RN 959664-76-7; STN Entry Date: Dec. 28, 2007; Benzo[b]thiophene-3-carboxylic acid, 4,5,6,7-tetrahydro-6,6-dimethyl-2-[[[[(5-methyl-1H-pyrazol-1-yl)sulfonyl]amino]carbonyl]amino]-, ethyl ester.
CAS RN 959670-14-5; STN Entry Date: Dec. 28, 2007; Benzo[b]thiophene-3-carboxylic acid, 2-[[[[(4-acetyl-1-piperazinyl)sulfonyl]amino]carbonyl]amino]-4,5,6,7-tetrahydro-, ethyl ester.
Chhabria et al. "Discovery of novel acyl Coenzyme A: Cholesterol Acyltransferase inhibitiors: Pharmacophore-based virtual screening, synthesis and pharmacology" Chemical Biology and Drug Design, 80(1): 106-113 (2012).
Coll et al., "A small-molecule inhibitor of the NLRP3 inflammasome for the treatment of inflammatory diseases," Nature Medicine, 21(3):248-255, (2015).
El-Akri et al. "Physicochemical 2D-Qsar and 3D molecular docking studies on N-chlorosulfonyl isocyanate analogs as sterol O-acyltransferase-1 "Soat-1" Inhibitors" Open Journal of Medicinal Chemistry, 3:100-120 (2013).
Laporte, et al., "Tetrahydrobenzothiophene inhibitors of hepatitis C Virus NS5B polymerase," Bioorganic & Medicinal Chemistry Letters, 16(1): 100-103, (2006).
Lather et al. "Prediciting Acyl-Coenzyme A: Cholesterol O-acyltransferase inhibitory activity: Computational approach using topological descriptors" Drug Design and Discovery, 18:117-122 (2003).
McManus et al. "Sulfamylurea hypoglycemic agents. I. Synthesis and screening" Journal of Medicinal Chemistry, 8(6): 766-776 (1965).
Patankar et al. "Prediction of IC50 values for ACAT inhibitors from molecular structure" J. Chem. Inf. Comput. Sci., 40:706-723 (2000).
Petersen, "New reactions of sulphonamides," Chemische Berichte, 83(6):551-558, (1950), English abstract.
Picard et al., "Inhibitors of Acyl-CoA:Cholesterol O-Acyltransferase. 17. Structure-Activity Relationships of Several Series of Compounds Derived from N-Chlorosulfonyl Isocyanate," J. Med. Chemn., 39(6):1243-1252, doi: 10.1021/JM9509455, (1996).
Rakel et al. "Beneficial effects of gliclazide modified release compared with glibenclamide on endothelial activation and low-grade inflammation in patients with type 2 diabetes" Diabetes, Obesity and Metabolism, 9(1):127-129 (2007).
Ronn et al. "New developments in the discovery of agents to treat Hepatitis C" Current Topics in Medicinal Chemistry, 8(7):533-562 (2008).
Sarges et al. "Sulfamylurea Hypoglycemic Agents. 6. High potency Derivatives" Journal of Medicinal Chemistry, 19(5):695-709 (1976).
Wiseman et al "Sulfamylurea hypoglycemic Agents. II. Drug Dynamic Studies" Journal of Medicinal Chemistry, 8(6): 777-781 (1965).
AU Application No. 2015900506, International-Type Search Report dated Jul. 21, 2015.
U.S. Appl. No. 16/535,002, Notice of Allowance dated May 19, 2021.
U.S. Appl. No. 16/629,006, Non-Finai Office Action dated Dec. 8, 2020.
WIPO Application No. PCT/EP2017/053498, PCT International Preliminary Report on Patentability dated Aug. 21, 2018.
WIPO Application No. PCT/EP2017/053498, PCT International Search Report dated Mar. 29, 2017.
WIPO Application No. PCT/EP2017/053498, PCT Written Opinion of the International Searching Authority dated Mar. 29, 2017.
WIPO Application No. PCT/EP2019/071628, PCT International Preliminary Report on Patentability dated Feb. 25, 2021.
WIPO Application No. PCT/EP2019/071628, PCT International Search Report and Written Opinion dated Nov. 8, 2020.
Balant, et al., "Metabolic Considerations in Prodrug Design," Burger's Medicinal Chemistry and Drug Discovery, 5th Edition, vol. 1; Principles and Practice, pp. 949-982, Editied by Manfred E. Wolff, © 1995 John Wiley & Sons, Inc.
Banker et al., Prodrugs, Modern Pharmaceutics, 3rd edition, Revised and Expanded, pp. 451 and 596, (1995).
Belikov, "Pharmaceutical chemistry", chapter 2.6 "The interconnection between chemical structure, properties of substances and their effect on the body", MEDpress-inform, Moscow, 2007, p. 27-29, Brief Statement of Relevance.
Bundgaard, "Design of Prodrugs," Chapter1, p. 1, (1985).
CAS RN 687986-77-2; May 31, 2004.
Disease—Wikipedia, retrieved from the internet on Feb. 2, 2022 at: https://en.wikipedia.org/wiki/Disease.
Ettmayer, et al., "Lessons learned from marketed and investigational prodrugs" J. Med. Chem., 47(10):2394-2404 (2004).
Han, "Targeted prodrug design to optimize drug delivery" AAPS Pharmsci. 2(1) Article 6: 1-11, (2000).
Himiceskij, Chemical Encyclopedia, (1983), p. 130-131, Brief Statement of Relevance.
Parajuli, et al., Prodrug as a novel approach of drug delivery—a review, Journal of Drug Delivery & Therapeutics, 2015, 5(3), pp. 5-9.
Silverman, Prodrugs and drug delivery systems, The organic chemistry of drug design and drug action, Chapter 8, pp. 352-400, 1992.
So, et al. "Evaluation of designed ligands by a multiple screening method: Application to glycogen phosphorylase inhibitors constructed with a variety of approaches" Journal of Computer Aided Design, 2001, 15, pp. 615-647.
Solvation—Wikipedia, retrieved from the internet on Jan. 15, 2022 at: https://en.wikipedia.org/wiki/Solvation.
Stella, "Prodrugs as theraputics" Expert Opinion of theraputic patents, 14(3): 277-280 (2004).
Testa, "Prodrug research: futile or fertile," Biochemical Pharmacology, 68, 2097-2106, (2004).
Zawilska, et al., Prodrugs: a challenge for the drug development, Pharmacological Reports, 2013, vol. 65, No. 1, pp. 1-14.
U.S. Appl. No. 17/267,800, Requirement for Restriction/Election dated Jun. 27, 2022.
CAS 256373-96-3; Feb. 18, 2000.
CAS RN 210826-40-7; Sep. 3, 1998.
Coll, et al., "The Cytokine Release Inhibitory Drug CRID3 Targets ASC Oligomerisation in the NLRP3 and AIM2 Inflammasomes," PloS ONE, vol. 6, Issue 12, e29539, (Dec. 2011) and correction.
U.S. Appl. No. 17/267,800, Non-Final Office Action dated Nov. 10, 2022.
U.S. Appl. No. 17/267,800, Final Office Action dated May 26, 2023.
JP Application 2021-507616 Notice of Reasons for Rejection dated Aug. 1, 2023, English translation only.

\* cited by examiner

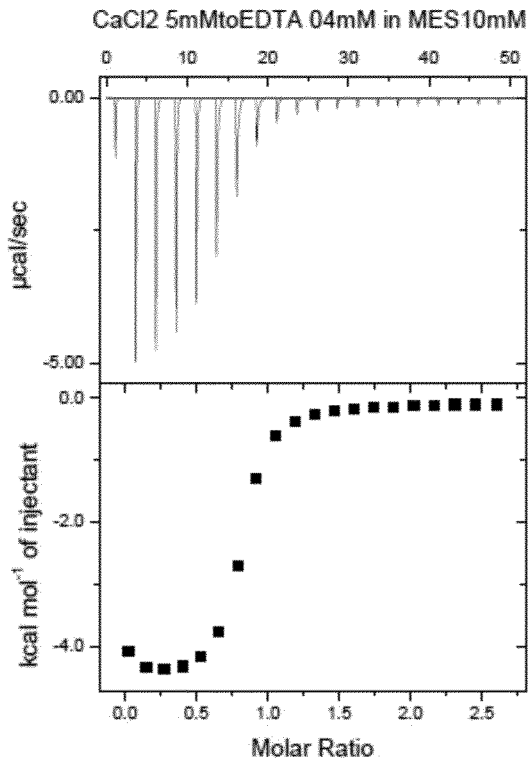
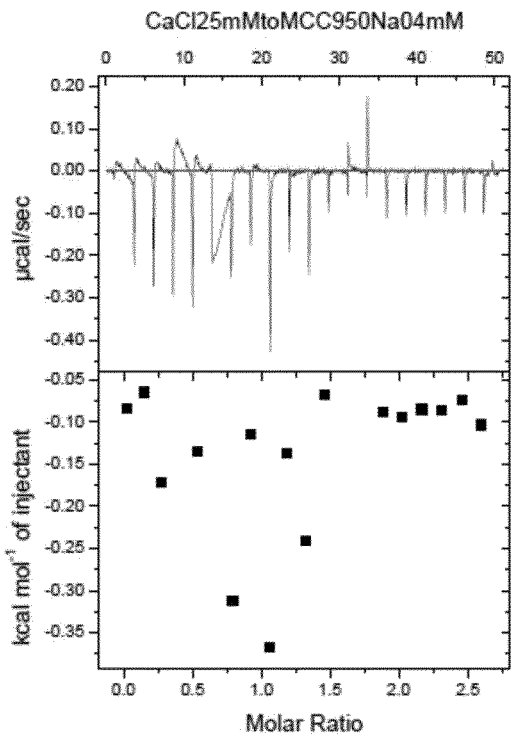
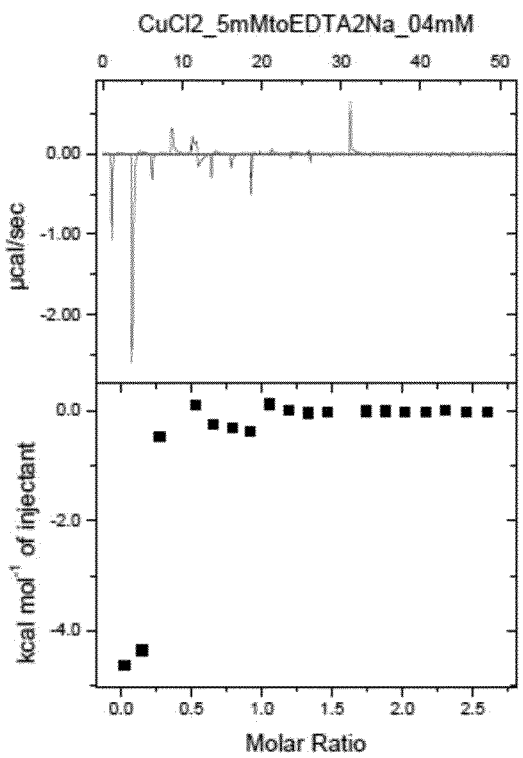
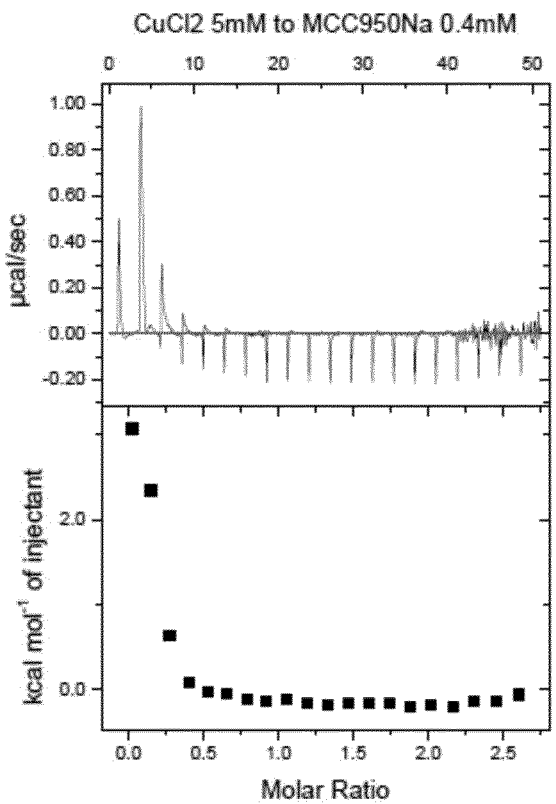

SULFONYLUREAS AND RELATED COMPOUNDS AND USE OF SAME

CROSS-REFERENCE TO RELATED APPLICATIONS

This application is a national stage entry of PCT/EP2017/053498 filed Feb. 16, 2017, which claims the benefit of AU Application No. 2016900535 filed, Feb. 16, 2016.

FIELD OF THE INVENTION

The invention relates to the field of medical treatment and diagnosis of disease. More particularly, this invention relates to novel sulfonylurea and related compounds and their use in treating, or identifying a disease or condition responsive to inhibition of NLRP3 or inhibition of the activation of NLRP3 or related components of the inflammatory process.

BACKGROUND TO THE INVENTION

Any reference to background art herein is not to be construed as an admission that such art constitutes common general knowledge in Australia or elsewhere.

The NOD-like receptor (NLR) family, pyrin domain-containing protein 3 (NLRP3) inflammasome is a component of the inflammatory process, and its aberrant activation is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the proinflammatory cytokines IL-1β and IL-18 to their active forms and mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cells driving a Th1 response.

Other intracellular pattern recognition receptors (PRRs) are also capable of forming inflammasomes. These include other NLR family members such as NLRP1 and NLRC4, as well as non-NLR PRRs such as the double-stranded DNA (dsDNA) sensors absent in melanoma 2 (AIM2) and interferon, gamma inducible protein 16 (IFI16). NLRP3-dependent IL-1β processing can also be activated by an indirect, non-canonical pathway downstream of caspase-11.

The inherited CAPS diseases Muckle-Wells syndrome (MWS), familial cold autoinflammatory syndrome and neo-natal-onset multisystem inflammatory disease are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using Nlrp3$^{-/-}$ mice, but there have also been insights into the specific activation of NLRP3 in these diseases. In type 2 diabetes, the deposition of islet amyloid polypeptide in the pancreas activates NLRP3 and IL-1β signaling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised NLRP3 inhibitors include parthenolide, 3,4-methylenedioxy-β-nitrostyrene and dimethyl sulfoxide (DMSO), although these agents have limited potency and are nonspecific.

Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

Certain diarylsulfonylurea-containing compounds have been identified as cytokine release inhibitory drugs (CRIDs) (Perregaux et al.; J. Pharmacol. Exp. Ther. 299, 187-197, 2001). CRIDs are a class of diarylsulfonylurea containing compounds that inhibit the post-translational processing of IL-1β. Post-translational processing of IL-1β is accompanied by activation of caspase-1 and cell death. CRIDs arrest activated monocytes so that caspase-1 remains inactive and plasma membrane latency is preserved.

Certain sulfonylurea-containing compounds are also disclosed as inhibitors of NLRP3 (Baldwin et al., J. Med. Chem., 59(5), 1691-1710, 2016).

There is a need to provide compounds with improved pharmacological and/or physiological and/or physicochemical properties and/or those that provide a useful alternative to known compounds.

SUMMARY OF INVENTION

According to a first aspect of the invention, there is provided a compound of formula (I), or a pharmaceutically acceptable salt, solvate or prodrug thereof:

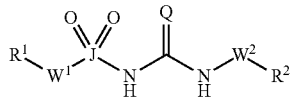

Formula (I)

wherein, Q is selected from O, S and Se;

J is S or Se;

$W^1$ and $W^2$, when present, are independently selected from N and C;

$R^1$ and $R^2$ are independently selected from the group consisting of hydrogen, $C_1$-$C_{12}$ alkyl, $C_2$-$C_{12}$ alkenyl, $C_2$-$C_{12}$ alkynyl, aryl, heterocyclyl, heteroaryl, cycloalkyl, cycloalkenyl, amino, amido, alkylthio, acyl, arylalkyl and acylamido, all of which may be optionally substituted; and wherein at least one of $W^1$ and $W^2$ is present and is a nitrogen atom and when $R^1$ or $R^2$ are cyclic then the respective $W^1$ or $W^2$ may form part of the ring structure.

According to a second aspect of the invention there is provided a pharmaceutical composition comprising a compound of the first aspect, or a pharmaceutically acceptable salt, solvate or prodrug thereof, and a pharmaceutically acceptable carrier, diluent and/or excipient.

A third aspect of the invention resides in a method of treatment or prevention of a disease, disorder or condition including the step of administering an effective amount of a compound of the first aspect, or a pharmaceutically effective salt, solvate or prodrug thereof, or the pharmaceutical composition of the second aspect to thereby treat or prevent the disease, disorder or condition.

A fourth aspect of the invention provides for a compound of the first aspect, or a pharmaceutically effective salt, solvate or prodrug thereof, or the pharmaceutical composition of the second aspect for use in the treatment or prevention of a disease, disorder or condition.

A fifth aspect of the invention provides for use of a compound of the first aspect, or a pharmaceutically effective salt, solvate or prodrug thereof, in the manufacture of a medicament for the treatment or prevention of a disease, disorder or condition.

In one embodiment, the disease, disorder or condition is responsive to inhibition of activation of the NLRP3 inflammasome.

In particular non-limiting embodiments of the above aspects, the disease, disorder or condition is a disease, disorder or condition of the immune system, the cardiovascular system, the endocrine system, the gastrointestinal tract, the renal system, the respiratory system, the central nervous system, is a cancer or other malignancy and/or is caused by or associated with a pathogen.

In a sixth aspect of the invention there is provided a method of diagnosing a disease, disorder or condition in a mammal including the step of administering a labelled compound of the first aspect, or a pharmaceutically effective salt, solvate or prodrug thereof, to the mammal or to a biological sample obtained from the mammal to facilitate diagnosis of the disease, disorder or condition in the mammal.

A seventh aspect of the invention resides in a method of modulating the activity of a biological target comprising the step of exposing the biological target to a compound of the first aspect, or a pharmaceutically acceptable salt thereof.

The biological target may be selected from the group consisting of the NLRP3 inflammasome, IL-1β, IL-17, IL-18, IL-1α, IL-37, IL-33 and Th17 cells.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein:

FIG. 1 is a series of isothermal titration calorimetry (ITC) showing a) control experiments: $Ca^{2+}$ binding to EDTA (top left) and $Cu^{2+}$ binding to EDTA (bottom left), together with b) data showing no binding of MCC950 (sodium salt) to $Ca^{2+}$ (top right), but significant binding to $Cu^{2+}$ (bottom right).

DETAILED DESCRIPTION

The present invention is predicated, at least in part, on the finding that certain sulfonyl ureas and related compounds have advantageous properties and show useful activity in the inhibition of activation of the NLRP3 inflammasome and/or inhibition of IL-1β and/or IL-17 and/or IL-18, and/or IL-1α, and/or IL-37, and/or IL-33 as well as interfere with or modulate the activity of T helper cells such as Th17. Particularly, the compounds of the invention are useful in the treatment of a wide range of disorders in which the inflammation process, or the NLRP3 inflammasome and/or IL-1β and/or IL-17 and/or IL-18, and/or IL-1α, and/or IL-37, and/or IL-33 and/or Th17 cells play a part.

Evidence from human CAPS patients and mouse models of CAPS has lead the present inventors to believe that NLRP3 inhibition will be a superior treatment over IL-1 biologics, as inhibition of all NLRP3-dependent processes will be more effective than inhibition of a single NLRP3-dependent process, such as IL-1 signalling.

Individuals with CAPS display dysregulated secretion of both IL-1β and IL-18, and CAPS patients treated with anti-IL-1 biologics have residual disease. Symptoms such as bony overgrowth and joint deformity are not prevented by IL-1 biologics. In addition, symptoms involving the central nervous system such as hearing loss are difficult to control using IL-1 biologics, which appear to poorly penetrate the central nervous system. Studies in mouse models of CAPS indicate that deficiency in either IL-1 signalling or IL-18 alone is insufficient to block systemic inflammation, particularly in older animals. In a severe model of CAPS, only a complete loss of caspase-1 signalling fully rescued the disease.

Specific inhibition of NLRP3 by sulfonylurea-containing compounds, such as those of the first aspect, may block all processes downstream of NLRP3, including ASC speck formation and caspase-8 and caspase-1 activation. Consequently, NLRP3 inhibition will block all caspase-1 dependent processes such as IL-1β, IL-18 and IL-37 processing and secretion, gasdermin D cleavage, pyroptosis, and release of IL-1α, IL-33 and HMGB. Furthermore, NLRP3-dependent extracellular release of the ASC speck will be blocked, and caspase-8-dependent pro-IL-1β and pro-IL-18 cleavage and apoptotic cell death will be prevented. Thus, specific inhibition of NLRP3 by compounds of the first aspect will prevent multiple downstream inflammatory signals and should therefore prove more effective as an anti-inflammatory therapy than IL-1 blockade alone.

Anti-IL-1 biologics block IL-1 derived from NLRP3-independent sources, such as IL-1 produced by other inflammasomes (e.g. NLRC4, NLRP1, NLRP6, AIM2), and IL-1 generated by the latter pathways may be important for host defence against pathogens. For example, patients receiving IL-1/IL-1R antagonists exhibit increased incidence of upper airway infections. Specific inhibition of NLRP3 by the present compounds may thus exert less generalised immunosuppression compared to anti-IL-1 biologics.

IL-1β and IL-18, generated by the NLRP3/caspase-1 axis, play critical roles in driving IL-17 production by CD4 Th17 cells and γδ T cells. IL-1β and IL-18 synergise with IL-23 to induce IL-17 production by memory CD4 Th17 cells and by γδ T cells in the absence of TCR engagement. IL-1-driven IL-17 has also been implicated in psoriasis, type I diabetes, rheumatoid arthritis, type 2 diabetes mellitus, atherosclerosis, obesity, gout, and recently, asthma.

In essence, each of these diseases has been shown to involve the activation of tissue macrophages, dendritic cells, or brain microglia, driven by the frustrated phagocytosis of metabolites that accumulate extracellularly. NLRP3 senses this phagocytic event, leading to IL-1 release, triggering inflammation to clear the offensive material. Disease will result if this process becomes chronic or over-activated, which explains why so many diseases have been shown to involve NLRP3. Inhibitors that act to prevent NLRP3 activation hence can have utility in IL-17 driven, as well as IL-1 driven diseases.

In this patent specification, the terms 'comprises', 'comprising', 'includes', 'including', or similar terms are intended to mean a non-exclusive inclusion, such that a method or composition that comprises a list of elements does not include those elements solely, but may well include other elements not listed.

Unless defined otherwise, all technical and scientific terms used herein have the same meaning as would be commonly understood by those of ordinary skill in the art to which this invention belongs.

The term "pharmaceutically acceptable salt", as used herein, refers to salts which are toxicologically safe for systemic or localised administration such as salts prepared from pharmaceutically acceptable non-toxic bases or acids including inorganic or organic bases and inorganic or organic acids. The pharmaceutically acceptable salts may be selected from the group including alkali and alkali earth, ammonium, aluminium, iron, glucosamine, chloride, sulphate, sulphonate, bisulphate, nitrate, citrate, tartrate, bitartrate, phosphate, carbonate, bicarbonate, malate, maleate, napsylate, fumarate, succinate, acetate, benzoate, terephthalate, palmoate, piperazine, pectinate and S-methyl methionine salts and the like.

The term "alkyl" refers to a straight-chain or branched alkyl substituent containing from, for example, 1 to about 12 carbon atoms, preferably 1 to about 9 carbon atoms, more preferably 1 to about 6 carbon atoms, even more preferably from 1 to about 4 carbon atoms, still yet more preferably from 1 to 2 carbon atoms. Examples of alkyl groups may be selected from the group consisting of methyl, ethyl, propyl, isopropyl, n-butyl, sec-butyl, isobutyl, tert-butyl, pentyl, isoamyl, 2-methylbutyl, 3-methylbutyl, hexyl, heptyl, 2-methylpentyl, 3-methylpentyl, 4-methylpentyl, 2-ethyl-butyl, 3-ethylbutyl, octyl, nonyl, decyl, undecyl, dodecyl and the like. The number of carbons referred to relates to the carbon backbone and carbon branching, but does not include carbon atoms belonging to any substituents, for example the carbon atoms of an alkoxy substituent branching off the main carbon chain. Substituted alkyl includes alkyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of "optionally substituted". An "alkylene" group is similarly defined as a divalent alkyl group.

The term "alkenyl" refers to unsaturated linear or branched hydrocarbon groups, having 2 to 12 carbon atoms, preferably 2 to 9 carbon atoms, more preferably 2 to 6 carbon atoms, and having at least one carbon-carbon double bond. Where appropriate, the alkenyl group may have a specified number of carbon atoms, for example, $C_2$-$C_6$ alkenyl which includes alkenyl groups having 2, 3, 4, 5 or 6 carbon atoms in linear or branched arrangements. The number of carbons referred to relates to the carbon backbone and carbon branching, but does not include carbon atoms belonging to any substituents. Examples of alkenyl groups may be selected from the group consisting of ethenyl, propenyl, isopropenyl, butenyl, s- and t-butenyl, pentenyl, hexenyl, hepta-1,3-dienyl, hexa-1,3-dienyl, nona-1,3,5-trienyl and the like. Substituted alkenyl includes alkenyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of "optionally substituted". An "alkenylene" group is similarly defined as a divalent alkenyl group.

The term "alkynyl" refers to unsaturated linear or branched hydrocarbon groups, having 2 to 12 carbon atoms, preferably 2 to 9 carbon atoms, more preferably 2 to 6 carbon atoms, and having at least one carbon-carbon triple bond. Where appropriate, the alkynyl group may have a specified number of carbon atoms, for example, $C_2$-$C_6$ alkynyl which includes alkynyl groups having 2, 3, 4, 5 or 6 carbon atoms in linear or branched arrangements. The number of carbons referred to relates to the carbon backbone and carbon branching, but does not include carbon atoms belonging to any substituents. Examples of alkynyl groups may be selected from the group consisting of ethynyl, propargyl, but-1-ynyl, but-2-ynyl and the like. Substituted alkynyl includes alkynyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of "optionally substituted". An "alkynylene" group is similarly defined as a divalent alkynyl group.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("$C_{1-10}$ alkoxy"). In further embodiments, alkoxy refers to oxygen-linked groups comprising 1 to 8 carbon atoms ("$C_{1-8}$ alkoxy"), 1 to 6 carbon atoms ("$C_{1-6}$ alkoxy"), 1 to 4 carbon atoms ("$C_{1-4}$ alkoxy") or 1 to 3 carbon atoms ("$C_{1-3}$ alkoxy").

The terms "cycloalkyl" and "cycloalkenyl" refer to saturated and unsaturated mono-cyclic, bicyclic or tricyclic carbon groups. Where appropriate, the cycloalkyl or cycloalkenyl group may have a specified number of carbon atoms, for example, $C_3$-$C_6$ cycloalkyl or cycloalkenyl includes within its scope a carbocyclic group having 3, 4, 5 or 6 carbon atoms. Examples of cycloalkyl and cycloalkenyl groups may be selected from the group consisting of cyclopropyl, cyclobutyl, cyclopentyl, cyclopentenyl, cyclohexyl, cyclohexenyl, cyclohexadienyl and the like. Substituted cycloalkyl or cycloalkenyl includes substitutions with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of "optionally substituted".

The term "alkylthio" as used herein means a thio group with one alkyl substituent (i.e., —S-alkyl), where alkyl is defined as above.

The term "amino" as used herein means a moiety represented by the structure $NR^{23}$, and includes primary amines, and secondary and tertiary amines substituted by alkyl (i.e., alkylamino). Thus, $R^{23}$ may represent, for example, two hydrogen atoms, two alkyl moieties, or one hydrogen atom and one alkyl moiety.

The term "aryl" refers to a monocyclic, bicyclic, tricyclic or other polycyclic carbon ring of up to 8 members in each ring, wherein at least one ring is aromatic as defined by the Hückel 4n+2 rule. The term includes polycyclic systems comprising saturated carbon rings or heteroaryl or heterocyclic groups so long as at least one ring is aryl, as described. An "arylene" group is similarly defined as a divalent aryl group.

The terms "aralkyl" and "arylalkyl" as used herein mean an aryl group as defined above linked to the molecule through an alkylene group as defined above.

For the purposes of the present invention, where a combination of groups is referred to as one moiety, for example, arylalkyl, arylalkenyl, arylalkynyl, alkylaryl, alkenylaryl or alkynylaryl, the last mentioned group contains the atom by which the moiety is attached to the rest of the molecule. A typical example of an arylalkyl group is benzyl.

The term "heteroaryl" refers to an aryl group containing from one or more (particularly one to four) non-carbon ring atom(s) (particularly N, O or S) or a combination thereof. A heteroaryl group may be optionally substituted at one or more carbon or nitrogen atom(s). Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5-membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having four heteroatoms (e.g., tetrazoles); 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heteroaryls with three heteroatoms (e.g., 1,3,5-triazine); and 6-membered heteroaryls with four heteroatoms. "Substituted heteroaryl" means a heteroaryl having one or more groups as substituents and including those defined under "optionally substituted". A "heteroarylene" group is similarly defined as a divalent heteroaryl group.

"Heterocyclyl" as used herein refers to a non-aromatic ring having 3 to 8 atoms in the ring, preferably 5 to 8 atoms in the ring, and of those atoms 1 to 4 are heteroatoms (particularly N, O or S). Heterocyclic rings may also be fused with one or more cyclic hydrocarbon, heterocyclic, aryl, or heteroaryl rings. Heterocyclic includes partially and fully saturated heterocyclic groups. Heterocyclic systems may be attached to another moiety via any number of carbon atoms or heteroatoms of the radical and may be both saturated and unsaturated. Non-limiting examples of heterocyclic groups include $C_4$-$C_6$ selenocycles, pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

The term "acyl" as used herein means $C(O)R^{19}$ wherein $R^{19}$ is alkyl, alkenyl, alkynyl, cycloalkyl, cycloalkenyl, aryl, aralkyl, heteroaryl or heterocyclyl.

The term "halo" as used herein refers to fluoro, chloro, bromo and iodo groups. Similarly the term "halogen" as used herein refers to fluorine, chlorine, bromine and iodine.

"Optionally substituted" in reference to a substituent group refers to substituent groups optionally substituted with one or more moieties, for example, those selected from the group consisting of optionally substituted $C_{1-10}$ alkyl (e.g., optionally substituted $C_{1-6}$ alkyl); optionally substituted $C_{3-6}$ cycloalkyl (e.g., optionally substituted cyclopropyl), optionally substituted hydroxylalkyl; optionally substituted $C_{1-10}$ alkoxy (e.g., optionally substituted $C_{1-6}$ alkoxy); optionally substituted $C_{2-10}$ alkenyl; optionally substituted $C_{2-10}$ alkynyl; optionally substituted $C_{6-12}$ aryl; aryloxy; optionally substituted heteroaryl; optionally substituted heterocyclyl; halo (e.g., Cl, F, Br, and I); hydroxyl; halogenated alkyl (e.g., $CF_3$, 2-Br-ethyl, $CH_2F$, $CH_2CF_3$, and $CF_2CF_3$); amino (e.g., $NH_2$, $NR^{24}H$, and $NR^{24}R^{25}$); alkylamino; arylamino; acyl; amido; CN; $NO_2$; $N_3$; $CH_2OH$; $CONH_2$; $CONR^{24}R^{25}$; $CO_2R^{24}$; $CH_2OR^{24}$; $NHCOR^{24}$; $NHCO_2R^{24}$; $C_{1-3}$ alkylthio; sulfate; sulfonic acid; sulfonate esters such as alkyl or aralkyl sulfonyl, including methanesulfonyl; phosphonic acid; phosphate; phosphonate; mono-, di-, or triphosphate esters; trityl or monomethoxytrityl; $R^{24}SO$; $R^{24}SO_2$; $CF_3S$; and $CF_3SO_2$; trialkylsilyl such as dimethyl-t-butylsilyl or diphenylmethylsilyl; and $R^{24}$ and $R^{25}$ are each independently selected from H or optionally substituted $C_{1-10}$ alkyl, $C_{1-6}$ alkyl or $C_{1-4}$ alkyl. Optional substituents also include cyclic structures such as cyclic hydrocarbon (e.g. cycloalkyl, cycloalkenyl), heterocyclic, aryl and heteroaryl rings, fused to the parent moiety.

Whenever a range of the number of atoms in a structure is indicated (e.g., a $C_1$-$C_{12}$, $C_1$-$C_{10}$, $C_1$-$C_9$, $C_1$-$C_6$, $C_1$-$C_4$, or $C_2$-$C_{20}$, $C_2$-$C_{12}$, $C_2$-$C_{10}$, $C_2$-$C_9$, $C_2$-$C_8$, $C_2$-$C_6$, $C_2$-$C_4$ alkyl, alkenyl, etc.), it is specifically contemplated that any subrange or individual number of carbon atoms falling within the indicated range also can be used. Thus, for instance, the recitation of a range of 1-12 carbon atoms (e.g., $C_1$-$C_{12}$), 1-9 carbon atoms (e.g., $C_1$-$C_9$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

According to a first aspect of the invention, there is provided a compound of formula (I), or a pharmaceutically acceptable salt, solvate or prodrug thereof:

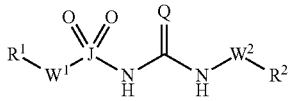

Formula (I)

wherein Q is selected from O, S and Se;
J is S or Se;
$W^1$ and $W^2$, when present, are independently selected from N and C;
$R^1$ and $R^2$ are independently selected from the group consisting of hydrogen, $C_1$-$C_{12}$ alkyl, $C_2$-$C_{12}$ alkenyl, $C_2$-$C_{12}$ alkynyl, aryl, heterocyclyl, heteroaryl, cycloalkyl, cycloalkenyl, amino, amido, alkylthio, acyl, arylalkyl and acylamido, all of which may be optionally substituted; and
wherein at least one of $W^1$ and $W^2$ is present and is a nitrogen atom and when $R^1$ or $R^2$ are cyclic then the respective $W^1$ or $W^2$ may form part of the ring structure.

It will be apparent to the skilled addressee that the structure of formula (I) covers compounds wherein either $W^1$ or $W^2$ is nitrogen as well as compounds wherein both $W^1$ and $W^2$ are nitrogen. Additionally, when $W^1$ and/or $W^2$ is nitrogen then that nitrogen may be part of a chain linking to $R^1$ or $R^2$ or may be an atom which forms part of a ring structure.

In preferred embodiments, $R^1W^1$— is $(R^1)_2N$— or $(R^1)HN$— or $(R^1)$—, and —$W^2R^2$ is —$N(R^2)_2$ or —$NH(R^2)$ or —$(R^2)$, provided that a nitrogen atom of $R^1W^1$— and/or a nitrogen atom of —$W^2R^2$ is linked to (i.e. bonded to) the remainder of the molecule.

In one embodiment, a sp$^3$ hybridised nitrogen atom of $R^1W^1$— is linked to J.

In another embodiment, a sp$^3$ hybridised nitrogen atom of —$W^2R^2$ is linked to the remainder of the molecule of formula (I).

In preferred embodiments, Q is O and J is S.

In one embodiment, $R^1$ and $R^2$ are independently $C_1$-$C_{10}$ alkyl which may be optionally substituted.

In an embodiment, $R^1$ and $R^2$ are independently $C_1$-$C_8$ alkyl which may be optionally substituted.

In a further embodiment, $R^1$ and $R^2$ are independently $C_1$-$C_6$ alkyl which may be optionally substituted.

In one embodiment, $R^1$ and $R^2$ are independently $C_1$-$C_{10}$ alkenyl which may be optionally substituted.

In a further embodiment, $R^1$ and $R^2$ are independently $C_1$-$C_8$ alkenyl which may be optionally substituted.

In an embodiment, $R^1$ and $R^2$ are independently $C_1$-$C_6$ alkenyl which may be optionally substituted.

In one embodiment, $R^1$ and $R^2$ are independently $C_1$-$C_{10}$ alkynyl which may be optionally substituted.

In a further embodiment, $R^1$ and $R^2$ are independently $C_1$-$C_8$ alkynyl which may be optionally substituted.

In one embodiment, $R^1$ and $R^2$ are independently $C_1$-$C_6$ alkynyl which may be optionally substituted.

In an embodiment, one or more hydrogens of the alkyl, alkenyl or alkynyl groups is deuterated.

In certain embodiments, $R^1$ and $R^2$ are independently $C_3$-$C_8$ cycloalkyl or cycloalkenyl which may each be optionally substituted.

In one embodiment, $R^1$ and $R^2$ are independently $C_4$-$C_7$ cycloalkyl or cycloalkenyl which may each be optionally substituted.

In one embodiment, $R^1$ and $R^2$ are independently selected from $C_5$ or $C_6$ cycloalkyl or cycloalkenyl, each of which may be optionally substituted.

In one embodiment, $R^1$ and $R^2$ are independently $C_6$-$C_8$ aryl which may be optionally substituted.

In one embodiment, $R^1$ and $R^2$ are independently $C_6$-$C_7$ aryl which may be optionally substituted.

In one embodiment, $W^2$ and $R^2$ may form an indacene group, including substituted, for example halogenated, and hydrogenated variants thereof.

In one embodiment, $W^2$ and $R^2$ may form a hexahydroindacene group, preferably a hexahydro-s-indacene group.

In one embodiment, $R^1$ and $R^2$ are independently $C_5$-$C_8$ heteroaryl which may be optionally substituted.

In one embodiment, $R^1$ and $R^2$ are independently $C_5$-$C_7$ heteroaryl which may be optionally substituted.

In one embodiment, $R^1$ and $R^2$ are independently selected from $C_5$ or $C_6$ heteroaryl, each of which may be optionally substituted.

In one embodiment, $R^1$ and $R^2$ are independently $C_3$-$C_8$ heterocyclyl which may be optionally substituted.

In one embodiment, $R^1$ and $R^2$ are independently $C_4$-$C_7$ heterocyclyl which may be optionally substituted.

In one embodiment, $R^1$ and $R^2$ are independently selected from $C_5$ or $C_6$ heterocyclyl, each of which may be optionally substituted.

It will be understood that $W^1$ and $W^2$ may independently represent —N— or —NH depending on the degree of substitution with $R^1$. That is, when $R^1$ is, for example, $C_3$ alkyl then $W^1$ may either be mono- or disubstituted with $C_3$ alkyl. Thus in all definitions where $R^1$ or $R^2$ are described as e.g. alkyl, alkenyl etc. then this may also be read as dialkyl, dialkenyl etc.

In one embodiment $W^1/R^1$ or $W^2/R^2$ may form a selenocycle.

In one embodiment —$W^2R^2$ is an aryl or a heteroaryl group, wherein the aryl or the heteroaryl group is substituted at the α and α' positions, wherein —$W^2R^2$ may optionally be further substituted. For example, —$W^2R^2$ may be a phenyl group substituted at the 2- and 6-positions. Typical substituents at the α and α' positions include alkyl, cycloalkyl, alkoxy, cycloalkoxy, alkenyl, cycloalkenyl, alkynyl, acyl, aryl, alkylaryl, alkoxyaryl, heteroaryl, heterocyclyl, arylalkyl and heteroarylalkyl groups. More typically, the substituents at the α and α' positions are independently selected from alkyl and cycloalkyl groups, such as $C_3$-$C_6$ branched or $C_3$-$C_6$ cyclic alkyl groups, e.g. isopropyl, cyclopropyl, cyclohexyl or t-butyl groups. Other typical substituents at the α and α' positions include cyclic hydrocarbon, heterocyclic, aryl or heteroaryl rings which are fused to the parent aryl or heteroaryl group across the α,β and/or α',β' positions respectively. Such fused aryl and fused heteroaryl groups are described in greater detail below.

As used herein, the nomenclature α, β, α', β' refers to the position of the atoms of the aryl or heteroaryl group relative to the point of attachment of the —$W^2R^2$ moiety to the remainder of the molecule. For example, where —$W^2R^2$ is a 1,2,3,5,6,7-hexahydro-s-indacen-4-yl moiety, the α, β, α' and β' positions are as follows:

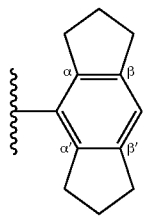 [SMILES: *c1c2c(cc3c1CCC3)CCC2]

In one embodiment —$W^2R^2$ is a fused aryl or a fused heteroaryl group, wherein the aryl or heteroaryl group is fused to one or more cyclic hydrocarbon, heterocyclic, aryl or heteroaryl rings, wherein —$W^2R^2$ may be optionally substituted.

In another embodiment, —$W^2R^2$ is a fused aryl or a fused heteroaryl group, wherein the aryl or heteroaryl group is fused to two or more cyclic hydrocarbon, heterocyclic, aryl or heteroaryl rings, wherein —$W^2R^2$ may be optionally substituted. Typically, the two or more cyclic hydrocarbon, heterocyclic, aryl or heteroaryl rings are each ortho-fused to the aryl or heteroaryl group, i.e. each fused cyclic hydrocarbon, heterocyclic, aryl or heteroaryl ring has only two atoms and one bond in common with the aryl or heteroaryl group.

In yet another embodiment, —$W^2R^2$ is a fused aryl or a fused heteroaryl group, wherein a first cyclic hydrocarbon, heterocyclic, aryl or heteroaryl ring is fused to the aryl or heteroaryl group across the α,β positions and a second cyclic hydrocarbon, heterocyclic, aryl or heteroaryl ring is fused to the aryl or heteroaryl group across the α',β' positions, and wherein —$W^2R^2$ may be optionally substituted.

Typically in any embodiment where —$W^2R^2$ is a fused aryl or a fused heteroaryl group, $R^1W^1$— is $(R^1)_2N$— or $R^1NH$—, J is S and Q is O, wherein $R^1$ is as previously defined.

In one embodiment, —$W^2R^2$ has a formula selected from:

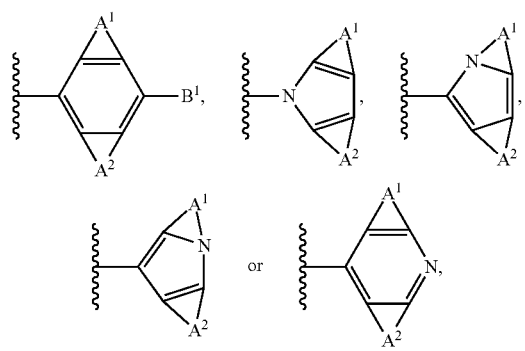

wherein $A^1$ and $A^2$ are each independently selected from an optionally substituted alkylene or alkenylene group, which may optionally include one or more heteroatoms N, O or S in its carbon skeleton, and wherein $B^1$ is hydrogen or any optional substituent. $B^1$ and any optional substituent attached to $A^1$ or $A^2$ may together with the atoms to which they are attached form a further fused cyclic hydrocarbon, heterocyclic, aryl or heteroaryl ring which may itself be optionally substituted. Similarly, any optional substituent attached to $A^1$ and any optional substituent attached to $A^2$ may also together with the atoms to which they are attached form a further fused cyclic hydrocarbon, heterocyclic, aryl or heteroaryl ring which may itself be optionally substituted.

Typically, $B^1$ is hydrogen or a halo, hydroxyl, —CN, —$NO_2$, $C_1$-$C_4$ alkyl, $C_1$-$C_4$ haloalkyl, $C_1$-$C_4$ alkoxy or $C_1$-$C_4$ haloalkoxy group.

Typically, any ring containing $A^1$ or $A^2$ is a five or a six membered ring.

In a further embodiment, —$W^2R^2$ has a formula selected from:

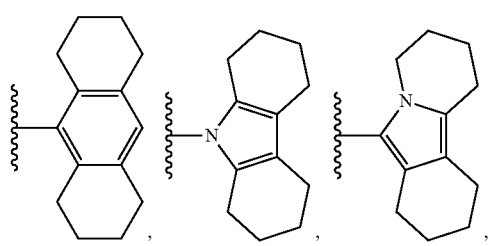

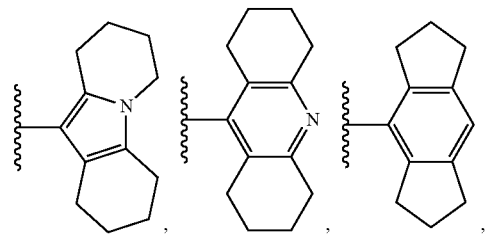

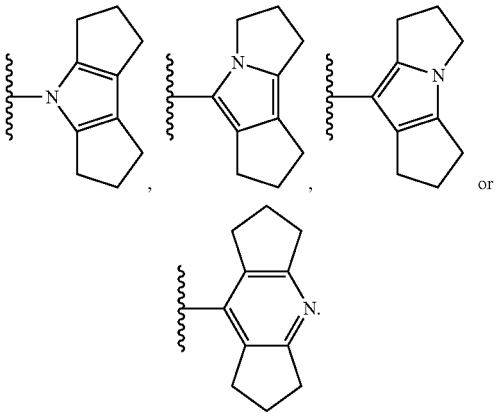

Examples of compounds where —$W^2R^2$ is a fused aryl or a fused heteroaryl group include the compounds of Examples 1-43 below and the compounds:

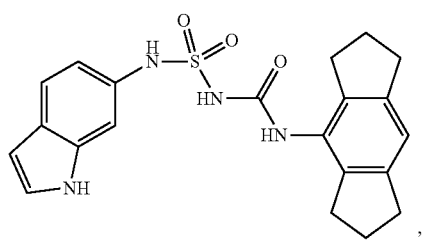

N-((1,2,3,5,6,7-hexahydro-s-indacen-4-yl)carbamoyl)(1H-indol-6-amine)sulfonamide

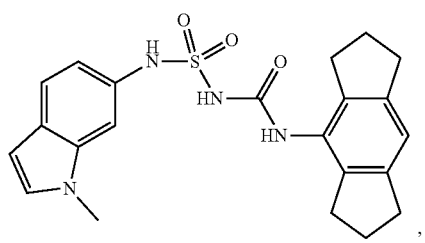

N-((1,2,3,5,6,7-hexahydro-s-indacen-4-yl)carbamoyl)(1-methyl-1H-indol-6-amine)sulfonamide

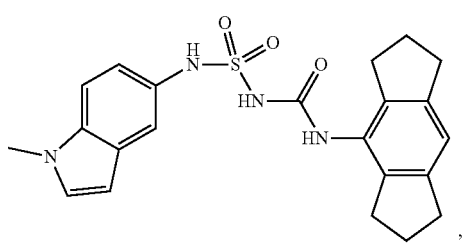

N-((1,2,3,5,6,7-hexahydro-s-indacen-4-yl)carbamoyl)(1-methyl-1H-indol-5-amine)sulfonamide

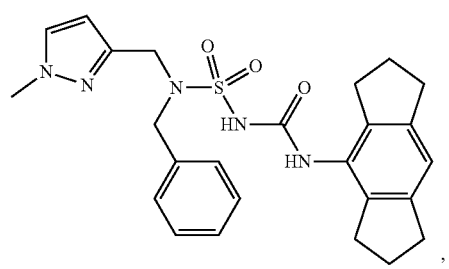

N-((1,2,3,5,6,7-hexahydro-s-indacen-4-yl)-carbamoyl)(N-benzyl-1-(1-methyl-1H-pyrazol-3-yl)methanamine)sulfonamide

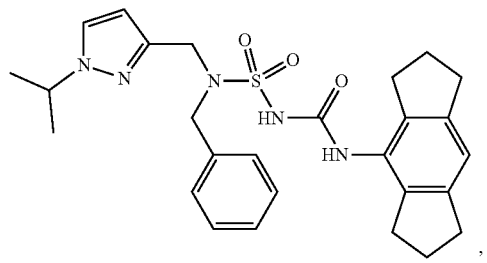

N-((1,2,3,5,6,7-hexahydro-s-indacen-4-yl)-carbamoyl)(N-benzyl-1-(1-isopropyl-1H-pyrazol-3-yl)methanamine)sulfonamide

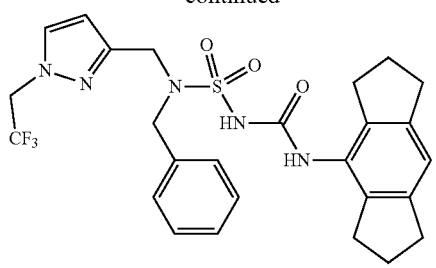

N-((1,2,3,5,6,7-hexahydro-s-indacen-4-yl)-carbamoyl)(N-benzyl-1-(1-(2,2,2-trifluoroethyl)-1H-pyrazol-3-yl)methanamine)sulfonamide

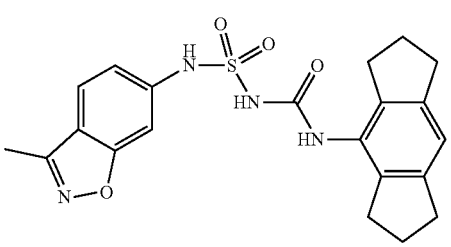

N-((1,2,3,5,6,7-hexahydro-s-indacen-4-yl)carbamoyl)(3-methylbenzo[d]isoxazol-6-amine)sulfonamide

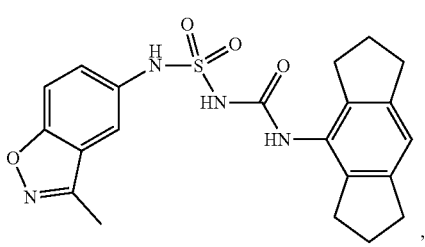

N-((1,2,3,5,6,7-hexahydro-s-indacen-4-yl)carbamoyl)(3-methylbenzo[d]isoxazol-5-amine)sulfonamide

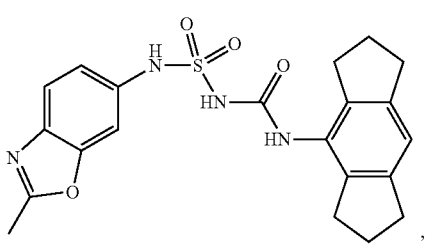

N-((1,2,3,5,6,7-hexahydro-s-indacen-4-yl)carbamoyl)(2-methylbenzo[d]oxazol-6-amine)sulfonamide

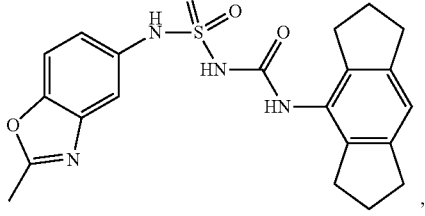

N-((1,2,3,5,6,7-hexahydro-s-indacen-4-yl)carbamoyl)(2-methylbenzo[d]oxazol-5-amine)sulfonamide -continued

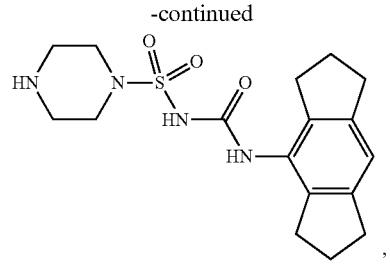

N-((1,2,3,5,6,7-hexahydro-s-indacen-4-yl)carbamoyl)piperazine-1-sulfonamide

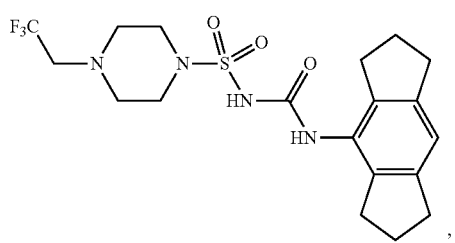

N-((1,2,3,5,6,7-hexahydro-s-indacen-4-yl)carbamoyl)-4-(2,2,2-trifluoroethyl)piperazine-1-sulfonamide

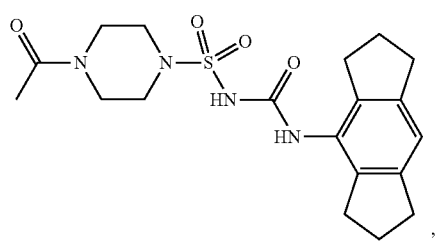

4-acetyl-N-((1,2,3,5,6,7-hexahydro-s-indacen-4-yl)carbamoyl)piperazine-1-sulfonamide

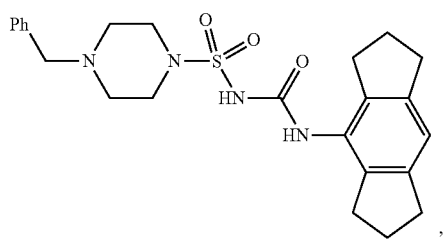

4-benzyl-N-((1,2,3,5,6,7-hexahydro-s-indacen-4-yl)carbamoyl)piperazine-1-sulfonamide

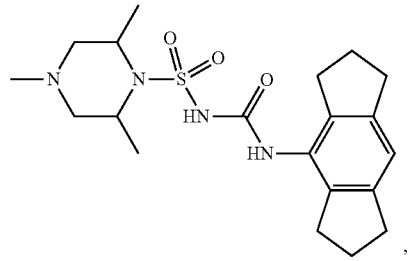

N-((1,2,3,5,6,7-hexahydro-s-indacen-4-yl)carbamoyl)-2,4,6-trimethylpiperazine-1-sulfonamide -continued

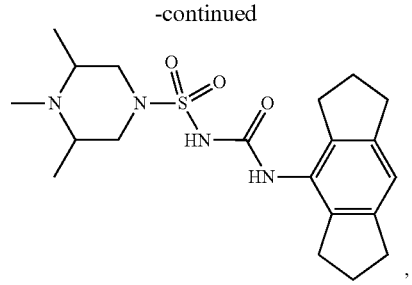

N-((1,2,3,5,6,7-hexahydro-s-indacen-4-yl)carbamoyl)-3,4,5-trimethylpiperazine-1-sulfonamide

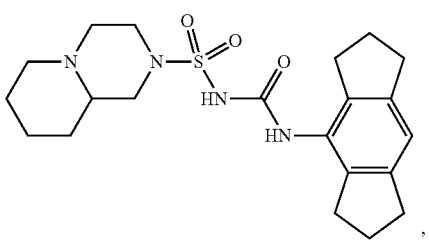

N-((1,2,3,5,6,7-hexahydro-s-indacen-4-yl)carbamoyl)octahydro-2H-pyrido[1,2-a]pyrazine-2-sulfonamide

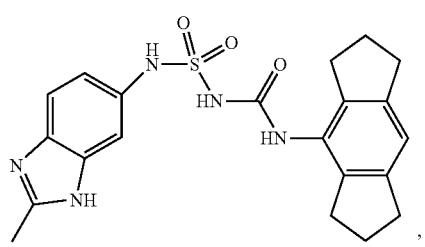

N-((1,2,3,5,6,7-hexahydro-s-indacen-4-yl)carbamoyl)(2-methyl-1H-benzo[d]imidazol-6-amine)sulfonamide

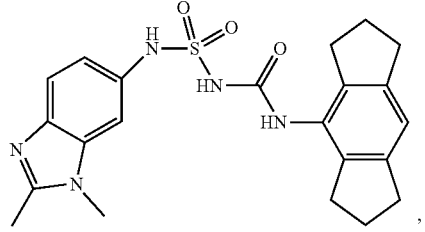

N-((1,2,3,5,6,7-hexahydro-s-indacen-4-yl)carbamoyl)(1,2-dimethyl-1H-benzo[d]imidazol-6-amine)sulfonamide

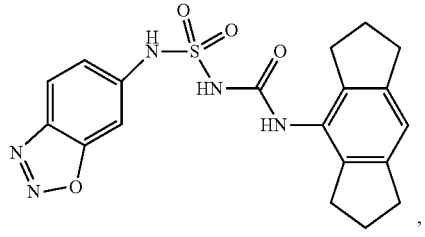

N-((1,2,3,5,6,7-hexahydro-s-indacen-4-yl)carbamoyl)(benzo[d][1,2,3]oxidazol-6-amine)sulfonamide -continued

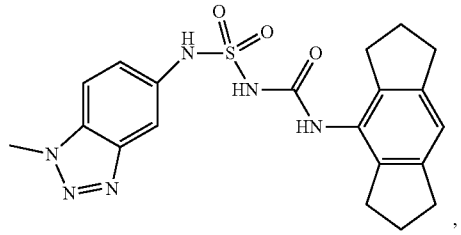

N-((1,2,3,5,6,7-hexahydro-s-indacen-4-yl)carbamoyl)(1-methyl-1H-benzo[d][1,2,3]triazol-5-amine)sulfonamide

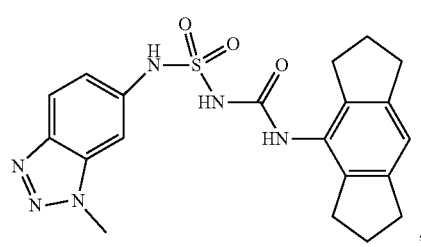

N-((1,2,3,5,6,7-hexahydro-s-indacen-4-yl)carbamoyl)(1-methyl-1H-benzo[d][1,2,3]triazol-6-amine)sulfonamide

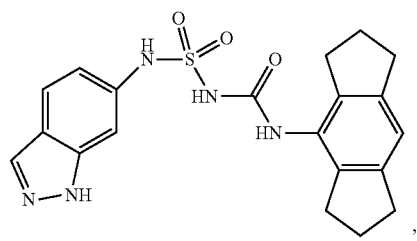

N-((1,2,3,5,6,7-hexahydro-s-indacen-4-yl)-carbamoyl)(1H-indazol-6-amine)sulfonamide

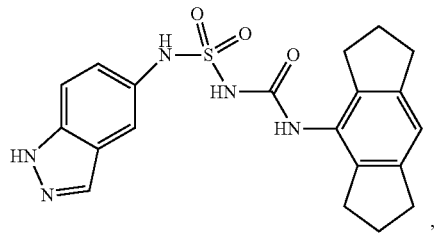

N-((1,2,3,5,6,7-hexahydro-s-indacen-4-yl)-carbamoyl)(1H-indazol-5-amine)sulfonamide

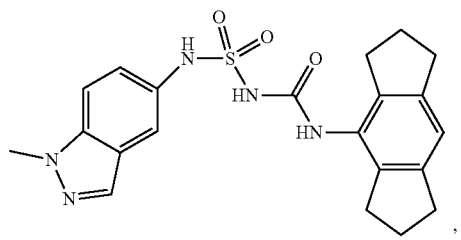

N-((1,2,3,5,6,7-hexahydro-s-indacen-4-yl)-carbamoyl)(1-methyl-1H-indazol-5-amine)sulfonamide -continued

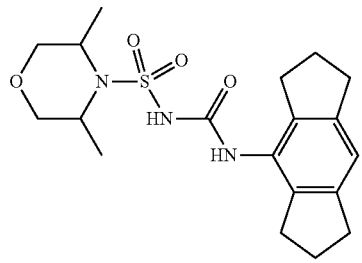

N-((1,2,3,5,6,7-hexahydro-s-indacen-4-yl)carbamoyl)-3-5-dimethylmorpholine-4-sulfonamide

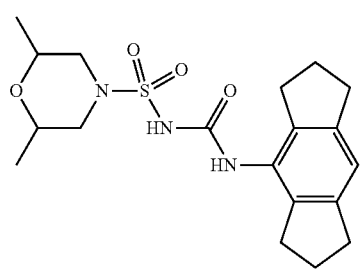

N-((1,2,3,5,6,7-hexahydro-s-indacen-4-yl)carbamoyl)-2-6-dimethylmorpholine-4-sulfonamide

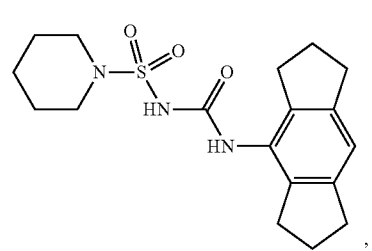

N-((1,2,3,5,6,7-hexahydro-s-indacen-4-yl)carbamoyl)piperidine-1-sulfonamide

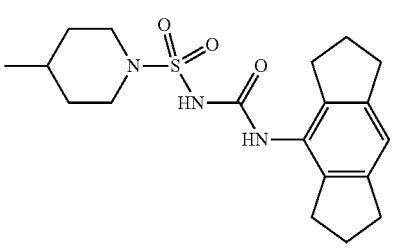

N-((1,2,3,5,6,7-hexahydro-s-indacen-4-yl)carbamoyl)-4-methylpiperidine-1-sulfonamide

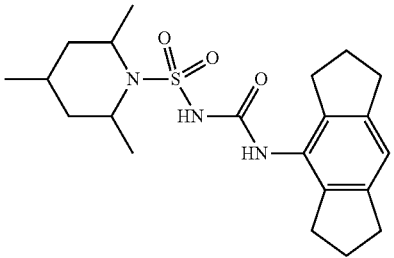

N-((1,2,3,5,6,7-hexahydro-s-indacen-4-yl)carbamoyl)-2,4,6-trimethylpiperidine-1-sulfonamide -continued

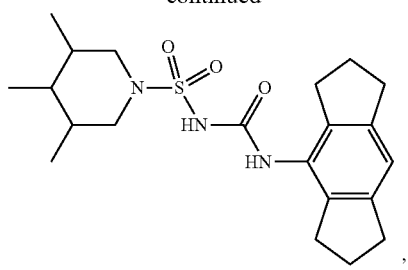

N-((1,2,3,5,6,7-hexahydro-s-indacen-4-yl)carbamoyl)-3,4,5-trimethylpiperidine-1-sulfonamide

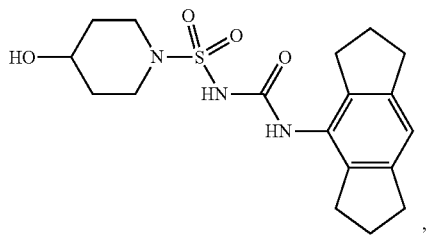

N-((1,2,3,5,6,7-hexahydro-s-indacen-4-yl)carbamoyl)-4-hydroxypiperidine-1-sulfonamide

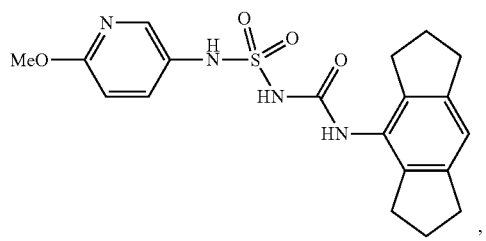

N-((1,2,3,5,6,7-hexahydro-s-indacen-4-yl)carbamoyl)(6-methoxypiperidin-3-amino)sulfonamide

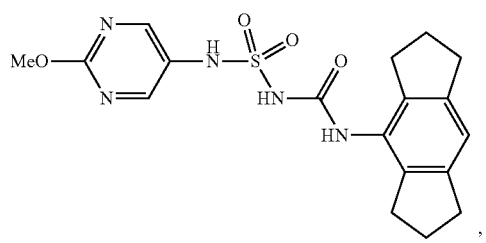

N-((1,2,3,5,6,7-hexahydro-s-indacen-4-yl)carbamoyl)(2-methoxypiperidin-5-amino)sulfonamide

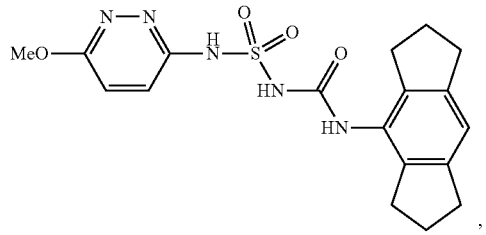

N-((1,2,3,5,6,7-hexahydro-s-indacen-4-yl)carbamoyl)(6-methoxypiperidin-3-amino)sulfonamide -continued

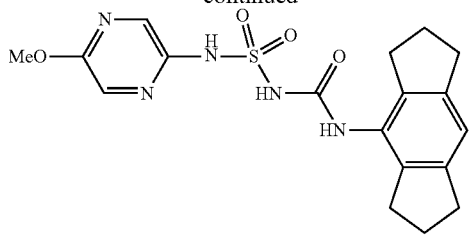

N-((1,2,3,5,6,7-hexahydro-s-indacen-4-yl)carbamoyl)(5-methoxypiperidin-2-amino)sulfonamide In one embodiment, $R^1W^1$— comprises a heteroaryl group, wherein $R^1W^1$— may be optionally substituted. Typically in any embodiment where $R^1W^1$-comprises a heteroaryl group, a nitrogen atom of $R^1W^1$— is linked to J. Typically, in any embodiment where $R^1W^1$— comprises a heteroaryl group and a nitrogen atom of $R^1W^1$— is linked to J, J is S, Q is O and —$W^2R^2$ is —$R^2$ wherein $R^2$ is as previously defined. Typically in any embodiment where $R^1W^1$— comprises a heteroaryl group, —$W^2R^2$ is an aryl or a heteroaryl group, wherein the aryl or the heteroaryl group is substituted at the α and α' positions and optionally at other positions. More typically, in any embodiment where $R^1W^1$— comprises a heteroaryl group, a nitrogen atom of $R^1W^1$— is linked to J and —$W^2R^2$ is an aryl group, wherein the aryl group is substituted at the α and α' positions and optionally at other positions.

In one embodiment, $R^1W^1$— is $R^1NH$— or $(R^1)_2N$— wherein at least one $R^1$ comprises a heteroaryl group, or two $R^1$ together with the nitrogen atom to which they are attached form a heteroaryl group or a cyclic group which is substituted with a heteroaryl group, wherein $R^1W^1$— may be optionally substituted.

In one embodiment, $R^1W^1$— is Het-L-NH— or Het-L-NR$^1$—, wherein Het is an optionally substituted heteroaryl group, -L- is a bond or an optionally substituted alkylene, alkenylene, alkynylene or arylene group, which may optionally include one or more heteroatoms N, O or S in its carbon skeleton, and $R^1$ is as previously defined. Typically, -L- is a bond or a $C_1$-$C_2$ alkylene group.

In one embodiment, Het is an optionally substituted monocyclic or bicyclic heteroaryl group. Typically, such a group is unsubstituted or substituted with one or more halo, alkyl, alkoxy, aryl, alkylaryl, alkoxyaryl, heteroaryl or halogenated alkyl groups.

In a further embodiment, Het is selected from an optionally substituted furanyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, triazinyl, indolizinyl, indolyl, isoindolyl, benzofuranyl, benzothiophenyl, indazolyl, benzimidazolyl, benzthiazolyl, purinyl, quinolinyl, isoquinolinyl, cinnolinyl, phthalazinyl, quinazolinyl, quinoxalinyl, naphthyridinyl or pteridinyl group. Typically, such a group is unsubstituted or substituted with one or more halo, alkyl, alkoxy, acyl, aryl, alkylaryl, alkoxyaryl, heteroaryl, arylalkyl, heteroarylalkyl, or halogenated alkyl groups.

Examples of compounds where $R^1W^1$— comprises a heteroaryl group include the compounds of Examples 4, 8, 13, 14, 15, 17-23, 27, 29, 30, 35, 39, 42 and 43 below and the compounds:

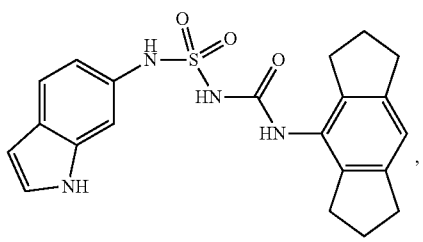

N-((1,2,3,5,6,7-hexahydro-s-indacen-4-yl)carbamoyl)(1H-indol-6-amine)sulfonamide

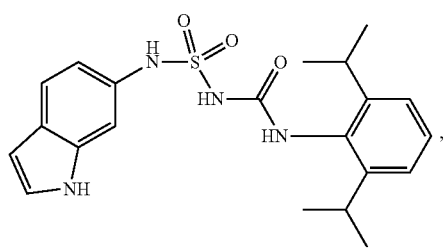

N-((2,6-diisopropylphenyl)carbamoyl)(1H-indol-6-amine)sulfonamide

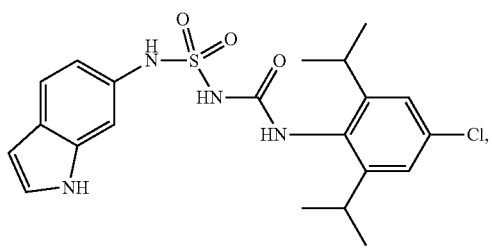

N-((4-chloro-2,6-diisopropylphenyl)carbamoyl)(1H-indol-6-amine)sulfonamide

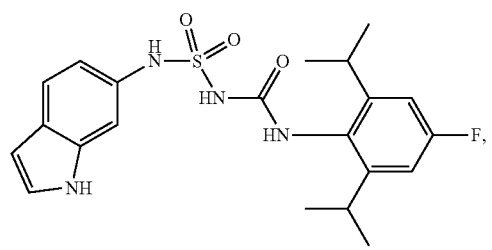

N-((4-fluoro-2,6-diisopropylphenyl)carbamoyl)(1H-indol-6-amine)sulfonamide

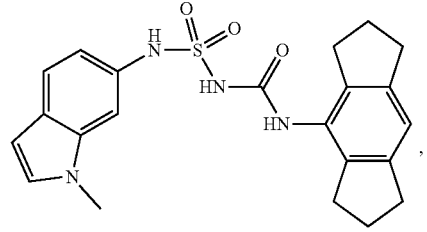

N-((1,2,3,5,6,7-hexahydro-s-indacen-4-yl)carbamoyl)(1-methyl-1H-indol-6-amine)sulfonamide

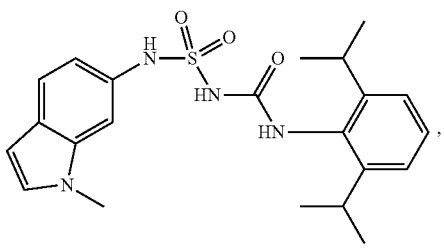

N-((2,6-diisopropylphenyl)carbamoyl)(1-methyl-1H-indol-6-amine)sulfonamide

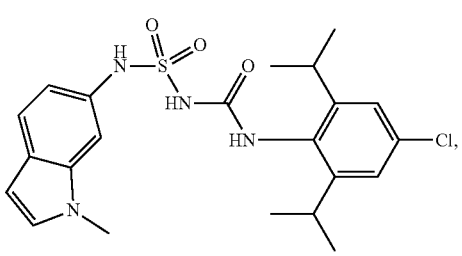

N-((4-chloro-2,6-diisopropylphenyl)carbamoyl)(1-methyl-1H-indol-6-amine)sulfonamide

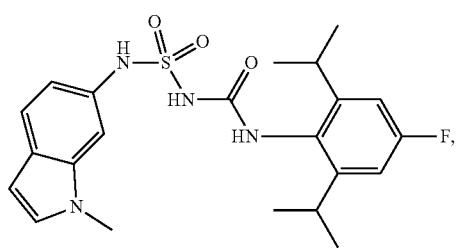

N-((4-fluoro-2,6-diisopropylphenyl)carbamoyl)(1-methyl-1H-indol-6-amine)sulfonamide

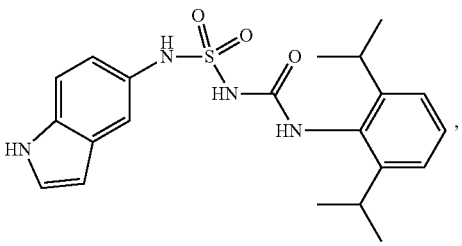

N-((2,6-diisopropylphenyl)carbamoyl)(1H-indol-5-amine)sulfonamide

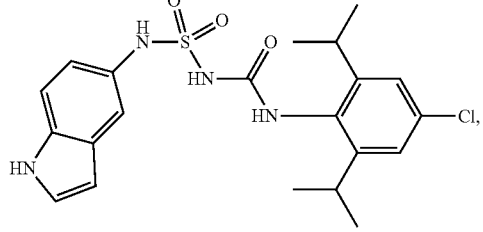

N-((4-chloro-2,6-diisopropylphenyl)carbamoyl)(1H-indol-5-amine)sulfonamide

-continued

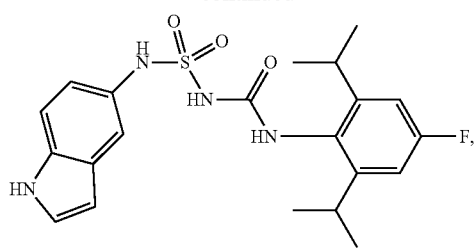

N-((4-fluoro-2,6-diisopropylphenyl)carbamoyl)
(1H-indol-5-amine)sulfonamide

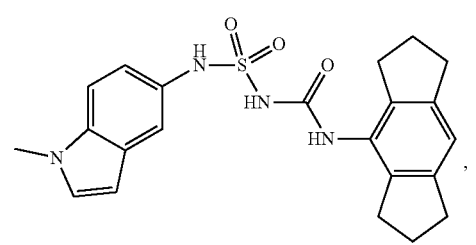

N-((1,2,3,5,6,7-hexahydro-s-indacen-4-
yl)carbamoyl)(1-methyl-
1H-indol-5-amine)sulfonamide

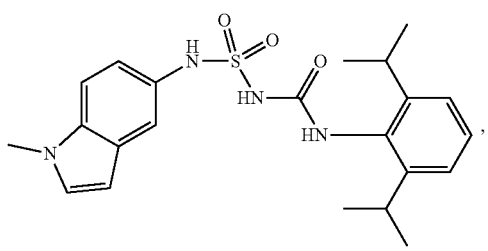

N-((2,6-diisopropylphenyl)carbamoyl)
(1-methyl-1H-indol-5-amine)sulfonamide

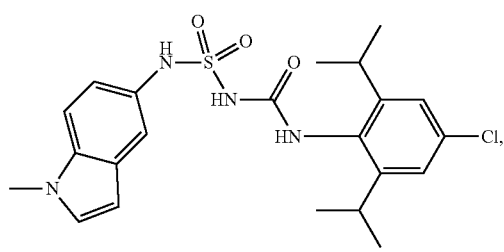

N-((4-chloro-2,6-diisopropylphenyl)carbamoyl)
(1-methyl-1H-indol-5-amine)sulfonamide

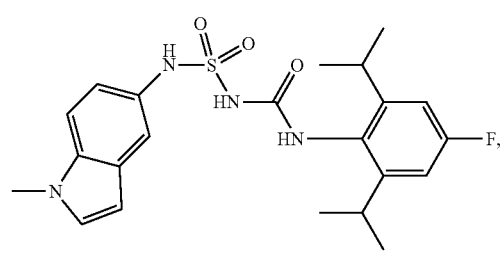

N-((4-fluoro-2,6-diisopropylphenyl)carbamoyl)
(1-methyl-1H-indol-5-amine)sulfonamide -continued

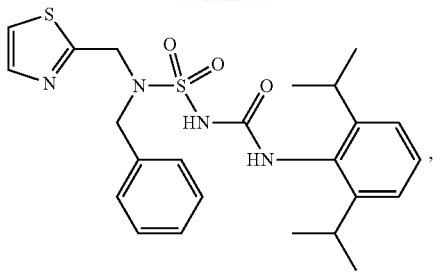

N-((2,6-diisopropylphenyl)carbamoyl)
(N-benzyl-1-(thiazol-2-yl)
methanamine)sulfonamide

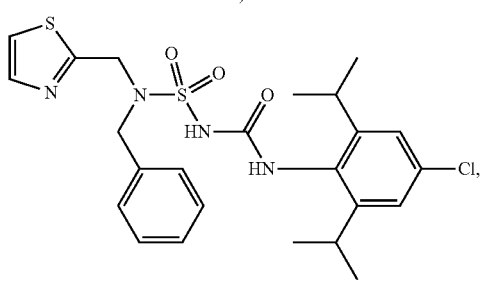

N-((4-chloro-2,6-diisopropylphenyl)carbamoyl)
(N-benzyl-1-(thiazol-2-yl)methanamine)sulfonamide

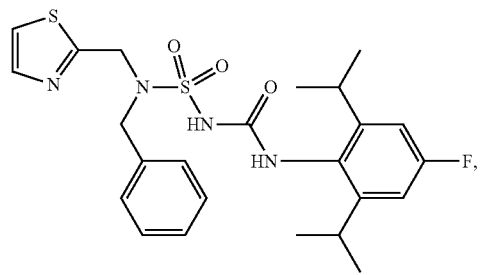

N-((4-fluoro-2,6-diisopropylphenyl)carbamoyl)
(N-benzyl-1-(thiazol-2-yl)methanamine)sulfonamide

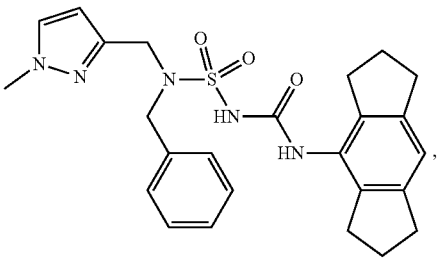

N-((1,2,3,5,6,7-hexadryo-s-indacen-4-yl)-
carbamoyl)(N-benzyl-1-(1-methyl-1H-pyrazol-3-
yl)methanamine)sulfonamide

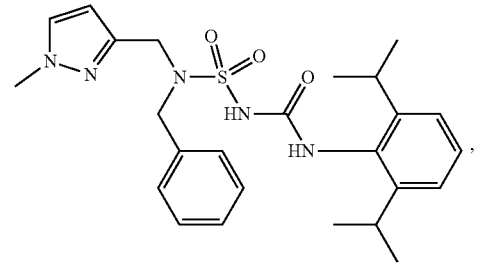

N-((2,6-diisopropylphenyl)carbamoyl)
(N-benzyl-1-(1-methyl-1H-pyrazol-3-yl)
methanamine)sulfonamide

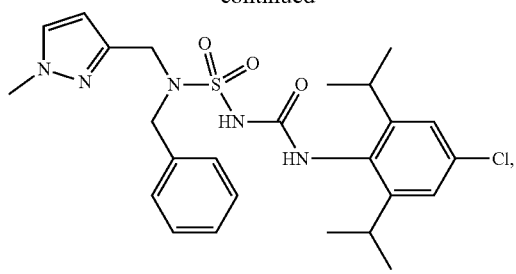

N-((4-chloro-2,6-diisopropylphenyl)carbamoyl)
(N-benzyl-1-(1-methyl-1H-pyrazol-3-yl)
methanamine)sulfonamide

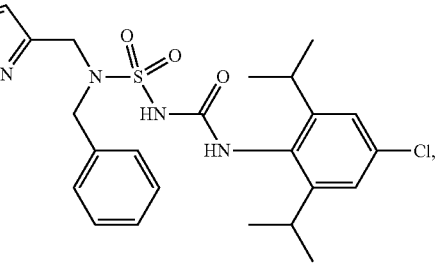

N-((4-chloro-2,6-diisopropylphenyl)carbamoyl)
(N-benzyl-1-(1-isopropyl-1H-pyrazol-3-yl)
methanamine)sulfonamide

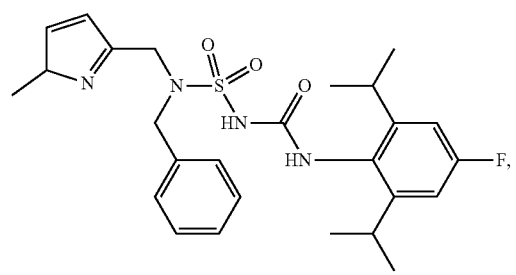

N-((4-fluoro-2,6-diisopropylphenyl)carbamoyl)
(N-benzyl-1-(1-methyl-1H-pyrazol-3-yl)
methanamine)sulfonamide

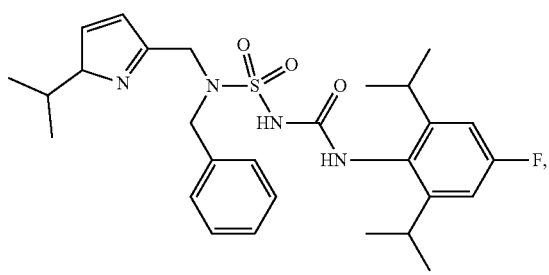

N-((4-fluoro-2,6-diisopropylphenyl)carbamoyl)
(N-benzyl-1-(1-isopropyl-1H-pyrazol-3-yl)
methanamine)sulfonamide

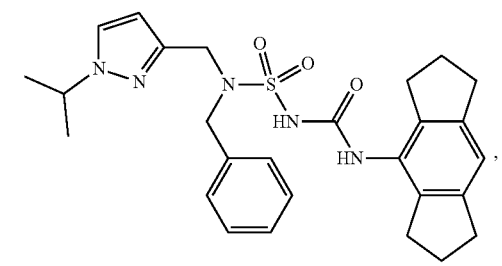

N-((1,2,3,5,6,7-hexadryo-s-indacen-4-yl)-
carbamoyl)(N-benzyl-1-(1-isopropyl-1H-pyrazol-3-
yl)methanamine)sulfonamide

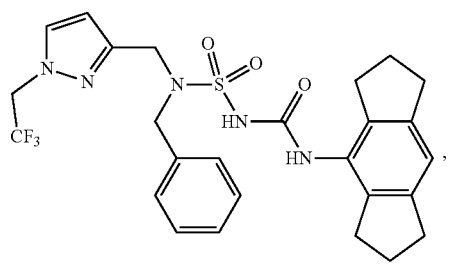

N-((1,2,3,5,6,7-hexadryo-s-indacen-4-yl)carbamoyl)
(N-benzyl-1-(1-(2,2,2-trifluoroethyl)-1H-pyrazol-3-yl)-
methanamine)sulfonamide

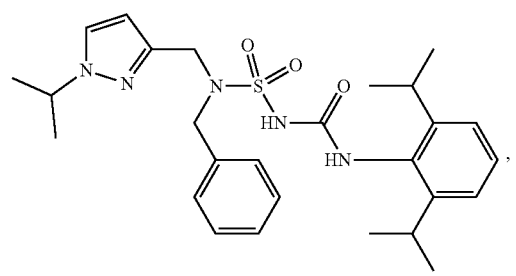

N-((2,6-diisopropylphenyl)carbamoyl)
(N-benzyl-1-(1-isopropyl-1H-pyrazol-3-yl)
methanamine)sulfonamide

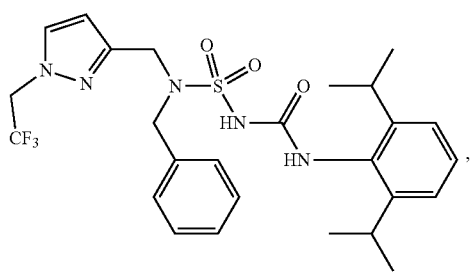

N-((2,6-diisopropylphenyl)carbamoyl)
(N-benzyl-1-(1-(2,2,2-trifluoroethyl)-1H-pyrazol-3-yl)-
methanamine)sulfonamide

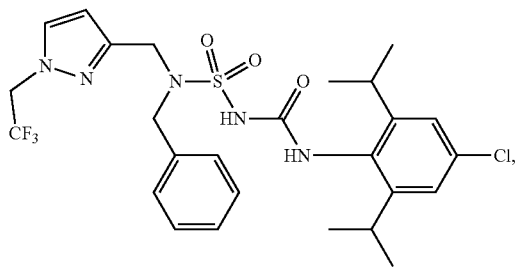

N-((4-chloro-2,6-diisopropylphenyl)carbamoyl)
(N-benzyl-1-(1-(2,2,2-trifluoroethyl-1H-pyrazol-3-yl)-
methanamine)sulfonamide

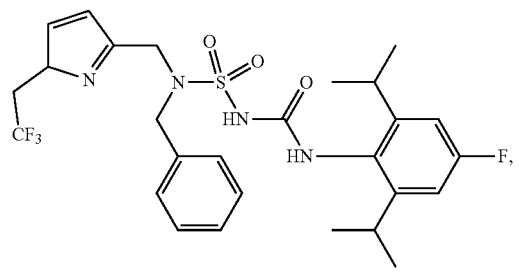

N-((4-fluoro-2,6-diisopropylphenyl)carbamoyl)
(N-benzyl-1-(1-(2,2,2-trifluoroethyl-1H-pyrazol-3-yl)-
methanamine)sulfonamide

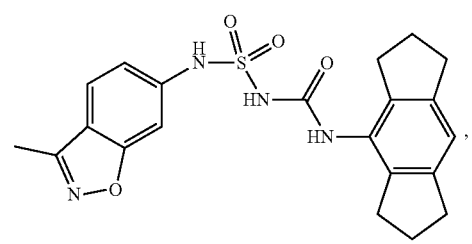

N-((1,2,3,5,6,7-hexadryo-s-indacen-4-
yl)carbamoyl)(3-methylbenzo[d]isoxazol-6-
amine)sulfonamide

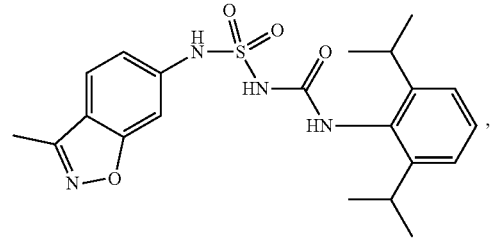

N-((2,6-diisopropylphenyl)carbamoyl)
(3-methylbenzo[d]isoxazol-6-amine)sulfonamide

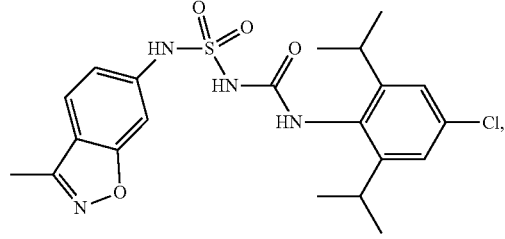

N-((4-chloro-2,6-diisopropylphenyl)carbamoyl)
(3-methylbenzo[d]isoxazol-6-amine)sulfonamide

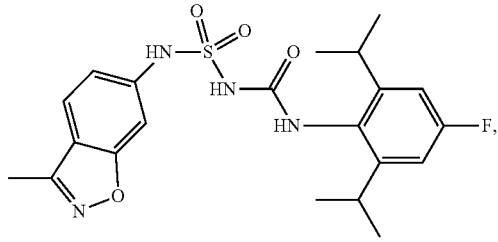

N-((4-fluoro-2,6-diisopropylphenyl)carbamoyl)
(3-methylbenzo[d]isoxazol-6-amine)sulfonamide

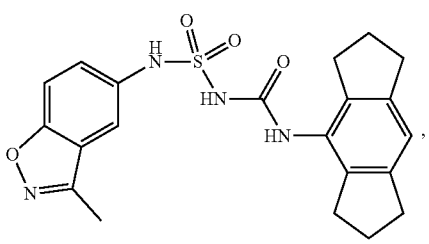

N-((1,2,3,5,6,7-hexadryo-s-indacen-4-
yl)carbamoyl)(3-methylbenzo[d]isoxazol-5-
amine)sulfonamide

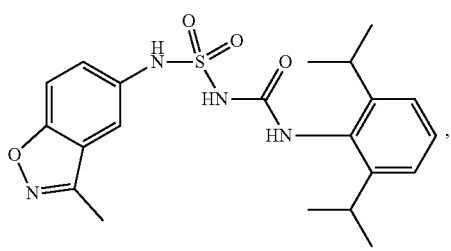

N-((2,6-diisopropylphenyl)carbamoyl)
(3-methylbenzo[d]isoxazol-5-amine)sulfonamide

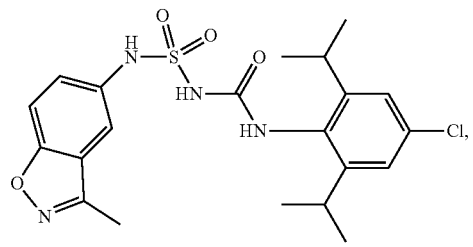

N-((4-chloro-2,6-diisopropylphenyl)carbamoyl)
(3-methylbenzo[d]isoxazol-5-amine)sulfonamide

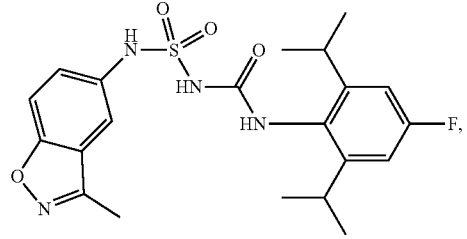

N-((4-fluoro-2,6-diisopropylphenyl)carbamoyl)
(3-methylbenzo[d]isoxazol-5-amine)sulfonamide

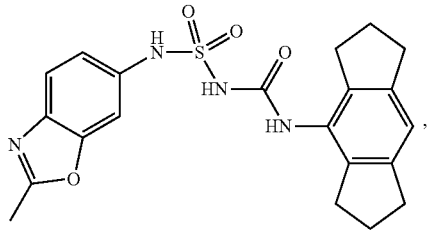

N-((1,2,3,5,6,7-hexadryo-s-indacen-4-yl)carbamoyl)(2-methylbenzo[d]oxazol-6-amine)sulfonamide

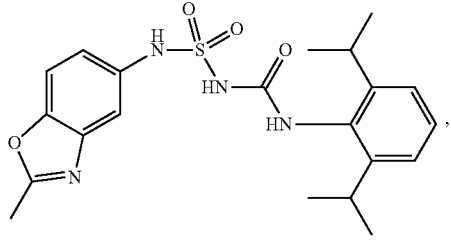

N-((2,6-diisopropylphenyl)carbamoyl)(2-methylbenzo[d]oxazol-5-amine)sulfonamide

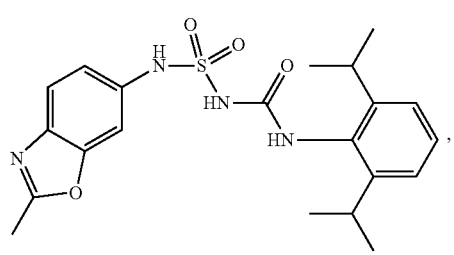

N-((2,6-diisopropylphenyl)carbamoyl)(2-methylbenzo[d]oxazol-6-amine)sulfonamide

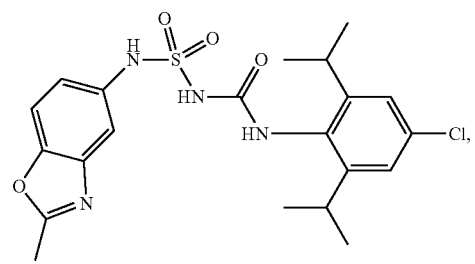

N-((4-chloro-2,6-diisopropylphenyl)carbamoyl)(2-methylbenzo[d]oxazol-5-amine)sulfonamide

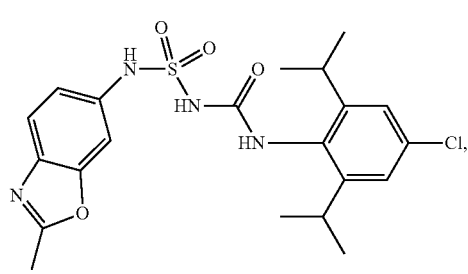

N-((4-chloro-2,6-diisopropylphenyl)carbamoyl)(2-methylbenzo[d]oxazol-6-amine)sulfonamide

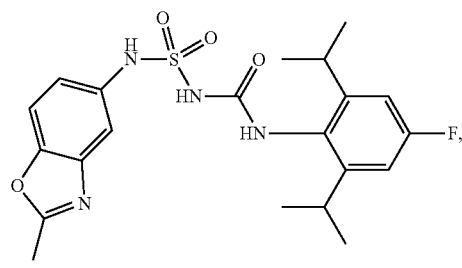

N-((4-fluoro-2,6-diisopropylphenyl)carbamoyl)(2-methylbenzo[d]oxazol-5-amine)sulfonamide

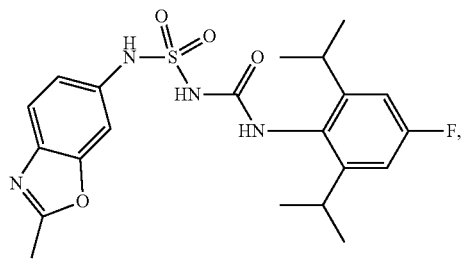

N-((4-fluoro-2,6-diisopropylphenyl)carbamoyl)(2-methylbenzo[d]oxazol-6-amine)sulfonamide

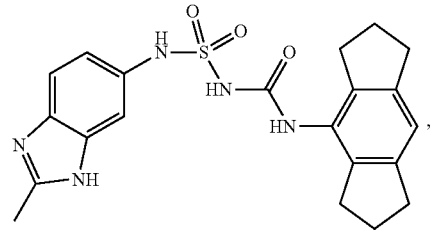

N-((1,2,3,5,6,7-hexadryo-s-indacen-4-yl)carbamoyl)(2-methyl-1H-benzo[d]imidazol-6-amine)sulfonamide

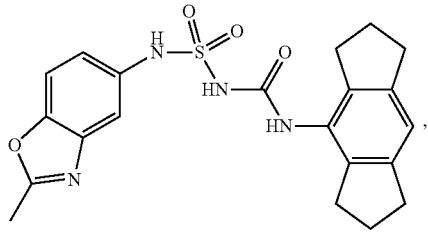

N-((1,2,3,5,6,7-hexadryo-s-indacen-4-yl)carbamoyl)(2-methylbenzo[d]oxazol-5-amine)sulfonamide

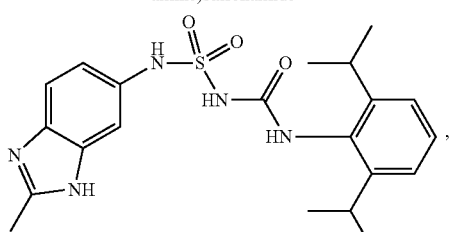

N-((2,6-diisopropylphenyl)carbamoyl)(2-methyl-1H-benzo[d]imidazol-6-amine)sulfonamide -continued

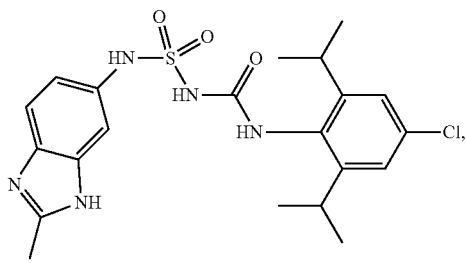

N-((4-chloro-2,6-diisopropylphenyl)carbamoyl)
(2-methyl-1H-benzo[d]imidazol-6-amine)sulfonamide

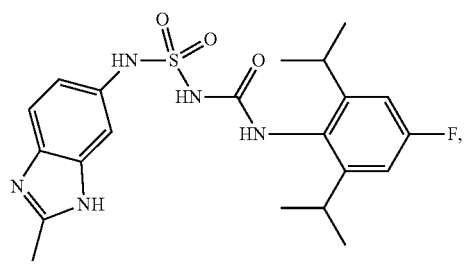

N-((4-fluoro-2,6-diisopropylphenyl)carbamoyl)
(2-methyl-1H-benzo[d]imidazol-6-amine)sulfonamide

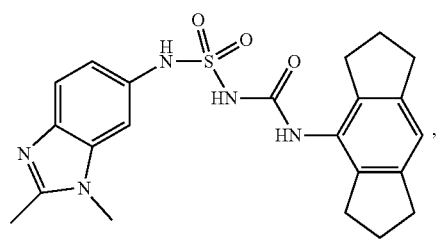

N-((1,2,3,5,6,7-hexadryo-s-indacen-4-
yl)carbamoyl)(1,2-dimethyl-1H-benzo[d]imidazol-6-
amine)sulfonamide

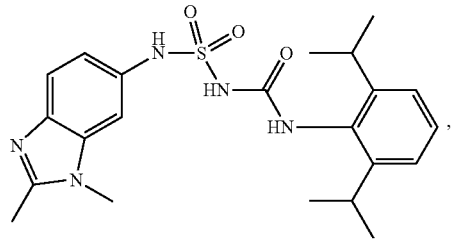

N-((2,6-diisopropylphenyl)carbamoyl)
(1,2-dimethyl-1H-benzo[d]imidazol-6-amine)sulfonamide

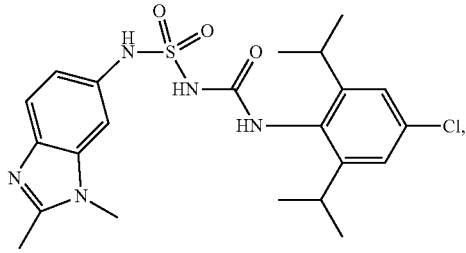

N-((4-chloro-2,6-diisopropylphenyl)carbamoyl)
(1,2-dimethyl-1H-benzo[d]imidazol-6-amine)sulfonamide -continued

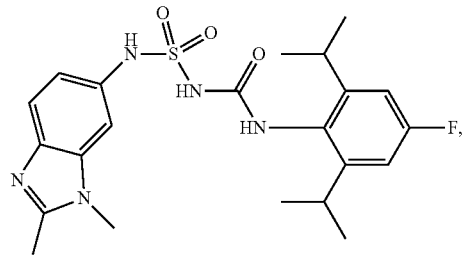

N-((4-fluoro-2,6-diisopropylphenyl)carbamoyl)
(1,2-dimethyl-1H-benzo[d]imidazol-6-amine)sulfonamide

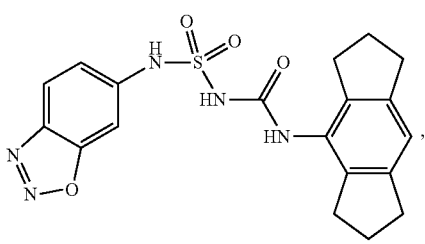

N-((1,2,3,5,6,7-hexadryo-s-indacen-4-
yl)carbamoyl)(benzo[d][1,2,3]oxadiazol-6-
amine)sulfonamide

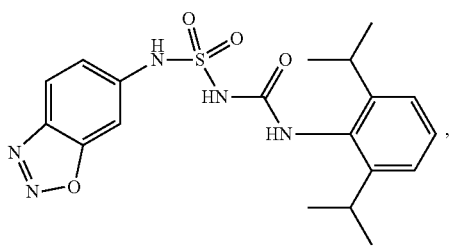

N-((2,6-diisopropylphenyl)carbamoyl)
(benzo[d][1,2,3]oxadiazol-6-amine)sulfonamide

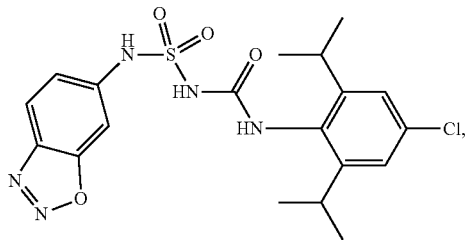

N-((4-chloro-2,6-diisopropylphenyl)carbamoyl)
(benzo[d][1,2,3]oxadiazol-6-amine)sulfonamide

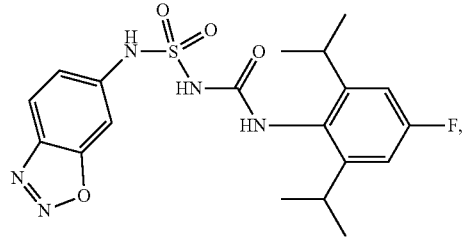

N-((4-fluoro-2,6-diisopropylphenyl)carbamoyl)
(benzo[d][1,2,3]oxadiazol-6-amine)sulfonamide

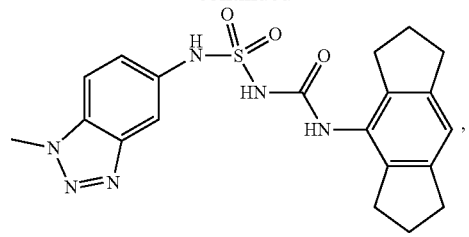

N-((1,2,3,5,6,7-hexadryo-s-indacen-4-yl)carbamoyl)(1-methyl-1H-benzo[d][1,2,3]triazol-5-amine)sulfonamide

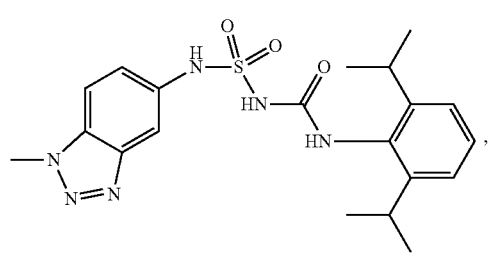

N-((2,6-diisopropylphenyl)carbamoyl)(1-methyl-1H-benzo[d][1,2,3]triazol-5-amine)sulfonamide

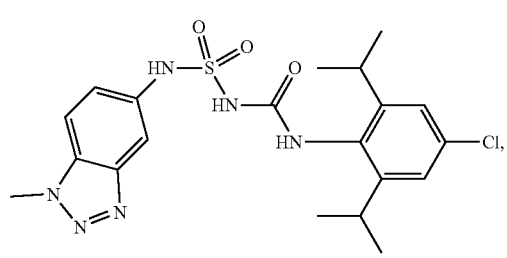

N-((4-chloro-2,6-diisopropylphenyl)carbamoyl)(1-methyl-1H-benzo[d][1,2,3]triazol-5-amine)sulfonamide

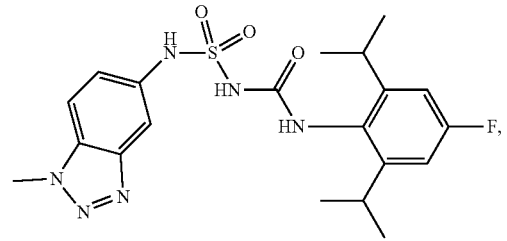

N-((4-fluoro-2,6-diisopropylphenyl)carbamoyl)(1-methyl-1H-benzo[d][1,2,3]triazol-5-amine)sulfonamide

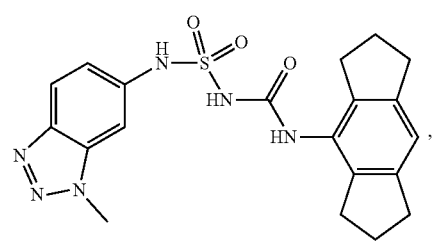

N-((1,2,3,5,6,7-hexadryo-s-indacen-4-yl)carbamoyl)(1-methyl-1H-benzo[d][1,2,3]triazol-6-amine)sulfonamide

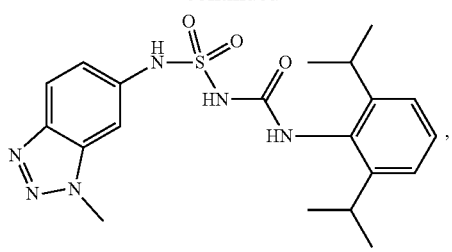

N-((2,6-diisopropylphenyl)carbamoyl)(1-methyl-1H-benzo[d][1,2,3]triazol-6-amine)sulfonamide

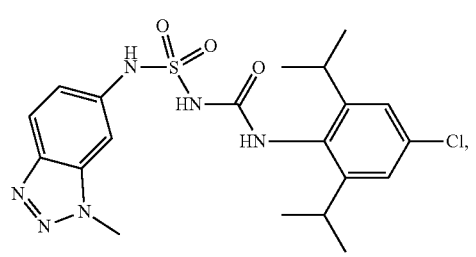

N-((4-chloro-2,6-diisopropylphenyl)carbamoyl)(1-methyl-1H-benzo[d][1,2,3]triazol-6-amine)sulfonamide

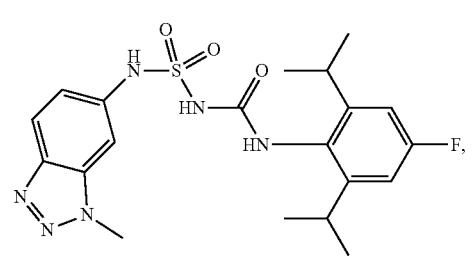

N-((4-fluoro-2,6-diisopropylphenyl)carbamoyl)(1-methyl-1H-benzo[d][1,2,3]triazol-6-amine)sulfonamide

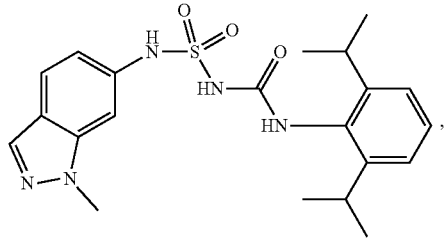

N-((2,6-diisopropylphenyl)carbamoyl)(1-methyl-1H-indazol-6-amine)sulfonamide

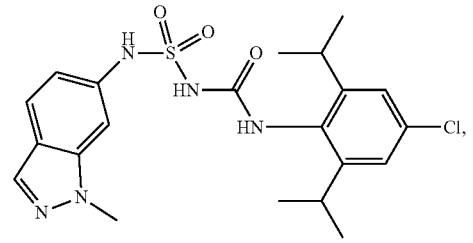

N-((4-chloro-2,6-diisopropylphenyl)carbamoyl)(1-methyl-1H-indazol-6-amine)sulfonamide -continued

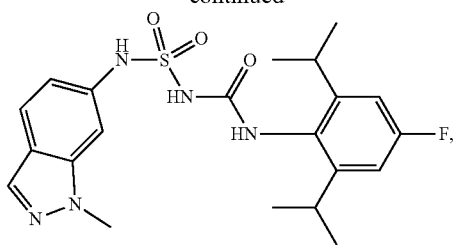

N-((4-fluoro-2,6-diisopropylphenyl)carbamoyl)
(1-methyl-1H-indazol-6-amine)sulfonamide

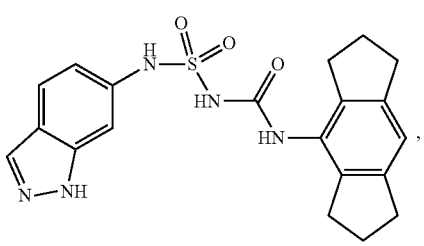

N-((1,2,3,5,6,7-hexadryo-s-indacen-4-yl)-
carbamoyl)(1H-indazol-6-amine)sulfonamide

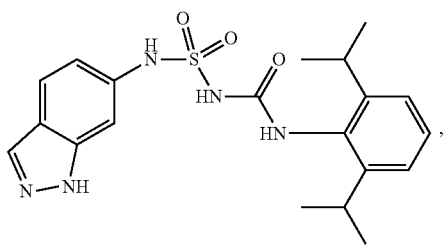

N-((2,6-diisopropylphenyl)carbamoyl)
(1H-indazol-6-amine)sulfonamide

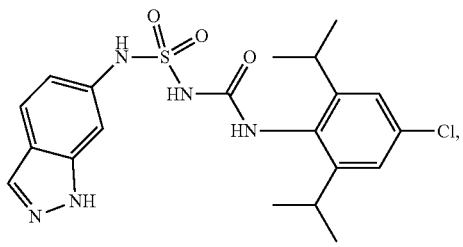

N-((4-chloro-2,6-diisopropylphenyl)carbamoyl)
(1H-indazol-6-amine)sulfonamide

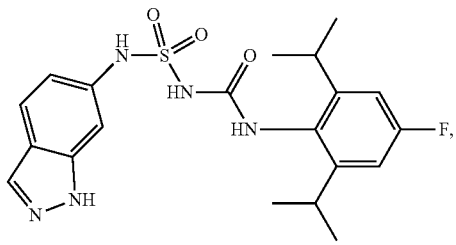

N-((4-fluoro-2,6-diisopropylphenyl)carbamoyl)
(1H-indazol-6-amine)sulfonamide

-continued

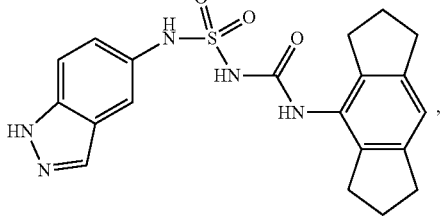

N-((1,2,3,5,6,7-hexadryo-s-indacen-4-yl)-
carbamoyl)(1H-indazol-5-amine)sulfonamide

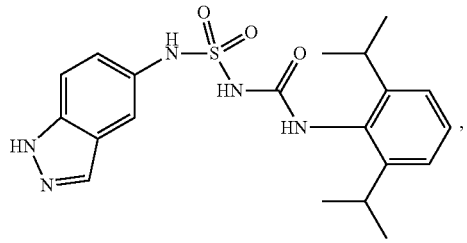

N-((2,6-diisopropylphenyl)carbamoyl)
(1H-indazol-5-amine)sulfonamide

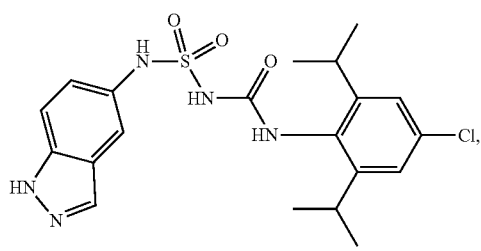

N-((4-chloro-2,6-diisopropylphenyl)carbamoyl)
(1H-indazol-5-amine)sulfonamide

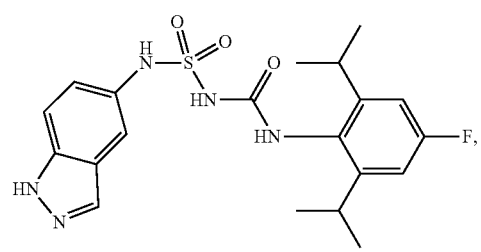

N-((4-fluoro-2,6-diisopropylphenyl)carbamoyl)
(1H-indazol-5-amine)sulfonamide

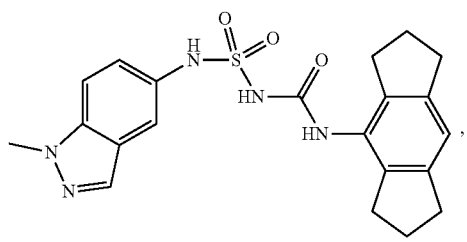

N-((1,2,3,5,6,7-hexadryo-s-indacen-4-yl)-
carbamoyl)(1-methly-1H-indazol-5-
amine)sulfonamide 37
-continued

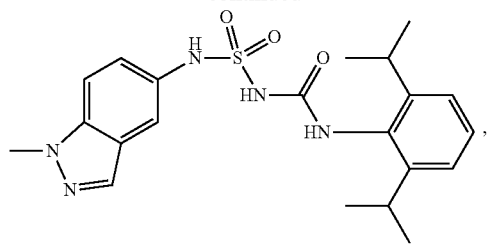

N-((2,6-diisopropylphenyl)carbamoyl)
(1-methyl-1H-indazol-5-amine)sulfonamide

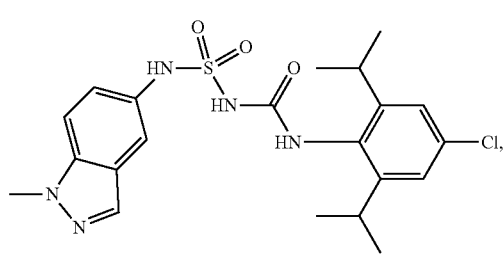

N-((4-chloro-2,6-diisopropylphenyl)carbamoyl)
(1-methyl-1H-indazol-5-amine)sulfonamide

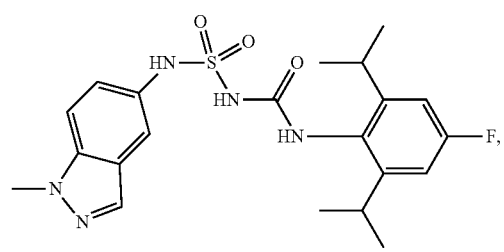

N-((4-fluoro-2,6-diisopropylphenyl)carbamoyl)
(1-methyl-1H-indazol-5-amine)sulfonamide

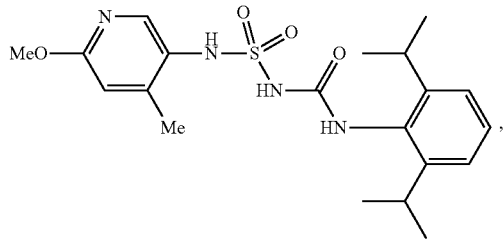

N-((2,6-diisopropylphenyl)carbamoyl)
(6-methoxy-4-methylpyridin-3-amino)sulfonamide

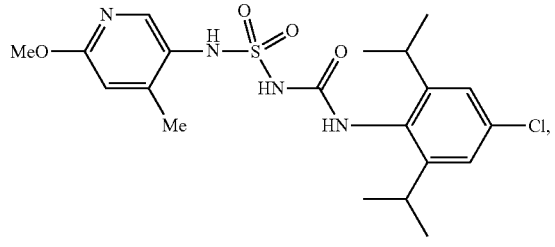

N-((4-chloro-2,6-diisopropylphenyl)carbamoyl)
(6-methoxy-4-methylpyridin-3-amino)sulfonamide 38
-continued

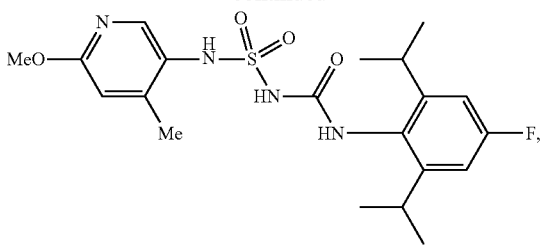

N-((4-fluoro-2,6-diisopropylphenyl)carbamoyl)
(6-methoxy-4-methylpyridin-3-amino)sulfonamide

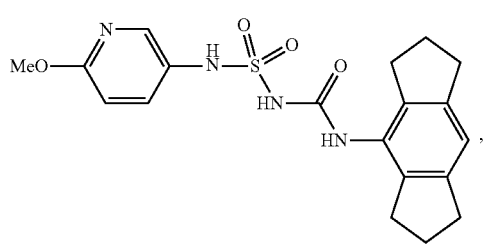

N-((1,2,3,5,6,7-hexadryo-s-indacen-4-yl)-
carbamoyl)(6-methoxypyridin-3-amino)sulfonamide

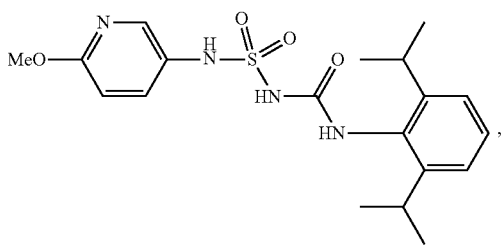

N-((2,6-diisopropylphenyl)carbamoyl)
(6-methoxypyridin-3-amino)sulfonamide

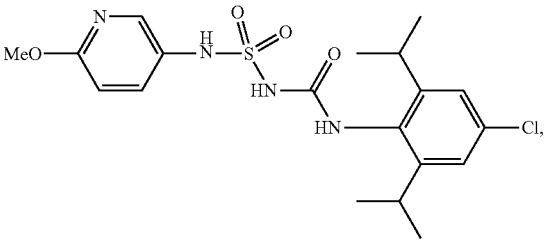

N-((4-chloro-2,6-diisopropylphenyl)carbamoyl)
(6-methoxypyridin-3-amino)sulfonamide

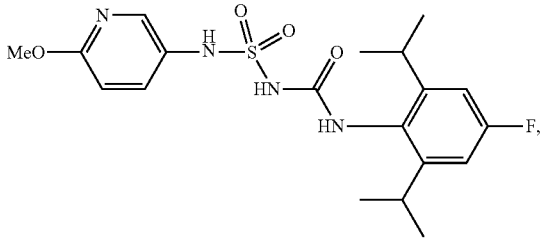

N-((4-fluoro-2,6-diisopropylphenyl)carbamoyl)
(6-methoxypyridin-3-amino)sulfonamide -continued

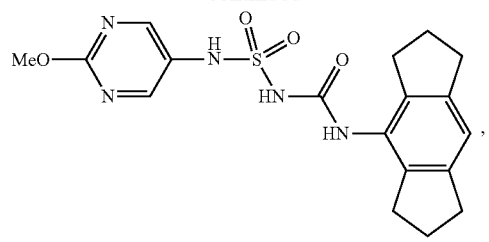

N-((1,2,3,5,6,7-hexadryo-s-indacen-4-yl)-carbamoyl)(2-methoxypyrimidin-5-amino)sulfonamide

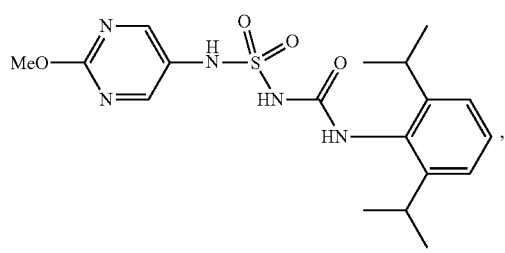

N-((2,6-diisopropylphenyl)carbamoyl)(2-methoxypyrimidin-5-amino)sulfonamide

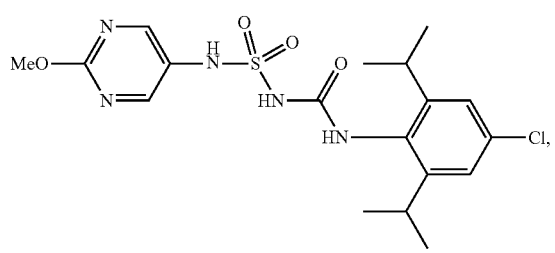

N-((4-chloro-2,6-diisopropylphenyl)carbamoyl)(2-methoxypyrimidin-5-amino)sulfonamide

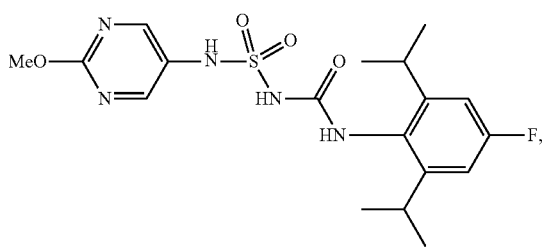

N-((4-fluoro-2,6-diisopropylphenyl)carbamoyl)(2-methoxypyrimidin-5-amino)sulfonamide

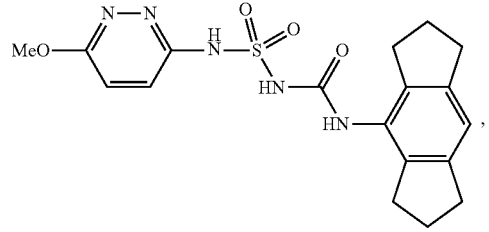

N-((1,2,3,5,6,7-hexadryo-s-indacen-4-yl)-carbamoyl)(6-methoyxypyridazin-3-amino)sulfonamide -continued

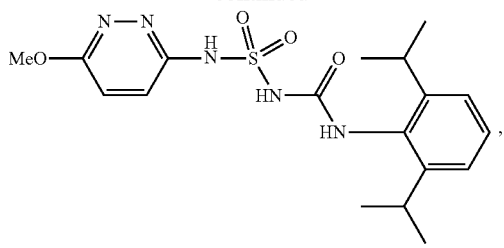

N-((2,6-diisopropylphenyl)carbamoyl)(6-methoyxypyridazin-3-amino)sulfonamide

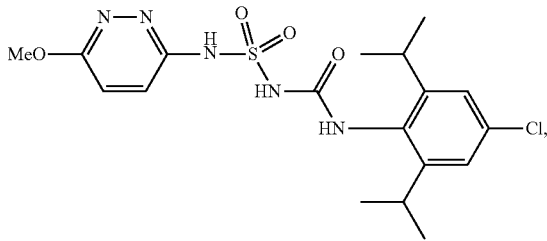

N-((4-chloro-2,6-diisopropylphenyl)carbamoyl)(6-methoxypyridazin-3-amino)sulfonamide

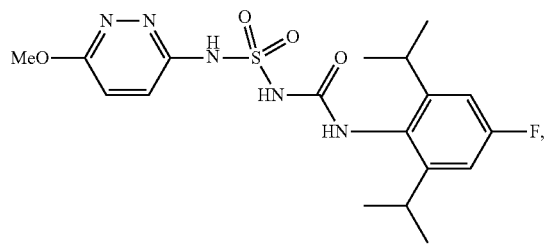

N-((4-fluoro-2,6-diisopropylphenyl)carbamoyl)(6-methoxypyridazin-3-amino)sulfonamide

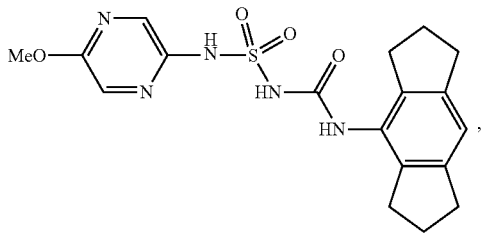

N-((1,2,3,5,6,7-hexadryo-s-indacen-4-yl)carbamoyl)(5-methoxypyrazin-2-amino)sulfonamide

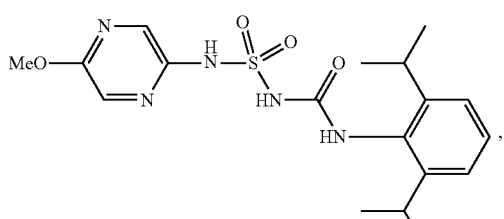

N-((2,6-diisopropylphenyl)carbamoyl)(5-methoxypyrazin-2-amino)sulfonamide

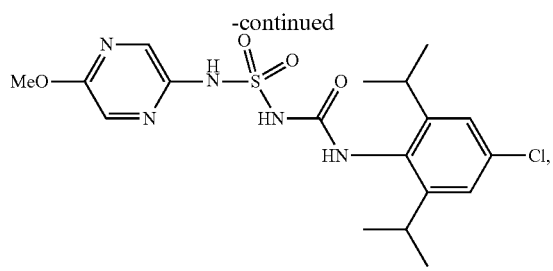

N-((4-chloro-2,6-diisopropylphenyl)carbamoyl)
(5-methoxypyrazin-2-amino)sulfonamide

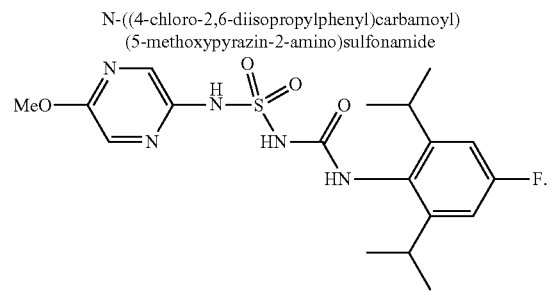

N-((4-fluoro-2,6-diisopropylphenyl)carbamoyl)
(5-methoxypyrazin-2-amino)sulfonamide In one embodiment, $R^1W^1$— comprises a heterocyclic group containing a nitrogen atom and at least one further heteroatom in the heterocyclic ring, wherein $R^1W^1$— may be optionally substituted. For example, $R^1W^1$— may comprise a heterocyclic group containing at least two nitrogen atoms in the heterocyclic ring, wherein $R^1W^1$— may be optionally substituted. Typically in any embodiment where $R^1W^1$— comprises a heterocyclic group containing a nitrogen atom and at least one further heteroatom in the heterocyclic ring, a nitrogen atom of $R^1W^1$— is linked to J, J is S, Q is O and —$W^2R^2$ is —$R^2$ wherein $R^2$ is as previously defined. Typically in any embodiment where $R^1W^1$— comprises a heterocyclic group containing a nitrogen atom and at least one further heteroatom, such as a nitrogen atom, in the heterocyclic ring, —$W^2R^2$ is an aryl or a heteroaryl group, wherein the aryl or the heteroaryl group is substituted at the α and α' positions and optionally at other positions.

In one embodiment, $R^1W^1$— is $(R^1)_2N$— wherein both $R^1$ and the nitrogen atom to which they are attached together form an optionally substituted heterocyclic group containing at least one further heteroatom N, O or S in the heterocyclic ring. Typically, $R^1W^1$— is $(R^1)_2N$— wherein both $R^1$ and the nitrogen atom to which they are attached together form an optionally substituted heterocyclic group containing at least one further nitrogen atom in the heterocyclic ring. Typically, the heterocyclic group is monocyclic or bicyclic.

In one embodiment, $R^1W^1$— is $(R^1)_2N$—, wherein $(R^1)_2N$— is an optionally substituted piperazinyl, morpholinyl or thiomorpholinyl group. Typically such a group is unsubstituted or substituted with one or more halo, alkyl, alkoxy, acyl, aryl, alkylaryl, alkoxyaryl, heteroaryl, arylalkyl, heteroarylalkyl, or halogenated alkyl groups.

Examples of compounds where $R^1W^1$— comprises a heterocyclic group containing a nitrogen atom and at least one further heteroatom in the heterocyclic ring include the compounds of Examples 1, 2, 13, 16, 17 and 41 below and the compounds:

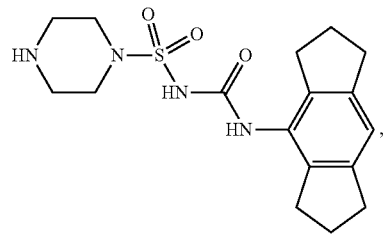

N-((1,2,3,5,6,7-hexahydro-s-indacen-4-yl)carbamoyl)piperazine-1-sulfonamide

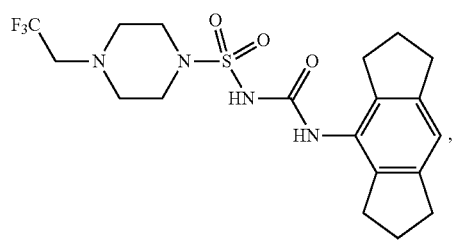

N-((1,2,3,5,6,7-hexahydro-s-indacen-4-yl)carbamoyl)-4-(2,2,2-trifluoroethyl)piperazine-1-sulfonamide

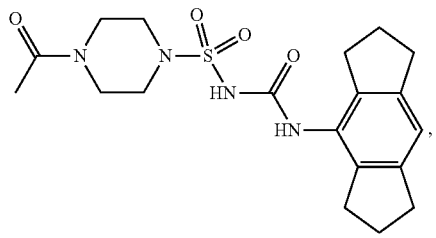

4-acetyl-N-((1,2,3,5,6,7-hexahydro-s-indacen-4-yl)carbamoyl)piperazine-1-sulfonamide

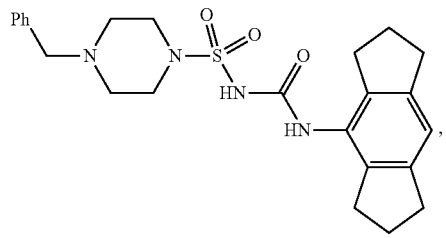

4-benzyl-N-((1,2,3,5,6,7-hexahydro-s-indacen-4-yl)carbamoyl)piperazine-1-sulfonamide

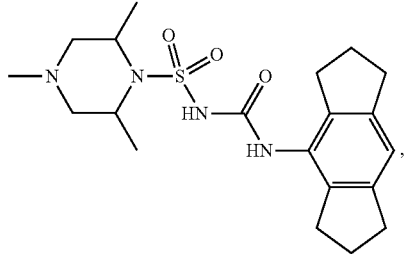

N-((1,2,3,5,6,7-hexahydro-s-indacen-4-yl)carbamoyl)-2,4,6-trimethylpiperazine-1-sulfonamide -continued

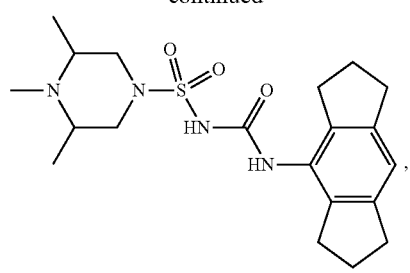

N-((1,2,3,5,6,7-hexahydro-s-indacen-4-yl)
carbamoyl)-
3,4,5-trimethylpiperazine-1-sulfonamide

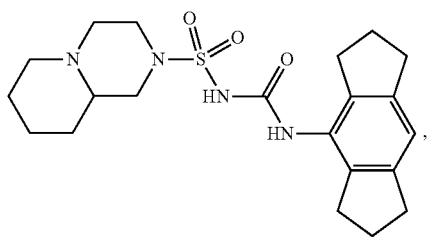

N-((1,2,3,5,6,7-hexahydro-s-indacen-4-
yl)carbamoyl)octahydro-2H-pyrido[1,2-a]pyrazine-2-
sulfonamide

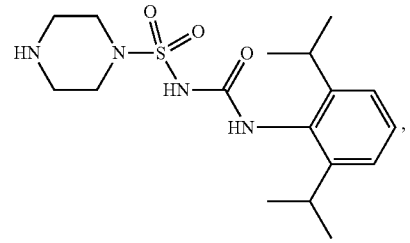

N-((2,6-diisopropylphenyl)carbamoyl)-
piperazine-1-sulfonamide

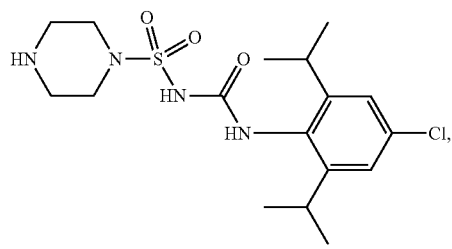

N-((4-chloro-2,6-diisopropylphenyl)carbamoyl)-
piperazine-1-sulfonamide

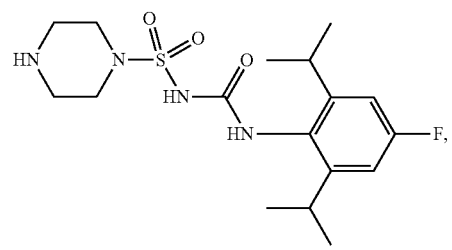

N-((4-fluoro-2,6-
diisopropylphenyl)carbamoyl)-
piperazine-1-sulfonamide

-continued

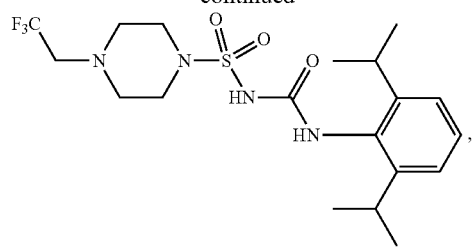

N-((2,6-diisopropylphenyl)carbamoyl)-
4-(2,2,2-trifluoroethyl)piperazine-1-sulfonamide

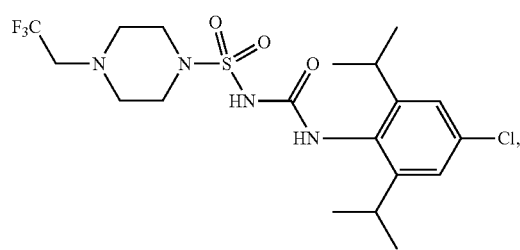

N-((4-chloro-2,6-diisopropylphenyl)carbamoyl)-
4-(2,2,2-trifluoroethyl)piperazine-1-sulfonamide

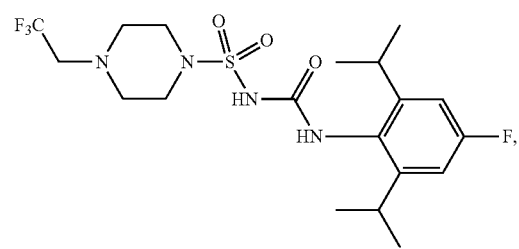

N-((4-fluoro-2,6-
diisopropylphenyl)carbamoyl)-4-(2,2,2-
trifluoroethyl)piperazine-1-sulfonamide

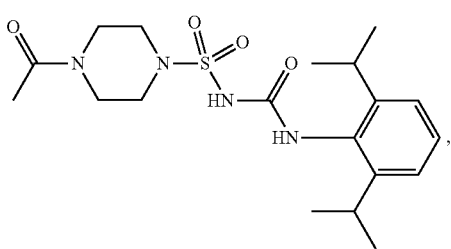

4-acetyl-N-((2,6-diisopropylphenyl)carbamoyl)-
piperazine-1-sulfonamide

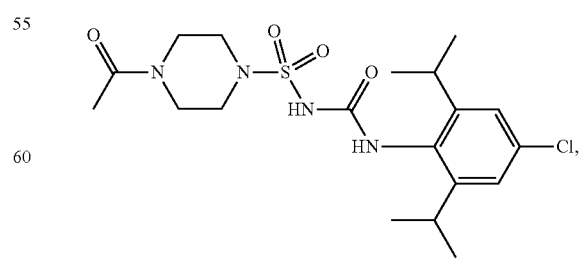

4-acetyl-N-((4-chloro-2,6-diisopropylphenyl)carbamoyl)-
piperazine-1-sulfonamide -continued

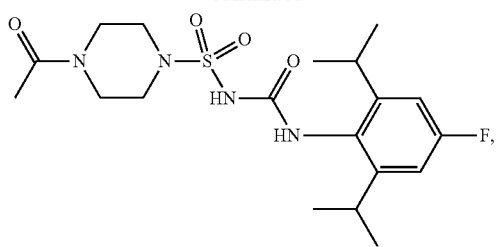

4-acetyl-N-((4-fluoro-2,6-diisopropylphenyl)carbamoyl)-
piperazine-1-sulfonamide

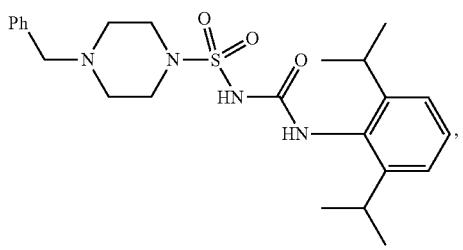

4-benzyl-N-((2,6-diisopropylphenyl)carbamoyl)-
piperazine-1-sulfonamide

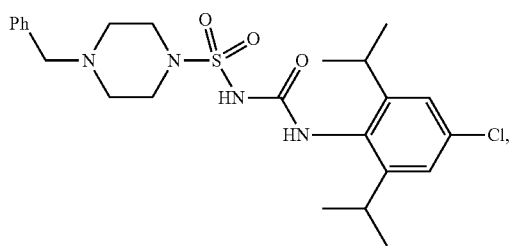

4-benzyl-N-((4-chloro-2,6-diisopropylphenyl)carbamoyl)-
piperazine-1-sulfonamide

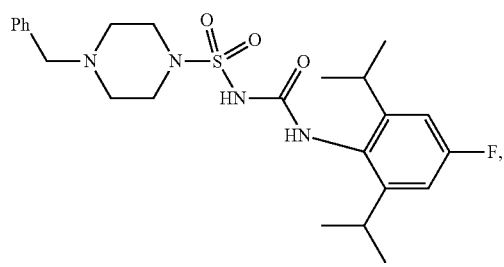

4-benzyl-N-((4-fluoro-2,6-
diisopropylphenyl)carbamoyl)-piperazine-1-
sulfonamide

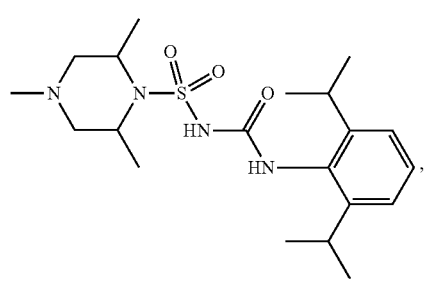

N-((2,6-diisopropylphenyl)carbamoyl)-
2,4,6-trimethylpiperazine-1-sulfonamide

-continued

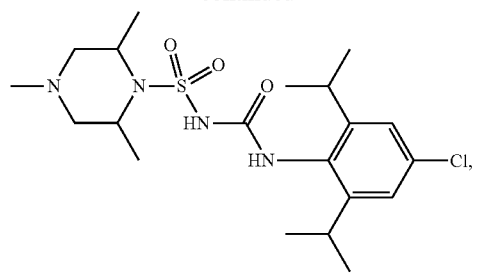

N-((4-chloro-2,6-diisopropylphenyl)carbamoyl)-
2,4,6-trimethylpiperazine-1-sulfonamide

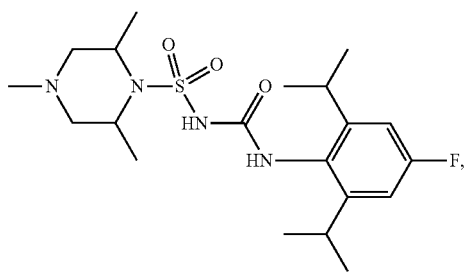

N-((4-fluoro-2,6-diisopropylphenyl)carbamoyl)-
2,4,6-trimethylpiperazine-1-sulfonamide

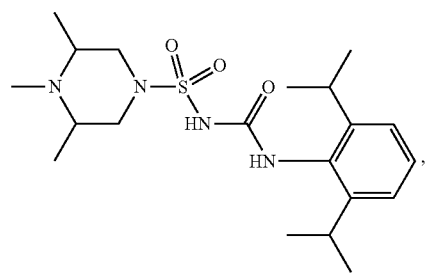

N-((2,6-diisopropylphenyl)carbamoyl)-
3,4,5-trimethylpiperazine-1-sulfonamide

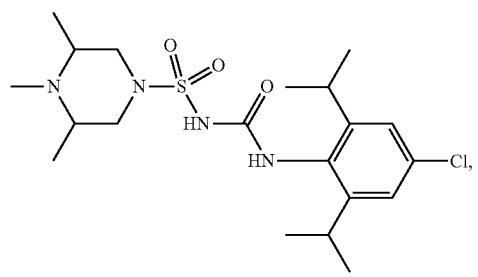

N-((4-chloro-2,6-diisopropylphenyl)carbamoyl)-
3,4,5-trimethylpiperazine-1-sulfonamide

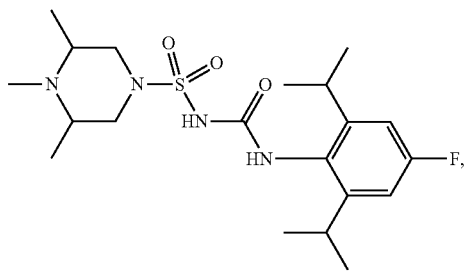

N-((4-fluoro-2,6-diisopropylphenyl)carbamoyl)-
3,4,5-trimethylpiperazine-1-sulfonamide

47

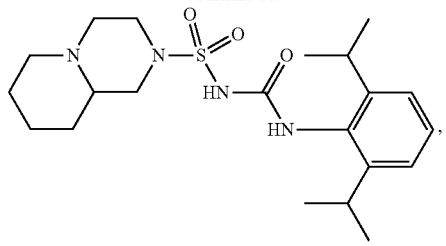

N-((2,6-diisopropylphenyl)carbamoyl)-
octahydro-2H-pyrido[1,2-a]pyrazine-2-sulfonamide

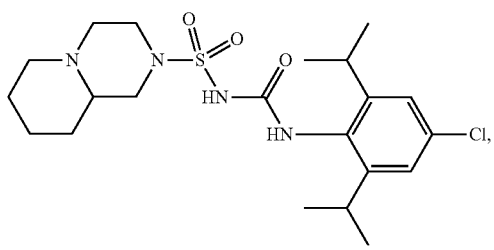

N-((4-chloro-2,6-diisopropylphenyl)carbamoyl)-
octahydro-2H-pyrido[1,2-a]pyrazine-2-sulfonamide

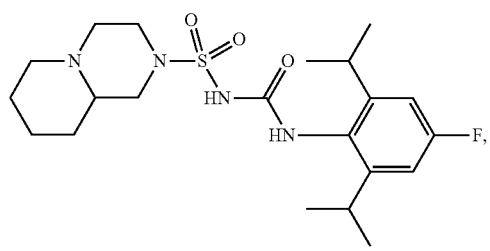

N-((4-fluoro-2,6-diisopropylphenyl)-
carbamoyl)octahydro-2H-pyrido[1,2-
a]pyrazine-2-sulfonamide

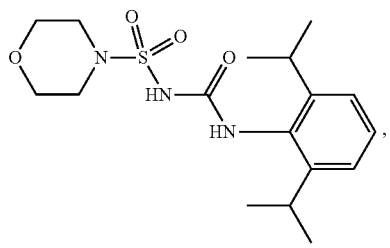

N-((2,6-diisopropylphenyl)carbamoyl)-
morpholine-4-sulfonamide

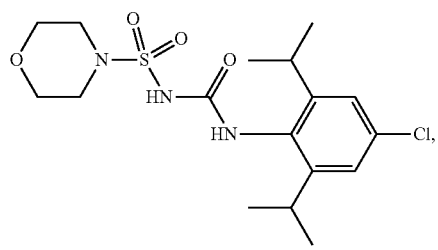

N-((4-chloro-2,6-diisopropylphenyl)carbamoyl)-
morpholine-4-sulfonamide

48

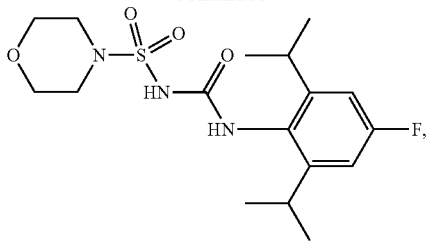

N-((4-fluoro-2,6-
diisopropylphenyl)carbamoyl)-morpholine-
4-sulfonamide

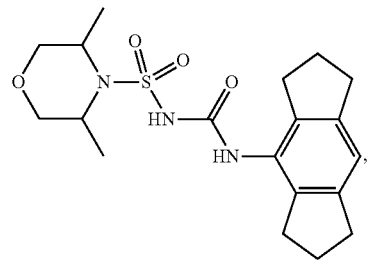

N-((1,2,3,5,6,7-hexahydro-s-indacen-
4-yl)carbamoyl)-3,5-
dimethylmorpholine-4-sulfonamide

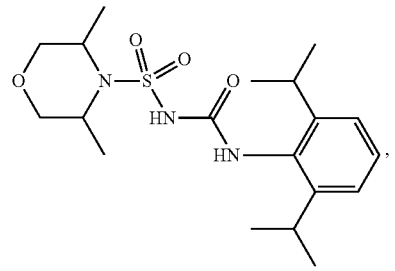

N-((2,6-diisopropylphenyl)carbamoyl)-
3,5-dimethylmorpholine-4-sulfonamide

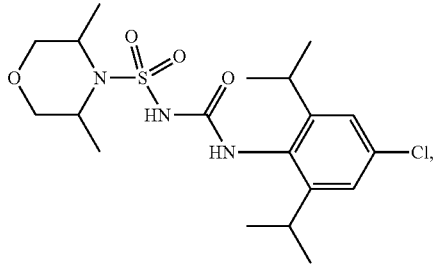

N-((4-chloro-2,6-diisopropylphenyl)carbamoyl)-
3,5-dimethylmorpholine-4-sulfonamide

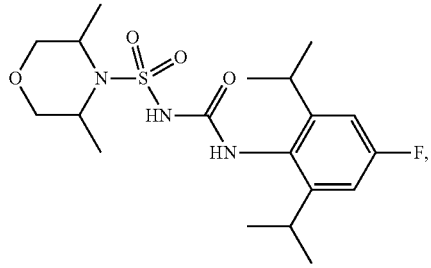

N-((4-fluoro-2,6-
diisopropylphenyl)carbamoyl)-3,5-
dimethylmorpholine-4-sulfonamide

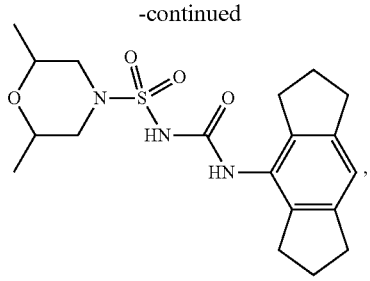

N-((1,2,3,5,6,7-hexahydro-s-indacen-4-yl)carbamoyl)-2,6-dimethylmorpholine-4-sulfonamide

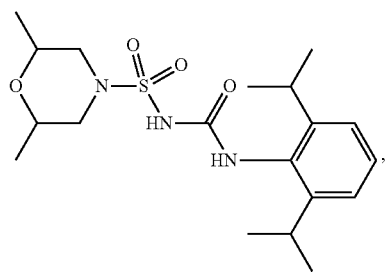

N-((2,6-diisopropylphenyl)carbamoyl)-2,6-dimethylmorpholine-4-sulfonamide

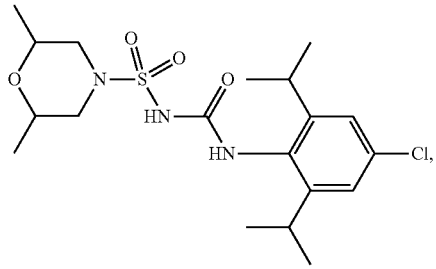

N-((4-chloro-2,6-diisopropylphenyl)carbamoyl)-2,6-dimethylmorpholine-4-sulfonamide

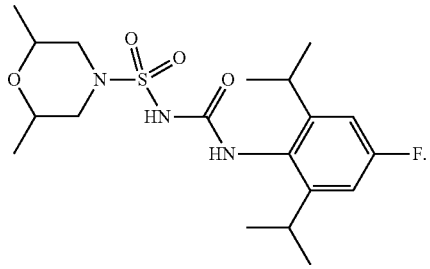

N-((4-fluoro-2,6-diisopropylphenyl)carbamoyl)-2,6-dimethylmorpholine-4-sulfonamide In one embodiment, $R^1W^1$— is $R^1NH$— or $(R^1)_2N$— wherein at least one $R^1$ comprises a fused bicyclic group, or two $R^1$ together with the nitrogen atom to which they are attached form a fused bicyclic group, wherein $R^1W^1$— may be optionally substituted. The fused bicyclic group may be optionally substituted and may be carbocyclic or heterocyclic. Both rings of the bicyclic group may be aromatic, or one ring may be aromatic and the other non-aromatic, or both rings may be non-aromatic. Typically in any embodiment where $R^1W^1$— is $R^1NH$— or $(R^1)_2N$— wherein at least one $R^1$ comprises a fused bicyclic group, or two $R^1$ together with the nitrogen atom to which they are attached form a fused bicyclic group, J is S, Q is O and —$W^2R^2$ is —$R^2$ wherein $R^2$ is as previously defined. Typically in any embodiment where $R^1W^1$— is $R^1NH$— or $(R^1)_2N$— wherein at least one $R^1$ comprises a fused bicyclic group, or two $R^1$ together with the nitrogen atom to which they are attached form a fused bicyclic group, —$W^2R^2$ is an aryl or a heteroaryl group, wherein the aryl or the heteroaryl group is substituted at the α and α' positions and optionally at other positions.

In one embodiment, $R^1W^1$— is Bic-L-NH— or Bic-L-NR^1—, wherein Bic is an optionally substituted fused bicyclic group, -L- is a bond or an optionally substituted alkylene, alkenylene, alkynylene or arylene group, which may optionally include one or more heteroatoms N, O or S in its carbon skeleton, and $R^1$ is as previously defined. Typically, -L- is a bond or a $C_1$-$C_2$ alkylene group.

In one embodiment, Bic comprises a 5-membered ring fused to a six-membered ring. Typically in such an embodiment, the six-membered ring is aromatic. Examples of such groups include optionally substituted indolyl, isoindolyl, indolinyl, indazolyl, indenyl, indanyl and 1,3-benzodioxolyl groups.

Examples of compounds where $R^1W^1$— is $R^1NH$— or $(R^1)_2N$— wherein at least one $R^1$ comprises a fused bicyclic group, or two $R^1$ together with the nitrogen atom to which they are attached form a fused bicyclic group, include the compounds of Examples 8, 28, 34, 36, 37, 38, 40, 42 and 43 below and the compounds:

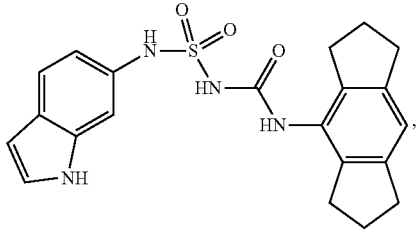

N-((1,2,3,5,6,7-hexahydro-s-indacen-4-yl)carbamoyl)(1H-indol-6-amine)sulfonamide

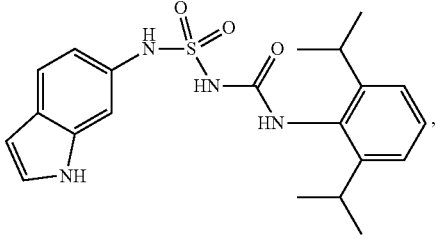

N-((2,6-diisopropylphenyl)carbamoyl)(1H-indol-6-amine)sulfonamide

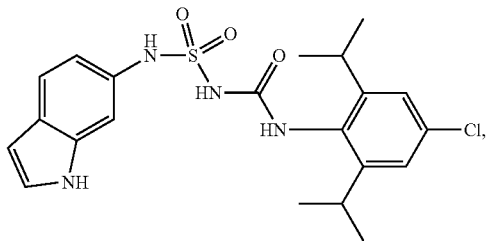

N-((4-chloro-2,6-diisopropylphenyl)carbamoyl)(1H-indol-6-amine)sulfonamide

-continued

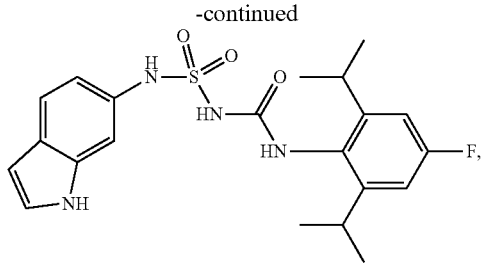

N-((4-fluoro-2,6-diisopropylphenyl)carbamoyl)
(1H-indol-6-amine)sulfonamide

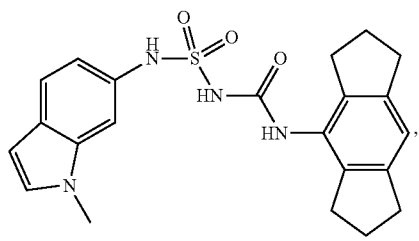

N-((1,2,3,5,6,7-hexahydro-s-indacen-4-
yl)carbamoyl)(1-methyl-1H-indol-6-
amine)sulfonamide

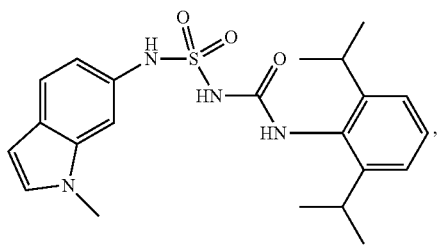

N-((2,6-diisopropylphenyl)carbamoyl)
(1-methyl-1H-indol-6-amine)sulfonamide

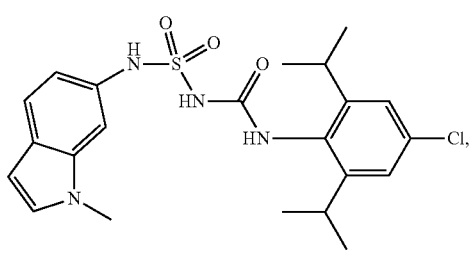

N-((4-chloro-2,6-diisopropylphenyl)carbamoyl)
(1-methyl-1H-indol-6-amine)sulfonamide

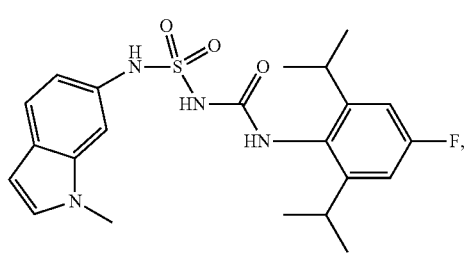

N-((4-fluoro-2,6-diisopropylphenyl)carbamoyl)
(1-methyl-1H-indol-6-amine)sulfonamide -continued

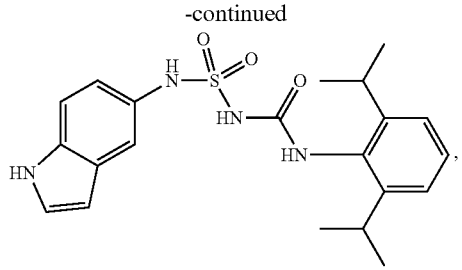

N-((2,6-diisopropylphenyl)carbamoyl)
(1H-indol-5-amine)sulfonamide

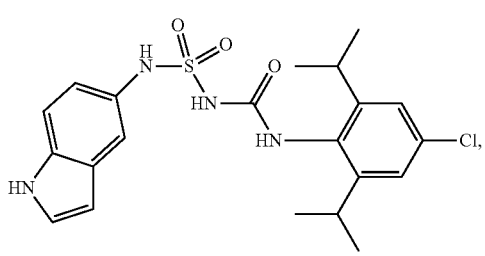

N-((4-chloro-2,6-diisopropylphenyl)carbamoyl)
(1H-indol-5-amine)sulfonamide

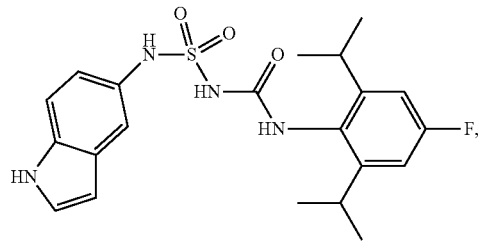

N-((4-fluoro-2,6-diisopropylphenyl)carbamoyl)
(1H-indol-5-amine)sulfonamide

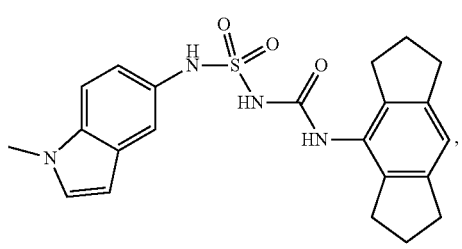

N-((1,2,3,5,6,7-hexahydro-s-indacen-4-
yl)carbamoyl)(1-methyl-
1H-indol-5-amine)sulfonamide

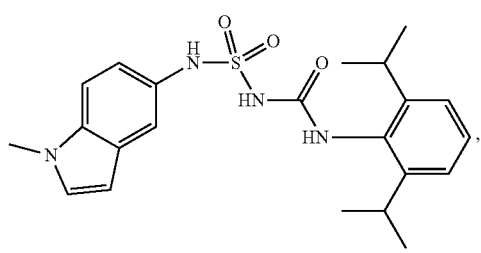

N-((2,6-diisopropylphenyl)carbamoyl)
(1-methyl-1H-indol-5-amine)sulfonamide

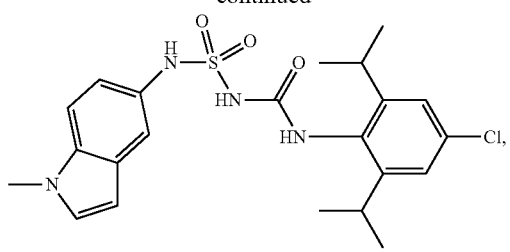

N-((4-chloro-2,6-diisopropylphenyl)carbamoyl)
(1-methyl-1H-indol-5-amine)sulfonamide

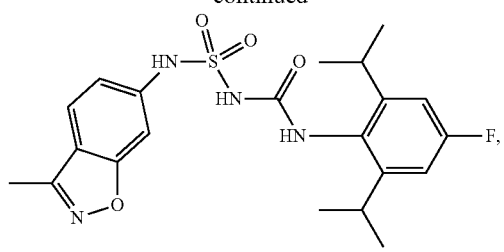

N-((4-chloro-2,6-diisopropylphenyl)carbamoyl)
(3-methylbenzo[d]isoxazol-6-amine)sulfonamide

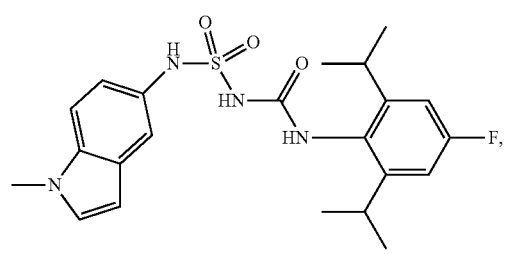

N-((4-fluoro-2,6-diisopropylphenyl)carbamoyl)
(1-methyl-1H-indol-5-amine)sulfonamide

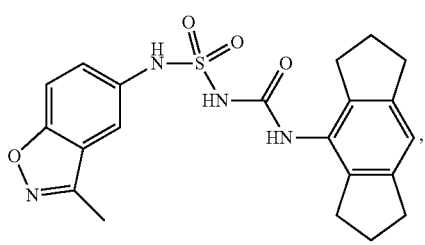

N-((1,2,3,5,6,7-hexahydro-s-indacen-4-
yl)carbamoyl)(3-methylbenzo[d]isoxazol-5-
amine)sulfonamide

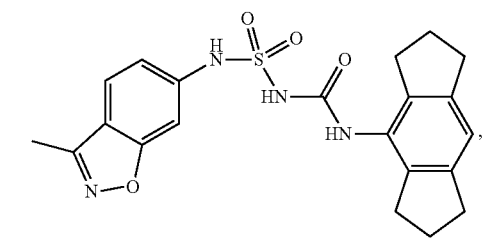

N-((1,2,3,5,6,7-hexahydro-s-indacen-4-
yl)carbamoyl)(3-methylbenzo[d]isoxazol-6-
amine)sulfonamide

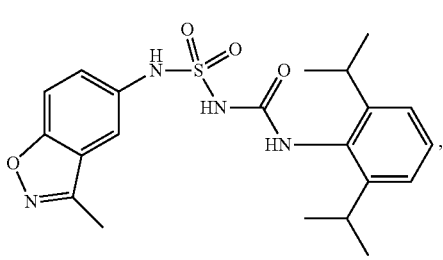

N-((2,6-diisopropylphenyl)carbamoyl)
(3-methylbenzo[d]isoxazol-5-amine)sulfonamide

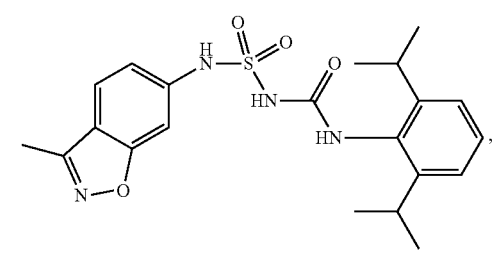

N-((2,6-diisopropylphenyl)carbamoyl)
(3-methylbenzo[d]isoxazol-6-amine)sulfonamide

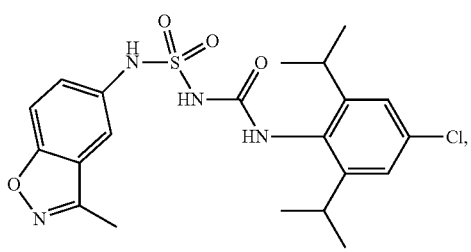

N-((4-chloro-2,6-diisopropylphenyl)carbamoyl)
(3-methylbenzo[d]isoxazol-5-amine)sulfonamide

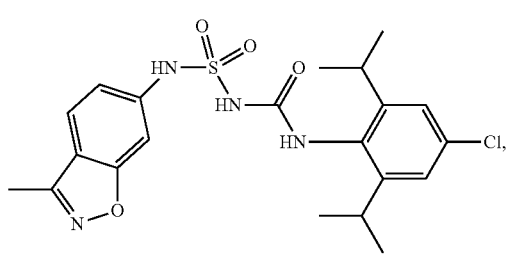

N-((4-chloro-2,6-diisopropylphenyl)carbamoyl)
(3-methylbenzo[d]isoxazol-6-amine)sulfonamide

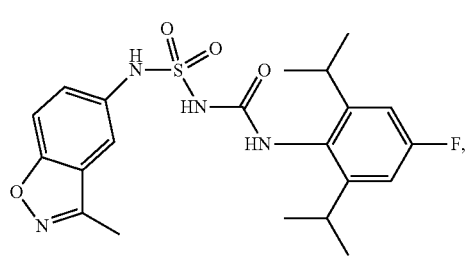

N-((4-fluoro-2,6-diisopropylphenyl)carbamoyl)
(3-methylbenzo[d]isoxazol-5-amine)sulfonamide -continued

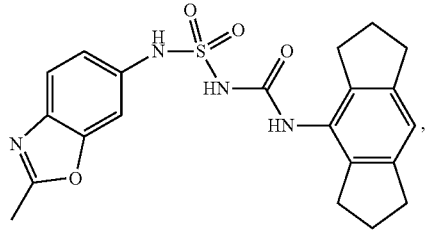

N-((1,2,3,5,6,7-hexahydro-s-indacen-4-yl)carbamoyl)(2-methylbenzo[d]oxazol-6-amine)sulfonamide

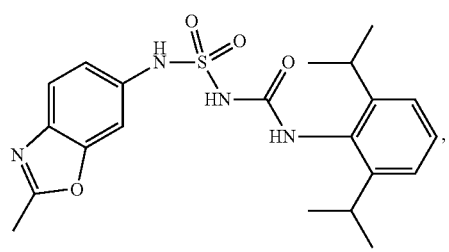

N-((2,6-diisopropylphenyl)carbamoyl)(2-methylbenzo[d]oxazol-6-amine)sulfonamide

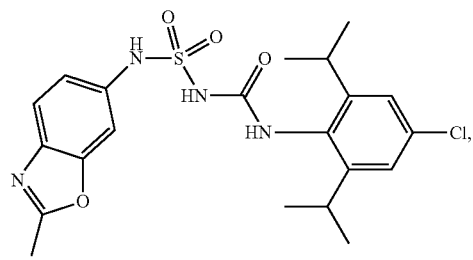

N-((4-chloro-2,6-diisopropylphenyl)carbamoyl)(2-methylbenzo[d]oxazol-6-amine)sulfonamide

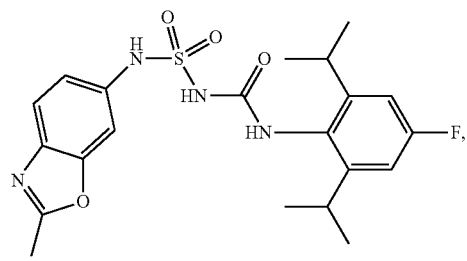

N-((4-fluoro-2,6-diisopropylphenyl)carbamoyl)(2-methylbenzo[d]oxazol-6-amine)sulfonamide

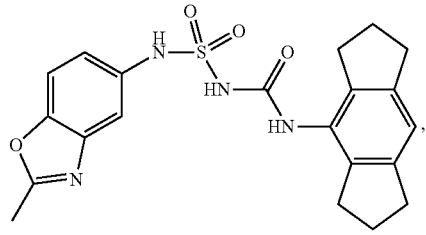

N-((1,2,3,5,6,7-hexahydro-s-indacen-4-yl)carbamoyl)(2-methylbenzo[d]oxazol-5-amine)sulfonamide -continued

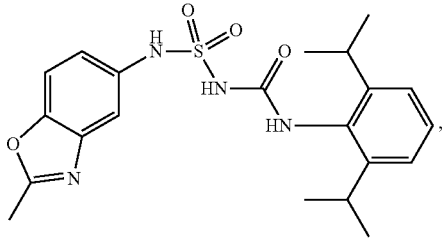

N-((2,6-diisopropylphenyl)carbamoyl)(2-methylbenzo[d]oxazol-5-amine)sulfonamide

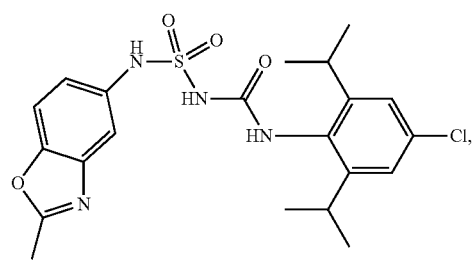

N-((4-chloro-2,6-diisopropylphenyl)carbamoyl)(2-methylbenzo[d]oxazol-5-amine)sulfonamide

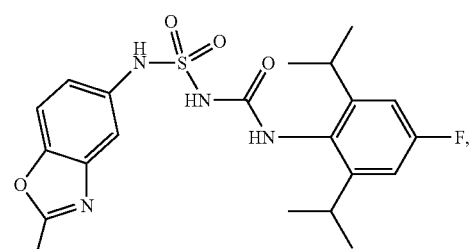

N-((4-fluoro-2,6-diisopropylphenyl)carbamoyl)(2-methylbenzo[d]oxazol-5-amine)sulfonamide

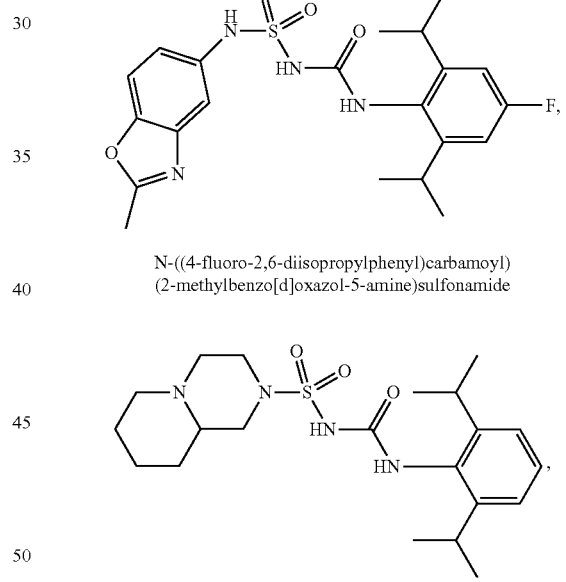

N-((2,6-diisopropylphenyl)carbamoyl)-octahydro-2H-pyrido[1,2-a]pyrazine-2-sulfonamide

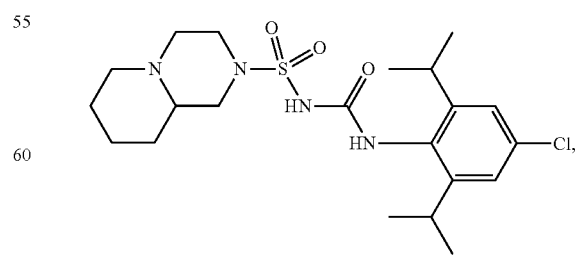

N-((4-chloro-2,6-diisopropylphenyl)carbamoyl)-octahydro-2H-pyrido[1,2-a]pyrazine-2-sulfonamide

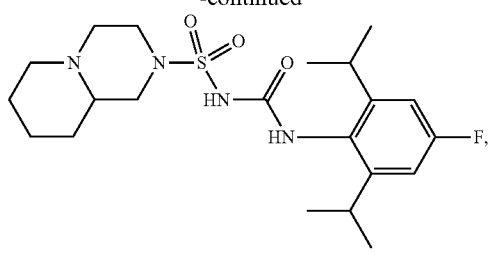

N-((4-fluoro-2,6-diisopropylphenyl)-
carbamoyl)octahydro-2H-pyrido[1,2-
a]pyrazine-2-sulfonamide

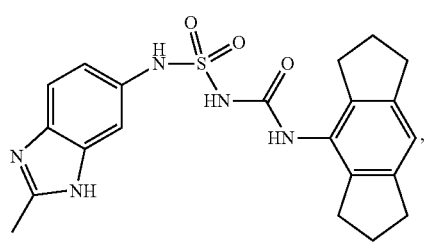

N-((1,2,3,5,6,7-hexahydro-s-indacen-4-
yl)carbamoyl)(2-methyl-1H-benzo[d]imidazol-6-
amine)sulfonamide

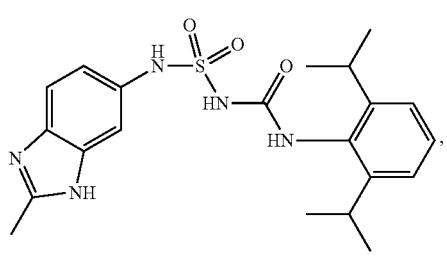

N-((2,6-diisopropylphenyl)carbamoyl)
(2-methyl-1H-benzo[d]imidazol-6-amine)sulfonamide

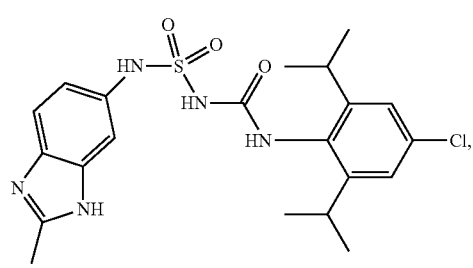

N-((4-chloro-2,6-diisopropylphenyl)carbamoyl)
(2-methyl-1H-benzo[d]imidazol-6-amine)sulfonamide

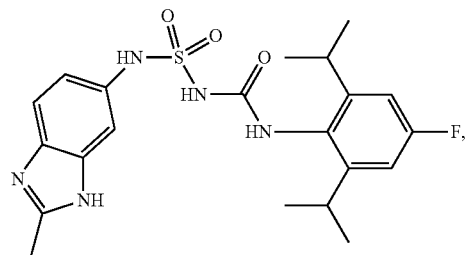

N-((4-fluoro-2,6-diisopropylphenyl)carbamoyl)
(2-methyl-1H-benzo[d]imidazol-6-amine)sulfonamide

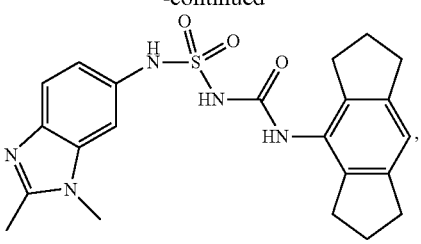

N-((1,2,3,5,6,7-hexahydro-s-indacen-4-
yl)carbamoyl)(1,2-dimethyl-1H-benzo[d]imidazol-6-
amine)sulfonamide

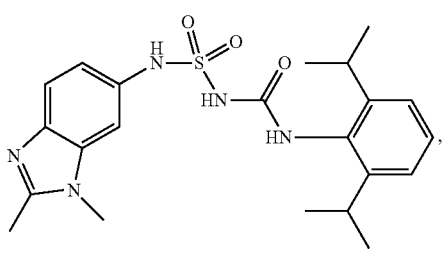

N-((2,6-diisopropylphenyl)carbamoyl)
(1,2-dimethyl-1H-benzo[d]imidazol-6-amine)
sulfonamide

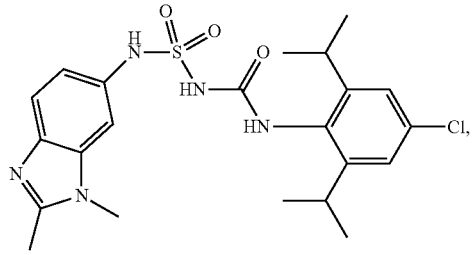

N-((4-chloro-2,6-diisopropylphenyl)carbamoyl)
(1,2-dimethyl-1H-benzo[d]imidazol-6-
amine)sulfonamide

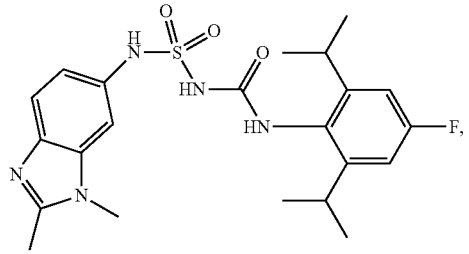

N-((4-fluoro-2,6-diisopropylphenyl)carbamoyl)
(1,2-dimethyl-1H-benzo[d]imidazol-6-
amine)sulfonamide

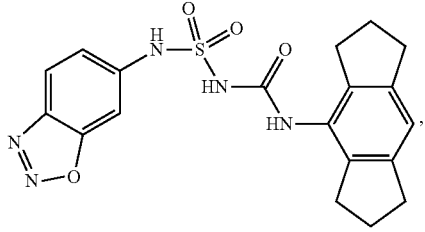

N-((1,2,3,5,6,7-hexahydro-s-indacen-4-
yl)carbamoyl)(benzo[d][1,2,3]oxadiazol-6-
amine)sulfonamide -continued

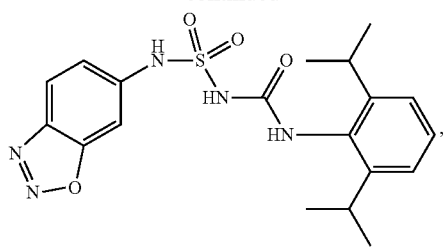

N-((2,6-diisopropylphenyl)carbamoyl)
(benzo[d][1,2,3]oxadiazol-6-amine)sulfonamide

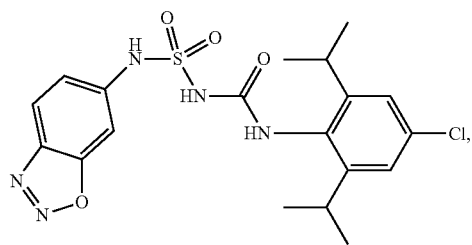

N-((4-chloro-2,6-diisopropylphenyl)carbamoyl)
(benzo[d][1,2,3]oxadiazol-6-amine)sulfonamide

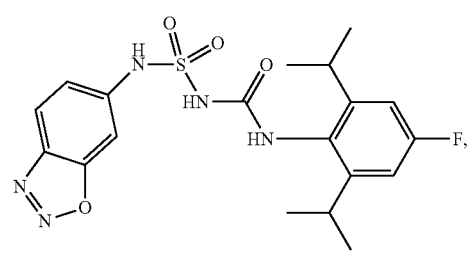

N-((4-fluoro-2,6-diisopropylphenyl)carbamoyl)
(benzo[d][1,2,3]oxadiazol-6-amine)sulfonamide

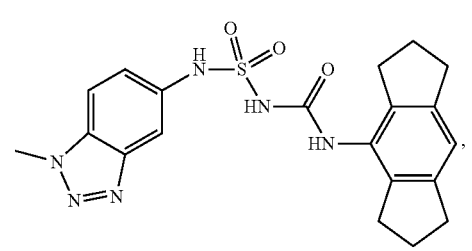

N-((1,2,3,5,6,7-hexahydro-s-indacen-4-
yl)carbamoyl)(1-methyl-1H-
benzo[d][1,2,3]triazol-5-amine)sulfonamide

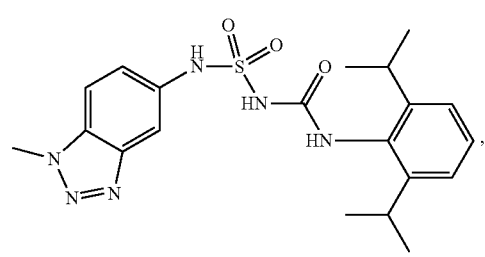

N-((2,6-diisopropylphenyl)carbamoyl)
(1-methyl-1H-benzo[d][1,2,3]triazol-5-amine)sulfonamide

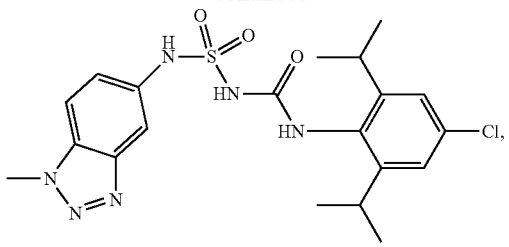

N-((4-chloro-2,6-diisopropylphenyl)carbamoyl)
(1-methyl-1H-benzo[d][1,2,3]triazol-5-
amine)sulfonamide

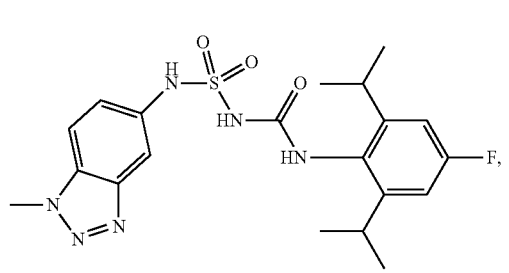

N-((4-fluoro-2,6-diisopropylphenyl)carbamoyl)
(1-methyl-1H-benzo[d][1,2,3]triazol-5-amine)sulfonamide

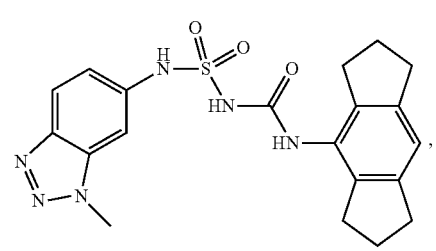

N-((1,2,3,5,6,7-hexahydro-s-indacen-4-
yl)carbamoyl)(1-methyl-1H-
benzo[d][1,2,3]triazol-5-amine)sulfonamide

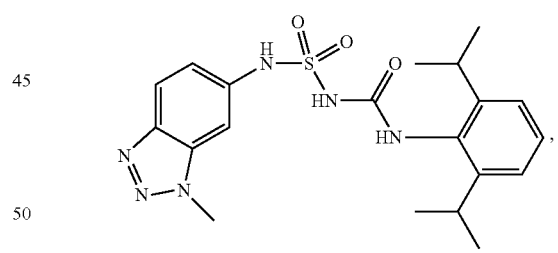

N-((2,6-diisopropylphenyl)carbamoyl)
(1-methyl-1H-benzo[d][1,2,3]triazol-6-amine)sulfonamide

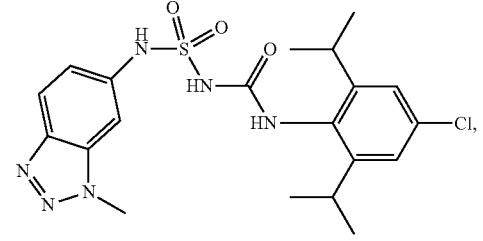

N-((4-chloro-2,6-diisopropylphenyl)carbamoyl)
(1-methyl-1H-benzo[d][1,2,3]triazol-6-
amine)sulfonamide -continued

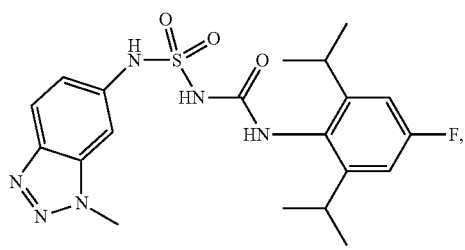

N-((4-fluoro-2,6-diisopropylphenyl)carbamoyl)
(1-methyl-1H-benzo[d][1,2,3]triazol-6-amine)sulfonamide

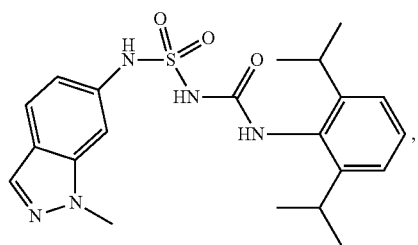

N-((2,6-diisopropylphenyl)carbamoyl)
(1-methyl-1H-indazol-6-amine)sulfonamide

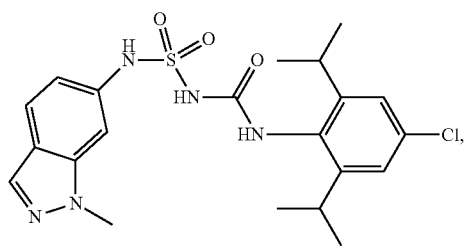

N-((4-chloro-2,6-diisopropylphenyl)carbamoyl)
(1-methyl-1H-indazol-6-amine)sulfonamide

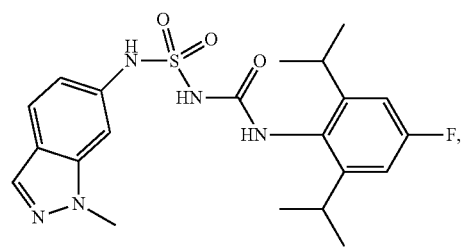

N-((4-fluoro-2,6-diisopropylphenyl)carbamoyl)
(1-methyl-1H-indazol-6-amine)sulfonamide

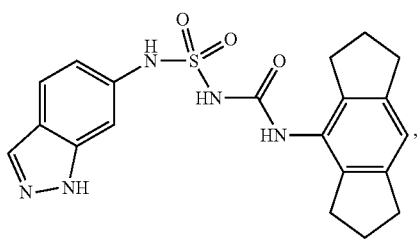

N-((1,2,3,5,6,7-hexahydro-s-indacen-4-yl)-
carbamoyl)(1H-indazol-6-amine)sulfonamide -continued

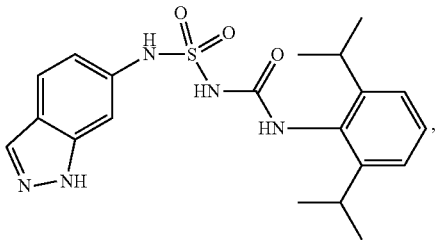

N-((2,6-diisopropylphenyl)carbamoyl)
(1H-indazol-6-amine)sulfonamide

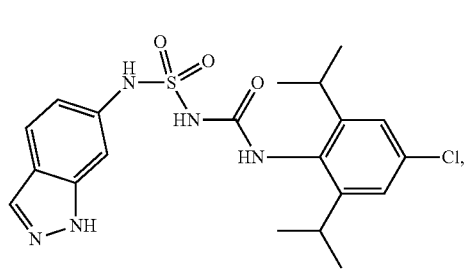

N-((4-chloro-2,6-diisopropylphenyl)carbamoyl)
(1H-indazol-6-amine)sulfonamide

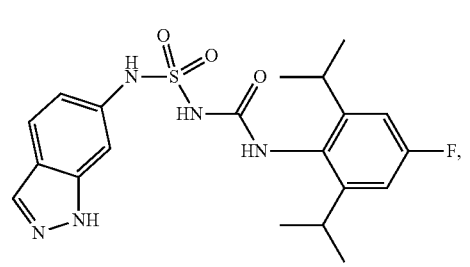

N-((4-fluoro-2,6-diisopropylphenyl)carbamoyl)
(1H-indazol-6-amine)sulfonamide

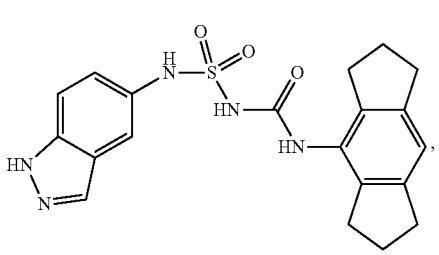

N-((1,2,3,5,6,7-hexahydro-s-indacen-4-yl)-
carbamoyl)(1H-indazol-5-amine)sulfonamide

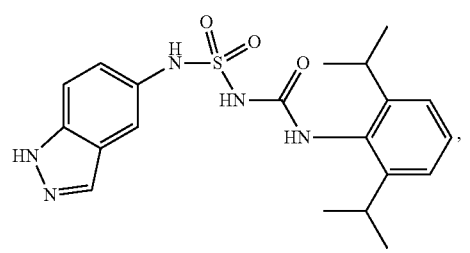

N-((2,6-diisopropylphenyl)carbamoyl)
(1H-indazol-5-amine)sulfonamide

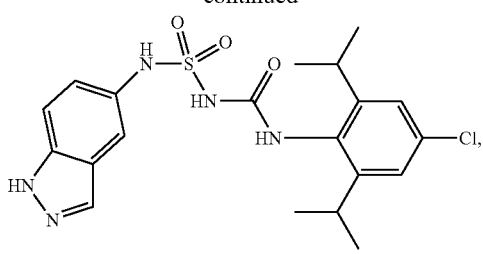

N-((4-chloro-2,6-diisopropylphenyl)carbamoyl)
(1H-indazol-5-amine)sulfonamide

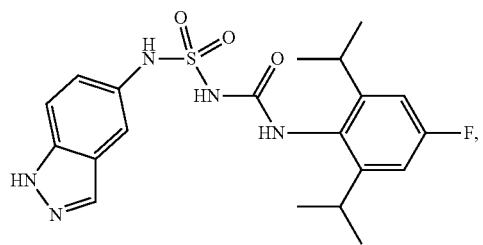

N-((4-fluoro-2,6-diisopropylphenyl)carbamoyl)
(1H-indazol-5-amine)sulfonamide

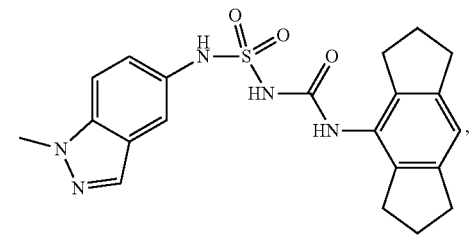

N-((1,2,3,5,6,7-hexahydro-s-indacen-4-yl)-
carbamoyl)(1-methyl-1H-indazol-5-
amine)sulfonamide

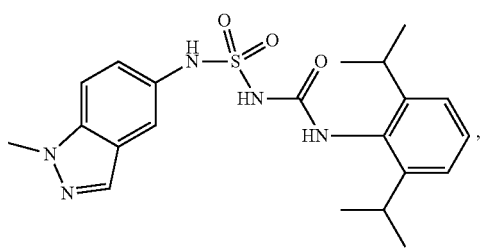

N-((2,6-diisopropylphenyl)carbamoyl)
(1-methyl-1H-indazol-5-amine)sulfonamide

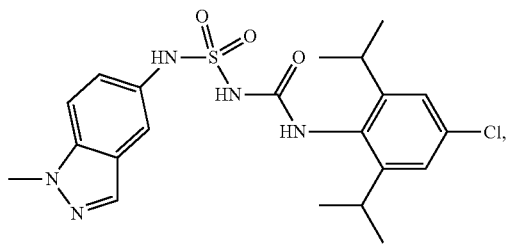

N-((4-chloro-2,6-diisopropylphenyl)carbamoyl)
(1-methyl-1H-indazol-5-amine)sulfonamide

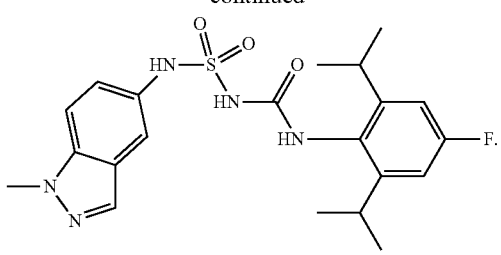

N-((4-fluoro-2,6-diisopropylphenyl)carbamoyl)
(1-methyl-1H-indazol-5-amine)sulfonamide In one embodiment, $R^1W^1$— is halo-substituted. Typically in such an embodiment, $R^1W^1$— is substituted with one or more fluoro and/or chloro groups. Typically in any embodiment where $R^1W^1$— is halo-substituted, a nitrogen atom of $R^1W^1$— is linked to J, J is S, Q is O and —$W^2R^2$ is —$R^2$ wherein $R^2$ is as previously defined. Typically in any embodiment where $R^1W^1$— is halo-substituted, —$W^2R^2$ is an aryl or a heteroaryl group, wherein the aryl or the heteroaryl group is substituted at the α and α' positions and optionally at other positions.

In one embodiment, $R^1W^1$— is Har-L-NH— or Har-L-$NR^1$—, wherein Har is an aryl or a heteroaryl group substituted with one or more halo, halogenated alkyl or halogenated alkoxy groups, wherein Har may optionally be further substituted, -L- is a bond or an optionally substituted alkylene, alkenylene, alkynylene or arylene group, which may optionally include one or more heteroatoms N, O or S in its carbon skeleton, and $R^1$ is as previously defined. Typically, -L- is a bond, a —O—($C_1$-$C_2$ alkylene)- group or a $C_1$-$C_2$ alkylene group.

In one embodiment, Har is a phenyl or toluyl group substituted with one or more chloro, fluoro, trifluoromethyl and/or trifluoromethoxy groups.

Examples of compounds where $R^1W^1$— is halo-substituted include the compounds of Examples 5, 6, 9-11 and 32 below and the compounds:

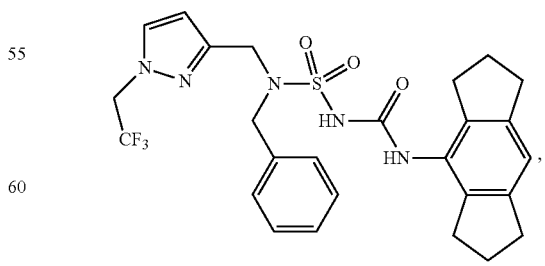

N-((1,2,3,5,6,7-hexahydro-s-indacen-4-yl)-
carbamoyl)(N-benzyl-1-(1-(2,2,2-trifluoroethyl)-1H-
pyrazol-3-yl)methanamine)sulfonamide

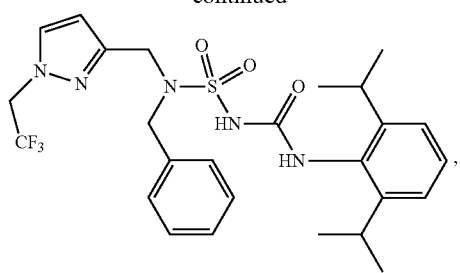

N-((2,6-diisopropylphenyl)carbamoyl)
(N-benzyl-1-(1-(2,2,2-trifluoroethyl)-1H-pyrazol-3-yl)-
methanamine)sulfonamide

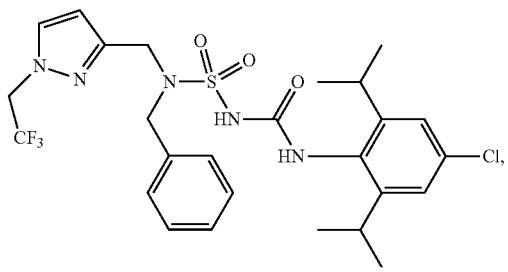

N-((4-chloro-2,6-diisopropylphenyl)carbamoyl)
(N-benzyl-1-(1-(2,2,2-trifluoroethyl)-1H-pyrazol-3-yl)-
methanamine)sulfonamide

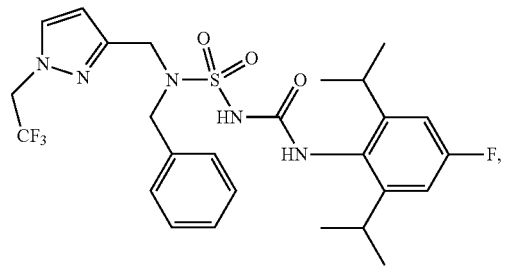

N-((4-fluoro-2,6-diisopropylphenyl)carbamoyl)
(N-benzyl-1-(1-(2,2,2-trifluoroethyl)-1H-pyrazol-3-yl)-
methanamine)sulfonamide

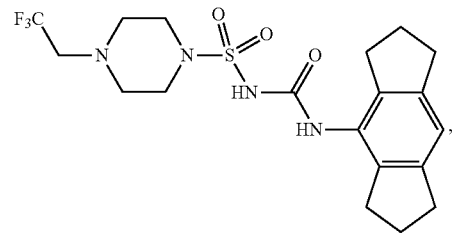

N-((1,2,3,5,6,7-hexahydro-s-indacen-4-yl)carbamoyl)-4-
(2,2,2-trifluoroethyl)piperazine-1-sulfonamide

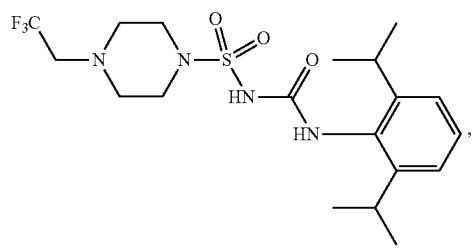

N-((2,6-diisopropylphenyl)carbamoyl)-
4-(2,2,2-trifluoroethyl)piperazine-1-sulfonamide

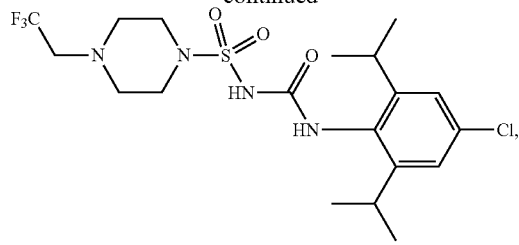

N-((4-chloro-2,6-diisopropylphenyl)carbamoyl)-
4-(2,2,2-trifluoroethyl)piperazine-1-sulfonamide

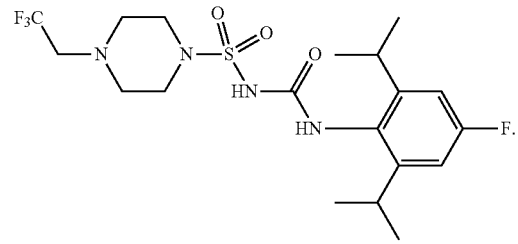

N-((4-fluoro-2,6-
diisopropylphenyl)carbamoyl)-4-(2,2,2-
trifluoroethyl)piperazine-1-sulfonamide In one embodiment, $R^1W^1$— is Het-X—$(CH_2)_m$—NH—, Ar—X—$(CH_2)_m$—NH—, Het-X—$(CH_2)_m$—$NR^1$— or Ar—X—$(CH_2)_m$—$NR^1$—; wherein Het is as defined above; Ar is an optionally substituted aryl group; —X— is a bond, —NH—, —S— or —O—; and m is 2-6. Typically m is 2-4. More typically m is 2. Typically in such an embodiment, J is S, Q is O and —$W^2R^2$ is —$R^2$ wherein $R^2$ is as previously defined. Typically in such an embodiment, —$W^2R^2$ is an aryl or a heteroaryl group, wherein the aryl or the heteroaryl group is substituted at the α and α' positions and optionally at other positions. Examples of compounds where $R^1W^1$— is Het-X—$(CH_2)_m$—NH—, Ar—X—$(CH_2)_m$—NH—, Het-X—$(CH_2)_m$—$NR^1$— or Ar—X—$(CH_2)_m$—$NR^1$— include the compounds of Examples 5, 15, 21 and 24-26 below.

In one embodiment, $R^1W^1$— is substituted with an alkylsulphonyl or a cyano group. For example, $R^1W^1$— may be $R^1NH$— or $(R^1)_2N$— wherein at least one $R^1$ is a cyano- or alkylsulphonyl-substituted aryl or arylalkyl group, which may optionally be substituted with further substituents. Typically in such an embodiment, a nitrogen atom of $R^1W^1$— is linked to J, J is S, Q is O and —$W^2R^2$ is —$R^2$ wherein $R_2$ is as previously defined. Typically in such an embodiment, —$W^2R^2$ is an aryl or a heteroaryl group, wherein the aryl or the heteroaryl group is substituted at the α and α' positions and optionally at other positions. Examples of compounds where $R^1W^1$— is substituted with an alkylsulphonyl or a cyano group include the compounds of Examples 7 and 33 below.

In one embodiment, $R^1W^1$— is $R^1N(Me)$-, wherein $R^1$ is an optionally substituted aryl or heteroaryl group. Typically in such an embodiment, J is S, Q is O and —$W^2R^2$ is —$R^2$ wherein $R^2$ is as previously defined. Typically in such an embodiment, —$W^2R^2$ is an aryl or a heteroaryl group, wherein the aryl or the heteroaryl group is substituted at the α and α' positions and optionally at other positions. An example of such a compound is the compound of Example 31 below.

In one embodiment, $R^1W^1$— is Am-M-NH— or Am-M-$NR^1$—, wherein Am is a primary, secondary or tertiary amino group, -M- is a branched alkylene, a cycloalkylene or a cycloalkyl-substituted alkylene group, and R¹ is as previously defined. Typically, Am is a dialkylamino group and -M- is a cycloalkyl-substituted alkylene group. Typically in such an embodiment, J is S, Q is O and —W²R² is —R² wherein R² is as previously defined. Typically in such an embodiment, —W²R² is an aryl or a heteroaryl group, wherein the aryl or the heteroaryl group is substituted at the α and α' positions and optionally at other positions. An example of such a compound is the compound of Example 12 below.

In one embodiment, R¹W¹— comprises a heterocyclic group, wherein the heterocyclic group is substituted with one or more hydroxyl, halo, alkyl, alkoxy, halogenated alkyl or halogenated alkoxy groups. Optionally the substituted heterocyclic group contains a single heteroatom in the heterocyclic ring, such as nitrogen. Alternatively the substituted heterocyclic group may contain two or more heteroatoms in the heterocyclic ring, such as nitrogen and one or more further heteroatoms selected from O, N or S. Typically, the substituted heterocyclic group is substituted with one or more hydroxyl or $C_1$-$C_4$ alkyl groups. Typically in any embodiment where R¹W¹— comprises a substituted heterocyclic group, a nitrogen atom of R¹W¹— is linked to J. Typically, in any embodiment where R¹W¹— comprises a substituted heterocyclic group and a nitrogen atom of R¹W¹— is linked to J, J is S, Q is O and —W²R² is —R² wherein R² is as previously defined. Typically, in any embodiment where R¹W¹— comprises a substituted heterocyclic group, —W²R² is an aryl or a heteroaryl group, wherein the aryl or the heteroaryl group is substituted at the α and α' positions and optionally at other positions. Specific examples of such compounds include the compounds of Examples 2 and 41 below and:

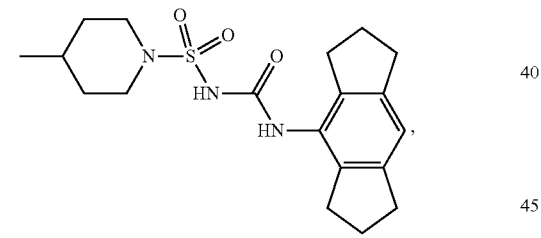

N-((1,2,3,5,6,7-hexahydro-s-indacen-4-yl)carbamoyl)-4-methylpiperidine-1-sulfonamie

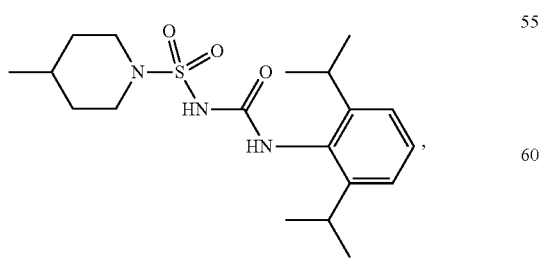

N-((2,6-diisopropylphenyl)carbamoyl)-4-methylpiperidine-1-sulfonamide

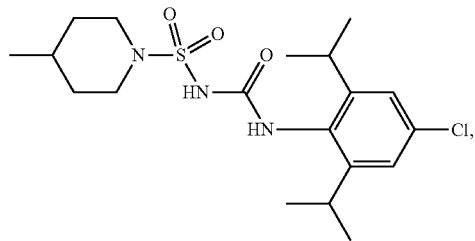

N-((4-chloro-2,6-diisopropylphenyl)carbamoyl)-4-methylpiperidine-1-sulfonamide

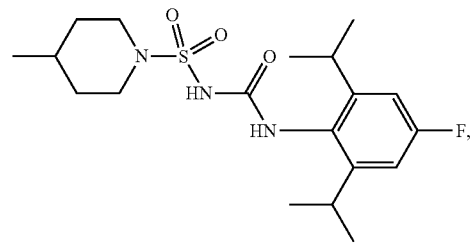

N-((4-fluoro-2,6-diisopropylphenyl)carbamoyl)-4-methylpiperidine-1-sulfonamide

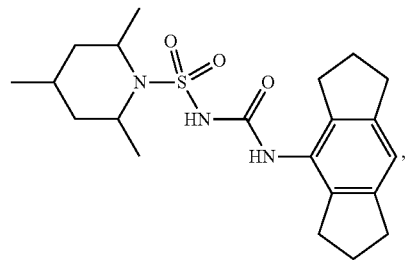

N-((1,2,3,5,6,7-hexahydro-s-indacen-4-yl)carbamoyl)-2,4,6-trimethylpiperidine-1-sulfonamide

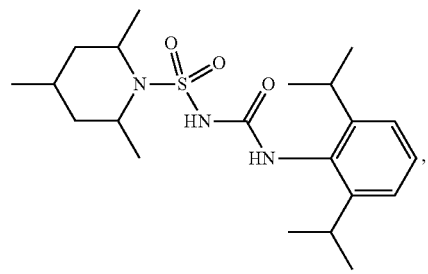

N-((2,6-diisopropylphenyl)carbamoyl)-2,4,6-trimethylpiperidine-1-sulfonamide

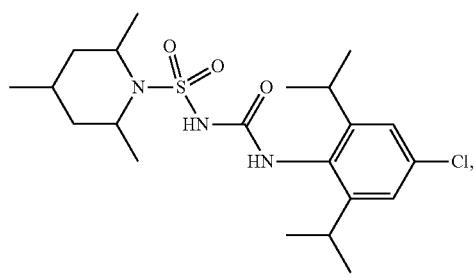

N-((4-chloro-2,6-diisopropylphenyl)carbamoyl)-2,4,6-trimethylpiperidine-1-sulfonamide -continued

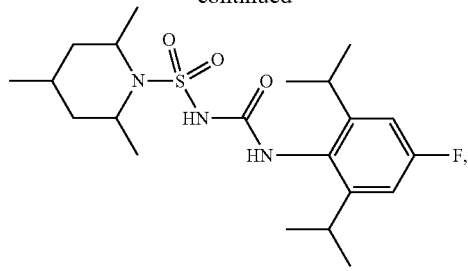

N-((4-fluoro-2,6-diisopropylphenyl)carbamoyl)-2,4,6-trimethylpiperidine-1-sulfonamide

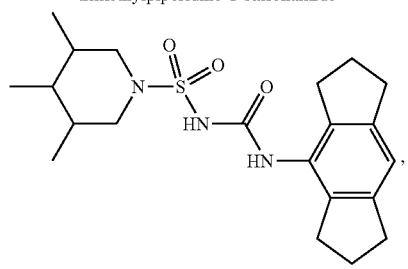

N-((1,2,3,5,6,7-hexahydro-s-indacen-4-yl)carbamoyl)-3,4,5-trimethylpiperidine-1-sulfonamide

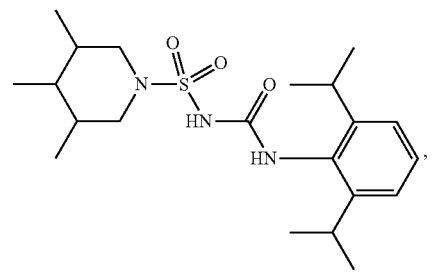

N-((2,6-diisopropylphenyl)carbamoyl)-3,4,5-trimethylpiperidine-1-sulfonamide

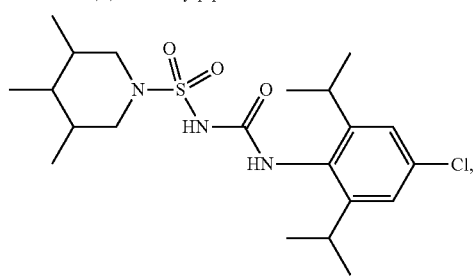

N-((4-chloro-2,6-diisopropylphenyl)carbamoyl)-3,4,5-trimethylpiperidine-1-sulfonamide

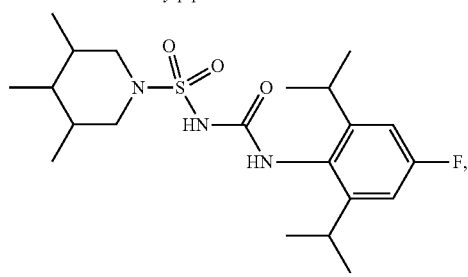

N-((4-fluoro-2,6-diisopropylphenyl)carbamoyl)-3,4,5-trimethylpiperidine-1-sulfonamide

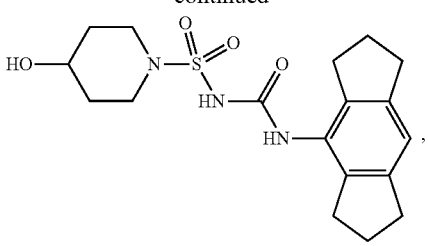

N-((1,2,3,5,6,7-hexahydro-s-indacen-4-yl)carbamoyl)-4-hydroxypiperidine-1-sulfonamide

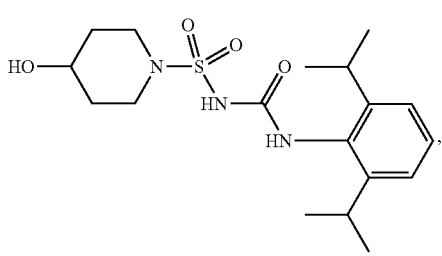

N-(2,6-diisopropylphenyl)carbamoyl)-4-hydroxypiperidine-1-sulfonamide

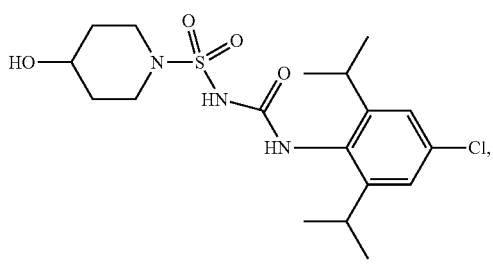

N-((4-chloro-2,6-diisopropylphenyl)carbamoyl)-4-hydroxypiperidine-1-sulfonamide

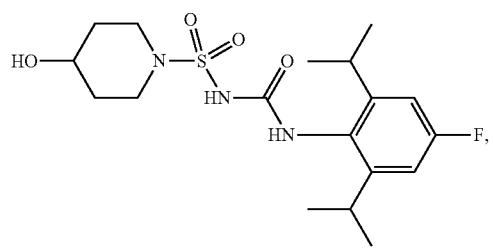

N-((4-fluoro-2,6-diisopropylphenyl)carbamoyl)-4-hydroxypiperidine-1-sulfonamide

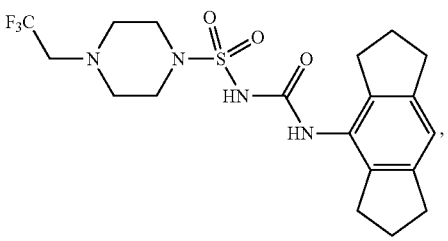

N-((1,2,3,5,6,7-hexahydro-s-indacen-4-yl)-carbamoyl)-4-(2,2,2-trifluoroethyl)piperazine-1-sulfonamide -continued

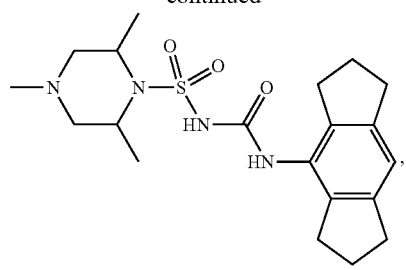

N-((1,2,3,5,6,7-hexahydro-s-indacen-4-yl)
carbamoyl)-
2,4,6-trimethylpiperazine-1-sulfonamide

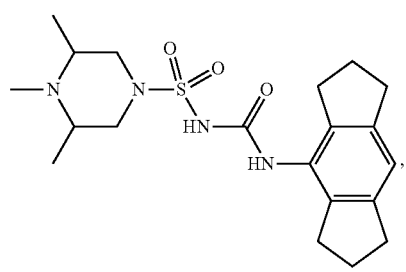

N-((1,2,3,5,6,7-hexahydro-s-indacen-4-yl)
carbamoyl)-
3,4,5-trimethylpiperazine-1-sulfonamide

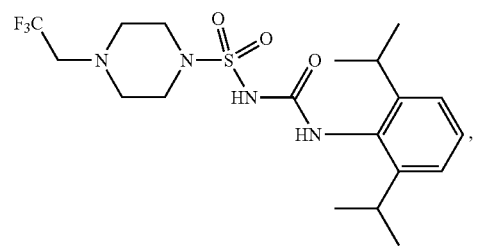

N-((2,6-diisopropylphenyl)carbamoyl)-
4-(2,2,2-trifluoroethyl)piperazine-1-sulfonamide

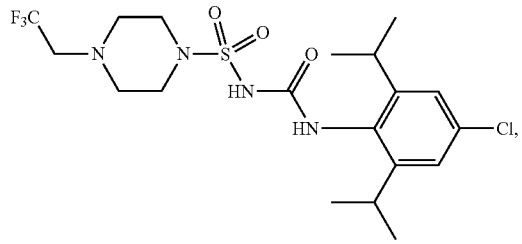

N-((4-chloro-2,6-diisopropylphenyl)carbamoyl)-
4-(2,2,2-trifluoroethyl)piperazine-1-sulfonamide

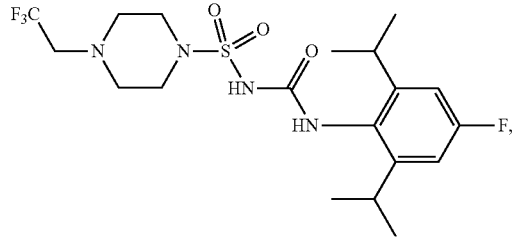

N-((4-fluoro-2,6-
diisopropylphenyl)carbamoyl)-4-(2,2,2-
trifluoroethyl)piperazine-1-sulfonamide -continued

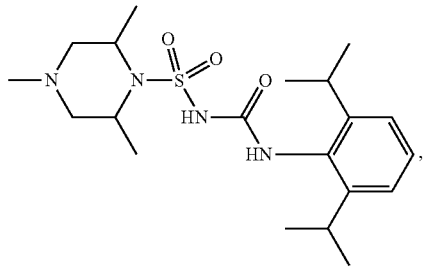

N-((2,6-diisopropylphenyl)carbamoyl)-
2,4,6-trimethylpiperazine-1-sulfonamide

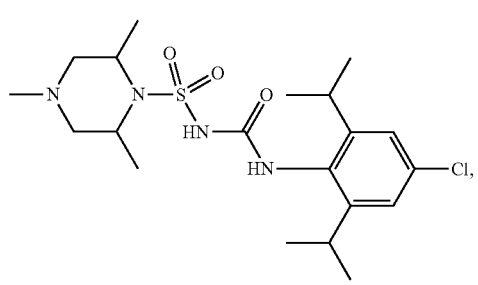

N-((4-chloro-2,6-diisopropylphenyl)carbamoyl)-
2,4,6-trimethylpiperazine-1-sulfonamide

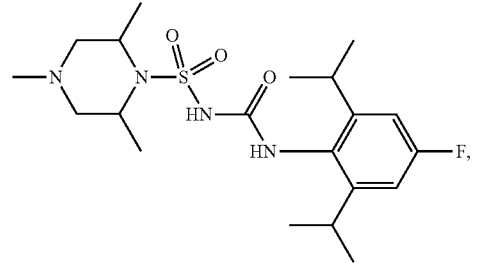

N-((4-fluoro-2,6-diisopropylphenyl)carbamoyl)-
2,4,6-trimethylpiperazine-1-sulfonamide

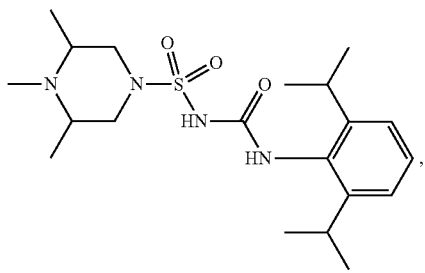

N-((2,6-diisopropylphenyl)carbamoyl)-
3,4,5-trimethylpiperazine-1-sulfonamide

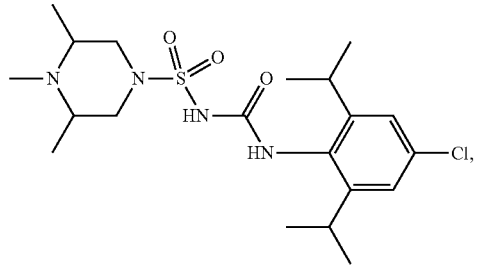

N-((4-chloro-2,6-diisopropylphenyl)carbamoyl)-
3,4,5-trimethylpiperazine-1-sulfonamide

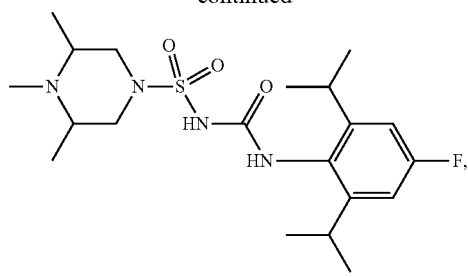

N-((4-chloro-2,6-diisopropylphenyl)carbamoyl)-
3,4,5-trimethylpiperazine-1-sulfonamide

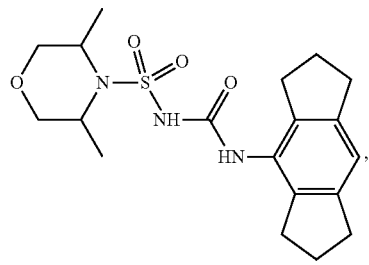

N-((1,2,3,5,6,7-hexahydro-s-indacen-
4-yl)-carbamoyl)-3,5-
dimethylmorpholine-4-sulfonamide

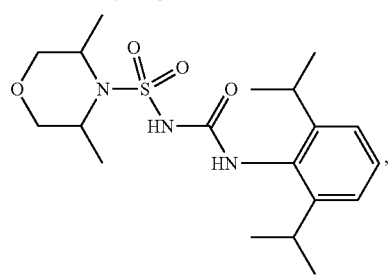

N-((2,6-diisopropylphenyl)carbamoyl)-
3,5-dimethylmorpholine-4-sulfonamide

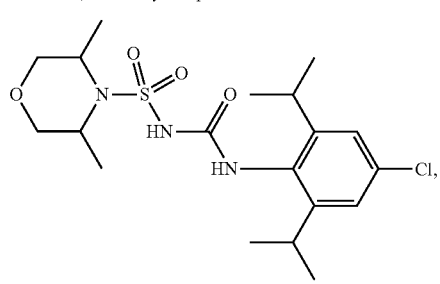

N-((4-chloro-2,6-diisopropylphenyl)carbamoyl)-
3,5-dimethylmorpholine-4-sulfonamide

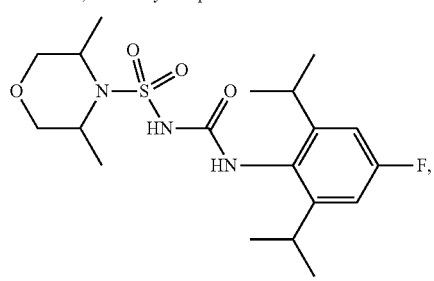

N-((4-fluoro-2,6-
diisopropylphenyl)carbamoyl)-3,5-
dimethylmorpholine-4-sulfonamide

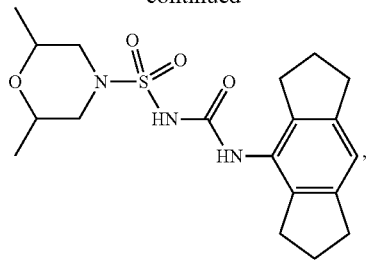

N-((1,2,3,5,6,7-hexahydro-s-indacen-4-
yl)-carbamoyl)-2,6-dimethylmorpholine-
4-sulfonamide

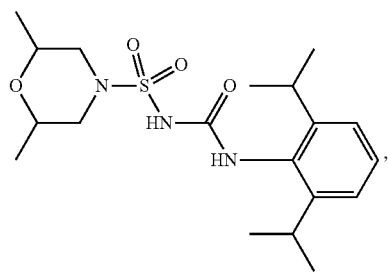

N-((2,6-diisopropylphenyl)carbamoyl)-
2,6-dimethylmorpholine-4-sulfonamide

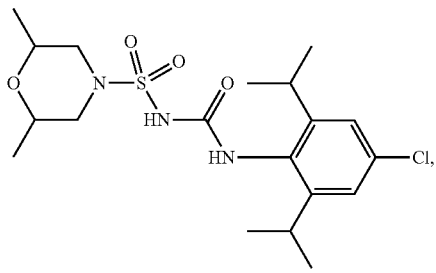

N-((4-chloro-2,6-diisopropylphenyl)carbamoyl)-
2,6-dimethylmorpholine-4-sulfonamide

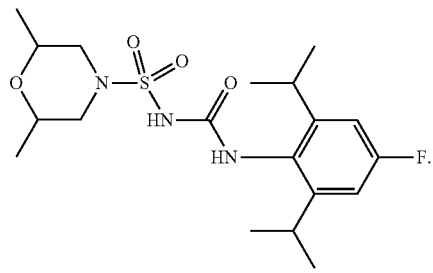

N-((4-fluoro-2,6-
diisopropylphenyl)carbamoyl)-2,6-
dimethylmorpholine-4-sulfonamide In one embodiment, when —W²R² is an aryl or a heteroaryl group, wherein the aryl or the heteroaryl group is substituted at the α and α' positions and optionally at other positions, —W²R² is halo substituted at a position other than the α and α' position of the aryl or the heteroaryl group. For example, —W²R² may be a phenyl group, wherein the phenyl group is fluoro, chloro and/or bromo substituted at one or more of the 3-, 4- and 5-positions, and substituted at the 2- and 6-positions with groups independently selected from alkyl, cycloalkyl, alkoxy, cycloalkoxy, alkenyl, cycloalkenyl, alkynyl, acyl, aryl, alkylaryl, alkoxyaryl, heteroaryl, heterocyclyl, arylalkyl and heteroarylalkyl groups. Examples of such compounds include:

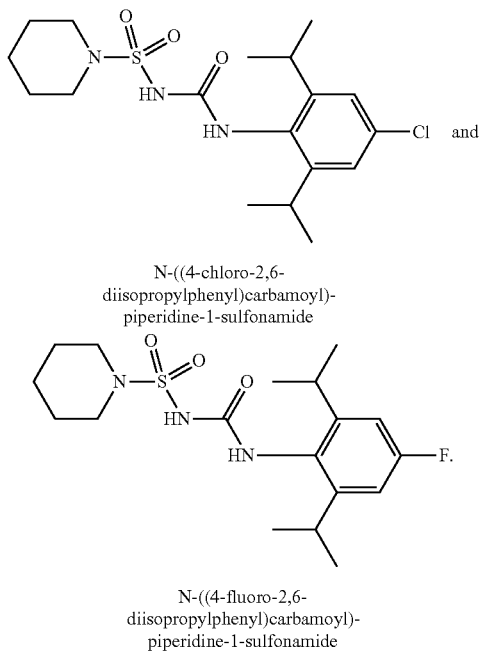

N-((4-chloro-2,6-diisopropylphenyl)carbamoyl)-piperidine-1-sulfonamide

N-((4-fluoro-2,6-diisopropylphenyl)carbamoyl)-piperidine-1-sulfonamide

In one embodiment, —$W^2R^2$ is an optionally substituted —$NHR^2$ or —$N(R^2)_2$ group, wherein optionally two $R^2$ together with the nitrogen atom to which they are attached may form a cyclic group, and $R^1W^1$— is Het, wherein Het is as defined above. Typically in such an embodiment, J is S and Q is O. Typically in such an embodiment, Het is an optionally substituted monocyclic or bicyclic heteroaryl group. More typically, Het is an optionally substituted five membered monocyclic heteroaryl group or an optionally substituted fused bicyclic heteroaryl group containing a five membered and a six membered ring.

In another embodiment, —$W^2R^2$ is an optionally substituted —$N(R^2)_2$ group, wherein the two $R^2$ together with the nitrogen atom to which they are attached form an optionally substituted cyclic aromatic group, such as an optionally substituted pyrrolyl, imidazolyl, pyrazolyl or triazolyl group. Typically in such an embodiment J is S, Q is O, and $R^1W^1$— is $R^1$— wherein $R^1$ is as previously defined. Typically, the pyrrolyl, imidazolyl, pyrazolyl or triazolyl group is substituted at least at the 2- and 5-positions, wherein the 2,5-disubstituents are each independently selected from alkyl, cycloalkyl, alkoxy, cycloalkoxy, alkenyl, cycloalkenyl, alkynyl, acyl, aryl, alkylaryl, alkoxyaryl, heteroaryl, heterocyclyl, arylalkyl and heteroarylalkyl groups. More typically, the 2,5-disubstituents are each independently selected from alkyl or cycloalkyl groups, such as $C_3$-$C_6$ branched or $C_3$-$C_6$ cyclic alkyl groups, e.g. isopropyl, cyclopropyl, cyclohexyl or t-butyl groups. Alternatively, —$W^2R^2$ may be

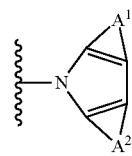

wherein $A^1$ and $A^2$ are each independently selected from an optionally substituted alkylene or alkenylene group, which may optionally include one or more heteroatoms N, O or S in its carbon skeleton. Typically, each ring containing $A^1$ or $A^2$ is a five or a six membered ring.

In a further embodiment, —$W^2R^2$ has a formula selected from

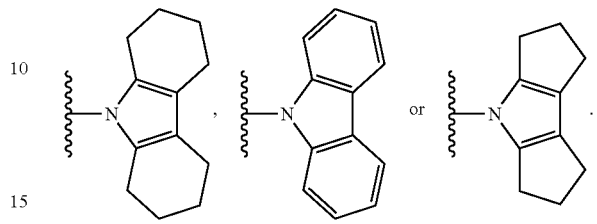

Example 4 below is an example of a compound where —$W^2R^2$ is an optionally substituted —$N(R^2)_2$ group, wherein the two $R^2$ together with the nitrogen atom to which they are attached form a cyclic aromatic group.

In one embodiment, $R^1W^1$— comprises a heterocyclic group, wherein the heterocyclic group contains a single heteroatom in the heterocyclic ring, such as a nitrogen atom, wherein $R^1W^1$— may be optionally substituted, and —$W^2R^2$ is a fused aryl or a fused heteroaryl group, wherein the aryl or heteroaryl group is fused to one or more cyclic hydrocarbon, heterocyclic, aryl or heteroaryl rings, wherein —$W^2R^2$ may be optionally substituted.

In another embodiment, $R^1W^1$— comprises a heterocyclic group containing a nitrogen atom and at least one further heteroatom in the heterocyclic ring, wherein $R^1W^1$— may be optionally substituted, wherein a nitrogen atom of $R^1W^1$— is linked to J, and wherein —$W^2R^2$ is a monocyclic aryl or a monocyclic heteroaryl group, wherein the monocyclic aryl or the monocyclic heteroaryl group is substituted at the α and α' positions, wherein the substituents at the α and α' positions are independently selected from alkyl, cycloalkyl, alkoxy, cycloalkoxy, alkenyl, cycloalkenyl, alkynyl, acyl, aryl, alkylaryl, alkoxyaryl, heteroaryl, heterocyclyl, arylalkyl and heteroarylalkyl groups, wherein —$W^2R^2$ may optionally be further substituted.

In one embodiment of the compound of formula (I), at least one of $W^1$ and $R^1$ or $W^2$ and $R^2$ combine to form a moiety selected from the group consisting of:

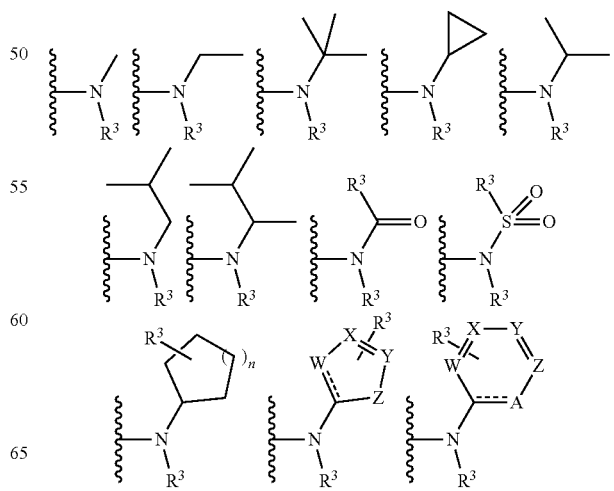

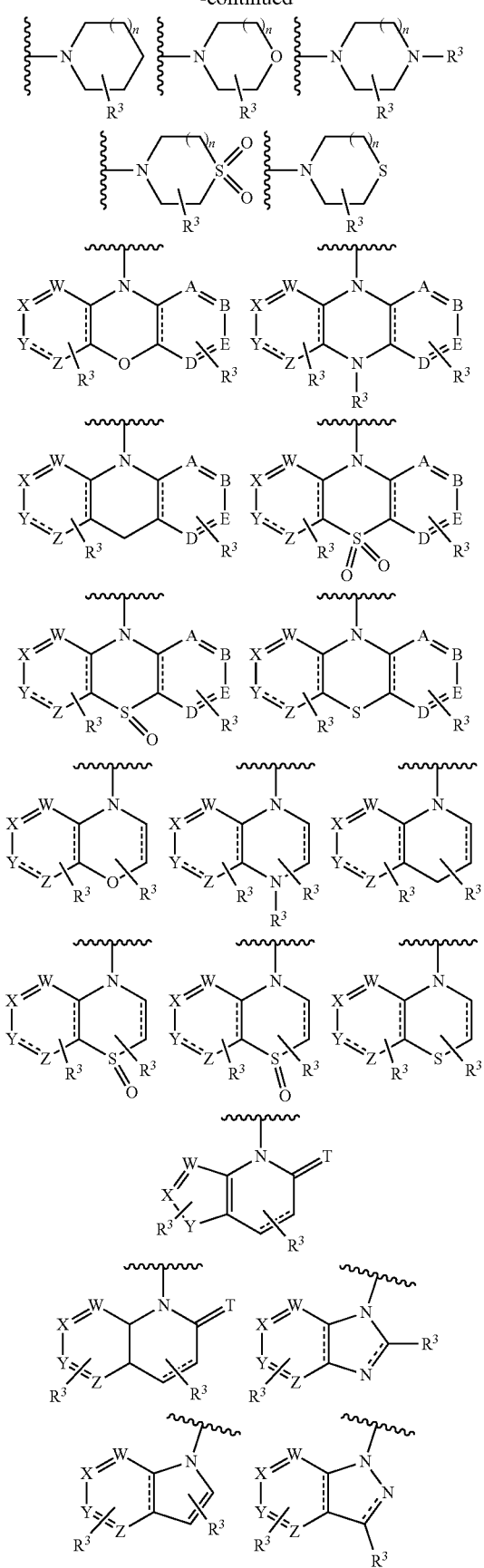

wherein, each dashed line may independently be a bond; T is O or S;

A, B, D, E, W, X, Y and Z, when present, may each be independently selected from O, C($R^3$), C($R^3$)$_2$, N, N($R^3$) and S;

each incidence of $R^3$ is independently selected from the group consisting of hydrogen, halide, cyano, $C_1$-$C_6$ alkyl, $C_1$-$C_6$ trifluoroalkyl, $C_1$-$C_6$ alkoxy, C=O, SO$_2$, acyl, amino, hydroxyl, $C_5$-$C_6$ heteroaryl, $C_5$-$C_6$ heterocyclyl and $C_3$-$C_6$ cycloalkyl, each of which may be optionally substituted as appropriate; and n is 0, 1, 2 or 3.

It will be appreciated that each ring shown in the above structures with an $R^3$ group extending therefrom indicates that an $R^3$ group may extend from one or more or all of the available positions on said ring for substitution.

Each of these 'nitrogen-linked' moieties may be combined with any of the 'carbon-linked' moieties described for the compound of the first aspect to form the respective $R^1$ and $R^2$ combination to give the final structure.

In one embodiment, the compound of formula (I) is selected from a compound of formula (II), (III), (IV), (V) or (VI) or a pharmaceutically acceptable salt, solvate or prodrug thereof:

Formula II

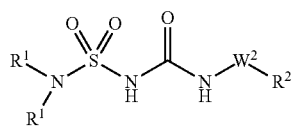

Formula III

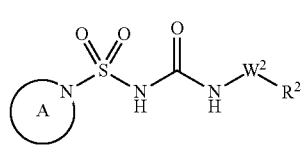

Formula IV

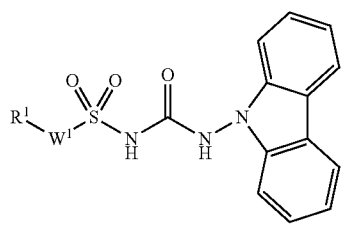

Formula V

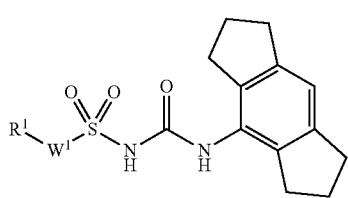

Formula VI

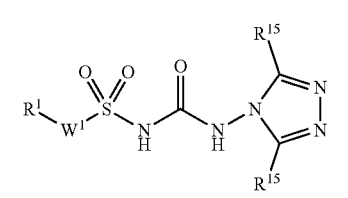

wherein $W^1$ and $W^2$, if present, and $R^1$ and $R^2$ are as described in any one or more of the embodiments described for the first aspect;

each incidence of $R^{15}$ is independently selected from $C_1$ to $C_4$ alkyl, $C_1$ to $C_4$ hydroxylalkyl and $C_3$ to $C_5$ cycloalkyl; and A is optionally substituted heteroaryl or heterocycle, as previously defined, linked to the sulfonyl sulphur through a ring nitrogen.

In one embodiment of any one of formula II to VI, $R^1$ or A may be selected from the group consisting of pyrazole, imidazole, triazole, tetrazole, pyrrole, morpholine, piperazine, 4-methyl piperazine, and fused bicyclics or tricyclics comprising a benzene ring fused with at least one 5-membered heterocycle, in one embodiment an indole, each of which may be substituted or unsubstituted.

In certain embodiments of any one of formula II to VI, $R^1$ or A may be pyrazole or triazole optionally substituted at a ring atom with a group selected from halo, isopropyl, morpholinyl, piperidinyl, and piperazinyl, each of which groups may themselves be optionally substituted with $C_1$-$C_6$ alkyl.

In one embodiment, $R^{15}$ is selected from isopropyl, cyclopropyl and $C_3$ to $C_5$ hydroxylalkyl.

In one embodiment, A is $C_3$-$C_8$ heteroaryl or heterocyclyl, each of which may be optionally substituted.

In one embodiment, A is $C_4$-$C_7$ heteroaryl or heterocyclyl, each of which may be optionally substituted.

In one embodiment, A is selected from $C_5$ or $C_6$ heteroaryl or heterocyclyl, each of which may be optionally substituted.

A may be selected from pyrazole, imidazole, triazole, tetrazole, pyrrole, morpholine, piperazine, 4-methyl piperazine, and fused bicyclics or tricyclics comprising a benzene ring fused with at least one 5-membered heterocycle, such as indole, all of which groups may be optionally substituted at a ring atom with a group selected from halo, isopropyl, morpholinyl, piperidinyl, and piperazinyl, each of which groups may themselves be optionally substituted with $C_1$-$C_6$ alkyl.

In one embodiment, the compound of formula (I), (II), (III), (IV) (V) or (VI) is selected from the group consisting of:

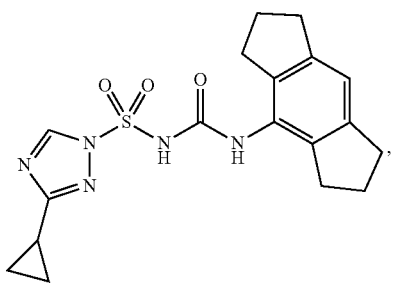

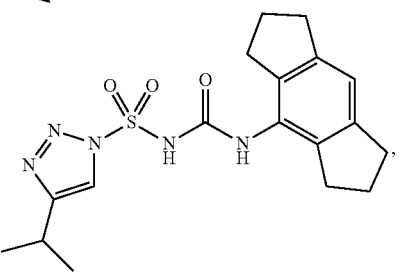

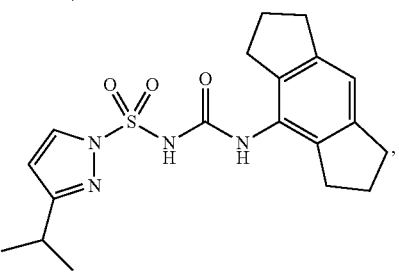

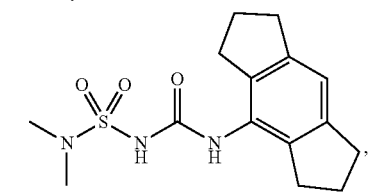

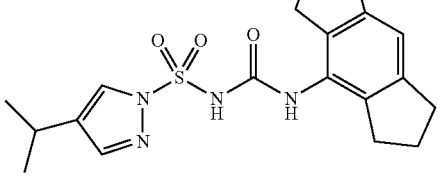

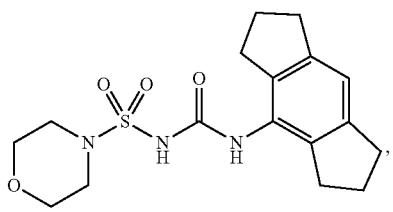

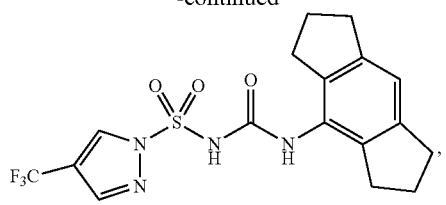
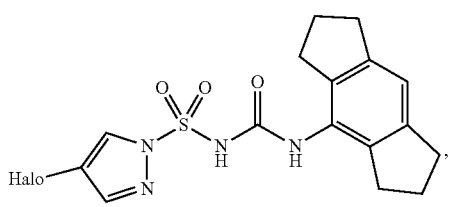
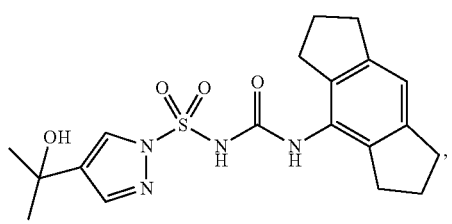
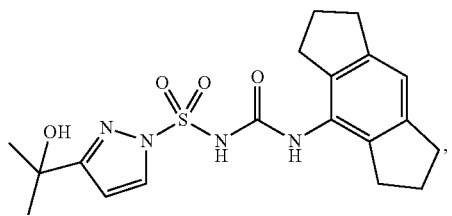
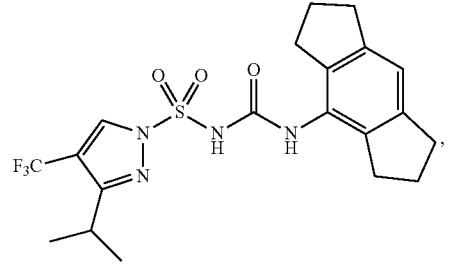
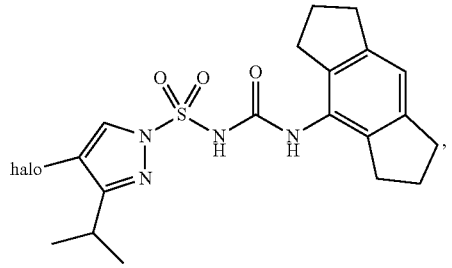
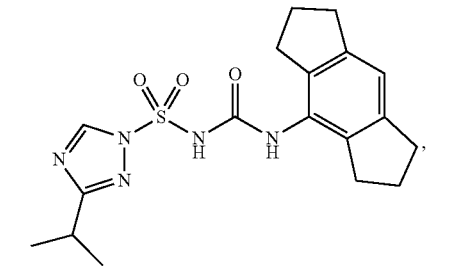
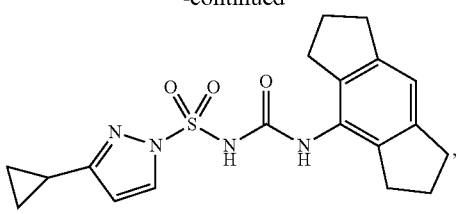
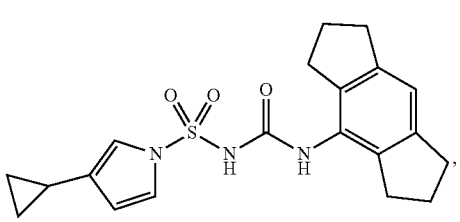
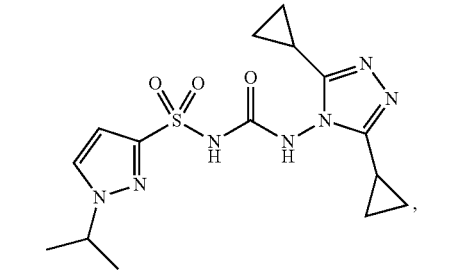
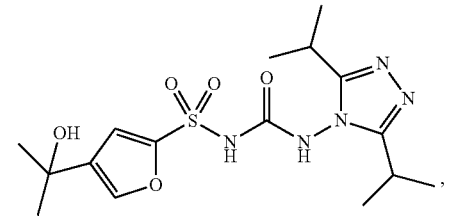
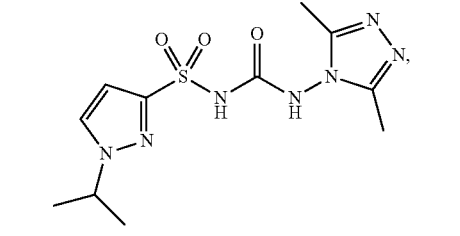
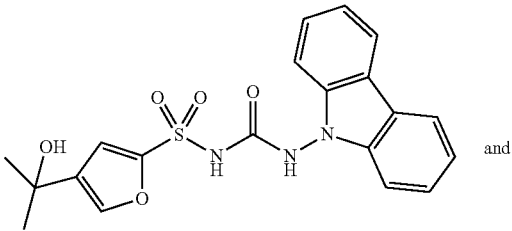
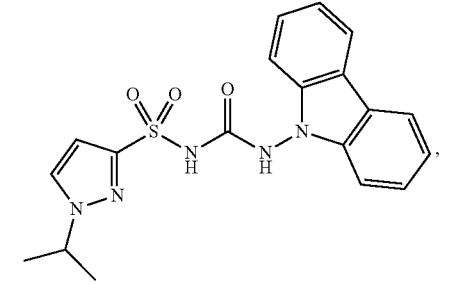

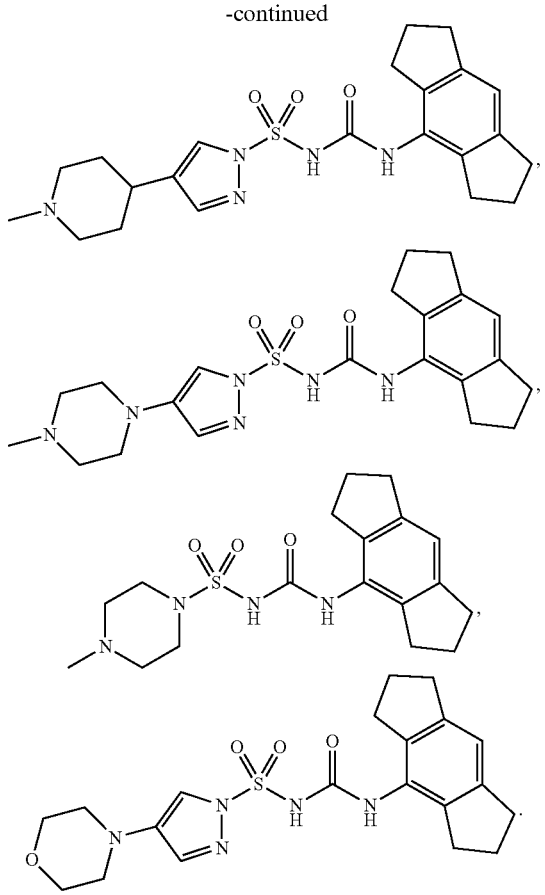

In one embodiment of the first aspect, when J is sulphur, Q is oxo, $W^2$ is carbon and $R^2$ is cycloalkane, heterocycle or aryl, then $R^2$ is not a monocyclic cycloalkane, heterocycle or aryl group.

In one embodiment of the first aspect, when J is sulphur, Q is oxo, and $W^2$ is carbon, then $R^2$ is not an alkyl group.

In one embodiment of the first aspect, when J is sulphur, Q is oxo, and $W^2$ is a carbon which is part of a ring system, then $R^2$ is not a substituted phenyl group.

In one embodiment of the first aspect, when J is sulphur, Q is oxo, $W^1$ and $R^1$ together form an alkylamine or dialkylamine and $W^2$ is a carbon which is part of a ring system, then $R^2$ is not a substituted or unsubstituted phenyl, a tetrahydrobenzothiophene, or other bicyclic thiophene, a pyridine or a pyrimidine group.

In one embodiment of the first aspect, when J is sulphur, Q is oxo, $W^1$ is a nitrogen as part of a piperidine or morpholine $R^1$ group and $W^2$ is a carbon which is part of a ring system, then $R^2$ is not a pyridine or pyrimidine group.

In one embodiment of the first aspect, when J is sulphur, Q is oxo, $W^1$ is a nitrogen as part of a piperidine, piperazine, morpholine, pyrazole, imidazole, pyrrolidine, isoquinoline or thienopyridine $R^1$ group and $W^2$ is a carbon which is part of a ring system, then $R^2$ is not a tetrahydrobenzothiophene, or other bicyclic thiophene, or a methyl-substituted pyridine group.

In one embodiment of the first aspect, when J is sulphur, Q is oxo, $W^1$ is a nitrogen and $W^2$ is a carbon which is part of a ring system, then $R^2$ may be an indacene, or substituted or hydrogenated variant thereof, or a phenyl substituted with at least one group selected from halo, $C_1$-$C_4$ alkyl and $C_3$-$C_5$ cycloalkyl.

In certain embodiments, the indacene may be a hexahydroindacene and the substituted phenyl group may be selected from 2,6-diisopropyl-4-chlorophenyl, 2,6-dicyclopropylphenyl and 2,6-dicyclopropyl-4-chloro-phenyl.

In one embodiment of the first aspect, when J is sulphur, Q is oxo, $W^1$ and $R^1$ together are selected from alkylamine, dialkylamine, arylamine, diarylamine, piperidine, morpholine, thiomorpholine, pyridine, pyrazole, azepine, hydroazepine, imidazole, pyrrolidine, isoquinoline or thienopyridine, then $W^2$ and $R^2$ together are not any group selected, independently, from substituted or unsubstituted phenyl, alkyl, cycloalkyl, pyrimidine, and a triazine group.

In one specific embodiment, the compound of formula (I), (II), (III), (IV), (V) or (VI) may not be a compound selected from the group consisting of:

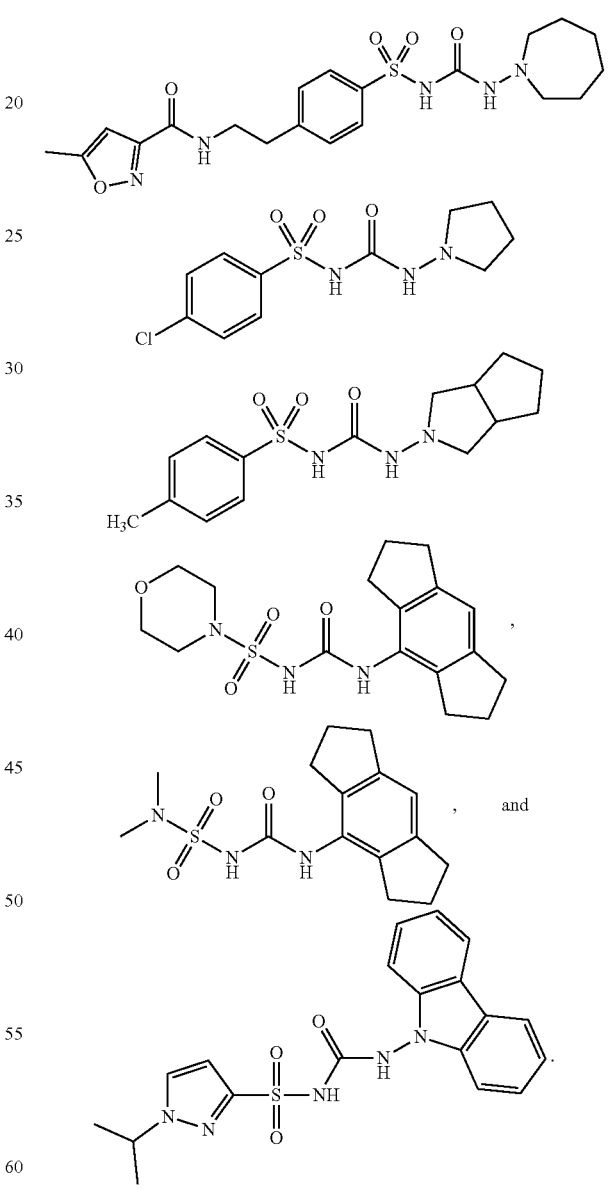

In one embodiment, the compound of formula (I) has a molecular weight of from 200 to 2000 Da. Preferably the compound of formula (I) has a molecular weight of from 300 to 1000 Da. More preferably, the compound of formula (I) has a molecular weight of from 350 to 500 Da.

The compounds of the present invention may provide one or more benefits over prior art sulfonyl ureas selected from: improved microsomal stability; improved permeability; reduced Pgp liability; reduced plasma protein binding; increased half-life; improved oral bioavailability; improved AUC; improved Cmax; reduced Cyp inhibition; and improved solubility.

In one embodiment, the compounds of formula (I) offer improved pharmacokinetic characteristics. CRID3, a known sulfonylurea, has a half-life of 3.2 hours (mouse) which may lead to substantial trough levels from QD or BD dosing when the t½ is extrapolated to man. The compounds of formula (I) may differ in, for example, their protein binding, metabolism and oral availability.

In one embodiment, the compounds of formula (I) have a tPSA of less than 90 Å$^2$.

In one further embodiment, the compounds of formula (I) have a tPSA of less than 90 Å$^2$ and a molecular weight of less than 405.

In some embodiments of the present invention, therapeutically inactive prodrugs are provided. Prodrugs are compounds which, when administered to a mammal, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

In certain embodiments, the compounds of formula (I) may exhibit improved properties compared to known antidiabetes drugs. Such compounds of formula (I) may be viewed as very potent versions of current sulfonylurea anti-diabetes drugs. Known diabetes drugs do not target NLRP3 to any therapeutically significant extent and so it would be necessary to use very high doses to have any significant effect on the NLRP3 inflammasome. The compounds of formula (I), show advantageously improved properties in a significant decrease in IC50 versus the NLRP3 inflammasome and additionally have the benefits, not realised by existing diabetes drugs, associated with NLRP3 inhibition such as improved wound healing and other advantages described herein.

In one embodiment, the compound of formula (I) displaying these improved properties is selected from the group consisting of:

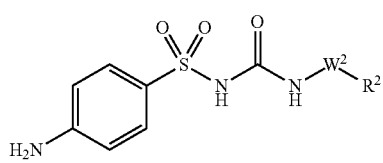

-continued

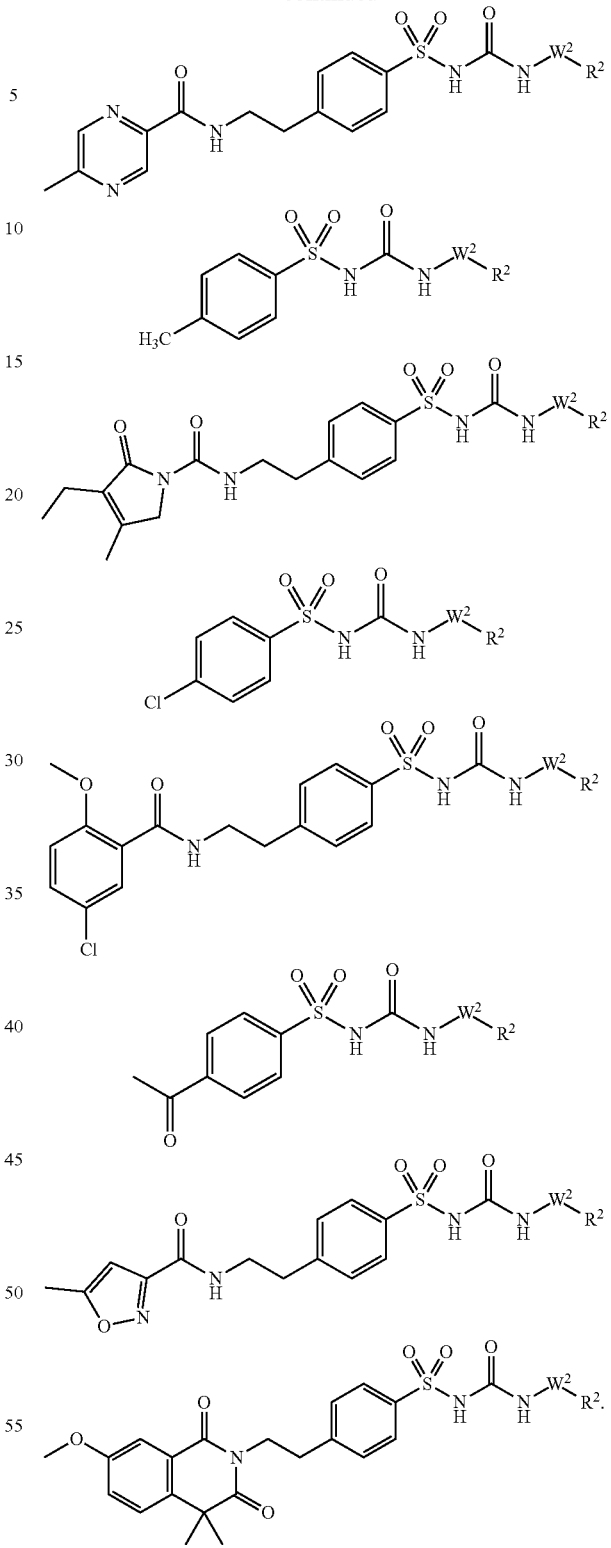

In a further embodiment, one or more of the compounds of formula (I) may be useful as photoswitchable compounds which may applied in a range of uses including but not limited to insulin release.

In certain embodiments of the invention one or more compounds of formula (I) may be appropriate for use as probes, such as photoaffinity probes, or as reactive intermediates which can be modified either directly or by means of a linking moiety to give biotinylated, fluorescent or photoaffinity probes. It will be appreciated that the compounds of formula (I) may be modified or derivatised by means well understood in the art to allow linkage to a molecule such as biotin, or a fluorescent group or photoaffinity label.

A number of prodrug ligands are known. In general, alkylation, acylation, or other lipophilic modification of one or more heteroatoms of the compound, such as a free amine or carboxylic acid residue, may reduce polarity and allow for the compound's passage into cells. Examples of substituent groups that can replace one or more hydrogen atoms on a free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphatidylcholine; phosphocholine; amino acid residues or derivatives; amino acid acyl residues or derivatives; peptides; cholesterols; or other pharmaceutically acceptable leaving groups which, when administered in vivo, provide the free amine. Any of these moieties can be used in combination with the disclosed active agents to achieve a desired effect.

In some embodiments, compounds with one or more chiral centers are provided. While racemic mixtures of compounds of the invention may be active, selective, and bioavailable, isolated isomers may be of interest as well.

The compounds disclosed herein as active agents may contain chiral centers, which may be either of the (R) or (S) configuration, or which may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds and prodrugs of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein and other similar tests which are well known in the art. Examples of methods that can be used to obtain optical isomers of the compounds according to the present invention include the following:
i) physical separation of crystals whereby macroscopic crystals of the individual enantiomers are manually separated. This technique may particularly be used when crystals of the separate enantiomers exist (i.e., the material is a conglomerate), and the crystals are visually distinct;
ii) simultaneous crystallization whereby the individual enantiomers are separately crystallized from a solution of the racemate, possible only if the latter is a conglomerate in the solid state;
iii) enzymatic resolutions whereby partial or complete separation of a racemate is achieved by virtue of differing rates of reaction for the enantiomers with an enzyme;
iv) enzymatic asymmetric synthesis, a synthetic technique whereby at least one step of the synthesis uses an enzymatic reaction to obtain an enantiomerically pure or enriched synthetic precursor of the desired enantiomer;
v) chemical asymmetric synthesis whereby the desired enantiomer is synthesized from an achiral precursor under conditions that produce asymmetry (i.e., chirality) in the product, which may be achieved using chiral catalysts or chiral auxiliaries;
vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;
vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;
viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;
ix) enantiospecific synthesis from non-racemic precursors whereby the desired enantiomer is obtained from non-chiral starting materials and where the stereochemical integrity is not or is only minimally compromised over the course of the synthesis;
x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;
xi) chiral gas chromatography whereby the racemate is volatilized and enantiomers are separated by virtue of their differing interactions in the gaseous mobile phase with a column containing a fixed non-racemic chiral adsorbent phase;
xii) extraction with chiral solvents whereby the enantiomers are separated by virtue of preferential dissolution of one enantiomer into a particular chiral solvent; and
xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compound optionally may be provided in a composition that is enantiomerically enriched, such as a mixture of enantiomers in which one enantiomer is present in excess, in particular, to the extent of 95% or more, 96% or more, 97% or more, 98% or more, or 99% or more, including 100%.

The terms (R), (S), (R,R), (S,S), (R,S) and (S,R) as used herein mean that the composition contains a greater proportion of the named isomer of the compound in relation to other isomers. In a preferred embodiment, these terms indicate that the composition contains at least 90% by weight of the named isomer and 10% by weight or less of the one or more other isomers; or more preferably about 95% by weight of the named isomer and 5% or less of the one or more other isomers. In some embodiments, the composition may contain at least 99% by weight of the named isomer and 1% or less by weight of the one or more other isomers, or may contain 100% by weight of the named isomer and 0% by weight of the one of more other isomers. These percentages are based on the total amount of the compound of the present invention present in the composition.

The compounds of the present invention may be utilized per se or in the form of a pharmaceutically acceptable ester, amide, salt, solvate, prodrug, or isomer. For example, the compound may be provided as a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature.

Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include those formed with propionic acid, glycolic acid, oxalic acid, malic acid, malonic acid, benzoic acid, cinnamic acid, mandelic acid, salicylic acid, and the like. Particular examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound or prodrug useful according to the present invention may be prepared in a similar manner using a pharmaceutically acceptable base, such as sodium hydroxide, potassium hydroxide, ammonium hydroxide, calcium hydroxide, triethylamine, or the like.

Esters of the active agent compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from an anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the methods of the invention may exist in different forms. For example, the compounds may exist in stable and metastable crystalline forms and isotropic and amorphous forms, all of which are intended to be within the scope of the present invention.

If a compound useful as an active agent according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound described herein as an active agent is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminium and lithium.

According to a second aspect of the invention there is provided a pharmaceutical composition comprising a compound of the first aspect disclosed herein, or a pharmaceutically acceptable salt, solvate or prodrug thereof, and a pharmaceutically acceptable carrier, diluent and/or excipient.

Suitably, the pharmaceutically acceptable carrier, diluent and/or excipient may be or include one or more of diluents, solvents, pH buffers, binders, fillers, emulsifiers, disintegrants, polymers, lubricants, oils, fats, waxes, coatings, viscosity-modifying agents, glidants and the like.

The salt forms of the compounds of the invention are especially useful due to their improved solubility.

In one embodiment, the pharmaceutical composition includes a cyclodextrin.

The cyclodextrin may be selected from alpha, beta or gamma cyclodextrins.

In one embodiment, the cyclodextrin is selected from a methyl cyclodextrin, a hydroxypropyl cyclodextrin and a sulfobutylether cyclodextrin.

It has been found that cyclodextrins provide significant advantages in formulation and delivery of the compounds of the invention.

Cyclodextrin formulations such as for example, one or more compounds of the invention with hydroxypropyl beta cyclodextrin or methyl beta cyclodextrin, may have uses in cholesterol sequestration/cholesterol lowering or via NLRP3 inhibition for Non-alcoholic steatohepatitis (NASH) and also in Alzheimer's Disease (AD).

Diluents may include one or more of microcrystalline cellulose, lactose, mannitol, calcium phosphate, calcium sulfate, kaolin, dry starch, powdered sugar, and the like. Binders may include one or more of povidone, starch, stearic acid, gums, hydroxypropylmethyl cellulose and the like. Disintegrants may include one or more of starch, croscarmellose sodium, crospovidone, sodium starch glycolate and the like. Solvents may include one or more of ethanol, methanol, isopropanol, chloroform, acetone, methylethyl ketone, methylene chloride, water and the like. Lubricants may include one or more of magnesium stearate, zinc stearate, calcium stearate, stearic acid, sodium stearyl fumarate, hydrogenated vegetable oil, glyceryl behenate and the like. A glidant may be one or more of colloidal silicon dioxide, talc or corn starch and the like. Buffers may include phosphate buffers, borate buffers and carbonate buffers, although without limitation thereto. Fillers may include one or more gels inclusive of gelatin, starch and synthetic polymer gels, although without limitation thereto. Coatings may comprise one or more of film formers, solvents, plasticizers and the like. Suitable film formers may be one or more of hydroxypropyl methyl cellulose, methyl hydroxyethyl cellulose, ethyl cellulose, hydroxypropyl cellulose, povidone, sodium carboxymethyl cellulose, polyethylene glycol, acrylates and the like. Suitable solvents may be one or more of water, ethanol, methanol, isopropanol, chloroform, acetone, methylethyl ketone, methylene chloride and the like. Plasticizers may be one or more of propylene glycol, castor oil, glycerin, polyethylene glycol, polysorbates, and the like.

Reference is made to the Handbook of Excipients $6^{th}$ Edition, Eds. Rowe, Sheskey & Quinn (Pharmaceutical Press), which provides non-limiting examples of excipients which may be useful according to the invention.

It will be appreciated that the choice of pharmaceutically acceptable carriers, diluents and/or excipients will, at least in part, be dependent upon the mode of administration of the formulation. By way of example only, the composition may be in the form of a tablet, capsule, caplet, powder, an inhalable liquid (e.g. solution, suspension), an injectable liquid, a suppository, a slow release formulation, an osmotic pump formulation or any other form that is effective and safe for administration.

Suitably, the pharmaceutical composition is for the treatment or prevention of a disease, disorder or condition in a mammal.

A third aspect of the invention resides in a method of treatment or prevention of a disease, disorder or condition including the step of administering an effective amount of a compound of the first aspect, or a pharmaceutically effective salt, solvate or prodrug thereof, or the pharmaceutical composition of the second aspect, to thereby treat or prevent the disease, disorder or condition.

A fourth aspect of the invention provides for a compound of the first aspect, or a pharmaceutically effective salt, solvate or prodrug thereof, or the pharmaceutical composition of the second aspect, for use in the treatment or prevention of a disease, disorder or condition.

A fifth aspect of the invention provides for use of a compound of the first aspect, or a pharmaceutically effective salt, solvate or prodrug thereof, in the manufacture of a medicament for the treatment or prevention of a disease, disorder or condition.

As generally used herein, the terms "administering" or "administration", and the like, describe the introduction of the compound or composition to a mammal such as by a particular route or vehicle. Routes of administration may include topical, parenteral and enteral which include oral, buccal, sub-lingual, nasal, anal, gastrointestinal, subcutaneous, intramuscular and intradermal routes of administration, although without limitation thereto.

By "treat", "treatment" or "treating" is meant administration of the compound or composition to a subject to at least ameliorate, reduce or suppress existing signs or symptoms of the disease, disorder or condition experienced by the subject.

By "prevent", "preventing" or "preventative" is meant prophylactically administering the formulation to a subject such as a mammal who does not exhibit signs or symptoms of a disease, disorder or condition, but who is expected or anticipated to likely exhibit such signs or symptoms in the absence of prevention. Preventative treatment may at least lessen or partly ameliorate expected symptoms or signs.

As used herein, "effective amount" refers to the administration of an amount of the relevant active agent sufficient to prevent the occurrence of symptoms of the condition being treated, or to bring about a halt in the worsening of symptoms or to treat and alleviate or at least reduce the severity of the symptoms. The effective amount will vary in a manner which would be understood by a person of skill in the art with patient age, sex, weight, etc. An appropriate dosage or dosage regime can be ascertained through routine trial.

As used herein, the terms "subject" or "individual" or "patient" may refer to any mammalian subject. Mammals may include, but are not restricted to, primates, livestock animals (e.g. sheep, cows, horses, donkeys, pigs), laboratory test animals (e.g. rabbits, mice, rats, guinea pigs, hamsters), companion animals (e.g. cats, dogs) and captive wild animals (e.g. foxes, deer, dingoes). A preferred subject is a human in need of treatment for a disease, disorder or condition as described herein. However, it will be understood that the aforementioned terms do not imply that symptoms are necessarily present.

In one particular embodiment, the disease, disorder or condition is one which is responsive to inhibition of activation of the NLRP3 inflammasome.

According to this embodiment, the compound of the first aspect, or pharmaceutically effective salt, solvate or prodrug thereof is a specific inhibitor of NLRP3.

In a further embodiment, the disease, disorder or condition is responsive to modulation of one or more of IL-1β, IL-17, IL-18, IL-1α, IL-37, IL-33 and Th17 cells.

In one embodiment, the modulation is inhibition of one or more of IL-1β, IL-17, IL-18, IL-1α, IL-37, and IL-33.

In one embodiment, the modulation of Th17 cells, is by inhibition of production and/or secretion of IL-17.

In general embodiments, the disease, disorder or condition is a disease, disorder or condition of the immune system, the cardiovascular system, the endocrine system, the gastrointestinal tract, the renal system, the respiratory system, the central nervous system, is a cancer or other malignancy and/or is caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is Type I diabetes which is an autoimmune disease and a disease of the endocrine system.

In one embodiment, the disease, disorder or condition is of the immune system. In particular embodiments, the disease, disorder or condition is an inflammatory disease, disorder or condition or an autoimmune disease, disorder or condition.

In one embodiment, the disease, disorder or condition is of the skin.

In one embodiment, the disease, disorder or condition is of the cardiovascular system.

In one embodiment, the disease, disorder or condition is a cancer, tumour or other malignancy. As used herein, cancers tumours and malignancies, refer to diseases disorders or conditions, or to cells or tissues associated with the diseases, disorders or conditions, characterized by aberrant or abnormal cell proliferation, differentiation and/or migration often accompanied by an aberrant or abnormal molecular phenotype that includes one or more genetic mutations or other genetic changes associated with oncogenesis, expression of tumour markers, loss of tumour suppressor expression or activity and/or aberrant or abnormal cell surface marker expression. In general embodiments, cancers, tumours and malignancies may include sarcomas, lymphomas, leukemias, solid tumours, blastomas, gliomas, carcinomas, melanomas and metastatic cancers, although without limitation thereto. A more comprehensive listing of cancers tumours and malignancies may be found at the National Cancer Institute's website http://www.cancer.gov/cancer-topics/types/alphalist.

In one embodiment, the disease, disorder or condition is of the renal system.

In one embodiment, the disease, disorder or condition is of the gastro-intestinal tract.

In one embodiment, the disease, disorder or condition is of the respiratory system.

In a further embodiment, the disease, disorder or condition is of the endocrine system.

In one embodiment, the disease, disorder or condition is of the central nervous system (CNS).

In one embodiment, the disease, disorder or condition is caused by, or is associated with, a pathogen. The pathogen may be a virus, a bacterium, a protist, a worm or a fungus or any other organism capable of infecting a mammal, although without limitation thereto.

Non-limiting examples of viruses include influenza virus, cytomegalovirus, Epstein Barr Virus, human immunodeficiency virus (HIV), alphavirus such as Chikungunya and Ross River virus, flaviviruses such as Dengue virus, Zika virus and papillomavirus, although without limitation thereto.

Non-limiting examples of pathogenic bacteria include *Staphylococcus aureus, Helicobacter pylori, Bacillus anthracis, Bordatella pertussis, Corynebacterium diptheriae, Clostridium tetani, Clostridium botulinum, Streptococcus pneumoniae, Streptococcus pyogenes, Listeria monocytogenes, Hemophilus influenzae, Pasteurelia multicida, Shigella dysenteriae, Mycobacterium tuberculosis, Mycobacterium leprae, Mycoplasma pneumoniae, Mycoplasma homrinis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* and *Yersinia pestis*, although without limitation thereto.

Non-limiting examples of protists include *Plasmodium, Babesia, Giardia, Entamoeba, Leishmania* and Trypanosomes, although without limitation thereto.

Non-limiting examples of worms include helminths inclusive of schistisimes, roundworms, tapeworms and flukes, although without limitation thereto.

Non-limiting examples of fungi include *Candida* and *Aspergillus* species, although without limitation thereto.

Further relevant diseases, disorders or conditions may be selected from the group consisting of those recited in the journal article Menu et al., Clinical and Experimental Immunology, 166, 1-15, 2011, found at: http://onlinelibrary.wiley.com/store/10.1111/j.1365-2249.2011.04440.x/asset/j.1365-2249.2011.04440.x.pdf?v=1&t=i60c1phf&s=d26f50a2622926cc6b4bc855bd911ae9dc9750cf.

In particular embodiments, the disease, disorder or condition is selected from the group consisting of constitutive inflammation including the cryopyrin-associated periodic syndromes (CAPS): Muckle-Wells syndrome (MWS), familial cold autoinflammatory syndrome (FCAS) and neonatal-onset multisystem inflammatory disease (NOMID); including autoinflammatory diseases: familial Mediterranean fever (FMF), TNF receptor associated periodic syndrome (TRAPS), mevalonate kinase deficiency (MKD), hyperimmunoglobulinemia D and periodic fever syndrome (HIDS), deficiency of interleukin 1 receptor (DIRA) antagonist, Majeed syndrome, pyogenic arthritis, pyoderma gangrenosum and acne syndrome (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID) and sideroblastic anemia with B-cell immunodeficiency, periodic fevers, and developmental delay (SIFD); autoimmune diseases including multiple sclerosis (MS), type-1 diabetes, psoriasis, rheumatoid arthritis, Behcet's disease, Sjogren's syndrome and Schnitzler syndrome; macrophage activation syndrome; Blau syndrome; respiratory diseases including chronic obstructive pulmonary disorder (COPD), asthma such as allergic asthma and steroid-resistant asthma, asbestosis, silicosis and cystic fibrosis; dermatitis including contact dermatitis; central nervous system diseases including Parkinson's disease, Alzheimer's disease, motor neuron disease, Huntington's disease, cerebral malaria and brain injury from pneumococcal meningitis; metabolic diseases including Type 2 diabetes, atherosclerosis, obesity, gout, pseudo-gout; ocular diseases including those of the ocular epithelium, age-related macular degeneration (AMD), uveitis, corneal infection and dry eye; kidney disease including chronic kidney disease, oxalate nephropathy, nephrocalcinosis and diabetic nephropathy; liver disease including non-alcoholic steatohepatitis (NASH) and alcoholic liver disease; inflammatory reactions in skin including contact hypersensitivity and sunburn; inflammatory reactions in the joints including osteoarthritis, systemic juvenile idiopathic arthritis, adult-onset Still's disease, relapsing polychondritis; viral infections including alpha virus (Chikungunya, Ross River) and flavivirus (Dengue, Zika), flu, HIV; hidradenitis suppurativa (HS) and other cyst-causing skin diseases; cancers including lung cancer metastasis, pancreatic cancers, gastric cancers, myelodisplastic syndrome, leukemia; polymyositis; stroke including ischemic stroke; myocardial infarction including recurrent myocardial infarction; congestive heart failure; embolism; cardiovascular disease; Graft versus Host Disease; hypertension; colitis; helminth infection; bacterial infection; abdominal aortic aneurism; wound healing; depression, psychological stress; ischaemia reperfusion injury and any disease where an individual has been determined to carry a germline or somatic non-silent mutation in NLRP3.

In one embodiment, the disease, disorder or condition is an autoinflammatory disease such as cryopyrin-associated periodic syndromes (CAPS), Muckle-Wells syndrome (MWS), familial cold autoinflammatory syndrome (FCAS), familial Mediterranean fever (FMF), Neonatal onset multi-system inflammatory disease (NOMID), Tumor Necrosis Factor (TNF) Receptor-Associated Periodic Syndrome (TRAPS), hyperimmunoglobulinemia D and periodic fever syndrome (HIDS), deficiency of interleukin 1 receptor antagonist (DIRA), Majeed syndrome, or pyogenic arthritis, pyoderma gangrenosum and acne syndrome (PAPA).

In another embodiment, the disease, disorder or condition is Parkinson's disease or Huntington's disease.

In another embodiment, the disease, disorder or condition is gout or juvenile idiopathic arthritis.

In another embodiment, the disease, disorder or condition is non-alcoholic steatohepatitis (NASH).

In another embodiment, the disease, disorder or condition is oxalate nephropathy or nephrocalcinosis.

In another embodiment, the disease, disorder or condition is uveitis.

In another embodiment, the disease, disorder or condition is hidradenitis suppurativa (HS).

In another embodiment, the disease, disorder or condition is myelodisplastic syndrome, macrophage activation syndrome, Schnitzler syndrome, adult-onset Still's disease, or Behget's Disease.

In one non-limiting example of those described, the disease, disorder or condition being treated is NASH. NLRP3 inflammasome activation is central to inflammatory recruitment in NASH, and inhibition of NLRP3 may both prevent and reverse liver fibrosis. Compounds of the present invention, by interrupting the function of NLRP3 inflammasomes in liver tissue, can cause histological reductions in liver inflammation, decreased recruitment of macrophages and neutrophils, and suppression of NF-κB activation. Inhibition of the NLRP3 can reduce hepatic expression of pro-IL-1β and normalized hepatic and circulating IL-1β, IL-6 and MCP-1 levels thereby assisting in treatment of the disease.

In a further non-limiting example of those described, the disease, disorder or condition being treated is severe steroid resistant (SSR) asthma. Respiratory infections induce an NLRP3 inflammasome/caspase-1/IL-1β signaling axis in the lungs that promotes SSR asthma. The NLRP3 inflammasome recruits, and activates, pro-caspase-1 to induce IL-1β responses. NLRP3 inflammasome-induced IL-1β responses are therefore important in the control of infections, however, excessive activation results in aberrant inflammation and has been associated with the pathogenesis of SSR asthma and COPD. The administration of compounds of the first aspect that target specific disease processes, are more therapeutically attractive than non-specifically inhibiting inflammatory responses with steroids or IL-1β. Targeting the NLRP3 inflammasome/caspase-1/IL-1β signaling axis with the compounds of the first aspect may therefore be useful in the treatment of SSR asthma and other steroid-resistant inflammatory conditions.

In one further non-limiting example of those described, the disease, disorder or condition being treated is Parkinson's disease. Parkinson's is the most common neurodegenerative movement disorder and is characterized by a selective loss of dopaminergic neurons, accompanied by the accumulation of mis-folded α-synuclein (Syn) into Lewy bodies that are pathological hallmarks of the disease. Chronic microglial neuroinflammation is evident early in the disease, and has been proposed to drive pathology.

A central role for microglial NLRP3 is postulated in Parkinson's progression. The NLRP3 inflammasome is activated by fibrillar Syn via a Syk kinase dependent mechanism, and also occurs in the absence of Syn pathology at the early stages of dopaminergic degeneration, and drives neuronal loss. The compounds of the first aspect may block NLRP3 inflammasome activation by fibrillar Syn or mitochondrial dysfunction and thereby confer effective neuroprotection of the nigrostriatal dopaminergic system and assist with treatment of Parkinson's.

In a sixth aspect of the invention there is provided a method of diagnosing a disease, disorder or condition in a mammal including the step of administering a labelled compound of the first aspect, or a pharmaceutically effective salt, solvate or prodrug thereof, to the mammal or to a biological sample obtained from the mammal to facilitate diagnosis of the disease, disorder or condition in the mammal.

Inflammasome activation, in particular that of the NLRP3 inflammasome, is known to drive initiation, progression and chronic development of a vast number of inflammatory diseases. The sulfonylureas and related compounds of the first aspect are potent and specific direct inhibitors of NLRP3. Accordingly, a chemical probe specific for NLRP3, which is present in immune cells during inflammation has potential utility in diagnosing inflammatory and other related diseases. An NRLP3 activation probe comprising a compound of the first aspect could act as an effective surrogate biomarker of inflammatory disease for ex vivo (blood) or in vivo (MRI, PET etc.) diagnostics. A compound of the first aspect (or a pharmaceutically effective salt, solvate or prodrug thereof) could also be used in other ex-vivo and/or in in-vitro diagnostic methods.

The use of the compounds of formula (I) in diagnosing inflammatory and other related diseases may be achieved by near infrared fluorescent imaging and ex vivo characterisation of immune cells by degree of inhibition of IL-1beta, pro-caspase 1 cleavage and IL-18 levels. In particular, peripheral blood monocytes (PMBCs), macrophages, dendritic cells, CD4+ T cells, Th17 cells, Th1 cells and Th2 cells are relevant. In vivo diagnostics may use magnetic resonance imaging (MRI), employing $^2$H (deuterium), $^{13}$C, $^{19}$F and/or $^{15}$N labelled variants of compounds of the present invention given to a patient IV, IM, SC, PO, topical, IT, etc.

In vivo diagnostics using positron emission tomography (PET) are also appropriate. PET is a molecular imaging technique that requires specific probes radiolabelled with short-lived positron emitting radionuclides. Typical isotopes include $^{11}C$, $^{13}N$, $^{15}O$, $^{18}F$, $^{64}Cu$, $^{62}Cu$, $^{124}I$, $^{76}Br$, $^{82}Rb$ and $^{68}Ga$, with $^{18}F$ being the most clinically utilized. In particular it is possible to produce in a simple manner a stable $^{64}Cu$ or $^{62}Cu$ salt of one or more of the compounds of formula (I) by simple ion exchange with a sodium (or other monovalent cation) salt of said compounds. This enables rapid preparation of a diagnostic probe for radioimaging, PET and the like whereby the intensity, location and temporal accretion of the diagnostic probe is able to identify the degree and/or the location of immune cells with activated NLRP3 as a surrogate biomarker of the patients inflammatory state, and site of inflammation within the body. They will also be useful for application to biological samples removed from the body i.e. in vitro diagnosis.

FIG. 1 evidences complex formation between the sodium form of MCC950 (CRID3), a sulfonylurea, and copper chloride by using isothermal titration calorimetry (ITC). The results show that copper (II) ions form a strong complex with MCC950, comparable to the complex with EDTAx2Na and much stronger than with EDTA free acid. Formation of MCC950:Cu(II) complex was endothermic with enthalpy being positive which suggests that the process was entropy driven with the presence of strong hydrophobic interactions. This is a strong indication that compounds of formula (I), bearing the same core functional sulfonyl and urea moieties, will achieve the same degree of complexation thereby proving for their use in diagnostics, as described above.

A seventh aspect of the invention resides in a method of modulating the activity of a biological target comprising the step of exposing the biological target to a compound of the first aspect, or a pharmaceutically effective salt, solvate or prodrug thereof. The method may be an ex-vivo or an in-vitro method.

The biological target may be selected from the group consisting of NLRP3 inflammasome, IL-1β, IL-17, IL-18, IL-1α, IL-37, IL-33 and Th17 cells. Preferably the target is NLRP3 inflammasome.

The modulation may be as described previously for the third to fifth aspects.

As generally used herein, a biological sample may include cells, tissues, fluids, molecules or other biological materials obtained, or obtainable, from a mammal. Non-limiting examples include urine, blood and fractions thereof such as serum, plasma, lymphocytes and erythrocytes, cerebrospinal fluid, PAP smears, nasal and ocular secretions, amniotic fluid, faeces, semen, tissue and/or organ biopsies and nucleic acid (e.g. DNA, RNA) or protein samples, although without limitation thereto.

The following experimental section describes in more detail the characterisation of certain of the compounds of the invention and their efficacy. The intention is to illustrate certain specific embodiments of the compounds of the invention and their efficacy without limiting the invention in any way.

EXPERIMENTAL

General Methods

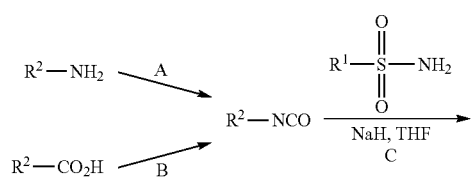

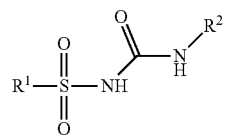

Method A:

A1: To a solution of $R^2$ amine intermediate (1 eq.) with or without base such as, but not exclusively, triethylamine (1.2 eq.) in an anhydrous aprotic solvent such as, but not exclusively, tetrahydrofuran or dichloromethane was added triphosgene (0.4 to 1.1 eq.). The reaction was stirred at ambient temperature or, where necessary, heated at reflux until completion, typically from 2 to 18 h.

A2: To di-t-butyldicarbonate (1.2-1.4 eq.) in anhydrous acetonitrile or THF was added DMAP (15-100 mol %), after 5 minutes, a solution of $R^2$ amine intermediate (1.0 eq.) in acetonitrile was added. The reaction mixture was stirred for 30-60 min at room temperature.

Method B:

B1: The $R^2$ carboxylic acid intermediate (1 eq.) was dissolved in an aprotic solvent such as toluene with or without 2 drops of DMF and a chlorinating agent such as thionyl chloride (2 eq.) added. The reaction mixture was heated at reflux until completion, then concentrated in vacuo to give the corresponding $R^2$ acid chloride intermediate.

Alternative methods or forming the acid chloride are also equally useful here for example the above procedure can be carried out without toluene and DMF thereby using thionyl chloride as both solvent and chlorinating agent.

The $R^2$ acid chloride intermediate was dissolved in acetone and added drop-wise to a solution of sodium azide (1.5 eq) in a water:acetone (50:50) solution at 0° C. Iced water was added to precipitate the resulting $R^2$ acylazide intermediate which was dissolved in toluene and dried (MgSO4) prior to adding the solution in a drop-wise fashion to anhydrous toluene at reflux while maintaining a constant flow of inert gas. The reaction was heated until completion, typically 2 h, to give the $R^2$ isocyanate.

B2: The $R^2$ acid chloride (formed as indicated in method B1) in dry $CH_2Cl_2$ was added $NaN_3$ (2.0 eq.) at 0° C. The reaction mixture was stirred at room temperature for 1 h and extracted into EtOAc. The organic layer was washed with $H_2O$ (15 mL), dried (MgSO4), and carefully evaporated to give acyl azide. The acyl azide was dissolved in dry toluene and heated to 100° C. for 2 h. The solvent was removed to give crude $R^2$ isocyanate.

Method C:

C1: $R^1$ sulfonamide intermediate (1 eq.) was dissolved in anhydrous THF and treated with NaH (1 eq.) under reduced pressure. The mixture was heated to reflux for 2 h then cooled to room temperature and $R^2$ isocyanate intermediate in THF added under nitrogen atmosphere. The reaction mixture was stirred at reflux until completion.

C2: $R^1$ sulfonamide intermediate (1 eq.) was dissolved in anhydrous THF or anhydrous methanol and treated with NaH (1 eq.) under reduced pressure. Once effervescence ceased the $R^2$ isocyanate intermediate was added and the reaction mixture was stirred at ambient temperature overnight.

C3: To $R^1$ sulfonamide intermediate (1 eq) in anhydrous THF (5 mL/mmol) was added NaH (1 eq) at 0° C. and stirred for 30 min to 2 h, or until completion, at ambient temperature under nitrogen atmosphere. Again cooled to 0° C., $R^2$ isocyanate (1.0 eq) in THF was added and stirred at ambient temperature until completion, typically 2 to 16 h.

C4: To crude $R^2$ isocyanate (1.0 eq) in anhydrous THF or DCM (5-11 mL/mmol) was added $R^1$ sulfonamide (1.0 eq) followed by base such as triethylamine, DIPEA, or DBU (1-2 eq) and the reaction mixture stirred at ambient temperature overnight.

C5: To $R^1$ sulfonamide intermediate (1 eq) in anhydrous MeOH (5 mL/mmol) was added NaOMe (1 eq) [alternatively: a 1.0 mM solution of freshly prepared sodium methoxide (1 eq) was added to a 1.0 mM solution of $R^1$ sulfonamide (1 eq) in anhydrous methanol]. The solvent was then removed in vacuo. The salt was suspended in anhydrous aprotic solvent such as acetonitrile or THF, the $R^2$ isocyanate (1.0 eq) in anhydrous aprotic solvent such as acetonitrile or THF was added and the mixture stirred at ambient temperature overnight. The solution was then heated at reflux until completion, typically 90 min.

$C_6$: $R^1$ sulfonamide (1.0 eq.) was dissolved in anhydrous THF under a nitrogen atmosphere. Solid sodium methoxide (1.0 eq mmol) was added in one portion. This mixture was stirred at ambient temperature for 3 h. A solution of the $R^2$ isocyanate (1.17 eq) in THF was added drop wise. The reaction mixture was stirred at room temperature overnight.

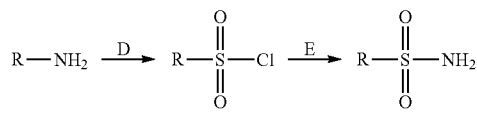

Method D:
A solution of amine (1.0 eq) in acetonitrile (7-12 mL/mmol) at 0° C. was treated with c.HCl (1.25-2.25 mL/mmol) in $H_2O$ (0.5-1.2 mL/mmol) followed by aqueous solution of $NaNO_2$ (1.2 eq) dissolved in $H_2O$ (0.3-0.5 mL/mmol of $NaNO_2$). The resulting solution was stirred at 0° C. for 45 min. AcOH (0.5-1.2 mL/mmol), $CuCl_2 \cdot 2H_2O$ (0.5 eq) and CuCl (0.05 eq) were sequentially added to the above mixture and purged with $SO_2$ gas for 20 min at 0° C. The resulting reaction mixture was stirred at 0° C.-10° C. until completion.

Method E:
E1: A solution of sulfonyl chloride (1 eq) in THF (10-20 mL/mmol) was cooled to −78° C. and ammonia gas was bubbled through the solution for 15 min, stirring was continued for a further 30 min then allowed to warm to ambient temperature and stirred for 2 h or until completion.

E2: A solution of sulfonyl chloride (1 eq) in acetone (20 mL/mmol) was treated with a solution of $NH_4HCO_3$ (4 eq) dissolved in water (1.5 mL/mmol of $NH_4HCO_3$) at ambient temperature and stirred for 4 h or until completion.

Method F

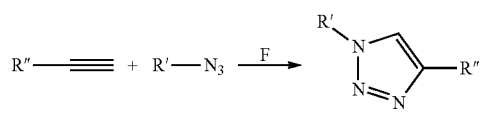

General Procedure for the Synthesis of Triazoles
Alkyne (1 eq) and azide (1.2 eq), 5 mol % $CuSO_4$, 10 mol % NaAsc solution in DMSO (500 μL) were stirred at room temperature until completion, typically 12 h.

Synthesis of $R^1$ Sulfonamide Intermediates:

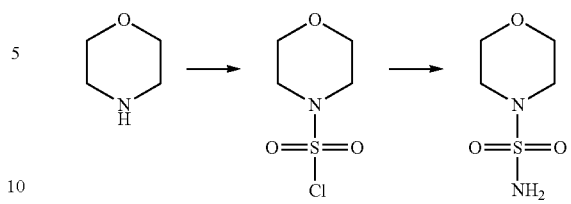

Morpholine (1.98 mL, 22.9 mmol) was added slowly to a mixture of sulfuryl chloride (5.5 mL, 68.8 mmol) in acetonitrile (15 mL) at ambient temperature. The resulting reaction mixture was heated to reflux for 24 h. The solvent was removed in vacuo and the residue azeotroped twice with toluene to give morpholine-4-sulfonyl chloride as a light yellow oil (2.8 g, 67%). The crude product was used directly in the next step without further purification. $^1H$ NMR (400 MHz, DMSO-$d_6$): δ 3.79 (t, J=4.0 Hz, 4H), 3.28 (t, J=4.0 Hz, 4H).

Morpholine-4-sulfonyl chloride (0.5 g, 4.3 mmol) in acetone (0.5 mL) was added to aq $NH_3$ (1.5 mL, $NH_4OH$ in $H_2O$, 28% $NH_3$ basis) at 0° C. and stirred at same temperature for 2 h. The solvent was removed in vacuo and the residue azeotroped twice with toluene. The residue was purified by column chromatography on silica gel using 2% MeOH-DCM eluent to give morpholine-4-sulfonamide as white solid (270 mg, 60%). $^1H$ NMR (400 MHz, DMSO-$d_6$): δ 6.82 (bs, 2H), 3.65 (t, J=4.0 Hz, 4H), 2.92 (t, J=4.0 Hz, 4H).

4-methylpiperazine-1-sulfonamide

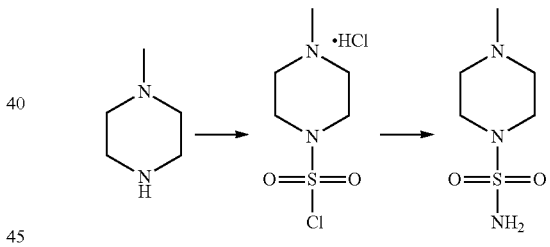

1-Methylpiperazine (2.0 g, 19.9 mmol) was added slowly to a mixture of sulfuryl chloride (4.83 mL, 59.9 mmol) in acetonitrile (15 mL) at room temperature, the resulting reaction mixture was heated to reflux for 24 h. The solvent was removed in vacuo and the residue azeotroped twice with toluene to give 4-methylpiperazine-1-sulfonyl chloride hydrochloride salt as a brown solid (2.1 g, crude). The crude product was used directly in the next step without purification. $^1H$ NMR (400 MHz, DMSO-$d_6$): δ=3.95 (bs, 2H), 3.60 (bs, 4H), 3.39-3.34 (m, 2H), 2.81 (3H, s).

To a solution of 4-methylpiperazine-1-sulfonyl chloride hydrochloride in acetone (5.0 mL) was added aq $NH_3$ (5.0 mL, $NH_4OH$ in $H_2O$, 28% $NH_3$ basis) at 0° C., the resulting reaction mixture was stirred at room temperature for about 2 h. The solvent was removed in vacuo and the residue azeotroped twice with toluene. The residue was purified by reverse phase column chromatography using acetonitrile/water as mobile phase to afford 4-methylpiperazine-1-sulfonamide as an off white solid (125 mg, 21%). $^1H$ NMR (400 MHz, DMSO-$d_6$): δ=6.71 (bs, 2H), 2.91 (t, J=4.0 Hz, 4H), 2.34 (t, J=4.0 Hz, 4H), 2.15 (s, 3H).

1-isopropyl-1H-pyrazole-3-sulfonamide

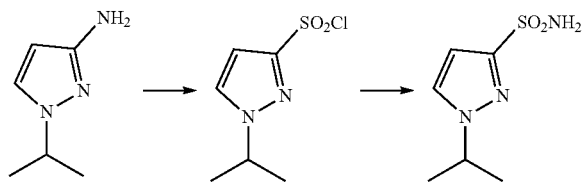

1-Isopropyl-1H-pyrazol-3-amine was reacted to 1-isopropyl-1H-pyrazole-3-sulfonyl chloride, a brown liquid, using general method D (0.5 g, 43%). $^1$H NMR (400 MHz, CDCl$_3$): δ=7.55 (s, 1H), 6.88 (s, 1H), 4.66-4.63 (m, 1H), 3.6 (br.s., 2H), 1.59 (d, J=6.8 Hz, 6H). LCMS (m/z): 209.0 (M+1)$^+$. The sulfonyl chloride was converted using general method E1 to give the titled compound as yellow solid (0.45 g, 82%). $^1$H NMR (300 MHz, DMSO-d$_6$): δ=7.9 (d, J=2.4 Hz, 1H), 7.36 (s, 2H), 6.55 (d, J=2.1 Hz, 1H), 4.57-4.53 (m, 1H), 1.42 (d, J=6.9 Hz, 6H). LCMS (m/z): 190.0 (M+1)$^+$.

Other R$^1$ sulphonamide intermediates are commercially available and/or may be prepared by routine synthetic methods. WO 2016/131098 for example (see pages 90-130) discloses the synthesis of the following R$^1$ sulphonamide intermediates which may be used in the synthesis of compounds of the present invention:
Cyclohexanesulfonamide
Cyclopentanesulfonamide
5-((dimethylamino)methyl)furan-2-sulfonamide
Furan-2-sulfonamide
5-methylfuran-2-sulfonamide
5-ethyl-N-((1,2,3,5,6,7-hexahydro-s-indacen-4-yl)carbamoyl)furan-2-sulfonamide
4-(prop-1-en-2-yl)furan-2-sulfonamide
d$_6$-4-(prop-1-en-2-yl)furan-2-sulfonamide
4-(prop-1-en-2-yl)furan-2-sulfonamide
4-(2-hydroxypropan-2-yl)-5-methylfuran-2-sulfonamide
d$_6$-4-(2-hydroxypropan-2-yl)-5-methylfuran-2-sulfonamide
1-benzyl-1H-1,2,4-triazole-3-sulfonamide
1-methyl-1H-pyrazole-3-sulfonamide
1-(trifluoromethyl)-1H-pyrazole-3-sulfonamide
1-isopropyl-1H-pyrazole-4-sulfonamide
1-cyclopropyl-1H-pyrazole-3-sulfonamide
1-(tert-butyl)-1H-pyrazole-3-sulfonamide
1-cyclohexyl-1H-pyrazole-3-sulfonamide
1-phenyl-1H-pyrazole-3-sulfonamide
1-benzyl-1H-pyrazole-3-sulfonyl chloride
1-(1-phenylethyl)-1H-pyrazole-3-sulfonamide
1-(2-(piperidin-1-yl)ethyl)-1H-pyrazole-3-sulfonamide
1,5-dimethyl-1H-pyrazole-3-sulfonamide
1-methyl-5-(trifluoromethyl)-1H-pyrazole-3-sulfonamide
1-isopropyl-5-(trifluoromethyl)-1H-pyrazole-3-sulfonamide
5-isopropyl-1-methyl-1H-pyrazole-3-sulfonamide
5-(2-hydroxypropan-2-yl)-1-methyl-1H-pyrazole-3-sulfonamide
1-benzyl-5-(2-hydroxypropan-2-yl)-1H-pyrazole-3-sulfonamide
5-(2-hydroxypropan-2-yl)-1-phenyl-1H-pyrazole-3-sulfonamide
5-(dimethylamino)naphthalene-1-sulfonamide
N-((1,2,3,5,6,7-hexahydro-s-indacen-4-yl)carbamoyl)-2,3-dihydrobenzo[b]thiophene-6-sulfonamide 1,1-dioxide
3-azidobenzenesulfonamide
N-(3-Sulfamoylphenyl)pent-4-ynamide
Benzene-1,3-disulfonamide
N$^1$,N$^1$-dimethylbenzene-1,3-disulfonamide
Methyl 3-sulfamoylbenzoate
3-(4-phenyl-1H-1,2,3-triazol-1-yl)benzenesulfonamide
N-(prop-2-yn-1-yl)-3-(4-sulfamoylphenyl)propanamide
benzo[d][1,3]dioxole-5-sulfonamide
Pyridine-4-sulfonamide
Pyridine-3-sulfonamide
Pyridine-2-sulfonamide
4-(trifluoromethyl)pyridine-2-sulfonamide
3-(3-(trifluoromethyl)-3H-diazirin-3-yl)benzenesulfonamide
2-(methyl(7-nitrobenzo[c][1,2,5]oxadiazol-4-yl)amino)-N-(4-sulfamoylphenethyl)acetamide
4-(2-(7-Nitrobenzo[c][1,2,5]oxadiazol-4-ylamino)ethyl)benzenesulfonamide
2-(7-(Dimethylamino)-2-oxo-2H-chromen-4-yl)-N-(4-sulfamoylphenethyl)acetamide Synthesis of R$^1$ and R$^2$ Amine Intermediates 9H-carbazol-9-amine

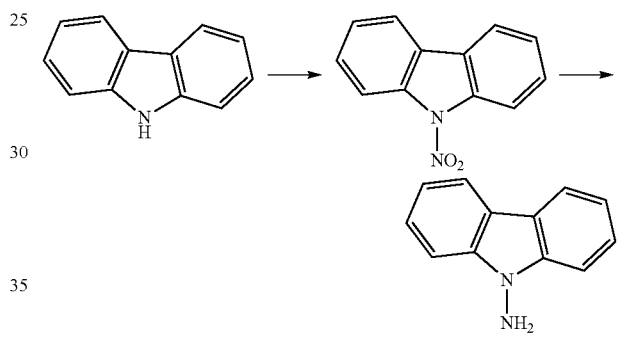

9H-carbazole (2.0 g, 12 mmol) was dissolved in acetonitrile (80 mL) and acetic acid (20 mL) then cooled to 0° C. and c.HCl:water (4:2, 6 mL) added. The solution was treated with a solution of sodium nitrite (1 g, 14.4 mmol) in water (4 mL) drop-wise over 10 mins. The reaction was stirred at 0-10° C. for 3 hours or until completion then diluted with water and extracted using ethyl acetate. The organics were washed with water, brine then dried (Na$_2$SO$_4$) and concentrated in vacuo to give 9-nitro-9H-carbazole as a yellow solid used directly in the next reaction step.

Zinc (9.7 g, 150 mmol) and ammonium chloride (8 g, 150 mmol) in THF (50 mL) and water (15 mL) was cooled to 0° C. and 9-nitro-9H-carbazole in THF (5 mL) was added dropwise and stirring continued for 2 h or until completion. The reaction was diluted using ethyl acetate and filtered through celite then the organic phase was washed using water, brine, dried (Na$_2$SO$_4$) and concentrated in vacuo. The crude product was purified by column chromatography on silica using 5% ethyl acetate:hexanes eluent to give the titled compound as a semi-solid (3.3 g, 42%). $^1$H NMR (400 MHz, DMSO-d$_6$) δ=8.10 (d, J=7.7 Hz, 1H), 7.59 (d, J=7.7 Hz, 1H), 7.45 (t, J=7.7 Hz, 1H), 7.17 (t, J=7.7 Hz, 1H), 5.83 (s, 1H).

Other R$^1$ and R$^2$ amine intermediates are commercially available and/or may be prepared by routine synthetic methods. WO 2016/131098 for example (see pages 130-157) discloses the synthesis of the following R$^1$ and R$^2$ amine intermediates which may be used in the synthesis of compounds of the present invention:

1-methyl-1H-pyrazol-3-amine HCl
1-(trifluoromethyl)-1H-pyrazol-3-amine
1-isopropyl-1H-pyrazol-3-amine
1-cyclopropyl-1H-pyrazol-3-amine
1-(tert-butyl)-1H-pyrazol-3-amine
1-cyclohexyl-1H-pyrazol-3-amine
1-phenyl-1H-pyrazol-3-amine
1-benzyl-1H-pyrazol-3-amine
1-(1-phenylethyl)-1H-pyrazol-3-amine
1-(2-(piperidin-1-yl)ethyl)-1H-pyrazol-3-amine
1,5-dimethyl-1H-pyrazol-3-amine
1-methyl-5-(trifluoromethyl)-1H-pyrazol-3-amine
1-methyl-5-(prop-1-en-2-yl)-1H-pyrazol-3-amine
Ethyl 1-benzyl-3-nitro-1H-pyrazole-5-carboxylate
Ethyl 1-benzyl-3-nitro-1H-pyrazole-5-carboxylate
3-(2,5-dimethyl-1H-pyrrol-1-yl)-1-phenyl-1H-pyrazole
8-bromo-1,2,3,5,6,7-hexahydro-s-indacen-4-amine
8-chloro-1,2,3,5,6,7-hexahydro-s-indacen-4-amine
8-methyl-1,2,3,5,6,7-hexahydro-s-indacen-4-amine
3,5,6,7-tetrahydro-2H-indeno[5,6-b]furan-8-amine
4-bromo-3,5,6,7-tetrahydro-2H-indeno[5,6-b]furan-8-amine
3,5,6,7-tetrahydro-2H-indeno[5,6-b]furan-4-amine
benzo[1,2-b:4,5-b']difuran-4-amine
3-(3-(trifluoromethyl)-3H-diazirin-3-yl)aniline Synthesis of $R^2$ Acid Intermediates $R^2$ acid intermediates are commercially available and/or may be prepared by routine synthetic methods. WO 2016/131098 for example (see pages 166-169) discloses the synthesis of the following $R^2$ acid intermediates which may be used in the synthesis of compounds of the present invention:

2,3,6,7-tetrahydrobenzo[1,2-b:4,5-b']difuran-4-carboxylic acid
Benzo[d][1,3]dioxole-4-carboxylic acid Compounds Example 1: N-((1,2,3,5,6,7-hexahydro-s-indacen-4-yl)carbamoyl) morpholine-4-sulfonamide

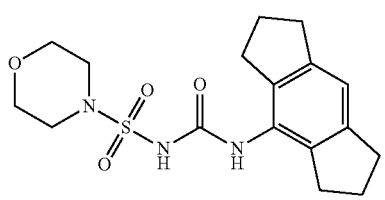 [SMILES: O=C(Nc1c2c(cc3c1CCC3)CCC2)NS(=O)(=O)N1CCOCC1]

4-Isocyanato-1,2,3,5,6,7-hexahydro-s-indacene (prepared using general method A2) and morpholine-4-sulfonamide were used in general method C2 to give the titled compound as a white solid (25 mg, 24%). $^1$H NMR (400 MHz, DMSO-d6): δ=7.98 (bs, 1H), 6.94 (s, 1H), 3.63 (t, J=4.0 Hz, 4H), 3.18 (t, J=4.0 Hz, 4H), 2.81 (t, J=8.0 Hz, 4H), 2.68 (t, J=8.0 Hz, 4H), 2.02-1.95 (m, 4H); LCMS Purity: >95%; LCMS (m/z): 366 [M+H]$^+$.

Example 2: N-((1,2,3,5,6,7-hexahydro-s-indacen-4-yl)carbamoyl)-4-methylpiperazine-1-sulfonamide

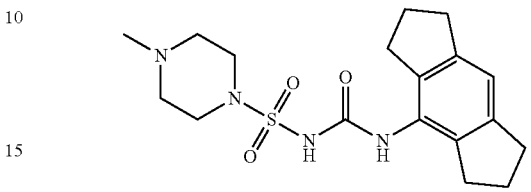

4-Isocyanato-1,2,3,5,6,7-hexahydro-s-indacene (prepared using general method A2) and 4-Methylpiperazine-1-sulfonamide were used in general method C3 to give the titled compound as a white solid (60 mg, 55%). $^1$H NMR (600 MHz, DMSO-d$_6$): δ=7.96 (bs, 1H), 6.94 (s, 1H), 3.20 (t, J=6.0 Hz, 4H), 2.80 (t, J=6.0 Hz, 4H), 2.69 (t, J=6.0 Hz, 4H), 2.37 (t, J=6.0 Hz, 4H), 2.19 (s, 3H), 2.00-1.95 (m, 4H). $^{13}$C NMR (150 MHz, DMSO-d$_6$): δ=150.6, 143.5, 137.4, 129.6, 118.1, 54.3, 46.5, 45.9, 32.9, 30.7, 25.5. LCMS Purity: >95%; LCMS (m/z): 379 [M+H]$^+$. HRMS calculated for $C_{18}H_{27}N_4O_3S_1$(M+H)$^+$ 379.1798, found 379.1795.

Example 3: N-[1,2,3,5,6,7-hexahydro-s-indacen-4-yl]-N'-[(dimethylamino) sulfonyl]urea

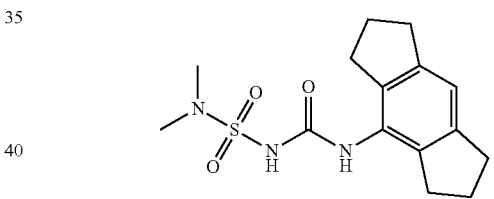

4-Isocyanato-1,2,3,5,6,7-hexahydro-s-indacene (prepared using general method A2) and N,N-dimethylsulfamide were used in general method C2 to give the titled compound as a white solid (29 mg, 31%). $^1$H NMR (400 MHz, DMSO-d6): δ=7.96 (s, 1H), 6.94 (s, 1H), 2.81 (t, J=8 Hz, 4H), 2.79 (s, 6H), 2.70 (t, J=8 Hz, 4H), 2.02-1.96 (m, 4H). $^{13}$C NMR (150 MHz, DMSO-d$_6$): δ=143.4, 142.9, 137.4, 125.1 117.9, 38.6, 32.9, 30.7, 25.5; LCMS (m/z): 324 [M+H]$^+$; HRMS calculated for $C_{15}H_{21}N_3O_3S_1$(M+H)$^+$, 324.13764, found 324.13891.

Example 4: N-((9H-carbazol-9-yl)carbamoyl)-1-isopropyl-1H-pyrazole-3-sulfonamide

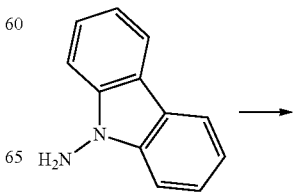

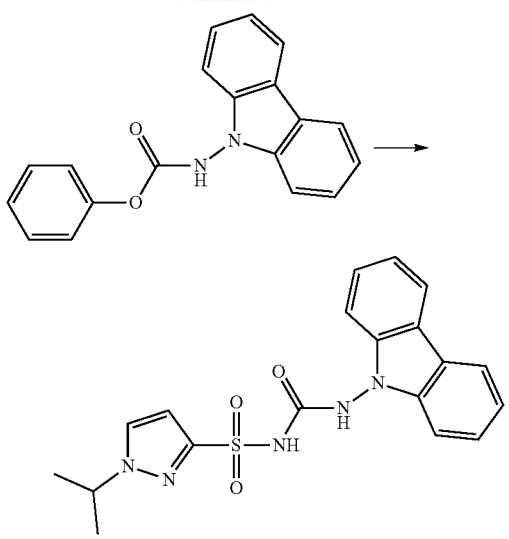

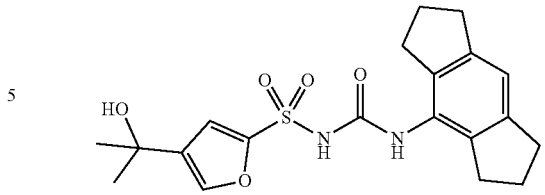

9H-carbazol-9-amine (1.0 g, 5.5 mmol) in THF (20 mL) was cooled to 0° C. and sodium hydride (0.45 g, 11 mmol) was added portion-wise. The reaction mixture was stirred for 30 mins then phenylchloroformate (1.72 g, 11 mmol) added drop-wise. The solution was allowed to warm to ambient temperature and stirred for a further 5 h. The reaction was quenched using NaHCO₃ (aq) and the solution extracted using ethyl acetate. The organic phase was washed using water, brine then dried (Na₂SO₄) and concentrated in vacuo. The crude phenyl (9H-carbazol-9-yl)carbamate was purified by column chromatography on silica using 10% EtOAc: hexanes eluent and the resulting white solid used directly in the next synthetic step.

1-Isopropyl-1H-pyrazole-3-sulfonamide (0.1 g, 0.53 mmol) in THF (10 mL) was treated with NaH (60 mg, 1.06 mmol) and the reaction heated to 80° C. for 2 h. The mixture was cooled to ambient temperature, phenyl (9H-carbazol-9-yl)carbamate (2 equivalents) added and the reaction heated once more to 80° C. for 2 h. On completion the reaction was diluted using sat. aq. NH₄Cl and extracted using ethyl acetate (2×25 mL). The combined organics were washed with water, brine, dried (Na₂SO₄) and concentrated in vacuo. The product was purified using preparative thin layer chromatography on silica with 50% EtOAc:hexane to give the titled product as a white solid (15 mg, 7%). $^1$H NMR (400 MHz, CD₃OD) δ 8.02 (d, J=7.7 Hz, 2H), 7.72 (s, 1H), 7.41-7.27 (m, 4H), 7.19 (t, J=7.4 Hz, 2H), 6.70 (s, 1H), 4.59 (m, 1H), 1.48 (d, J=6.6 Hz, 6H).

Copper Complexation of MCC950

Complex formation between the sodium form of MCC950 and copper chloride was tested and detected by using isothermal titration calorimetry (ITC). MCC950 (also known as CRID3) is a sulphonylurea having the formula:

An autoITC 200 (GE life sciences) was used to measure the change in heat induced by Cu$^{2+}$-MCC950 interactions and data analysed using the MicroCal Origin version 7.0 software package adapted for auto-ITC data analysis.

Copper chloride (5 or 2.5 mM of CuCl2) dissolved in water (miliQ water; Elga) was titrated into a cell containing 0.4 mM MCC950Na also dissolved in water. The titration consisted of 19×2 µL injections at 25° C. As a control EDTA was used, in free acid form or as a sodium di-salt, at a concentration of 0.4 mM. Experiments were replicated three times and results were averaged. Thermograms and binding isotherms were used to determine the enthalpy (ΔH), binding constants (K), stoichiometry (N), and entropy (TΔS) using a single-site binding model. The change in standard Gibbs free energy (ΔG) was calculated using the Gibbs-Helmholz thermodynamic equation: ΔG=−RTlnK, where R is the ideal gas constant (1.985 cal mol$^{-1}$K$^{-1}$) and T is the temperature (298 K).

Copper (II) ions were seen to form a strong complex with MCC950, comparable to the complex with EDTAx2Na and much stronger than with EDTA free acid. Formation of MCC950:Cu(II) complex was endothermic with enthalpy being positive thereby suggesting that the process was entropy driven with the presence of strong hydrophobic interactions. The thermodynamics are displayed in the table below and results are also shown in FIG. 1:

| Complex | N | K ($10^4$ M$^{-1}$) | ΔH (kcal mol$^{-1}$) | TΔS (kcal mol$^{-1}$) | ΔG (kcal mol$^{-1}$) |
|---|---|---|---|---|---|
| MCC950 × Na:CuCl2 | 0.31 ± 0.00 | 5.69 ± 0.3 | 6.56 ± 0.15 | 13.04 ± 0.12 | −6.48 ± 0.03 |

Biological Testing Methodology

NLRP3 inhibition assays

The following assays can be used to determine inhibitory activity of test compounds on the NLRP3 inflammasome using common stimuli such as adenosine triphosphate, nigericin, LeuLeu-OMe or monosodium urate crystals (MSU).

Cell Culture

To generate HMDM (Human Monocyte Derived Macrophages), human monocytes are isolated from buffy coat blood using Ficoll-Plaque Plus (GE Healthcare) and density centrifugation. CD14$^+$ cell selection is performed using MACS magnetic beads (Miltenyi Biotec). Isolated CD14$^+$ monocytes are differentiated in culture for 7 days with 10 ng/ml human CSF-1 (Miltenyi Biotec) in Iscove's modified Dulbecco's medium (IMDM) containing L-glutamine supplemented with 10% FBS and 1% penicillin/streptomycin (Life Technologies) as described by Croker et al 2013 *Immunol Cell Biol* 91:625. Stably transfected ASC-cerulean macrophages as described by Hett et al. (Nat. Chem. Biol., 9, 398-405, 2013) are cultured in DMEM supplemented with 10% FCS and 1% P/S.

NLRP3 Inflammasome Activation Assays

HMDM are seeded at 1×10$^5$/ml. The following day the overnight medium is replaced and cells are stimulated with *Escherichia coli* serotype 0111:B4 (Sigma Aldrich) for 3 h.

Medium is removed and replaced with serum free medium (SFM) containing test compound 30 min prior to NLRP3 stimulation. Cells are then stimulated with: adenosine 5'-triphosphate disodium salt hydrate (5 mM 1 h), nigericin (10 µM 1 h), LeuLeu-OMe (1 mM 2 h) or MSU (200 µg/ml 15 h). ATP can be sourced from Sigma Aldrich, nigericin and MSU from Invivogen and LeuLeu-Ome from Chem-Impex International.

Measurement of IL-1β, IL-18, TNFα and Cell Death

For ELISA and cell death assays cells are seeded in 96 well plates. Supernatants are removed and analysed using ELISA kits according to the manufacturer's instructions (DuoSet® R&D Systems, ReadySetGo!® eBioscience, BD OptEIA™, or Perkin Elmer AlphaLISA®). Cell death is assessed by measurement of LDH release relative to a 100% cell lysis control using the CytoTox96® non-radioactive cytotoxicity assay (Promega).

Murine Studies on Compound Levels in Blood Plasma and Brain

General Experimental:

Carbutamide was purchased from Sigma Aldrich (Catalogue No. 381578). Acetonitrile was Chromasolv® HPLC grade (Sigma Aldrich, Sydney, Australia), the formic acid was AR grade 99%-100% Normapur (VWR International Pty Ltd, Brisbane, Australia), DMSO was ReagentPlus® grade (D5879, Sigma Aldrich, Sydney, Australia) and the $H_2O$ Milli-Q was filtered. The HPLC vial and polypropylene inserts from Agilent Technologies (Melbourne, Australia), while the 1.5 mL Eppendorf tubes Protein LoBind Tubes were from VWR International Pty Ltd (Brisbane, Australia).

Preparation of Precipitation Solution:

100 mL ACN and 5 µL of 10 mM carbutamide in DMSO (ACN with 135 ng/mL carbutamide MS internal standard).

Preparation of Standard Curve in Plasma:

A 1 mg/mL of test compound in 10 mM $NH_4HCO_3$ was prepared and diluted 10-fold to give a 100,000 ng/mL stock solution. A series of 10-fold dilutions of the 100,000 ng/mL stock solution with 10 mM $NH_4HCO_3$ gave concentrations of 10,000, 1,000, 100 and 10 ng/mL. The 100,000 ng/mL stock solution was diluted to 3:7 with 10 mM $NH_4HCO_3$ to give a concentration of 30,000 ng/mL and a series of 10-fold dilutions gave concentrations of 3,000, 300, 30 and 3 ng/mL.

20 µL of test compound-containing solution and 160 µL precipitation solution were added to 20 µL of mouse plasma in a low binding Eppendorf tube. The samples were vortexed, allowed to stand at 4° C. for 10 mins and centrifuged at 14,000×g for 8 min. 150 µL of the supernatant was transferred to an HPLC vial insert. The samples were stored at 4° C. until analysis.

Preparation of Standard Curve in Brain Homogenate:

The sample solutions prepared for the plasma standard curve were used for the brain homogenate standard curve.

The mouse brain homogenate from the saline control was thawed and vortexed for 3 min or until homogenous, sonicated for 1 min. When the foam settled, 50 µL of mouse brain homogenate was transferred into an Eppendorf tube, followed by 50 µL of test compound in 10 mM $NH_4HCO_3$, 150 µL of $H_2O$ and 500 µL of ice cold precipitation solution with vortexing after every addition. The standards were allowed to stand at 4° C. for 10 mins and then centrifuged at 14,000×g for 8 min. 200 µL of the supernatant was transferred to HPLC vial insert ensuring that no air bubbles were present and the samples stored at 4° C. until analysis.

Dosing of Mice and Transcardial Perfusion

Dosing:
Oral gavage at 20 mg/kg
Time Point:
2 hour

Prepare stock compounds for dosing at 4 mg/ml in sterile PBS. Mice were weighed and dosed by oral gavage at 20 mg/kg for each compound. After 2 hours mice were anesthetized using a combination of Zoletil (50 mg/kg) and Xylazine (10 mg/kg) and blood was collected by cardiac puncture into tubes containing 20 µL of 100 mM EDTA. The blood was centrifuged at 2000×g for 15 minutes at 4° C. to collect plasma.

Preparation of Plasma Samples for Analysis:

20 µL of $NH_4HCO_3$ and 160 µL precipitation solution were added to 20 µL of mouse plasma in a low binding Eppendorf tube. The samples were vortexed, allowed to stand at 4° C. for 10 mins and centrifuged at 14,000×g for 8 min. 150 µL of the supernatant was transferred to an HPLC vial insert ensuring that no air bubbles were present. The samples were stored at 4° C. until analysis.

Brain Homogenate Preparation:

The brains of mice were perfused with PBS for 5 minutes then dissected and weighed. Brain homogenate was prepared by homogenizing total brain (0.5 g) with 4 volumes (2 ml) of deionized water and stored at −20° C. before analysis. The homogenate was thawed, vortexed for 3 min or until homogenous, and sonicated for 1 min. When the foam settled, 50 µL of mouse brain homogenate was transferred into an Eppendorf tube, followed by 50 µL of 10 mM $NH_4HCO_3$, 150 µL of $H_2O$ and 500 µL of ice cold precipitation solution with vortexing after every addition. 200 µL of the supernatant was transferred to HPLC vial insert ensuring that no air bubbles were present and the samples stored at 4° C. until analysis.

Preparation of Brain Samples for Analysis:

50 µL of mouse brain was transferred into an Eppendorf tube, followed by 50 µL of 10 mM $NH_4HCO_3$, 150 µL of $H_2O$ and 500 µL of ice cold precipitation solution with vortexing after every addition. The solutions were allowed to stand at 4° C. for 10 mins and then centrifuged at 14,000×g for 8 min. 200 µL of the supernatant was transferred to HPLC vial insert ensuring that no air bubbles were present and the samples stored at 4° C. until analysis.

LC-MS/MS:

The samples were analysed on an AB Sciex 4000QTrap MS with 2 Shimadzu Nexera LC-30AD Solvent Delivery Units, Shimadzu Nexera SIL-30AC Auto-Sampler, Shimadzu Prominence DGU-20$A_5$ Degasser, Shimadzu Prominence CBM-20A System Controller and Shimadzu Prominence CTO-20A Column Oven. The column oven was set to 40° C., while the Autosampler was set to 15° C. 2 µL injections were made and MS analyses were undertaken in Selected Reaction Monitoring (SRM) mode using Turbo Spray (−)-ESI with Low Resolution Q1 and Low Resolution Q3. MS parameters: CUR: 30.00, IS: −4300.00, TEM: 500.00, GS1: 50.00, GS2: 50.00, ihe: ON, CAD: High, DP −60.00, EP −10.00, CXP −15.00. MCC950 SRM: Q1 403.2 to Q3 204.3 Da, dwell 150 msec, CE −27 and carbutamide (IS) SRM: Q1 270.0 to Q3 171.0 Da, dwell 100 msec, CE −25. HPLC Column: Waters Atlantis® T3 5 µm 2.1×50 mm with Atlantis® T3 5 µm 2.1×10 mm guard column. Flow rates and solvent: 0.35 ml/min, solvent A: 0.1% formic acid in $H_2O$, solvent B: 0.1% formic acid in ACN; isocratic 2% B from 0→2 mins, gradient 2%→100% B from 2→5 mins, isocratic 100% from 5→9 mins, gradient 100%→2% B from 9→9.1 mins and isocratic 2% B from 9.1→13 mins. The peak areas from the SRM data for carbutamide and test compound were analysed using the AB Sciex's Analyst software using the Quantitation Wizard. The peak area was plotted against the ng/mL concentration in 20 μL 3 to 30,000 ng/mL test compound solutions and the lower and upper range of linear response was determined. These data were then plotted in Microsoft Excel and the linear response equation used to determine the test compound concentration in the 20 μL plasma solutions. Similarly, for the brain homogenate samples, the peak areas of the 50 μL 3 to 3,000 ng/mL test compound solutions were used to determine the test compound concentration in the 50 μL brain homogenate solutions.

Results

TABLE 1

Topological Polar Surface Area (tPSA) and molecular weight of select compounds.

| Ex | Compound structure | Compound name | tPSA | M.W. |
|----|---|---|---|---|
| 1 | 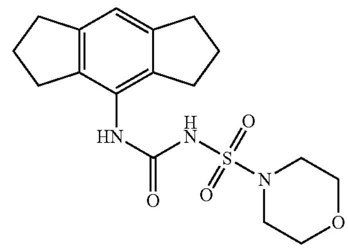 [SMILES: O=C(Nc1c2c(cc3c1CCC3)CCC2)NS(=O)(=O)N1CCOCC1] | N-((1,2,3,5,6,7-hexahydro-s-indacen-4-yl)carbamoyl)morpholine-4-sulfonamide | 88 | 365 |
| 2 | 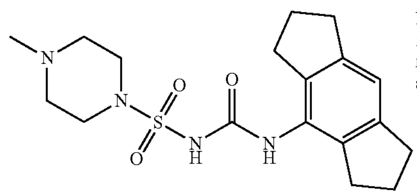 | N-((1,2,3,5,6,7-hexahydro-s-indacen-4-yl)carbamoyl)-4-methylpiperazine-1-sulfonamide | 90 | 378 |
| 3 | 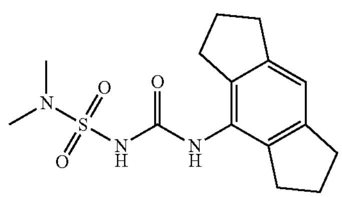 [SMILES: CN(C)S(=O)(=O)NC(=O)Nc1c2c(cc3c1CCC3)CCC2] | N-[1,2,3,5,6,7-hexahydro-s-indacen-4-yl]-N'-[(dimethylamino)sulfonyl]urea | 79 | 323 |
| 4 | 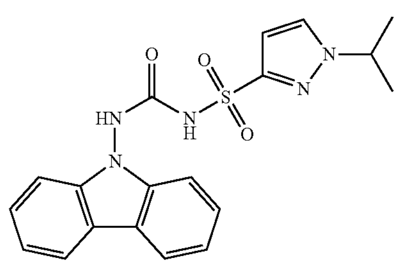 [SMILES: CC(C)n1ccc(S(=O)(=O)NC(=O)Nn2c3ccccc3c3ccccc32)n1] | N-((9H-carbazol-9-yl)carbamoyl)-1-isopropyl-1H-pyrazole-3-sulfonamide | 106 | 397 |

TABLE 2

Inhibition of IL-1β release IC50 in nM cell based assay using

| Ex | Name | Chem Formula | HRMS formula | HRMS Calc | HRMS found | Avg. IL-1β IC50 HMDM (nM) |
|----|---|---|---|---|---|---|
| 2 | N-((1,2,3,5,6,7-hexahydro-s-indacen-4-yl)carbamoyl)-4-methylpiperazine-1-sulfonamide | C18H26N4O3S | C18H27N4O3S1 | 379.1798 | 379.1795 | +++ |

TABLE 2-continued

Inhibition of IL-1β release IC50 in nM cell based assay using

| Ex | Name | Chem Formula | HRMS formula | HRMS Calc | HRMS found | Avg. IL-1β IC50 HMDM (nM) |
|---|---|---|---|---|---|---|
| 4 | N-((9H-carbazol-9-yl)carbamoyl)-1-isopropyl-1H-pyrazole-3-sulfonamide | C19H19N5O3S | C19H20N5O3S | 398.1281 | 398.1282 | ++ |

HMDM (<1 μM = '+++'/<10 μM = '++'/<50 μM = '+'). (ESI+ for all compounds)

Examples 5-43

Nuclear magnetic resonance (NMR) spectra were recorded at 400 MHZ; the chemical shifts are reported in parts per million. Spectra were recorded using a Bruker Avance III spectrometer at 400 MHz fitted with a BBO 5 mm liquid probe.

Mass spectra were recorded with a Waters Acquity UPLC system equipped with Acquity UPLC BEH. Mobile phases typically consisted of acetonitrile mixed with water containing 10 mM ammonium bicarbonate.

Preparative HPLC was carried out using a Waters Xbridge BEH C18, 5 μm, 19×50 mm column using a gradient MeCN in aqueous 10 mM ammonium bicarbonate. Fractions were collected following detection by mass with positive and negative ion electrospray detector on a Waters FractionLynx LCMS.

((1,2,3,5,6,7-Hexahydro-s-indacen-4-yl)carbamoyl)sulfamoyl chloride

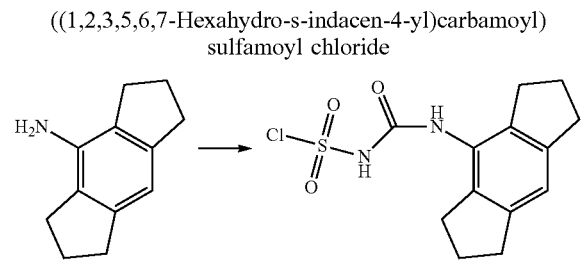

A stirred solution of chlorosulfonyl isocyanate (2.63 ml, 30.3 mmol) in diethyl ether (20 mL) was cooled to −20° C., then a solution of 1,2,3,5,6,7-hexahydro-s-indacen-4-amine (5 g, 28.9 mmol) in diethyl ether (100 mL) was added slowly over 10 minutes. The reaction was stirred for 1 hour, then most of the ether removed in vacuo. Iso-hexane (200 mL) was added and the mixture was sonicated for 5 minutes. The solid was filtered and dried overnight to afford the title compound (7.5 g).

1H NMR (400 MHz, CDCl₃) δ 7.95 (s, 1H), 7.10 (s, 1H), 2.93 (t, J=7.5 Hz, 4H), 2.86 (t, J=7.4 Hz, 4H), 2.11 (p, J=7.4 Hz, 4H) (exchangeable proton not visible).

General Procedure

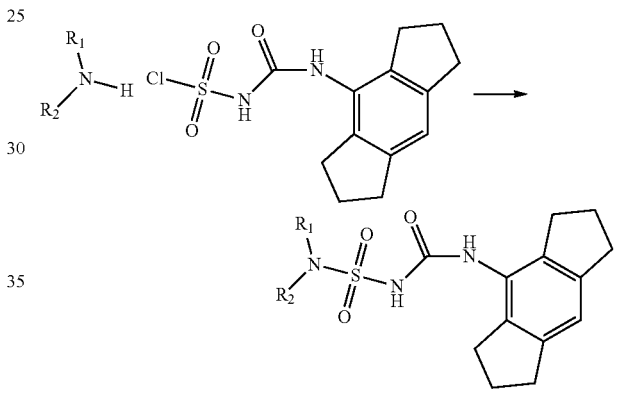

Amines (0.1 mmol) were pre-dissolved in DMA (0.5 mL), then 4-methylmorpholine (0.040 g, 0.400 mmol) was added. A solution of ((1,2,3,5,6,7-hexahydro-s-indacen-4-yl)carbamoyl)sulfamoyl chloride (0.025 g, 0.08 mmol) in THF (1 mL) was added to each well, the reactions were capped and shaken overnight at room temperature. The samples were purified by RPHPLC; Waters X-Bridge BEH C18 prep column, 5 μm, 10×50 mm, Basic (0.1% ammonium bicarbonate) 6.5 min method, 10-40% acetonitrile. Examples 5-40 shown in Table 3 below were prepared this way.

TABLE 3

| Ex | Structure | Exact mass | LCMS Mass ion | Retention time |
|---|---|---|---|---|
| 5 | 1-{[2-(2-chlorophenoxy)ethyl]sulfamoyl}-3-(1,2,3,5,6,7-hexahydro-s-indacen-4-yl)urea | 449.1 | 450.1 | 1.3 |

TABLE 3-continued

| Ex | Structure | Exact mass | LCMS Mass ion | Retention time |
|---|---|---|---|---|
| 6 | 1-{[(4-chloro-2-fluorophenyl)methyl]sulfamoyl}-3-(1,2,3,5,6,7-hexahydro-s-indacen-4-yl)urea | 437.1 | 438.1 | 1.3 |
| 7 | 3-(1,2,3,5,6,7-hexahydro-s-indacen-4-yl)-1-{[(3-methanesulfonylphenyl)methyl]sulfamoyl}urea | 463.1 | 464.1 | 1.03 |
| 8 | 1-(1,2,3,5,6,7-hexahydro-s-indacen-4-yl)-3-[(1H-indol-2-ylmethyl)sulfamoyl]urea | 424.2 | 425.2 | 1.24 |
| 9 | 1-{[(4-chloro-2-methylphenyl)methyl]sulfamoyl}-3-(1,2,3,5,6,7-hexahydro-s-indacen-4-yl)urea | 433.1 | 434.1 | 1.36 |
| 10 | 3-(1,2,3,5,6,7-hexahydro-s-indacen-4-yl)-1-({[2-(trifluoromethoxy)phenyl]methyl}sulfamoyl)urea | 469.1 | 470.1 | 1.35 |
| 11 | 3-(1,2,3,5,6,7-hexahydro-s-indacen-4-yl)-1-{[(2,4,6-trifluorophenyl)methyl]sulfamoyl}urea | 439.1 | 440.1 | 1.21 |

TABLE 3-continued

| Ex | Structure | Exact mass | LCMS Mass ion | Retention time |
|---|---|---|---|---|
| 12 | 1-[({1-[ethyl(methyl)amino]cyclohexyl}methyl)sulfamoyl]-3-(1,2,3,5,6,7-hexahydro-s-indacen-4-yl)urea | 448.3 | 449.3 | 1.09 |
| 13 | 3-(1,2,3,5,6,7-hexahydro-s-indacen-4-yl)-1-({4-[2-(thiophen-2-yl)ethyl]piperazin-1-yl}sulfonyl)urea | 474.2 | 475.2 | 1.29 |
| 14 | 1-[(furan-2-ylmethyl)sulfamoyl]-3-(1,2,3,5,6,7-hexahydro-s-indacen-4-yl)urea | 375.1 | 376.1 | 1.09 |
| 15 | 3-(1,2,3,5,6,7-hexahydro-s-indacen-4-yl)-1-{[2-(1,3-thiazol-2-yl)ethyl]sulfamoyl}urea | 406.1 | 407.1 | 1.01 |
| 16 | 3-(1,2,3,5,6,7-hexahydro-s-indacen-4-yl)-1-{[4-(propan-2-yl)piperazin-1-yl]sulfonyl}urea | 406.2 | 407.2 | 1.05 |

TABLE 3-continued

| Ex | Structure | Exact mass | LCMS Mass ion | Retention time |
|---|---|---|---|---|
| 17 | 1-[(furan-2-ylmethyl)[2-(morpholin-4-yl)ethyl]sulfamoyl]-3-(1,2,3,5,6,7-hexahydro-s-indacen-4-yl)urea | 488.2 | 489.2 | 1.24 |
| 18 | 3-{[2-(dimethylamino)ethyl](thiophen-3-ylmethyl)sulfamoyl}-1-(1,2,3,5,6,7-hexahydro-s-indacen-4-yl)urea | 462.2 | 463.2 | 1.27 |
| 19 | 1-[benzyl(1,3-thiazol-2-ylmethyl)sulfamoyl]-3-(1,2,3,5,6,7-hexahydro-s-indacen-4-yl)urea | 482.1 | 483.2 | 1.29 |
| 20 | 1-(1,2,3,5,6,7-hexahydro-s-indacen-4-yl)-3-{methyl[(2-phenyl-1,3-thiazol-4-yl)methyl]sulfamoyl}urea | 482.1 | 483.2 | 1.47 |
| 21 | 3-(1,2,3,5,6,7-hexahydro-s-indacen-4-yl)-1-({2-[3-(pyridin-3-yl)-1,2,4-oxadiazol-5-yl]ethyl}sulfamoyl)urea | 468.2 | 469.2 | 0.96 |

TABLE 3-continued

| Ex | Structure | Exact mass | LCMS Mass ion | Retention time |
|---|---|---|---|---|
| 22 | 3-({[3-(3,4-dimethoxyphenyl)-1,2,4-oxadiazol-5-yl]methyl}sulfamoyl)-1-(1,2,3,5,6,7-hexahydro-s-indacen-4-yl)urea | 513.2 | 514.2 | 1.13 |
| 23 | 3-(1,2,3,5,6,7-hexahydro-s-indacen-4-yl)-1-[(thiophen-2-ylmethyl)sulfamoyl]urea | 391.1 | 392.1 | 1.09 |
| 24 | 3-(1,2,3,5,6,7-hexahydro-s-indacen-4-yl)-1-{[2-(4-methylphenoxy)ethyl]sulfamoyl}urea | 429.2 | 430.2 | 1.5 |
| 25 | 3-(1,2,3,5,6,7-hexahydro-s-indacen-4-yl)-1-[(3-phenylpropyl)sulfamoyl]urea | 413.2 | 414.2 | 1.38 |
| 26 | 3-(1,2,3,5,6,7-hexahydro-s-indacen-4-yl)-1-{[2-(2-methylphenoxy)ethyl]sulfamoyl}urea | 429.2 | 430.2 | 1.5 |

TABLE 3-continued

| Ex | Structure | Exact mass | LCMS Mass ion | Retention time |
|---|---|---|---|---|
| 27 | 3-(1,2,3,5,6,7-hexahydro-s-indacen-4-yl)-1-{[4-(2-methyl-1H-imidazol-1-yl)phenyl]sulfamoyl}urea | 451.2 | 452.2 | 1.09 |
| 28 | 1-(2,3-dihydro-1H-indole-1-sulfonyl)-3-(1,2,3,5,6,7-hexahydro-s-indacen-4-yl)urea | 397.1 | 398.2 | 1.21 |
| 29 | 3-(1,2,3,5,6,7-hexahydro-s-indacen-4-yl)-1-[methyl(pyridin-4-ylmethyl)sulfamoyl]urea | 400.2 | 401.2 | 0.91 |
| 30 | 3-(1,2,3,5,6,7-hexahydro-s-indacen-4-yl)-1-[(pyridin-4-ylmethyl)sulfamoyl]urea | 386.1 | 387.1 | 0.93 |
| 31 | 3-(1,2,3,5,6,7-hexahydro-s-indacen-4-yl)-1-[methyl(phenyl)sulfamoyl]urea | 385.1 | 386.2 | 1.21 |

TABLE 3-continued

| Ex | Structure | Exact mass | LCMS Mass ion | Retention time |
|---|---|---|---|---|
| 32 | 1-{[(4-fluorophenyl)methyl](methyl)sulfamoyl}-3-(1,2,3,5,6,7-hexahydro-s-indacen-4-yl)urea | 417.2 | 418.2 | 1.22 |
| 33 | 1-[(3-cyano-4-methylphenyl)sulfamoyl]-3-(1,2,3,5,6,7-hexahydro-s-indacen-4-yl)urea | 410.1 | 411.1 | 1.13 |
| 34 | 3-[(1,3-diethyl-6-methyl-2-oxo-2,3-dihydro-1H-1,3-benzodiazol-5-yl)sulfamoyl]-1-(1,2,3,5,6,7-hexahydro-s-indacen-4-yl)urea | 497.2 | 498.2 | 1.1 |
| 35 | 3-(1,2,3,5,6,7-hexahydro-s-indacen-4-yl)-1-[(6-methoxy-4-methylpyridin-3-yl)sulfamoyl]urea | 416.2 | 417.2 | 1.1 |
| 36 | 1-[(6-acetyl-2H-1,3-benzodioxol-5-yl)sulfamoyl]-3-(1,2,3,5,6,7-hexahydro-s-indacen-4-yl)ure | 457.1 | 458.1 | 1.11 |

TABLE 3-continued

| Ex | Structure | Exact mass | LCMS Mass ion | Retention time |
|---|---|---|---|---|
| 37 | 1-[(2,3-dihydro-1H-inden-4-yl)sulfamoyl]-3-(1,2,3,5,6,7-hexahydro-s-indacen-4-yl)urea | 411.2 | 412.2 | 1.27 |
| 38 | 1-[(4,7-dimethyl-2-oxo-2H-chromen-6-yl)sulfamoyl]-3-(1,2,3,5,6,7-hexahydro-s-indacen-4-yl)urea | 467.2 | 468.2 | 1.09 |
| 39 | 1-[(2,4-dimethylpyridin-3-yl)sulfamoyl]-3-(1,2,3,5,6,7-hexahydro-s-indacen-4-yl)urea | 400.2 | 401.2 | 1.02 |
| 40 | 1-{[2-(2,3-dihydro-1H-indol-1-yl)ethyl]sulfamoyl}-3-(1,2,3,5,6,7-hexahydro-s-indacen-4-yl)urea | 440.2 | 441.2 | 1.38 |

Example 41: N-((1,2,3,5,6,7-Hexahydro-s-indacen-4-yl)carbamoyl)-4-methyl-piperazine-1-sulfonamide

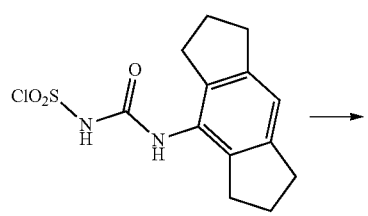

-continued

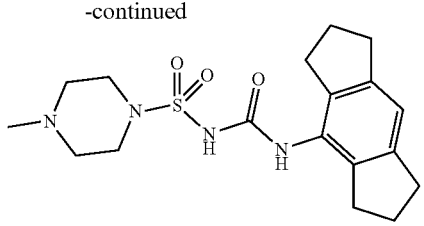

1-Methylpiperazine (70 μl, 0.631 mmol) was added to a suspension of ((1,2,3,5,6,7-hexahydro-s-indacen-4-yl)carbamoyl)sulfamoyl chloride (50 mg, 0.159 mmol) in THF (1 mL). The reaction mixture was stirred at room temperature overnight. DMF (1 mL) was added to aid solubility, the mixture was stirred for a further 1 hour, then filtered through a plug of cotton wool and purified by preparative HPLC to afford the title compound (2.8 mg) as a colourless solid.

$^1$H NMR (400 MHz, D$_2$O/NaOD) δ 6.82 (s, 1H), 2.89 (br s, 4H), 2.59 (t, J=7.5 Hz, 4H), 2.48 (t, J=7.3 Hz, 4H), 2.26 (br s, 4H), 1.97 (s, 3H), 1.76 (p, J=7.5 Hz, 4H).

LCMS m/z 379 (M+H)$^+$ (ES$^+$); 377 (M−H)$^−$ (ES$^−$)

Example 42: 1-(1,2,3,5,6,7-Hexahydro-s-indacen-4-yl)-3-[(1-methyl-1H-indazol-6-yl)sulfamoyl]urea

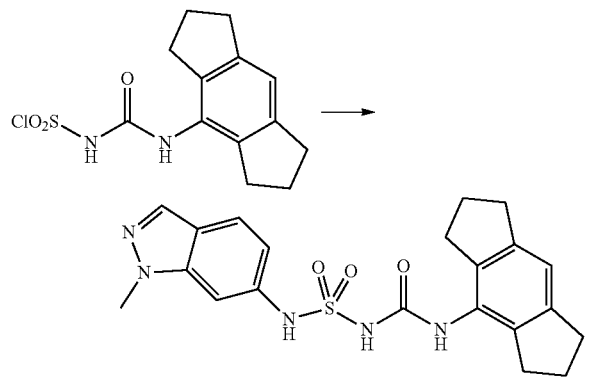

((1,2,3,5,6,7-hexahydro-s-indacen-4-yl)carbamoyl)sulfamoyl chloride (75 mg, 0.238 mmol) was added to a solution of 1-methyl-1H-indazol-6-amine (105 mg, 0.715 mmol) in THF (2 mL). The mixture was stirred for 6 hours, filtered, then purified by preparative HPLC to afford the title compound (2.3 mg).

$^1$H NMR (400 MHz, D$_2$O/NaOD) δ 7.53 (s, 1H), 7.19 (d, J=8.8 Hz, 1H), 6.77 (s, 1H), 6.60 (s, 1H), 6.46 (dd, J=8.7, 1.8 Hz, 1H), 2.37 (t, J=7.5 Hz, 4H), 2.36 (s, 3H), 1.97 (t, J=7.5 Hz, 4H), 1.41 (p, J=7.5 Hz, 4H).

LCMS m/z 426 (M+H)$^+$ (ES$^+$); 424 (M−H)$^−$ (ES$^−$)

Example 43: 3-(1,2,3,5,6,7-Hexahydro-s-indacen-4-yl)-1-[(1H-indol-5-yl)sulfamoyl]urea

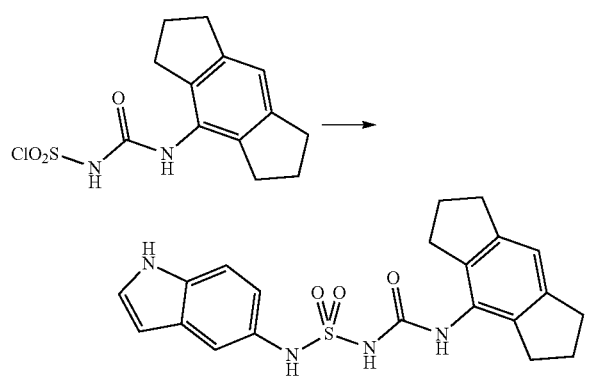

1H-Indol-5-amine (84 mg, 0.635 mmol) and triethylamine (150 µl, 1.076 mmol) were dissolved in THF (2 mL). ((1,2,3,5,6,7-Hexahydro-s-indacen-4-yl)carbamoyl) sulfamoyl chloride (100 mg, 0.318 mmol) was then added as a solid, the mixture was stirred for 30 minutes, filtered and purified by preparative HPLC to afford the title compound (7 mg) as a pale brown solid.

$^1$H NMR (400 MHz, DMSO-d6) δ 11.11 (s, 1H), 9.85 (s, 1H), 9.70 (s, 1H), 7.64 (s, 1H), 7.41 (d, J=2.0 Hz, 1H), 7.37 (t, J=2.8 Hz, 1H), 7.34 (d, J=8.6 Hz, 1H), 7.00 (dd, J=8.6, 2.0 Hz, 1H), 6.94 (s, 1H), 6.39-6.36 (m, 1H), 2.81 (t, J=7.4 Hz, 4H), 2.58 (t, J=7.4 Hz, 4H), 1.95 (p, J=7.5 Hz, 4H).

LCMS m/z 411 (M+H)$^+$ (ES$^+$); 409 (M−H)$^−$ (ES$^−$)

Biological Assay

NLRP3 and Pyroptosis

It is well established that the activation of NLRP3 leads to cell pyroptosis and this feature plays an important part in the manifestation of the clinical disease (Yan-gang Liu et al., Cell Death & Disease, 2017, 8(2), e2579; Alexander Wree et al., Hepatology, 2014, 59(3), 898-910; Alex Baldwin et al., Journal of Medicinal Chemistry, 2016, 59(5), 1691-1710; Ema Ozaki et al., Journal of Inflammation Research, 2015, 8, 15-27; Zhen Xie & Gang Zhao, Neuroimmunology Neuroinflammation, 2014, 1(2), 60-65; Mattia Cocco et al., Journal of Medicinal Chemistry, 2014, 57(24), 10366-10382; T. Satoh et al., Cell Death & Disease, 2013, 4, e644). Therefore, it is anticipated that inhibitors of NLRP3 will block pyroptosis, as well as the release of pro-inflammatory cytokines (e.g. IL-1β) from the cell.

THP-1 Cells: Culture and Preparation

THP-1 cells (ATCC #TIB-202) were grown in RPMI containing L-glutamine (Gibco #11835) supplemented with 1 mM sodium pyruvate (Sigma #S8636) and penicillin (100 units/ml)/streptomycin (0.1 mg/ml) (Sigma #P4333) in 10% Fetal Bovine Serum (FBS) (Sigma #F0804). The cells were routinely passaged and grown to confluency (~10$^6$ cells/ml). On the day of the experiment, THP-1 cells were harvested and resuspended into RPMI medium (without FBS). The cells were then counted and viability (>90%) checked by Trypan blue (Sigma #T8154). Appropriate dilutions were made to give a concentration of 625,000 cells/ml. To this diluted cell solution was added LPS (Sigma #L4524) to give a 1 µg/ml Final Assay Concentration (FAC). 40 µl of the final preparation was aliquoted into each well of a 96-well plate. The plate thus prepared was used for compound screening.

THP-1 Cells Pyroptosis Assay

The following method step-by-step assay was followed for compound screening.

1. Seed THP-1 cells (25,000 cells/well) containing 1.0 µg/ml LPS in 40 µl of RPMI medium (without FBS) in 96-well, black walled, clear bottom cell culture plates coated with poly-D-lysine (VWR #734-0317)
2. Add 5 µl compound (8 points half-log dilution, with 10 µM top dose) or vehicle (DMSO 0.1% FAC) to the appropriate wells
3. Incubate for 3 hrs at 37° C. in 5% CO$_2$
4. Add 5 µl nigericin (Sigma #N7143) (FAC 5 µM) to all wells
5. Incubate for 1 hr at 37° C. and 5% CO$_2$
6. At the end of the incubation period, spin plates at 300×g for 3 mins and remove supernatant
7. Then add 50 µl of resazurin (Sigma #R7017) (FAC 100 µM resazurin in RPMI medium without FBS) and incubate plates for a further 1-1.5 h at 37° C. and 5% CO$_2$
8. Plates were read in an Envision reader at Ex 560 nm and Em 590 nm
9. IC$_{50}$ data is fitted to a non-linear regression equation (log inhibitor vs response-variable slope 4-parameters)

96-Well Plate Map

|   | 1 | 2 | 3 | 4 | 5 | 6 | 7 | 8 | 9 | 10 | 11 | 12 |
|---|---|---|---|---|---|---|---|---|---|----|----|----|
| A | High | Comp 1 | Comp 2 | Comp 3 | Comp 4 | Comp 5 | Comp 6 | Comp 7 | Comp 8 | Comp 9 | Comp 10 | Low |
| B | High | Comp 1 | Comp 2 | Comp 3 | Comp 4 | Comp 5 | Comp 6 | Comp 7 | Camp S | Comp 9 | Comp 10 | Low |
| C | High | Comp 1 | Comp 2 | Comp 3 | Comp 4 | Comp 5 | Comp 6 | Comp 7 | Comp 8 | Comp 9 | Comp 10 | Low |
| D | High | Comp 1 | Comp 2 | Comp 3 | Comp 4 | Comp 5 | Comp 6 | Comp 7 | Comp 8 | Comp 9 | Comp 10 | Low |
| E | High | Comp 1 | Comp 2 | Comp 3 | Comp 4 | Comp 5 | Comp 6 | Comp 7 | Comp 8 | Comp 9 | Comp 10 | Low |
| F | High | Comp 1 | Comp 2 | Comp 3 | Comp 4 | Comp 5 | Comp 6 | Comp 7 | Comp 8 | Comp 9 | Comp 10 | Low |
| G | High | Comp 1 | Comp 2 | Comp 3 | Comp 4 | Comp 5 | Comp 6 | Comp 7 | Comp 8 | Comp 9 | Comp 10 | Low |
| H | High | Comp 1 | Comp 2 | Comp 3 | Comp 4 | Comp 5 | Comp 6 | Comp 7 | Comp 8 | Comp 9 | Comp 10 | Low |
|   | High | MCC950 (10 uM) | | | Compound 8-point half-log dilution | | | | | | | |
|   | Low | Drug free control | | | | | | | | | | |

The results of the pyroptosis assay performed are summarised in Table 4 below.

TABLE 4

Results of pyroptosis assay

| Example No. | $IC_{50}$ (nM) | Example No. | $IC_{50}$ (nM) |
|---|---|---|---|
| 5 | ++ | 6 | ++ |
| 7 | ++ | 8 | not measured |
| 9 | not measured | 10 | not measured |
| 11 | ++ | 12 | ++ |
| 13 | ++ | 14 | ++ |
| 15 | ++ | 16 | not measured |
| 17 | + | 18 | ++ |
| 19 | +++ | 20 | ++ |
| 21 | ++ | 22 | not measured |
| 23 | ++ | 24 | ++ |
| 25 | ++ | 26 | ++ |
| 27 | ++ | 28 | ++ |
| 29 | ++ | 30 | + |
| 31 | ++ | 32 | ++ |
| 33 | ++ | 34 | ++ |
| 35 | +++ | 36 | ++ |
| 37 | ++ | 38 | not measured |
| 39 | ++ | 40 | ++ |
| 41 | not measured | 42 | +++ |
| 43 | +++ | | |

(<1 μM = '+++'/<10 μM = '++'/<50 μM = '+')

The invention claimed is:

1. A compound of formula (II) or (III), or a pharmaceutically acceptable salt or solvate thereof:

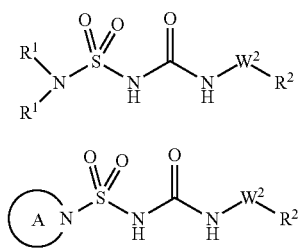

Formula II

Formula III wherein:
$R^1$ is independently selected from the group consisting of hydrogen, $C_1$-$C_{12}$ alkyl, $C_2$-$C_{12}$ alkenyl, $C_2$-$C_{12}$ alkynyl, aryl, heterocyclyl, heteroaryl, cycloalkyl, cycloalkenyl, amino, amido, alkylthio, acyl, arylalkyl and acylamido, all of which may be optionally substituted; and
A is heteroaryl or heterocyclyl, each of which is optionally substituted and linked to the sulfonyl sulphur through a ring nitrogen; and
$W^2$ and $R^2$ form an indacene group or a substituted or hydrogenated variant thereof.

2. A compound of formula (II) or (III), or a pharmaceutically acceptable salt or solvate thereof:

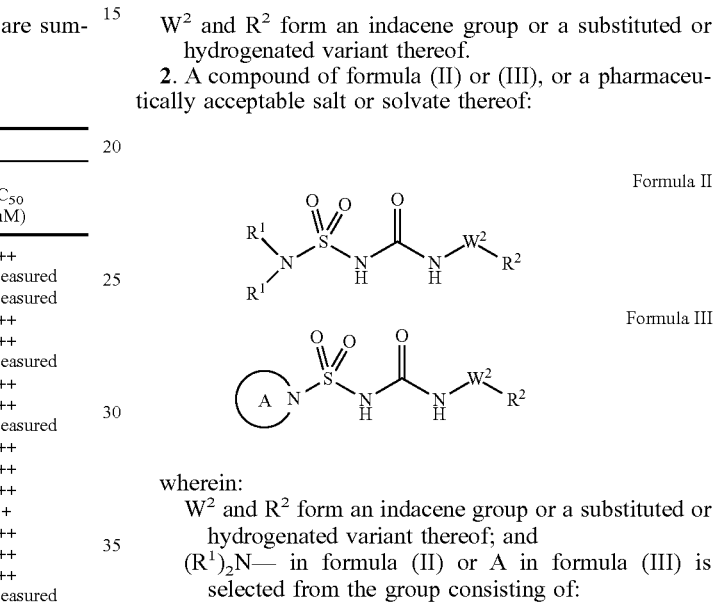

Formula II

Formula III wherein:
$W^2$ and $R^2$ form an indacene group or a substituted or hydrogenated variant thereof; and
$(R^1)_2N$— in formula (II) or A in formula (III) is selected from the group consisting of:

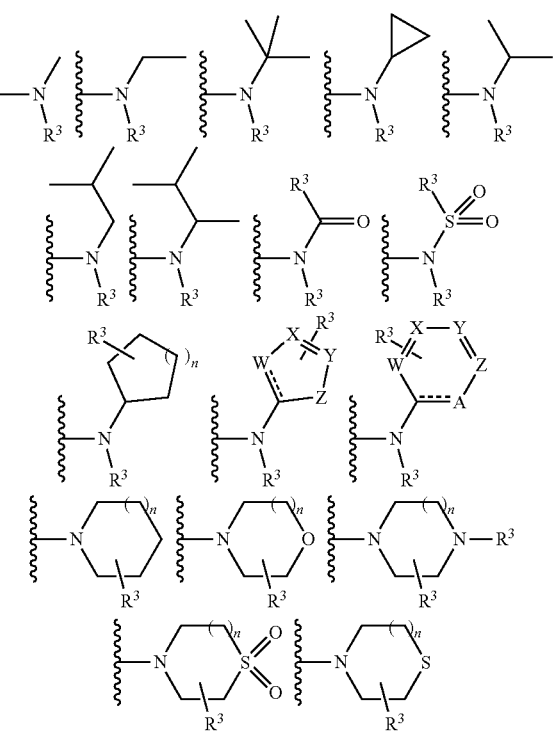

-continued

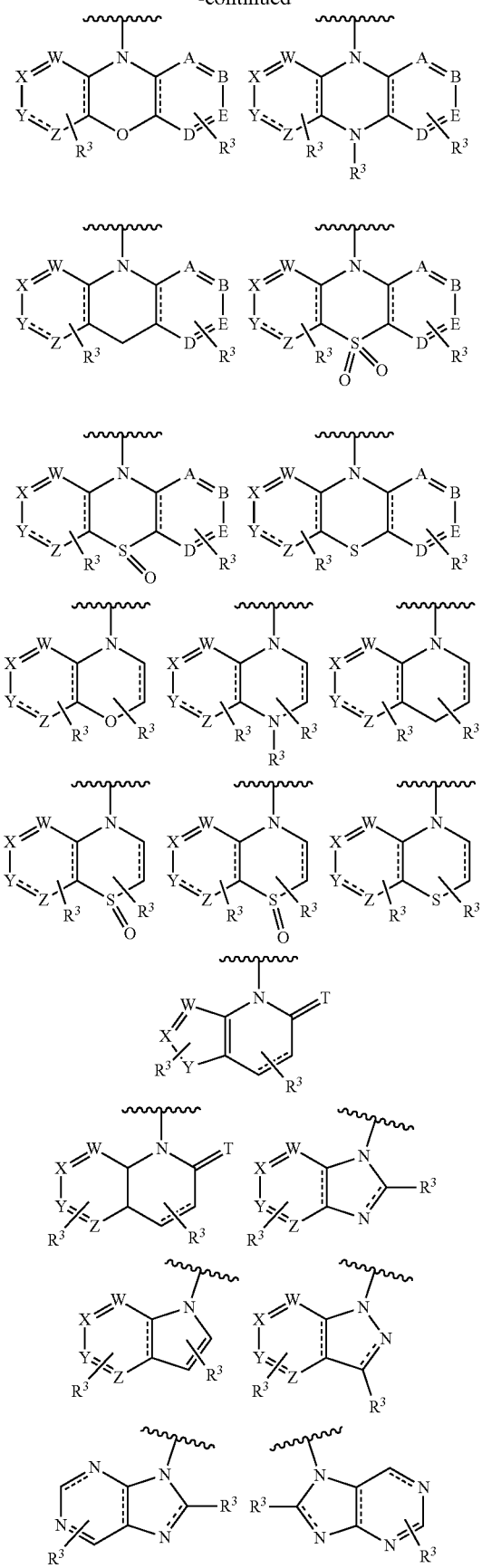

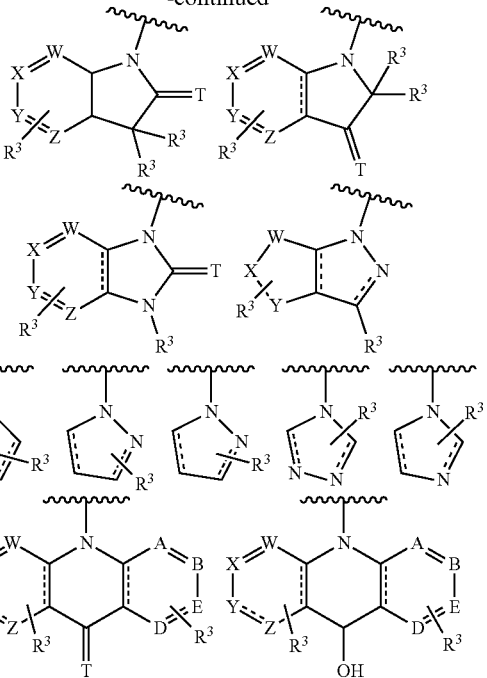

wherein:
each dashed line may independently be a bond;
T is O or S;
A, B, D, E, W, X, Y and Z, when present, are each independently selected from O, C(R³), C(R³)₂, N, N(R³) and S;
each incidence of R³ is independently selected from the group consisting of hydrogen, halide, cyano, $C_1$-$C_6$ alkyl, $C_1$-$C_6$ trifluoroalkyl, $C_1$-$C_6$ alkoxy, C=O, SO₂, acyl, amino, hydroxyl, $C_5$-$C_6$ heteroaryl, $C_5$-$C_6$ heterocyclyl and $C_3$-$C_6$ cycloalkyl, each of which may be optionally substituted; and
n is 0, 1, 2 or 3.

3. A compound of formula (II) or (III), or a pharmaceutically acceptable salt or solvate thereof:

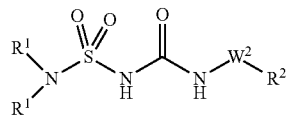

Formula II

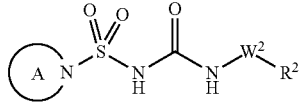

Formula III wherein:
each R¹ is independently selected from a hydrogen atom and pyrazole, imidazole, triazole, tetrazole, pyrrole, morpholine, piperazine, 4-methyl piperazine, and fused bicyclics or tricyclics comprising a benzene ring fused with at least one 5-membered heterocycle, each of which groups may be optionally substituted at a ring atom with a group selected from halo, isopropyl, morpholinyl, piperidinyl, and piperazinyl, each of which groups may themselves be optionally substituted with $C_1$-$C_6$ alkyl;

A is selected from pyrazole, imidazole, triazole, tetrazole, pyrrole, morpholine, piperazine, 4-methyl piperazine, and fused bicyclics or tricyclics comprising a benzene ring fused with at least one 5-membered heterocycle, each of which groups may be optionally substituted at a ring atom with a group selected from halo, isopropyl, morpholinyl, piperidinyl, and piperazinyl, each of which groups may themselves be optionally substituted with $C_1$-$C_6$ alkyl; and $W^2$ and $R^2$ form an indacene group or a substituted or hydrogenated variant thereof.

4. A pharmaceutical composition comprising the compound of claim 1, or the pharmaceutically acceptable salt or solvate thereof, and a pharmaceutically acceptable carrier, diluent and/or excipient.

5. A method of treating or preventing a disease, disorder or condition in a subject including the step of administering an effective amount of the compound of claim 1, or the pharmaceutically acceptable salt or solvate thereof, to the subject thereby treating or preventing the disease, disorder or condition, wherein the disease, disorder or condition is responsive to inhibition of activation of the NLRP3 inflammasome.

6. The method of claim 5, wherein the disease, disorder or condition is:
  (i) a disease, disorder or condition of the immune system;
  (ii) an inflammatory disease, disorder or condition or an autoimmune disease, disorder or condition;
  (iii) a disease, disorder or condition of the skin;
  (iv) a disease, disorder or condition of the cardiovascular system;
  (v) a cancer, tumour or other malignancy;
  (vi) a disease, disorder or condition of the renal system;
  (vii) a disease, disorder or condition of the gastro-intestinal tract;
  (viii) a disease, disorder or condition of the respiratory system;
  (ix) a disease, disorder or condition of the endocrine system; and/or
  (x) a disease, disorder or condition of the central nervous system (CNS).

7. The method of claim 5, wherein the disease, disorder or condition is selected from the group consisting of;
  (i) constitutive inflammation, autoinflammatory diseases, autoimmune disease respiratory diseases, central nervous system diseases, metabolic diseases, ocular diseases, kidney disease, liver disease, inflammatory reactions in skin, inflammatory reactions in the joints, viral infections, and cancers; or
  (ii) cryopyrin-associated periodic syndromes (CAPS); Muckle-Wells syndrome (MWS); familial cold autoinflammatory syndrome (FCAS); neonatal-onset multisystem inflammatory disease (NOMID); familial Mediterranean fever (FMF); TNF receptor associated periodic syndrome (TRAPS); mevalonate kinase deficiency (MKD); hyperimmunoglobulinemia D and periodic fever syndrome (HIDS); deficiency of interleukin 1 receptor antagonist (DIRA); Majeed syndrome; pyogenic arthritis, pyoderma gangrenosum and acne syndrome (PAPA); haploinsufficiency of A20 (HA20); pediatric granulomatous arthritis (PGA); PLCG2-associated antibody deficiency and immune dysregulation (PLAID); autoinflammation, PLCG2-associated antibody deficiency and immune dysregulation (APLAID); sideroblastic anemia with B-cell immunodeficiency, periodic fevers, and developmental delay (SIFD); multiple sclerosis (MS); type-1 diabetes; psoriasis; rheumatoid arthritis; Behcet's disease; Sjogren's syndrome; Schnitzler syndrome; chronic obstructive pulmonary disorder (COPD); steroid-resistant asthma; asbestosis; silicosis; cystic fibrosis; Parkinson's disease; Alzheimer's disease; motor neuron disease; Huntington's diseases; cerebral malaria; brain injury from pneumococcal meningitis; Type 2 diabetes; atherosclerosis; obesity; gout; pseudo-gout; ocular diseases of the ocular epithelium; age-related macular degeneration (AMD); corneal infection; dry eye; chronic kidney disease; oxalate nephropathy; diabetic nephropathy; non-alcoholic steatohepatitis (NASH); alcoholic liver disease; contact hypersensitivity; sunburn; osteoarthritis; systemic juvenile idiopathic arthritis; adult-onset Still's disease; relapsing polychondritis; infections with alpha virus (Chikungunya, Ross River); infection with flavivirus (Dengue, Zika); flu; HIV; hidradenitis suppurativa (HS); cyst-causing skin diseases; lung cancer metastasis; pancreatic cancers; gastric cancers; myelodysplastic syndrome; leukemia; polymyositis; stroke; myocardial infarction; Graft versus Host Disease; hypertension; colitis; helminth infection; bacterial infection; abdominal aortic aneurysm; wound healing; depression; psychological stress; ischaemia reperfusion injury; and diseases where an individual has been determined to carry a germline or somatic non-silent mutation in NLRP3.

8. The method of claim 5, wherein the subject is a mammal, such as a human subject.

9. A method of diagnosing a disease, disorder or condition in a mammal including the step of administering the compound of claim 1, or the pharmaceutically acceptable salt or solvate thereof, which compound, pharmaceutically acceptable salt or solvate is labelled, to the mammal or to a biological sample obtained from the mammal to facilitate diagnosis of the disease, disorder or condition in the mammal, wherein the disease, disorder or condition is responsive to inhibition of activation of the NLRP3 inflammasome.

10. A method of modulating the activity of a biological target comprising the step of exposing the biological target to the compound of claim 1, or the pharmaceutically acceptable salt or solvate thereof, wherein the biological target is selected from the group-consisting of the NLRP3 inflammasome, IL-1β and IL-18.

11. A compound or a pharmaceutically acceptable salt or solvate thereof, which is any of:

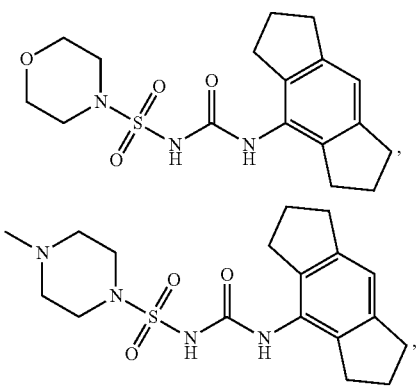

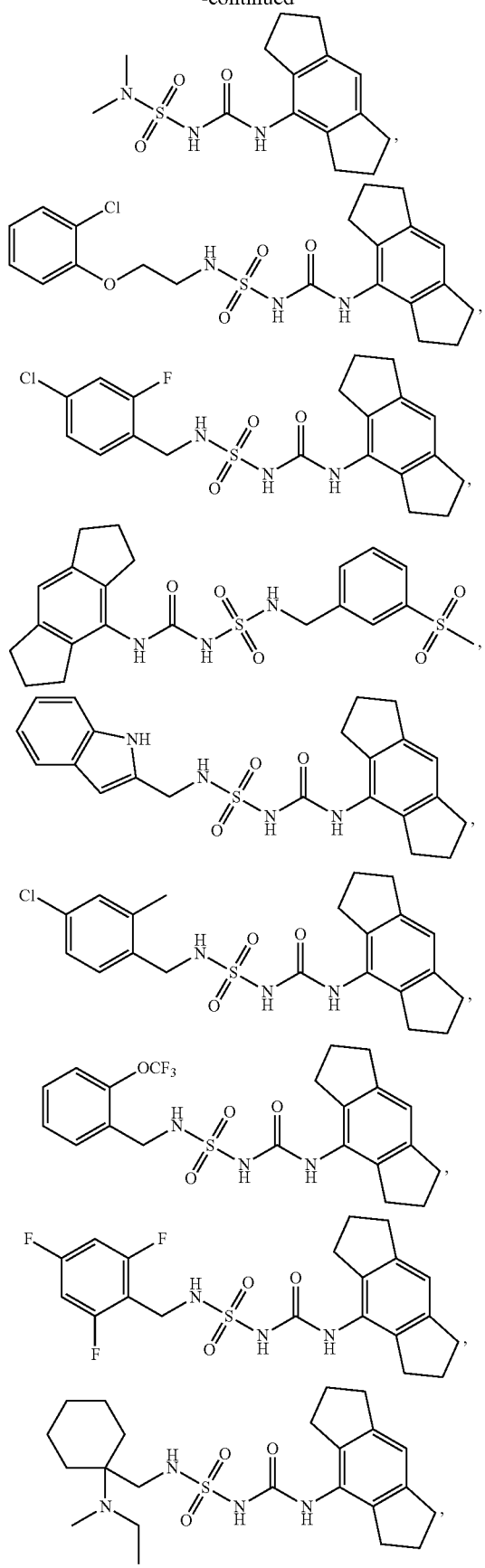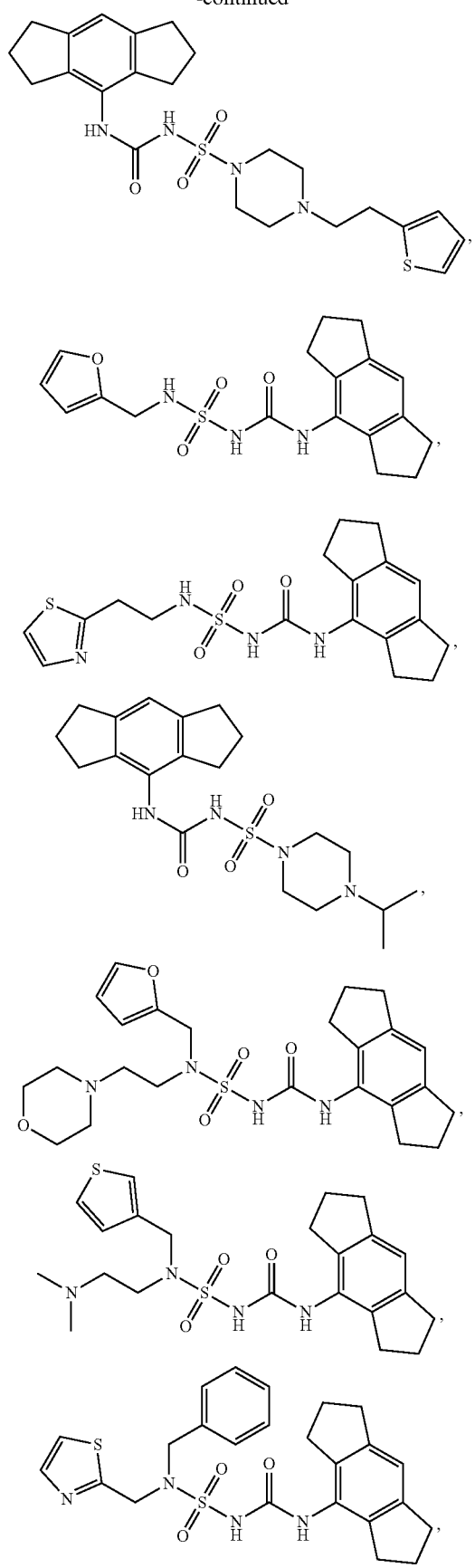

137
-continued
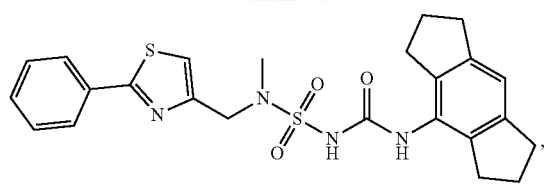
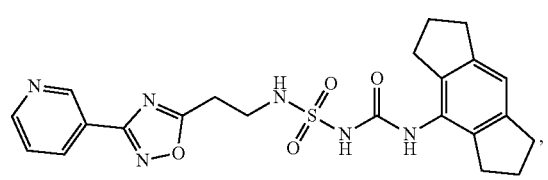
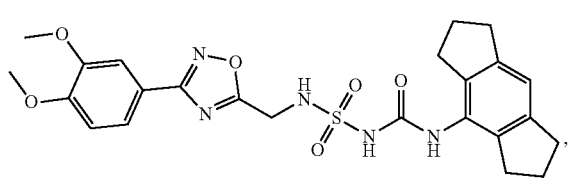
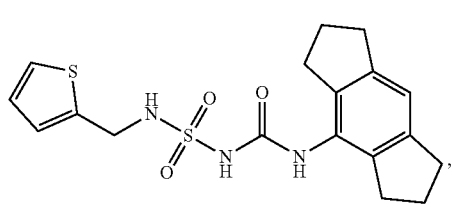
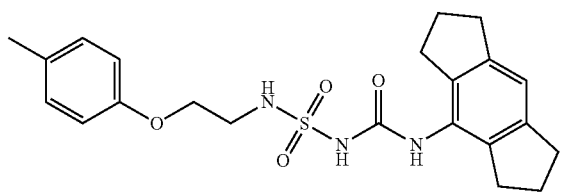
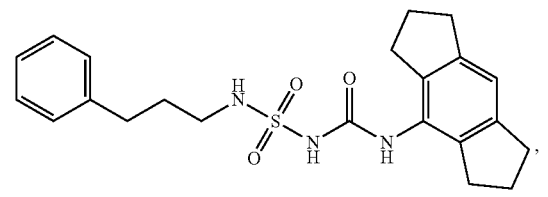
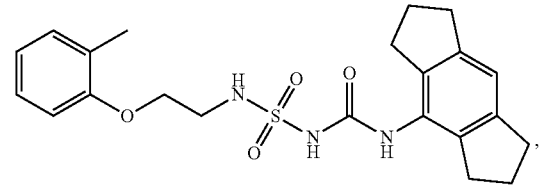
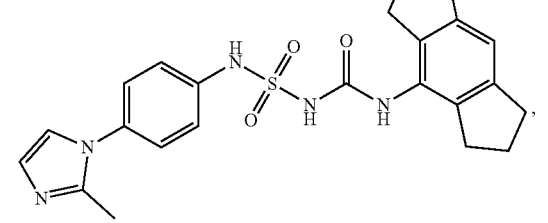
138
-continued
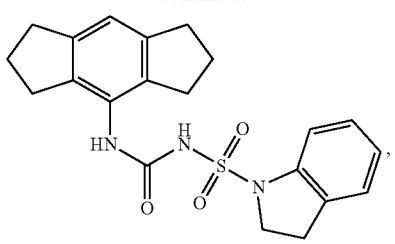
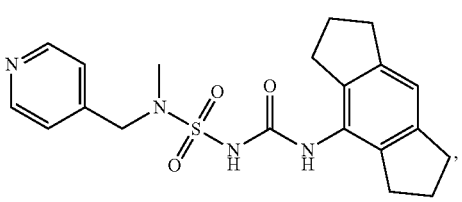
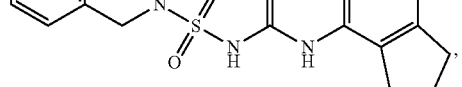
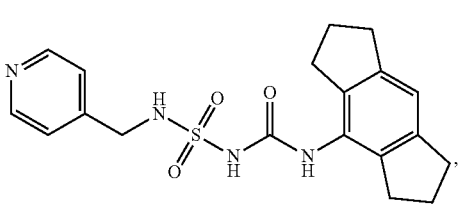
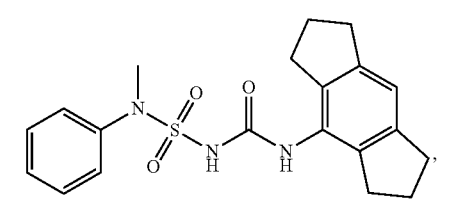
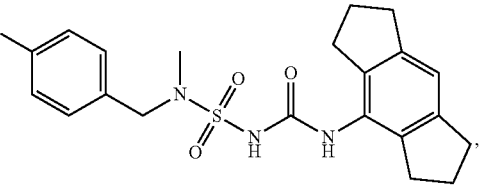
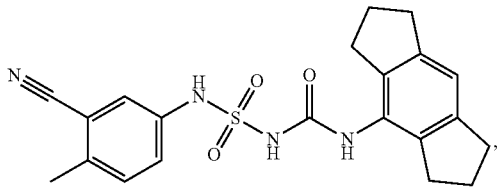
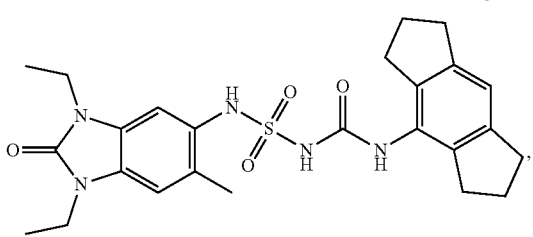

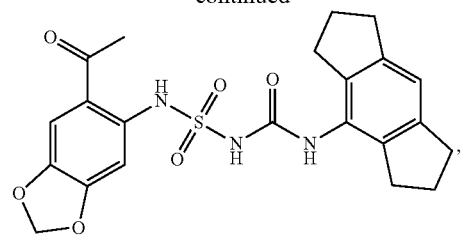
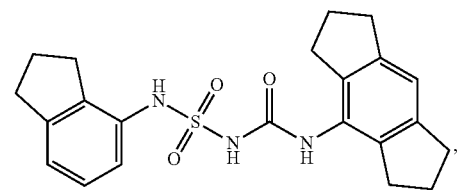
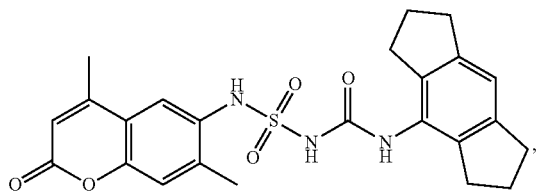
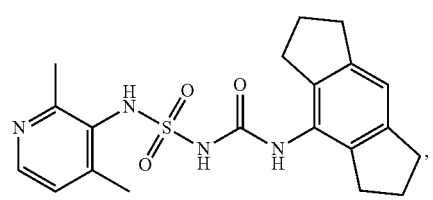
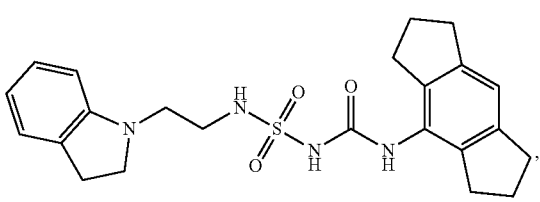
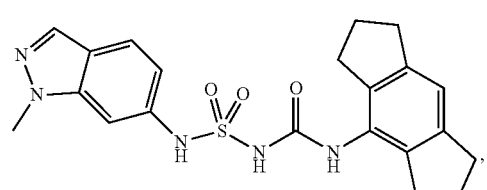
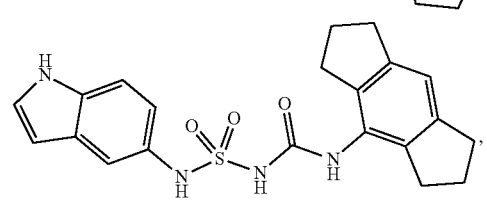
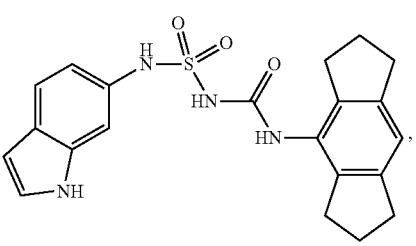
N-((1,2,3,5,6,7-hexahydro-s-indacen-4-yl)carbamoyl)
(1H-indol-6-amine)sulfonamide
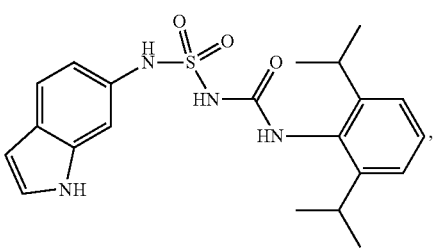
N-((2,6-diisopropylplyphenyl)carbamoyl)
(1H-indol-6-amine)sulfonamide
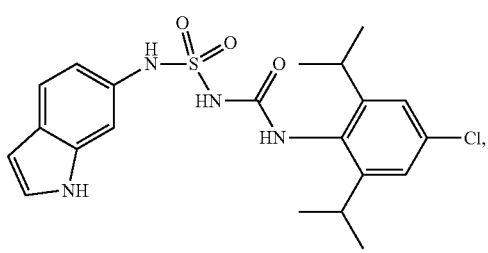
N-((4-chloro-2,6-diisopropylphenyl)carbamoyl)
(1H-indol-6-amine)sulfonamide
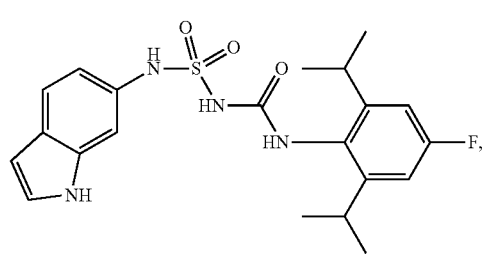
N-((4-fluoro-2,6-diisopropylphenyl)carbamoyl)
(1H-indol-6-amine)sulfonamide
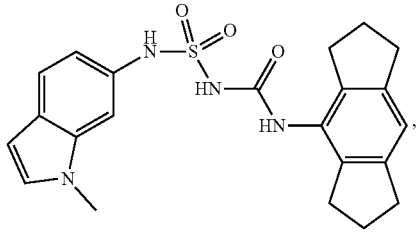
N-((1,2,3,5,6,7-hexahydro-s-indacen-4-
yl)carbamoyl)(1-methyl-1H-indol-6-
amine)sulfonamide -continued

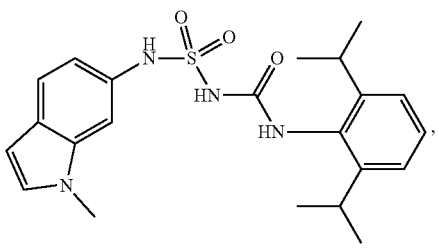

N-((2,6-diisopropylphenyl)carbamoyl)
(1-methyl-1H-indol-6-amine)sulfonamide

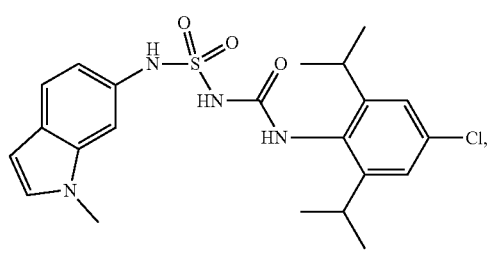

N-((4-chloro-2,6-diisopropylphenyl)carbamoyl)
(1-methyl-1H-indol-6-amine)sulfonamide

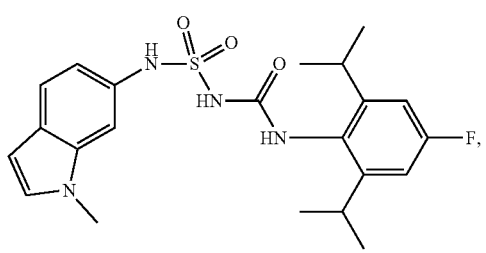

N-((4-fluoro-2,6-diisopropylphenyl)carbamoyl)
(1-methyl-1H-indol-6-amine)sulfonamide

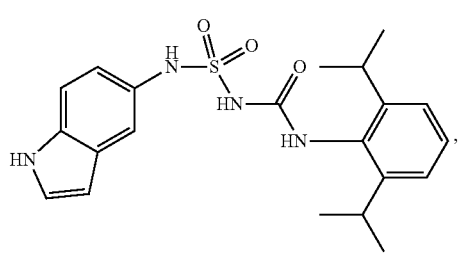

N-((2,6-diisoporpylphenyl)carbamoyl)
(1H-indol-5-amine)sulfonamide

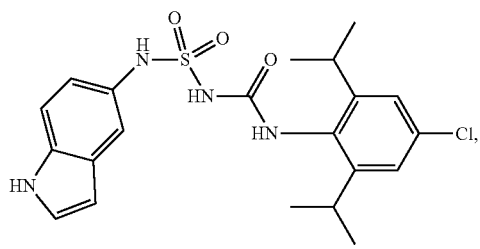

N-((chloro-2,6-diisopropylphenyl)carbamoyl)
(1H-indol-5-amine)sulfonamide

-continued

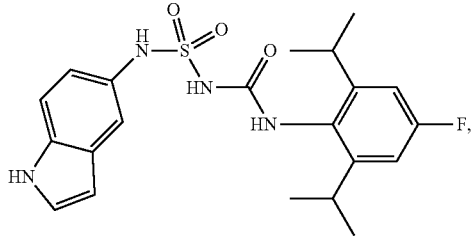

N-((4-fluoro-2,6-diisopropylphenyl)carbamoyl)
(1H-indol-5-amine)sulfonamide

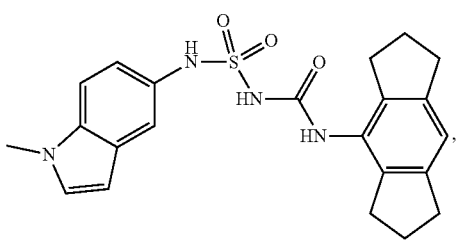

N-((1,2,3,5,6,7-hexahydro-s-indacen-4-
yl)carbamoyl)(1-methyl-1H-indol-5-amine)sulfonamide

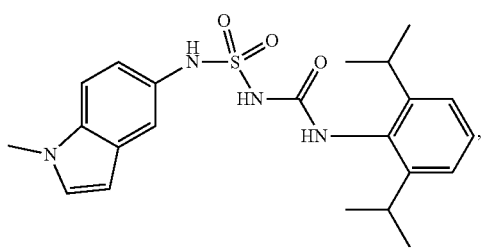

N-((2,6-diisopropylphenyl)carbamoyl)
(1-methyl-1H-indol-5-amine-sulfonamide

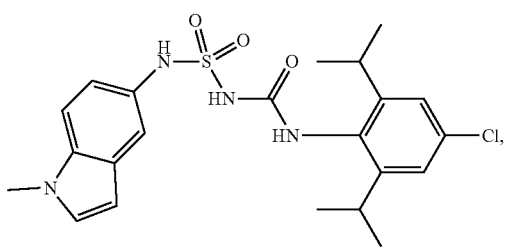

N-((4-chloro-2,6-diisopropylphenyl)carbamoyl)
(1-methyl-1H-indol-5-amine)sulfonamide

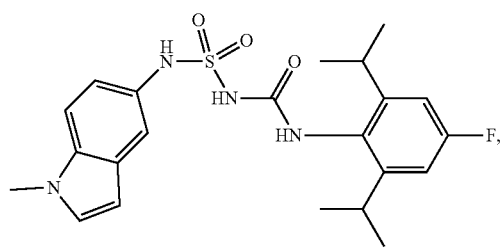

N-((4-fluoro-2,6-diisopropylphenyl)carbamoyl)
(1-methyl-1H-indol-5-amine)sulfonamide

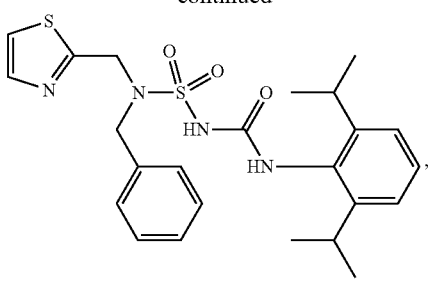

N-((2,6-diisoprpylphenyl)carbamoyl)
(n-benzyl-1-(thiazol-2-yl)methanamine)sulfonamide

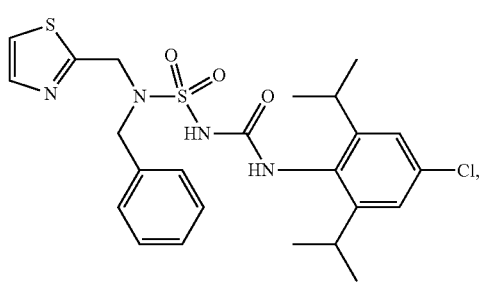

N-((4-chloro-2,6-diisopropylphenyl)carbamoyl)
(N-benzyl-1-(thiazol-2-yl)methanamine)sulfonamide

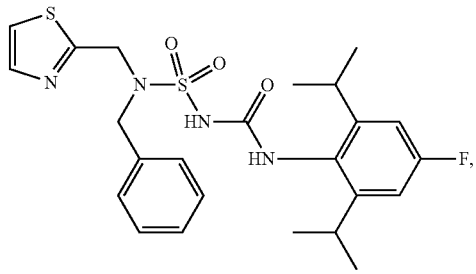

N-((4-fluoro-2,6-diisopropylphenyl)carbamoyl)
(N-benzyl-1-(thiazol-2-yl)methanamine)sulfonamide

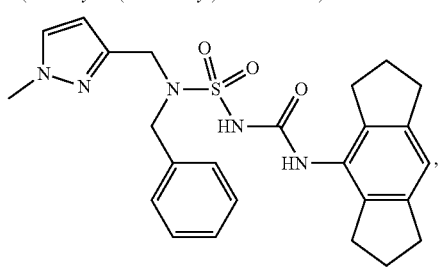

N-((1,2,3,5,6,7-hexahydro-s-indacen-4-yl)-
carbamoyl)(N-benzyl-1-(1-methyl-1H-pyrazol-3-
yl)methanamine)sulfonamide

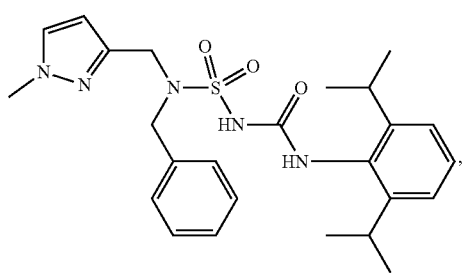

N-((2,6-diisoprpylphenyl)carbamoyl)
(N-benzyl-1-(1-methyl-1H-pyrazol-3-yl)-
methanamine)sulfonamide

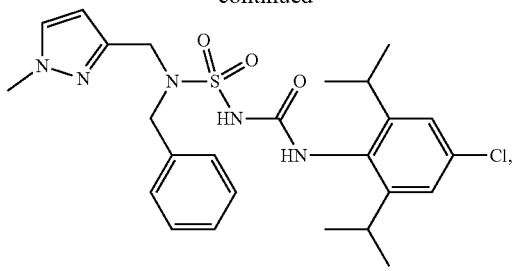

N-((4-chloro-2,6-diisopropylphenyl)carbamoyl)
(N-benzyl-1-(1-methyl-1H-pyrazol-3-yl)-
methanamine)sulfonamide

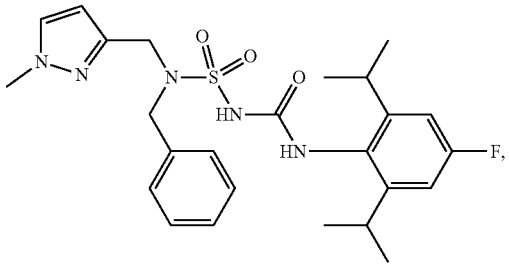

N-((4-fluoro-2,6-diisopropylphenyl)carbamoyl)
(N-benzyl-1-(1-methyl-1H-pyrazol-3-yl)-
methanamine)sulfonamide

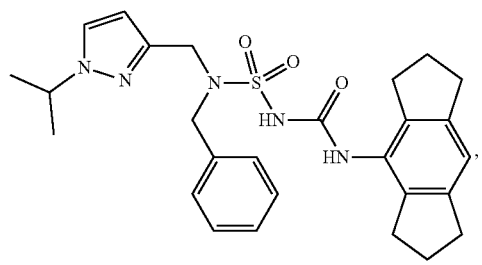

N-((1,2,3,5,6,7-hexahydro-s-indacen-4-yl)-
carbamoyl)(N-benzyl-1-(1-isopropyl-1H-pyrazol-3-
yl)methanamine)sulfonamide

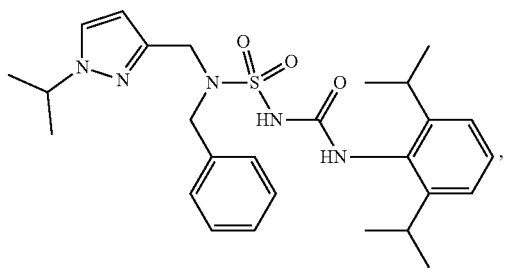

N-((2,6-diisopropylphenyl)carbamoyl)
(N-benzyl-1-(1-isopropyl-1H-pyrazol-3-yl)-
methanamine)sulfonamide

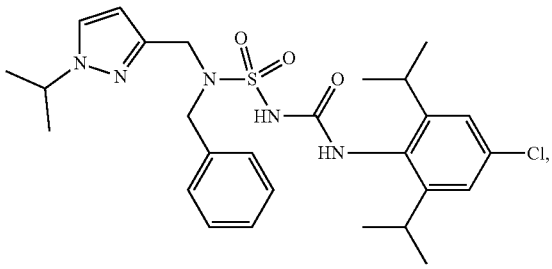

N-((4-chloro-2,6-diisopropylphenyl)carbamoyl)
(N-benzyl-1-(1-isopropyl-1H,pyrazol-3-yl)-
methanamine)sulfonamide

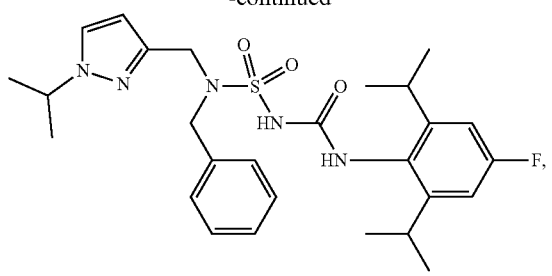

N-((4-fluoro-2,6-diisopropylphenyl)carbamoyl)
(N-benzyl-1-(1-isopropyl-1H-pyrazol-3-yl)-
methanamine)sulfonamide

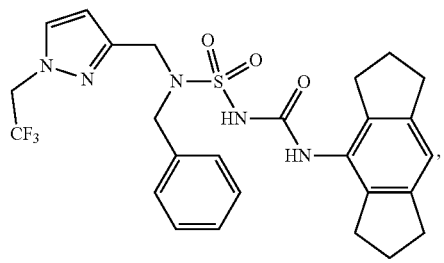

N-((1,2,3,5,6,7-hexahydro-s-indacen-4-yl)-
carbamoyl)(N-benzyl-1-(1-(2,2,2-trifluomethyl)-1H-
pyrazol-3-yl)methanamine)sulfonamide

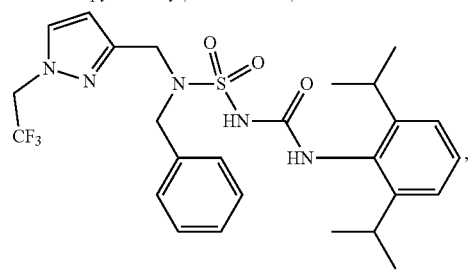

N-((2,6-diisoprpylphenyl)carbamoyl)
(N-benzyl-1-(1-(2,2,2-trifluoroethyl)-1H-pyrazol-3-yl)-
methanamine)sulfonamide

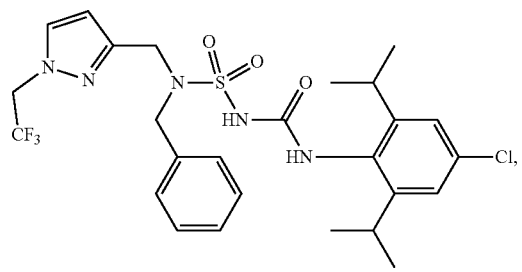

N-((4-chloro-2,6-diisopropylphenyl)carbamoyl)
(N-benzyl-1-(2,2,2-trifluoroethyl)-1H-pyrazol-3-yl)-
methanamine)sulfonamide

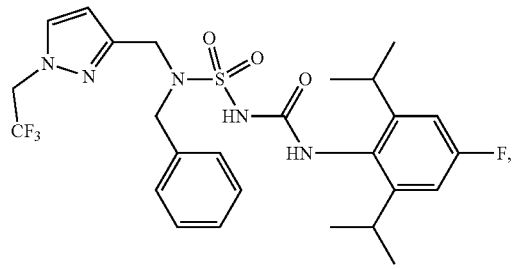

N-((4-fluoro-2,6-diisoprpylphenyl)carbamoyl)
(N-benzyl-1-(1-(2,2,2-trifluoroethyl)-1H-pyrazol-3-yl)-
methanamine)sulfonamide

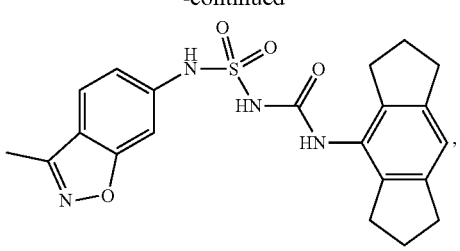

N-((1,2,3,5,6,7-hexahydro-2-indacen-4-
yl)carbamoyl)(3-methylbenzo[d]isoxazol-6-
amine)sulfonamide

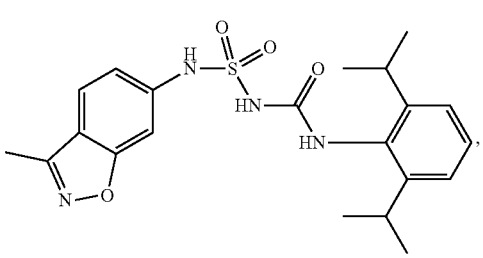

N-((2,6-diisopropylphenyl)carbamoyl)
(3-methylbenzo[d]isoxazol-6-amine)sulfonamide

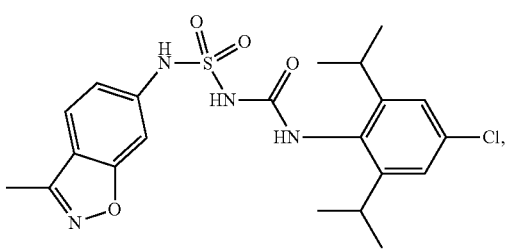

N-((4-chloro-2,6-diisopropylphenyl)carbamoyl)
(3-methylbenzo[d]isoxazol-6-amine)sulfonamide

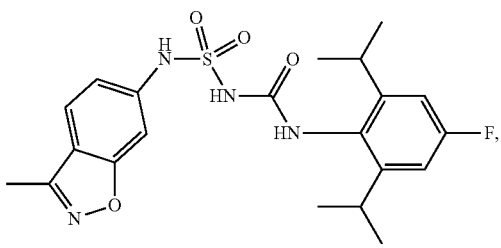

N-((4-fluoro-2,6-diisopropylphenyl)carbamoyl)
(3-methylbenzo[d]isoxazol-6-amine)sulfonamide

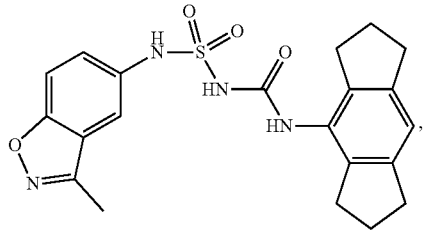

N-((1,2,3,5,6,7-hexahydro-s-indacen-4-
yl)carbamoyl)(3-methylbenzo[d]idoxazol-5-
amine)sulfonamide

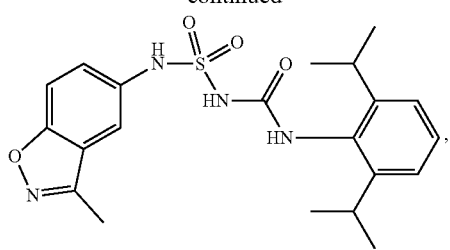

N-((2,6-diisopropylphenyl)carbamoyl)
(3-methylbenzo[d]isoxazol-5-amine)sulfonamide

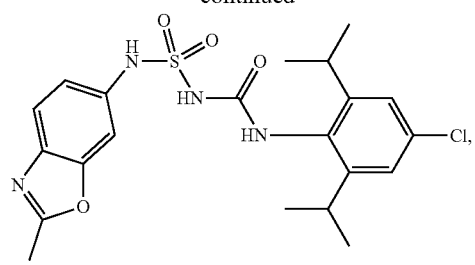

N-((4-chloro-2,6-diisopropylphenyl)carbamoyl)
(2-methylbenzo[d]oxazol-6-amine)sulfonamide

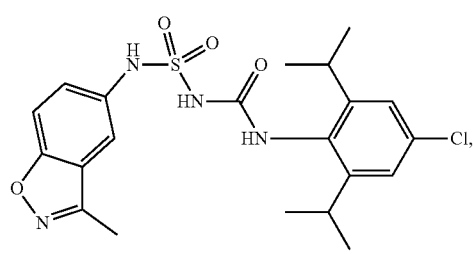

N-((4-chloro-2,6-diisopropylphenyl)carbamoyl)
(3-methylbenzo[d]isoxazol-5-amine)sulfonamide

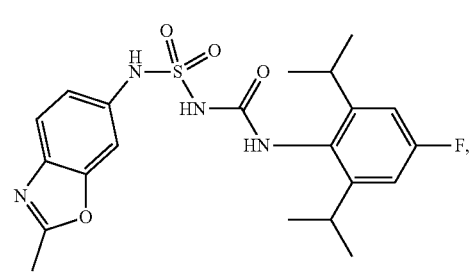

N-((4-fluoro-2,6-diisoprpylphenyl)carbamoyl)
(2-methylbenzo[d]oxazol-6-amine)sulfonamide

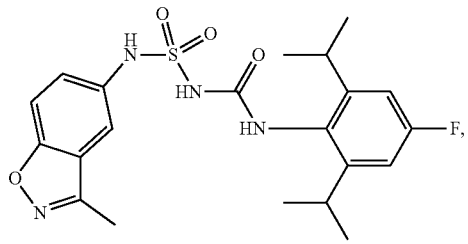

N-((4-fluoro-2,6-diisopropylphenyl)carbamoyl)
(3-methylbenzo[d]isoxazol-5-amine)sulfonamide

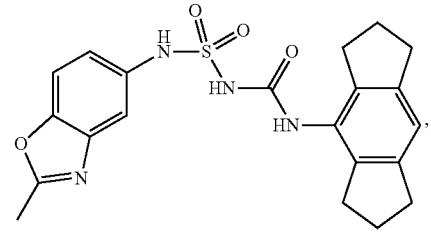

N-((1,2,3,5,6,7-hexahydro-s-indacen-4-
yl)carbamoyl)(2-methylbenzo[d]oxazol-5-
amine)sulfonamide

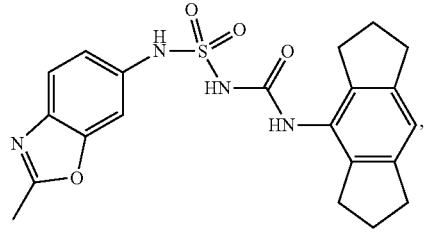

N-((1,2,3,5,6,7-hexahydro-5-indacen-4-
yl)carbamoyl)2-methylbenzo[d]oxazol-6-
amine)sulfonamide

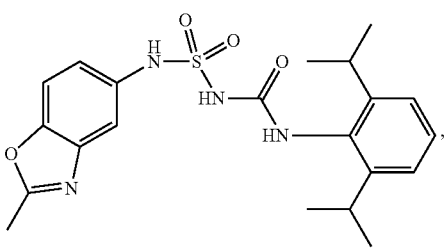

N-((2,6-diisopropylphenyl)carbamoyl)
(2-methylbenzo[d]oxazol-5-amine)sulfonamide

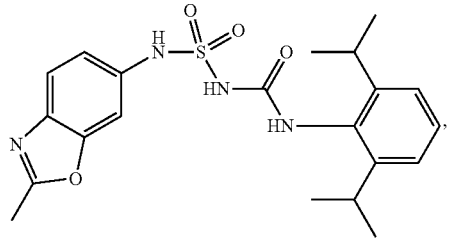

N-((2,6-diisopropylphenyl)carbamoyl)
(2-methylbenzo[d]oxazol-6-amine)sulfonamide

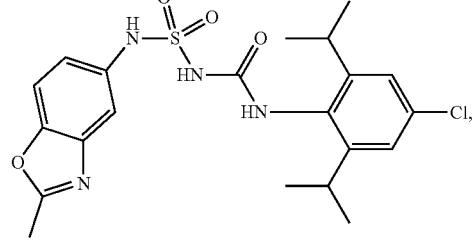

N-((4-chloro-2,6-diisoprpylphenyl)carbamoyl)
(2-methylbenzo[d]oxazol-5-amine)sulfonamide

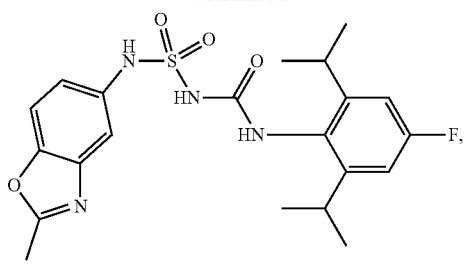

N-((4-fluoro-2,6-diisopropylphenyl)carbamoyl)
(2-methylbenzo[d]oxazol-5-amine)sulfonamide

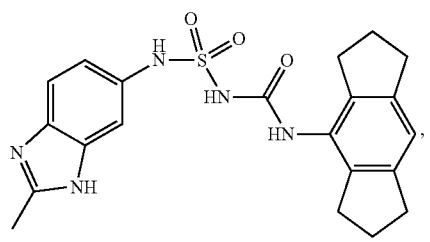

N-((1,2,3,5,6,7-hexahydro-s-indacen-4-
yl)carbamoyl)(2-methyl-1H-benzo[d]imidazol-6-
amine)sulfonamide

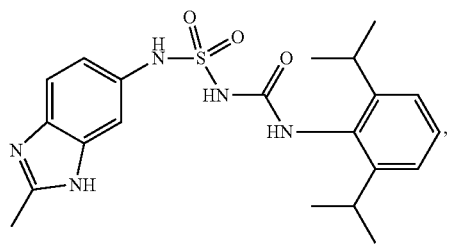

N-((2,6-diisoprpylphenyl)carbamoyl)
(2-methyl-1H-benzo[d]imidazol-6-amine)sulfonamide

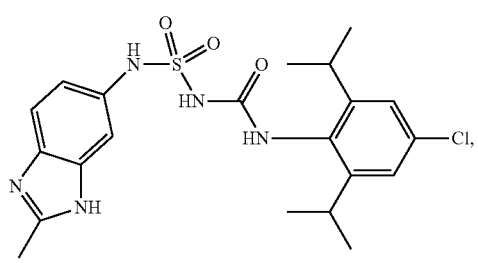

N-((4-chloro-2,6-diisopropylphenyl)carbamoyl)
(2-methyl-1H-benzo[d]imidazol-6-amine)sulfonamide

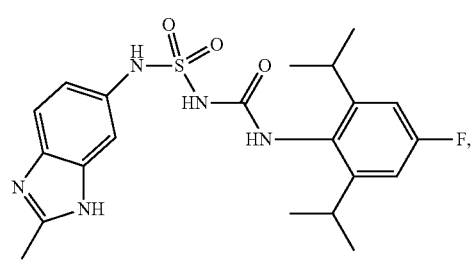

N-((4-fluoro-2,6-diisopropylphenyl)carbamoyl)
(2-methyl-1H-benzo[d]imidazol-6-amine)sulfonamide

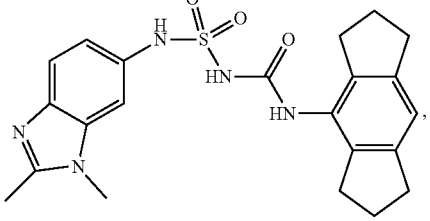

N-((1,2,3,5,6,7-hexahydro-s-indacen-4-
yl)carbamoyl)(1,2-dimethyl-1H-benzo[d]imidazol-6-
amine)sulfonamide

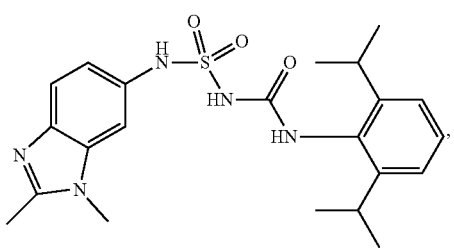

N-((2,6-diisopropylphenyl)carbamoyl)
(1,2-dimethyl-1H-benzo[d]imidazol-6-amine)sulfonamide

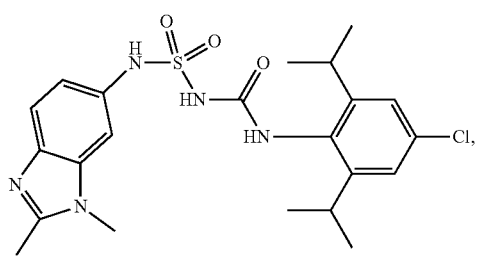

N-((4-chloro-2,6-diisopropylphenyl)carbamoyl)
(1,2-dimethyl-1H-benzo[d]imidzaol-6-
amine)sulfonamide

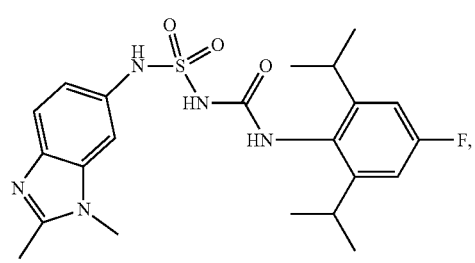

N-((4-fluoro-2,6-diisopropylphenyl)carbamoyl)
(1,2-dimethyl-1H-benzo[d]imidazol-6-amine)sulfonamide

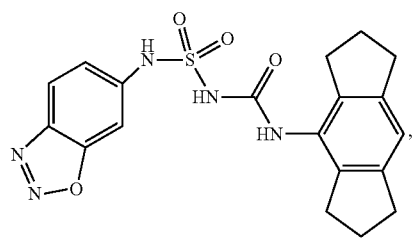

N-((1,2,3,5,6,7-hexahydro-s-indacen-4-
yl)carbamoyl)benzo[d][1,2,3]oxadiazol-6-
amine)sulfonamide

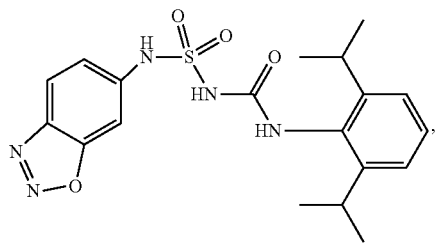

N-((2,6-diisopropylphenyl)carbamoyl)
(benzo[d][1,2,3]oxadiazol-6-amine)sulfonamide

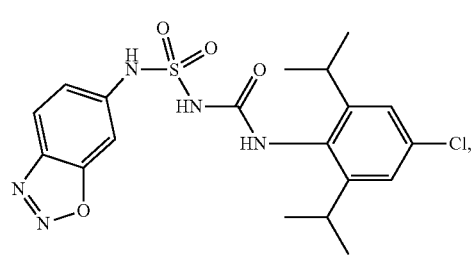

N-((4-chloro-2,6-diisopropylphenyl)carbamoyl)
(benzo[d][1,2,3]oxadiazol-6-amine)sulfonamide

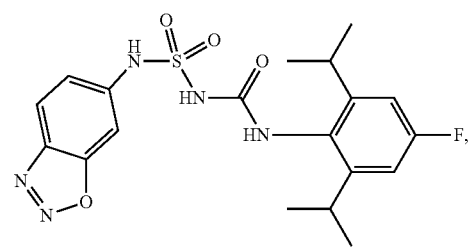

N-((4-fluoro-2,6-diisopropylphenyl)carbamoyl)
(benzo[d][1,2,3]oxadiazol-6-amine)sulfonamide

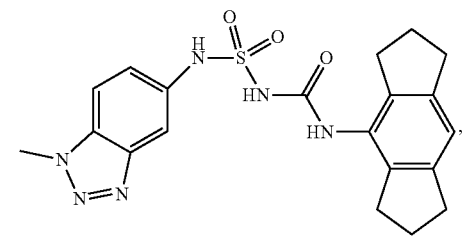

N-((1,2,3,5,6,7-hexahydro-s-indacen-4-
yl)carbamoyl)(1-methyl-1H-
benzo[d][1,2,3]triazol-5-amine)sulfonamide

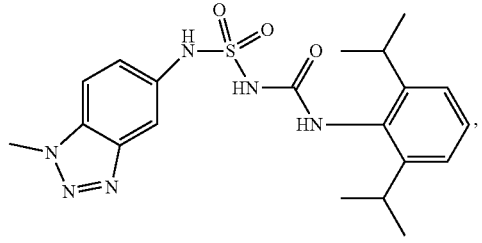

N-((2,6-diisopropylphenyl)carbamoyl)
(1-methyl-1H-benzo[d][1,2,3]triazol-5-amine)sulfonamide

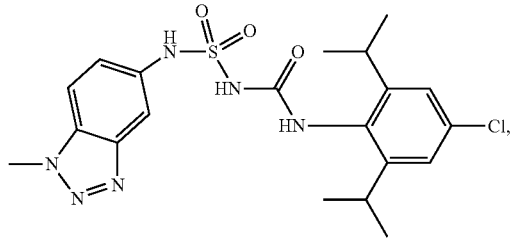

N-((4-chloro-2,6-diisopropylphenyl)carbamoyl)
(1-methyl-1H-benzo[d][1,2,3]triazol-5-
amine)sulfonamide

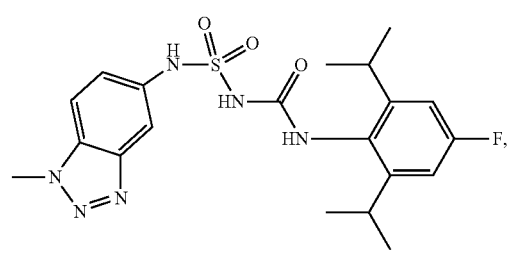

N-((4-fluoro-2,6-diisopropylphenyl)carbamoyl)
(1-methyl-1H-benzo[d][1,2,3]triazol-5-amine)sulfonamide

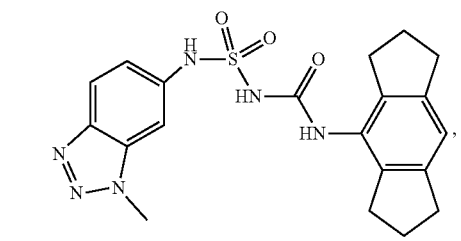

N-((1,2,3,5,6,7-hexahydro-s-indacen-4-
yl)carbmoyl)(1-methyl-1H-benzo[d][1,2,3]triazol-6-amine)
sulfonamide

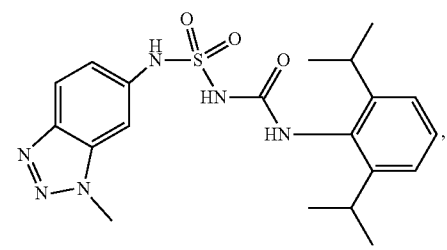

N-((2,6-diisopropylphenyl)carbamoyl)
(1-methyl-1H-benzo[d][1,2,3]triazol-6-amine)sulfonamide

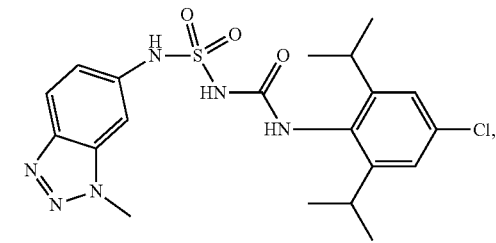

N-((4-chloro-2,6-diisopropylphenyl(carbamoyl)
(1-methyl-1H-benzo[d][1,2,3]triazol-6-
amine)sulfonamide -continued

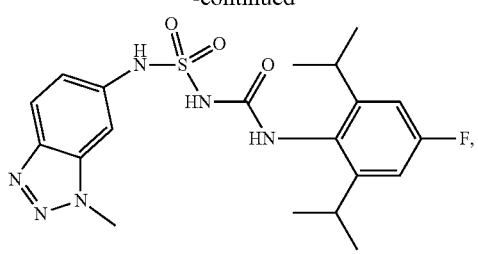

N-((4-fluoro-2,6-diisopropylphenyl)carbamoyl)
(1-methyl-1H-benzo[d][1,2,3]triazol-6-amine)sulfonamide

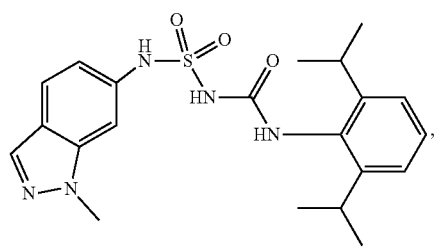

N-((2,6-diisopropylphenyl)carbamoyl)
(1-methyl-1H-indazol-6-amine)sulfonamide

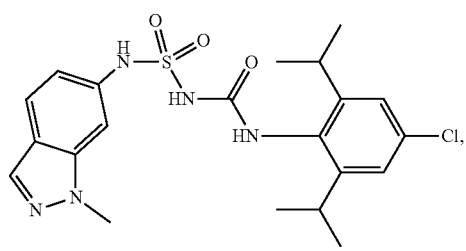

N-((4-chloro-2,6-diisopropylphenyl)carbamoyl)
(1-methyl-1H-indazol-6-amine)sulfonamide

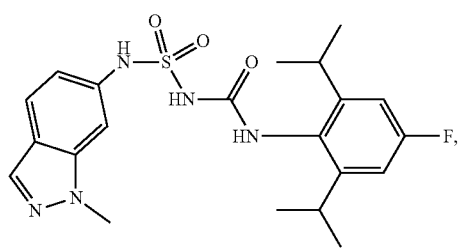

N-((4-fluoro-2,6-diisopropylphenyl)carbamoyl)
(1-methyl-1H-indazol-6-amine)sulfonamide

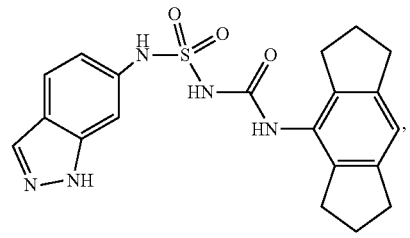

N-((1,2,3,5,6,7-hexahydro-s-indacen-4-yl)-
carbamoyl)(1H-indazol-6-amine)sulfonamide -continued

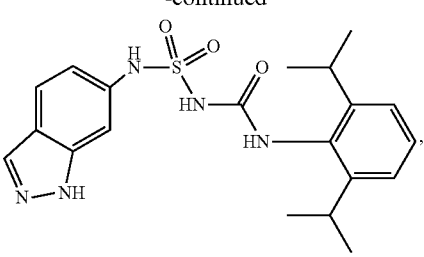

N-((2,6-diisopropylphenyl)carbamoyl)
(1H-indazol-6-amine)sulfonamide

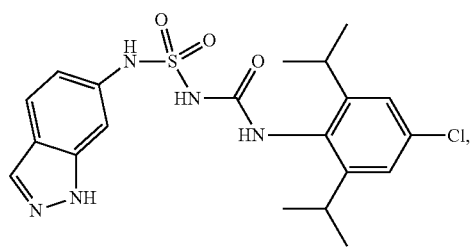

N-((4-chloro-2,6-diisopropylphenyl)carbamoyl)
(1H-indazol-6-amine)sulfonamide

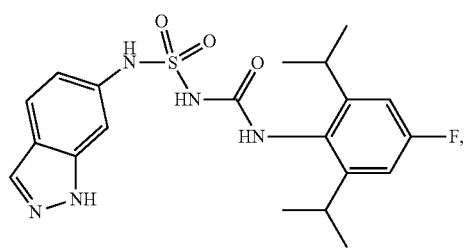

N-((4-fluoro-2,6-diisopropylphenyl)carbamoyl)
(1H-indazol-6-amine)sulfonamide

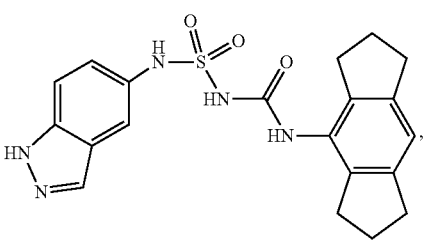

N-((1,2,3,5,6,7-hexahydro-s-indacen-4-yl)-
carbamoyl)(1H-indazol-5-amine)sulfonamide)

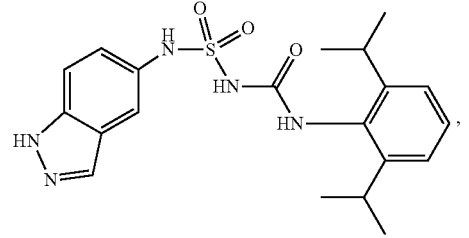

N-((2,6-diisopropylphenyl)carbamoyl)
(1H-indazol-5-amine)sulfonamide

-continued

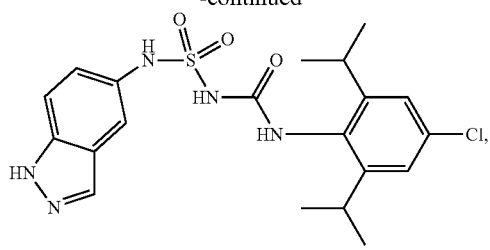

N-((4-chloro-2,6-diisopropylphenyl)carbamoyl)
(1H-indazol-5-amine)sulfonamide

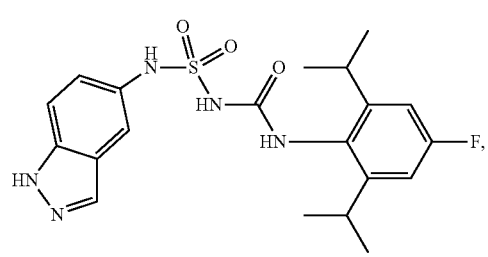

N-((4-fluoro-2,6-diisopropylphenyl)carbamoyl)
(1H-indazol-5-amine)sulfonamide

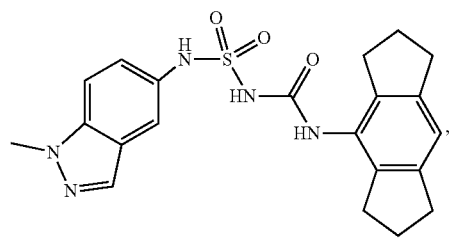

N-(1,2,3,5,6,7-hexahydro-s-indacen-4-yl)-
carbamoyl)(1-methyl-1H-indazol-5-
amine)sulfonamide

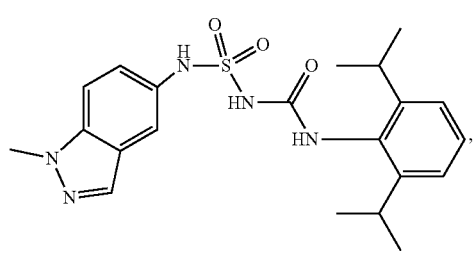

N-((2,6-diisopropylphenyl)carbamoyl)
(1-methyl-1H-indazol-5-amine)sulfonamide

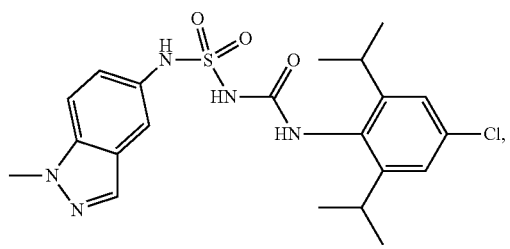

N-((4-chloro-2,6-diisopropylphenyl)carbamoyl)
(1-methyl-1H-indazol-5-amine)sulfonamide -continued

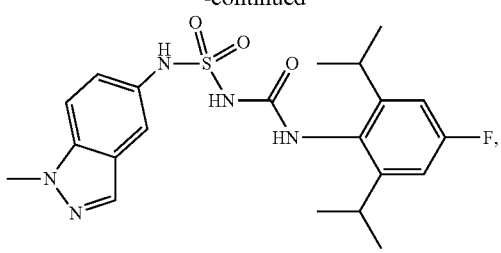

N-((4-fluoro-2,6-diisopropylphenyl)carbamoyl)
(1-methyl-1H-indazol-5-amine)sulfonamide

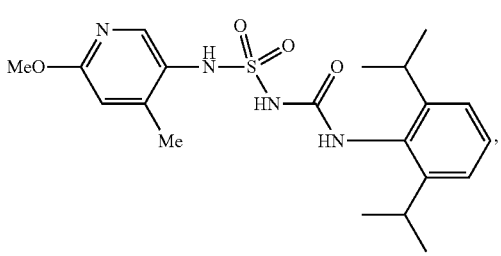

N-((2,6-diisopropylphenyl)carbamoyl)
(6-methoxy-4-methylpyridin-3-amino)sulfonamide

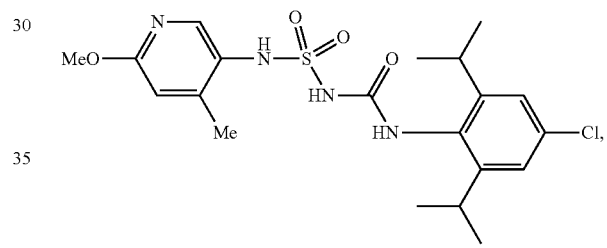

N-((4-chloro-2,6-diisopropylphenyl)carbamoyl)
(6-methoxy-4-methylpyridin-3-amino)sulfonamide

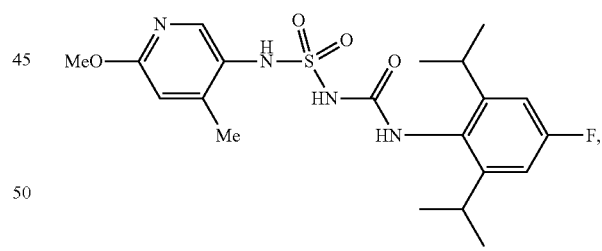

N-((4-fluoro-2,6-diisopropylphenyl)carbamoyl)(6-
methoxy-4-methylpyridin-3-amino)sulfonamide

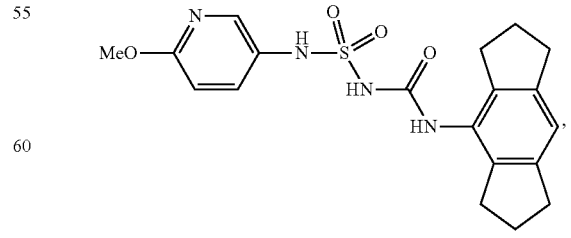

N-((1,2,3,5,6,7-hexahydro-s-indacen-4-
yl)carbamoyl)(6-methoxypyridin-3-
amino)sulfonamide

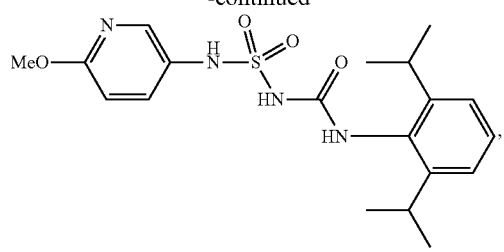

N-((2,6-diisopropylphenyl)carbamoyl)
(6-methoxypyridin-3-amino)sulfonamide

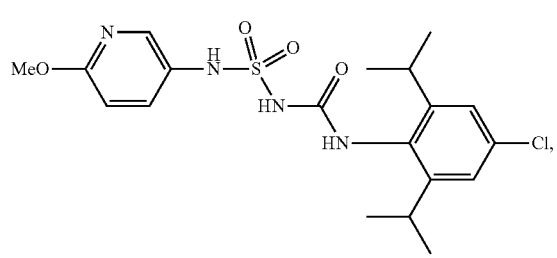

N-((4-chloro-2,6-diisopropylphenyl)carbamoyl)
(6-methoxypyridin-3-amino)sulfonamide

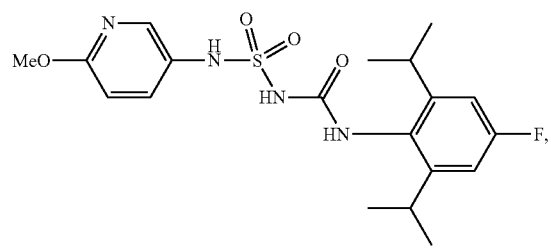

N-((4-fluoro-2,6-diisopropylphenyl)carbamoyl)
(6-methoxypyridin-3-amino)sulfonamide

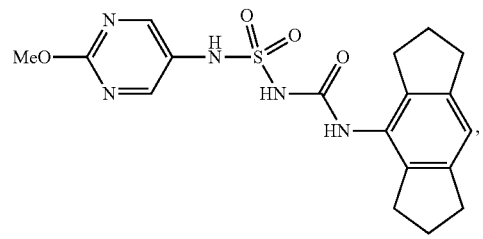

N-((1,2,3,5,6,7-hexahydro-s-indacen-4-
yl)carbamoyl)(2-methoxypyrimidin-5-
amino)sulfonamide

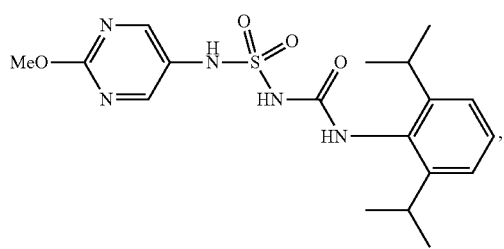

N-((2,6-diisopropylphenyl)carbamoyl)
(2-methoxypyrimidin-5-amino)sulfonamide

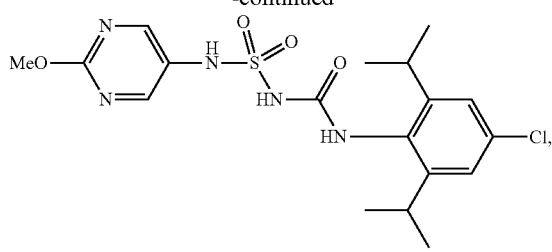

N-((4-chloro-2,6-diisopropylphenyl)carbamoyl)
(2-methoxypyrimidin-5-amino)sulfonamide

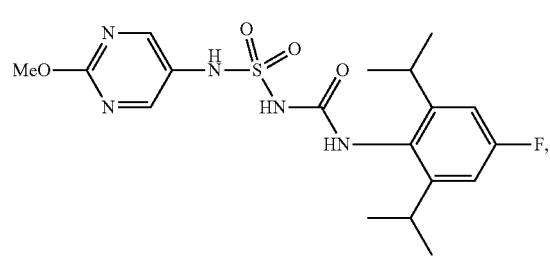

N-((4-fluoro-2,6-diisopropylphenyl)carbamoyl)
(2-methoxypyrimidin-5-amino)sulfonamide

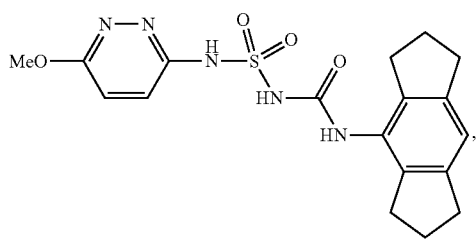

N-((1,2,3,5,6,7-hexahydro-s-indacen-4-
yl)carbamoyl)(6-methoxypyridazin-3-
amino)sulfonamide

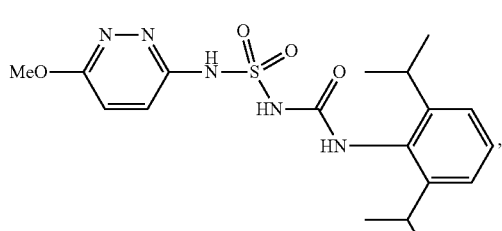

N-((2,6-diisopropylphenyl)carbamoyl)
(6-methoxypyridazin-3-amino)sulfonamide

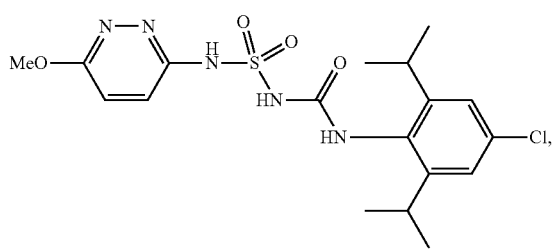

N-((4-chloro-2,6-diisopropylphenyl)carbamoyl)
(6-methoxypyridazin-3-amino)sulfonamide

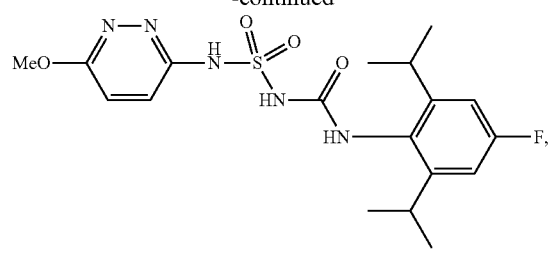

N-((4-fluoro-2,6-diisopropylphenyl)carbamoyl)
(6-methoxypyridazin-3-amino)sulfonamide

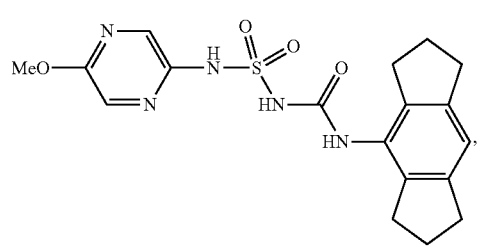

N-((1,2,3,5,6,7-hexahydro-s-indacen-4-
yl)carbamoyl)(5-methoxypyrazin-2-
amino)sulfonamide

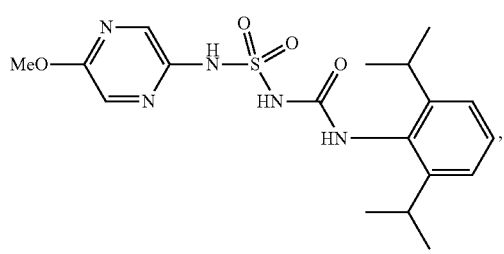

N-((2,6-diisopropylphenyl)carbamoyl)
(5-methoxypyrazin-2-amino)sulfonamide

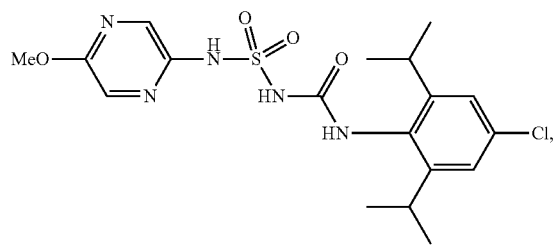

N-((4-chloro-2,6-diisopropylphenyl)carbamoyl)
(5-methoxypyrazin-2-amino)sulfonamide

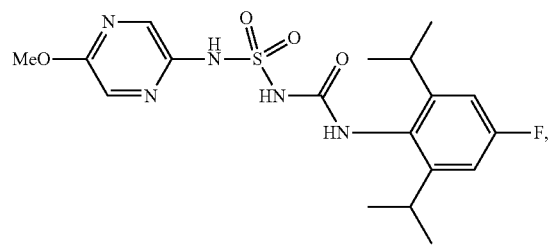

N-((4-fluoro-2,6-diisopropylphenyl)carbamoyl)
(5-methoxypyrazin-2-amino)sulfonamide

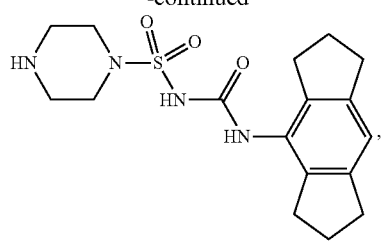

N-((1,2,3,5,6,7-hexahydro-s-indacen-4-
yl)carbamoyl)piperazine-1-sulfonamide

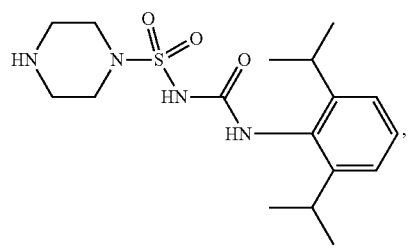

N-((2,6-diisopropylphenyl)carbamoyl)
-piperazine-1-sulfonamide

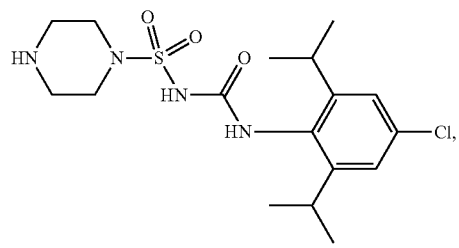

N-((4-chloro-2,6-diisopropylphenyl)carbamoyl)
-piperazine-1-sulfonamide

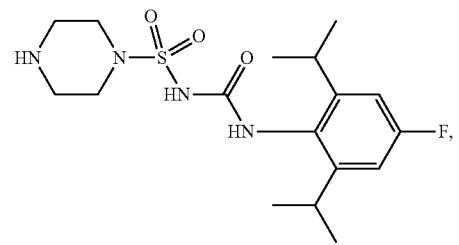

N-((4-fluoro-2,6-
diisopropylphenyl)carbamoyl)-
piperazine-1-sulfonamide

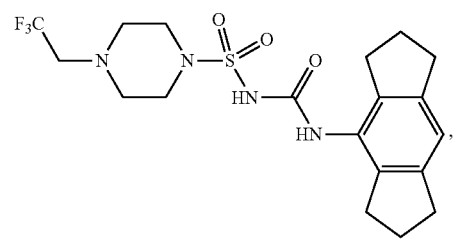

N-((1,2,3,5,6,7-hexahydro-s-indacen-4-yl)carbamoyl)-4-
(2,2,2-trifluoroethyl)piperazine-1-sulfonamide

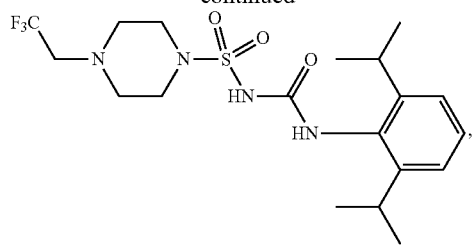

N-((2,6-diisopropylphenyl)carbamoyl)
-4-(2,2,2-trifluoroethyl)piperazine-1-sulfonamide

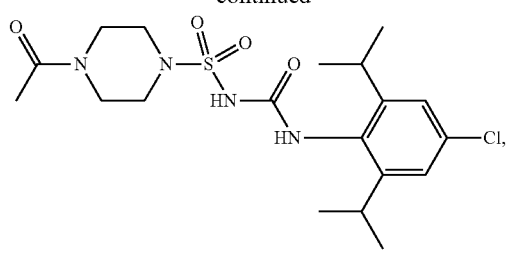

4-acetyl-N-((4-chloro-2,6-diisopropylphenyl)carbamoyl)
-piperazine-1-sulfonamide

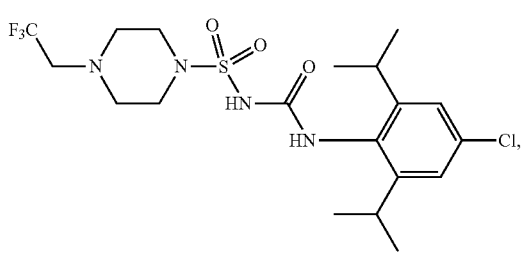

4-((4-chloro-2,6-diisopropylphenyl)carbamoyl)
-4-(2,2,2-trifluoroethyl)piperazine-1-sulfonamide

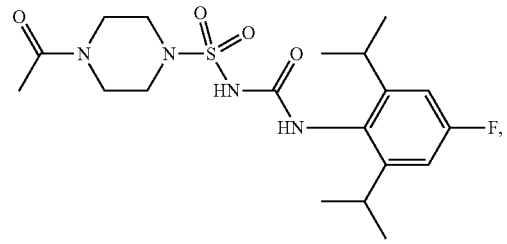

4-acetyl-N-((4-fluoro-2,6-diisopropylphneyl)carbamoyl)
-piperazine-1-sulfonamide

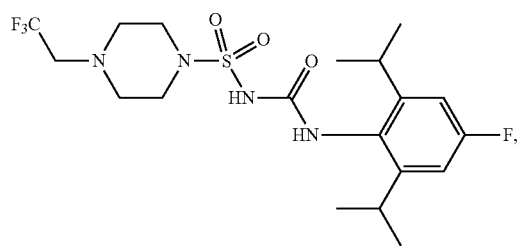

N-((4-fluoro-2,6-
diisopropylphenyl)carbamoyl)-4-(2,2,2-
trifluoroethyl)piperazine-1-sulfonamide

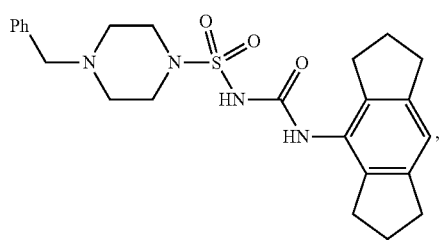

4-benzyl-N-((1,2,3,5,6,7-hexahydro-s-indacen-4-
yl)carbamoyl)piperazine-1-sulfonamide

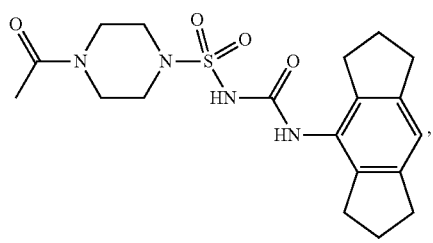

4-acetyl-N-((1,2,3,5,6,7-hexahydro-s-indacen-4-
yl)carbamoyl)piperazine-1-sulfonamide

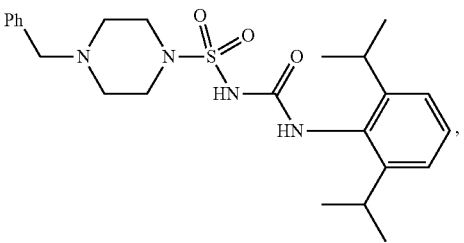

4-benzyl-N-((2,6-diisopropylphenyl)carbamoyl)
-piperazine-1-sulfonamide

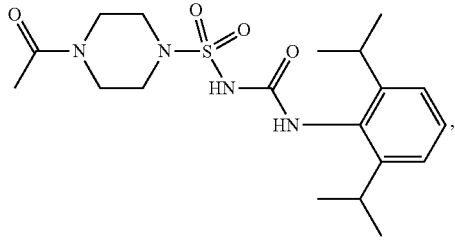

4-acetyl-N-((2,6-diisopropylphenyl)carbamoyl)
-piperazine-1-sulfonamide

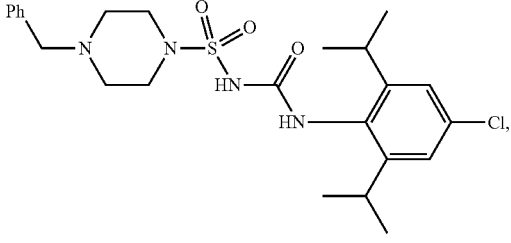

4-phenyl-N-((4-chloro-2,6-diisopropylphenyl)carbamoyl)
-piperazine-1-sulfonamide

163

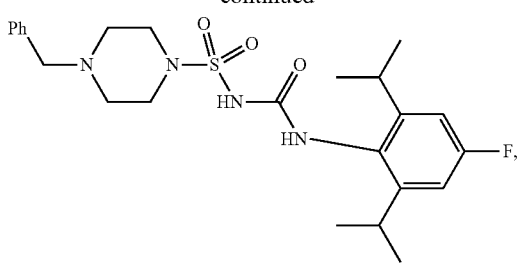

4-benzyl-N-((4-fluoro-2,6-diisopropylphenyl)carbamoyl)-piperazine-1-sulfonamide

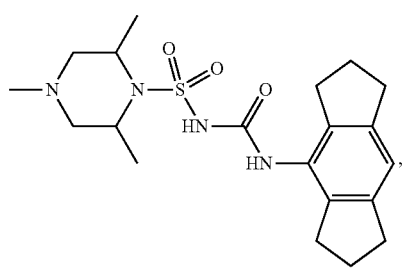

N-((1,2,3,5,6,7-hexahydro-s-indacen-4-yl)carbamoyl)-2,4,6-trimethylpiperazine-1-sulfonamide

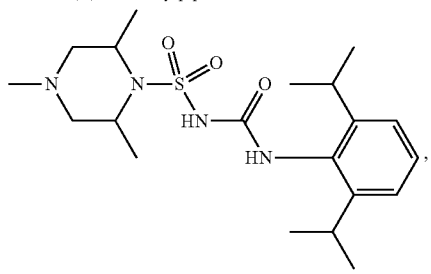

N-((2,6-diisopropylphenyl)carbamoyl)-2,4,6-trimethylpiperazine-1-sulfonamide

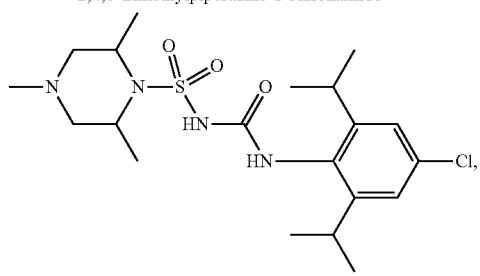

N-((4-chloro-2,6-diisopropylphenyl)carbamoyl)-2,4,6-trimethylpiperazine-1-sulfonamide

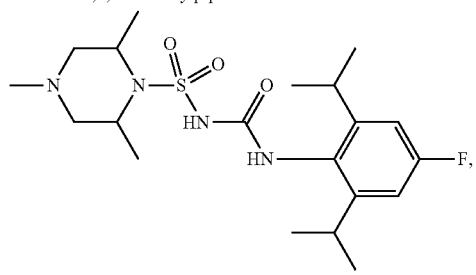

N-((4-fluoro-2,6-diisopropylphenyl)-carbamoyl)-2,4,6-trimethylpiperazine-1-sulfonamide

164

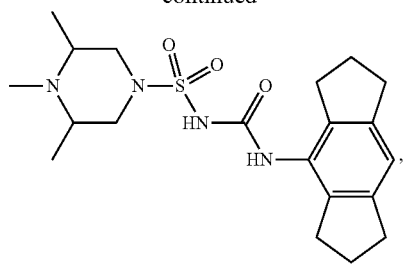

N-((1,2,3,5,6,7-hexahydro-s-indacen-4-yl)carbamoyl)-3,4,5-trimethylpiperazine-1-sulfonamide

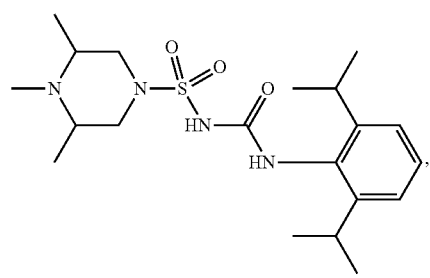

N-((2,6-diisopropylphenyl)carbamoyl)-3,4,5-trimethylpiperazine-1-sulfonamide

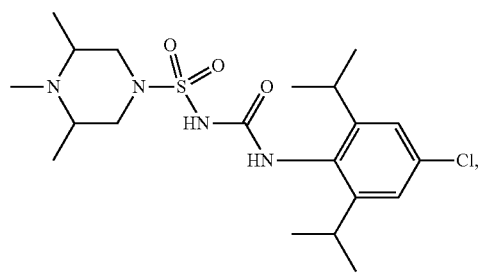

N-((4-chloro-2,6-diisopropylphenyl)carbamoyl)-3,4,5-trimethylpiperazine-1-sulfonamide

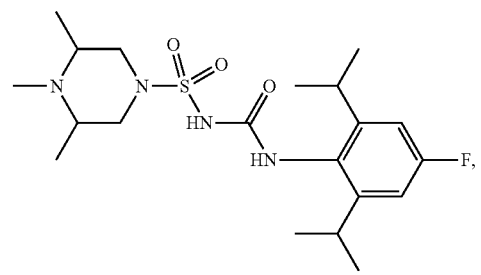

N-((4-fluoro-2,6-diisopropylphenyl)carbamoyl)-3,4,5-trimethylpiperazine-1-sulfonamide

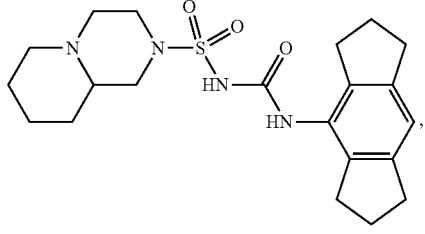

N-((1,2,3,5,6,7-hexahydro-s-indacen-4-yl)carbamoyl)octahydro-2H-pyrido[1,2-a]pyrazine-2-sulfonamide

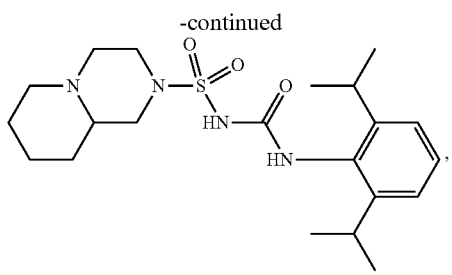

N-((2-6-diisopropylphenyl)carbamoyl)-
octahydro-2H-pyrido[1,2-a]pyrazine-2-sulfonamide

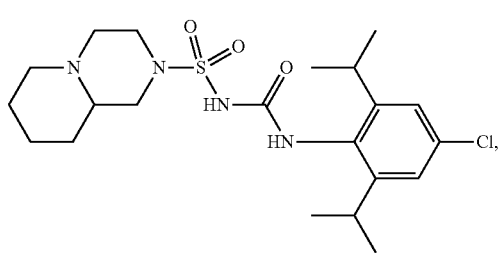

N-((4-chloro-2,6-diisopropylphenyl)carbamoyl)
-octahydro-2H-pyrido[1,2-a]pyrazine-2-sulfonamide

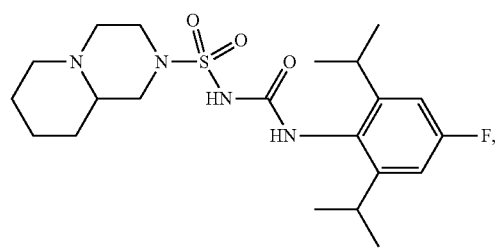

N-((4-fluoro-2,6-diisopropylphenyl)-
carbamoyl)octahydro-2H-pyrido[1,2-
a]pyrazine-2-sulfonamide

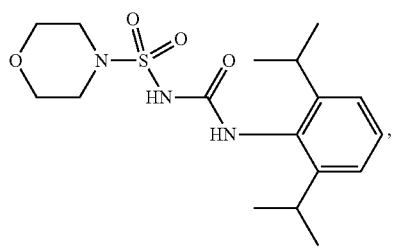

N-((2,6-diisopropylphenyl)carbamoyl)
-morpholine-4-sulfonamide

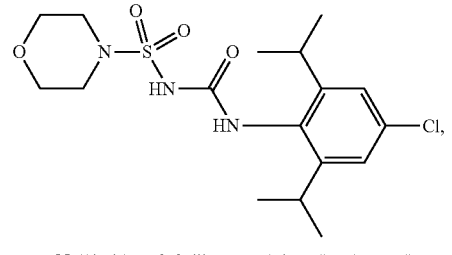

N-((4-chloro-2,6-diisopropylphenyl)carbamoyl)
-morpholine-4-sulfonamide

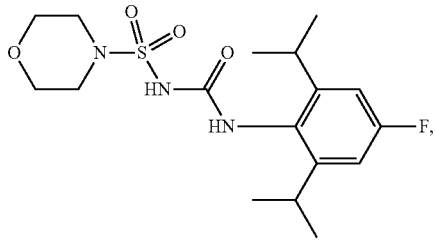

N-((4-fluoro-2,6-
diisopropylphenyl)carbamoyl)morpholine-
4-sulfonamide

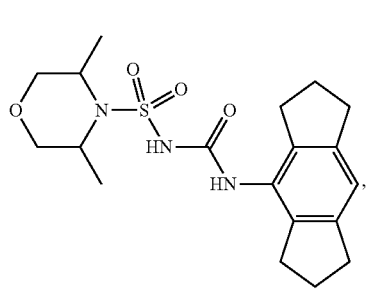

N-((1,2,3,5,6,7-hexahydro-s-indacen-
4-yl)carbamoyl)-3,5-
dimethylmorpholine-4-sulfonamide

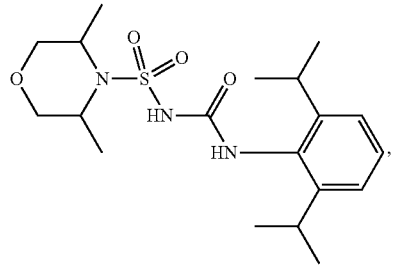

N-((2,6-diisopropylphenyl)carbamoyl)
-3,5-dimethylmorpholine-4-sulfonamide

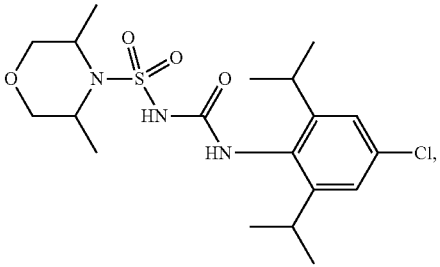

N-((4-chloro-2,6-diisopropylphenyl)carbamoyl)
-3,5-dimethylmorpholine-4-sulfonamide

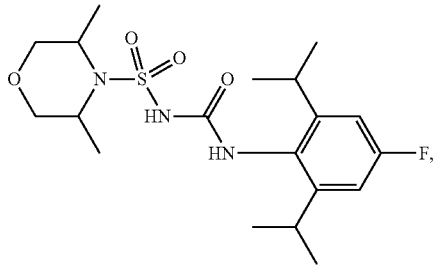

N-((4-fluoro-2,6-
diisopropylphenyl)carbamoyl)-3,5-
dimethylmorpholine-4-sulfonamide

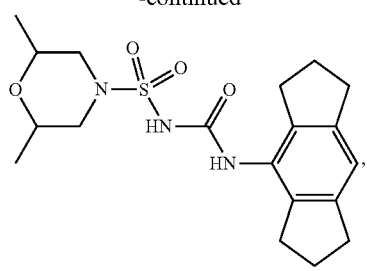

N-((1,2,3,5,6,7-hexahydro-s-indacen-4-yl)carbamoyl)-2,6-dimethylmorpholine-4-sulfonamide

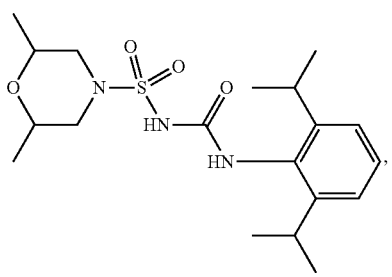

N-((2,6-diisopropylphenyl)carbamoyl)-2,6-dimethylmorpholine-4-sulfonamide

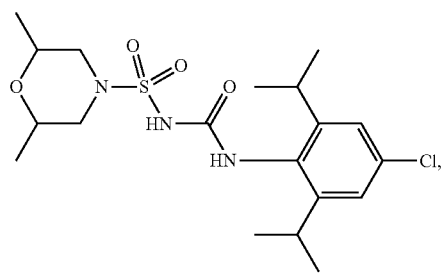

N-((4-chloro-2,6-diisopropylphenyl)carbamoyl)-2,6-dimethylmorpholine-4-sulfonamide

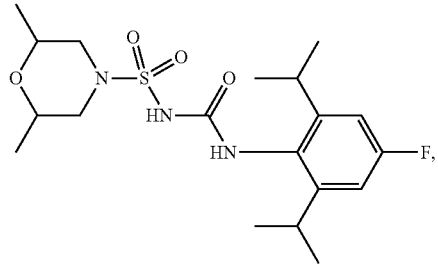

N-((4-fluoro-2,6-diisopropylphenyl)carbamoyl)-2,6-dimethylmorpholine-4-sulfonamide

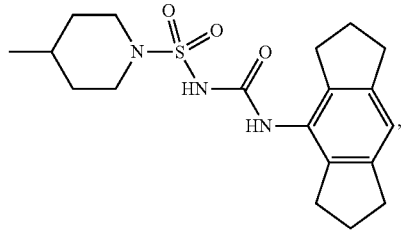

N-((1,2,3,5,6,7-hexahydro-s-indacen-4-yl)carbamoyl)-4-methylpiperadine-1-sulfonamide

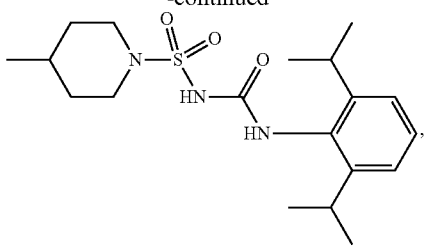

N-((2,6-diisopropylphenyl)carbamoyl)-4-methylpiperadine-1-sulfonamide

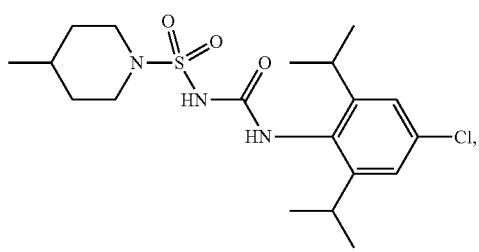

N-((4-chloro-2,6-diisopropylphenyl)carbamoyl)-4-methylpiperadine-1-sulfonamide

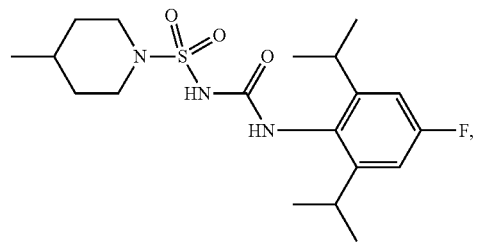

N-((4-fluoro-2,6-diisopropylphenyl)carbamoyl)-4-methylpiperadine-1-sulfonamide

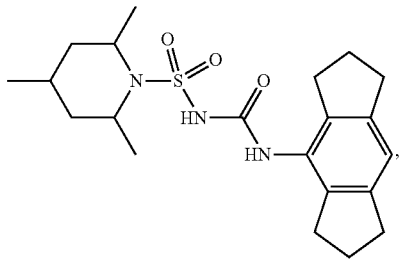

N-((1,2,3,5,6,7-hexahydro-s-indacen-4-yl)carbamoyl)-2,4,6-trimethylpiperadine-1-sulfonamide

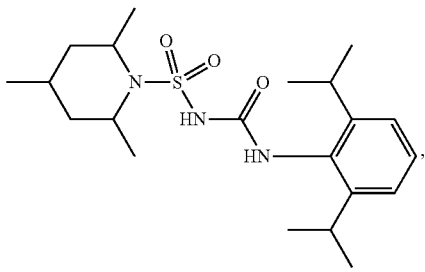

N-((2,6-diisopropylphenyl)carbamoyl)-2,4,6-trimethylpiperadine-1-sulfonamide

-continued

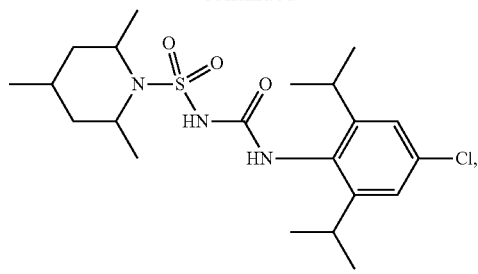

N-((4-chloro-2,6-diisopropylphenyl)carbamoyl)
-2,4,6-trimethylpiperadine-1-sulfonamide

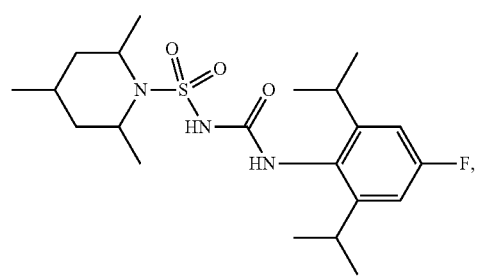

N-((4-fluoro-2,6-
diisopropylphenyl)carbamoyl)-2,4,6-
trimethylpiperadine-1-sulfonamide

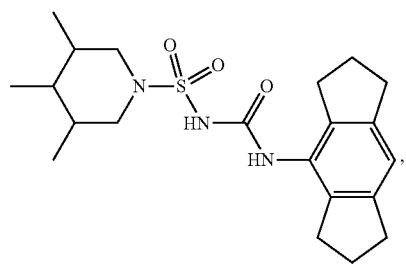

N-((1,2,3,5,6,7-hexahydro-s-indacen-4-
yl)carbamoyl)-3,4,5-trimethylpiperadine-1-
sulfonamide

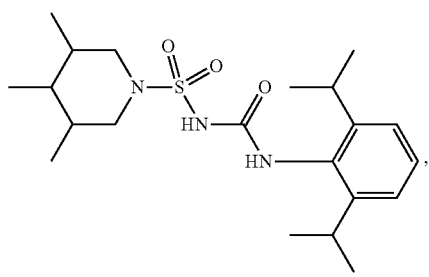

N-((2,6-diisopropylphenyl)carbamoyl)
-3,4,5-trimethylpiperadine-1-sulfonamide

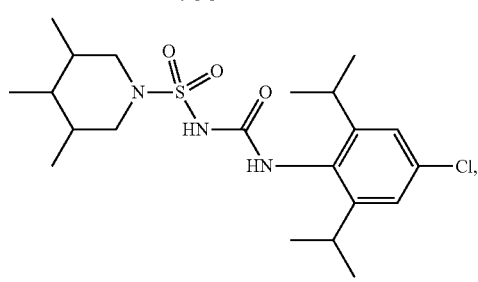

N-((4-chloro-2,6-diisopropylphenyl)carbamoyl)
-3,4,5-trimethylpiperadine-1-sulfonamide -continued

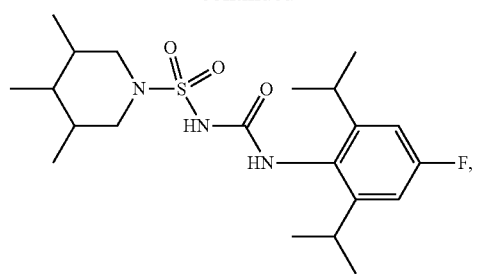

N-((4-fluoro-2,6-
diisopropylphenyl)carbamoyl)-3,4,5-
trimethylpiperadine-1-sulfonamide

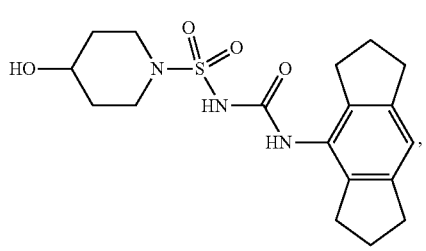

N-((1,2,3,5,6,7-hexahydro-s-indacen-4-
yl)carbamoyl)-4-hydroxypiperadine-1-
sulfonamide

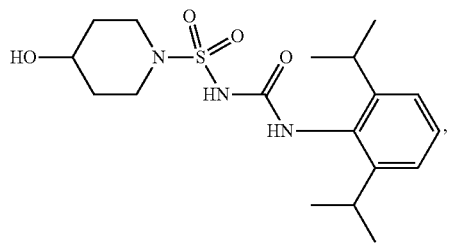

N-((2,6-diisopropylphenyl)carbamoyl)
-4-hydroxypiperadine-1-sulfonamide

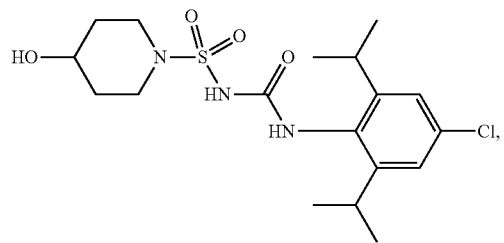

N-((4-chloro-2,6-diisopropylphenyl)carbamoyl)
-4-hydroxypiperidine-1-sulfonate

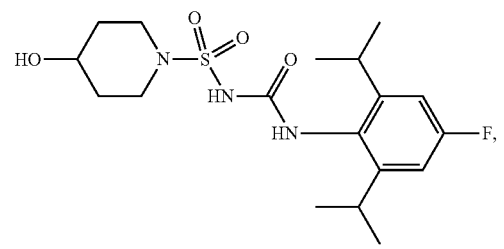

N-((4-fluoro-2,6-diisopropylphenyl)carbamoyl)
-4-hydroxypiperadine-1-sulfonamide

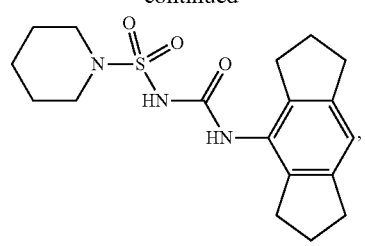
N-((1,2,3,5,6,7-hexahydro-s-indacen-4-yl)carbamoyl)piperadine-1-sulfonamide
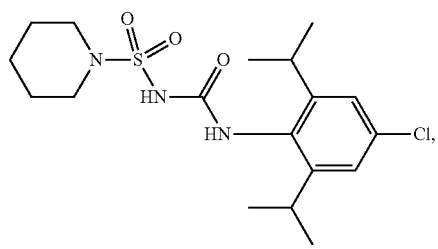
N-((4-chloro-2,6-diisopropylphenyl)carbamoyl)-piperadine-1-sulfonamide
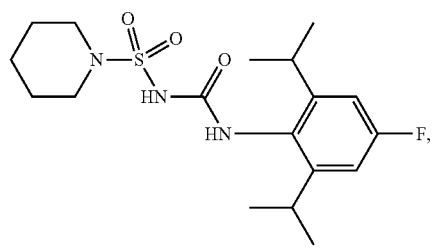
N-((4-fluoro-2,6-diisopropylphenyl)carbamoyl)piperadine-1-sulfonamide
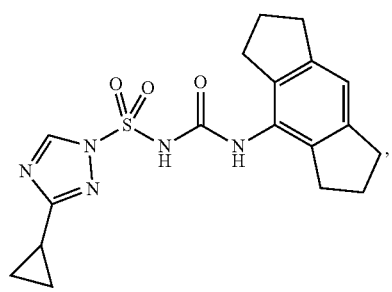
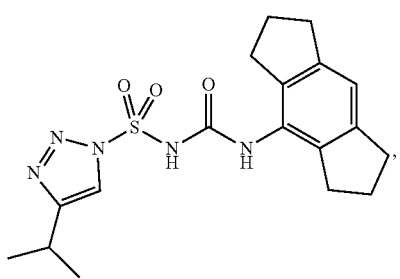
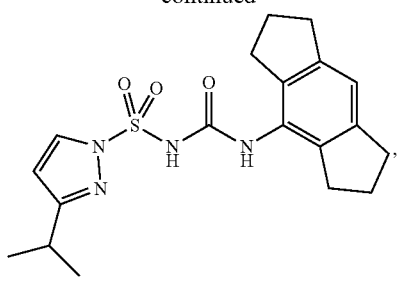
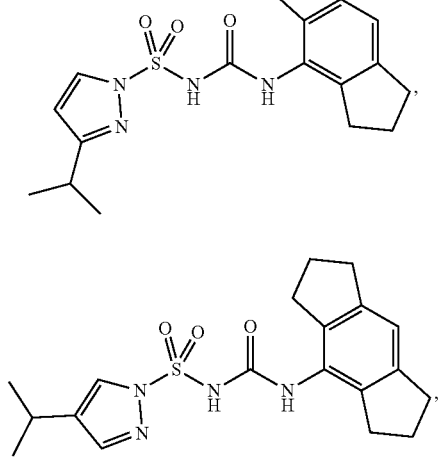
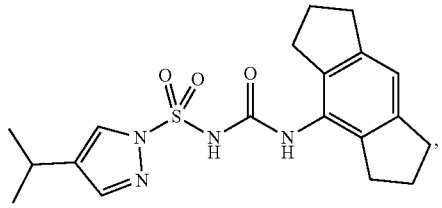
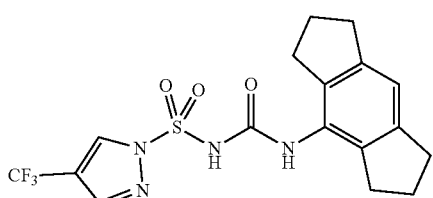
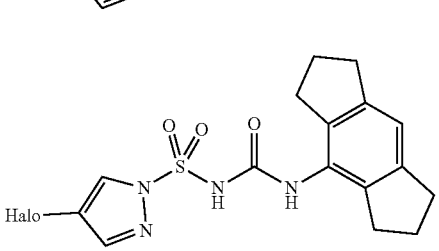
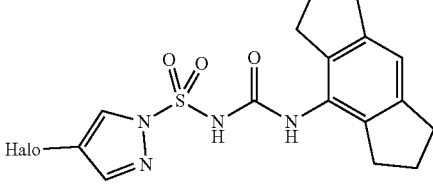
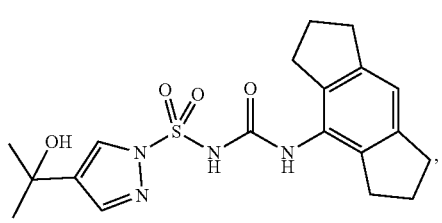
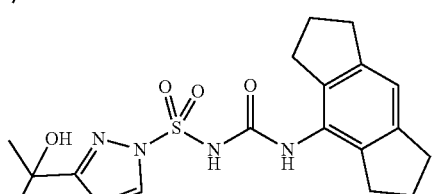
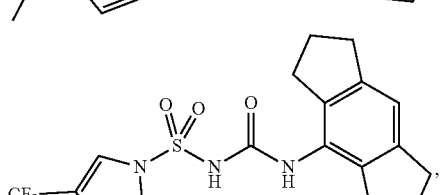

-continued

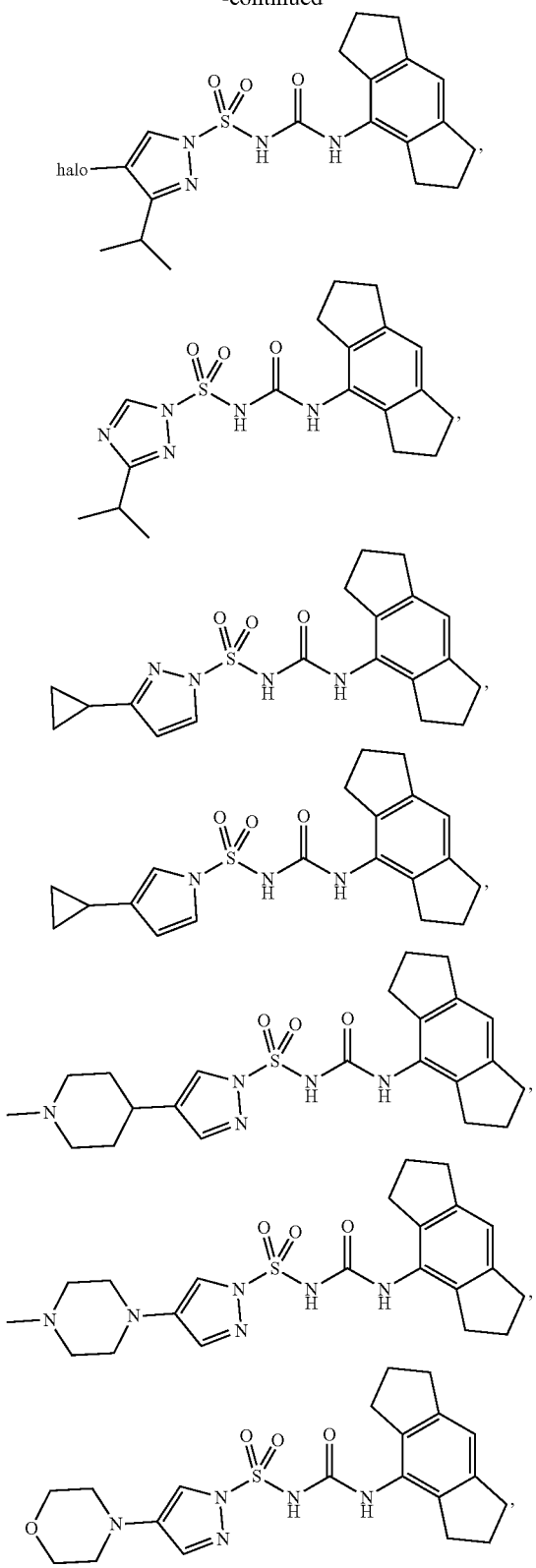

or a pharmaceutically acceptable salt or solvate thereof.

12. The compound of claim 3, wherein one or both $R^1$ or A is selected from pyrazole or triazole, optionally substituted at a ring atom with a group selected from halo, isopropyl, morpholinyl, piperidinyl, and piperazinyl, each of which groups may themselves be optionally substituted with $C_1$-$C_6$ alkyl.

13. The compound of claim 1, wherein $W^2$ and $R^2$ form a hexahydro-indacene group.

14. The compound of claim 2, wherein $W^2$ and $R^2$ form a hexahydro-indacene group.

15. The compound of claim 3, wherein $W^2$ and $R^2$ form a hexahydro-indacene group.

16. The compound of claim 1, wherein any optional substituent is independently selected from the group consisting of $C_{1-10}$ alkyl; $C_{3-6}$ cycloalkyl; hydroxylalkyl; $C_{1-10}$ alkoxy; $C_{2-10}$ alkenyl; $C_{2-10}$ alkynyl; $C_{6-12}$ aryl; aryloxy; heteroaryl; heterocyclyl; halo; hydroxyl; halogenated alkyl; amino; alkylamino; arylamino; acyl; amido; CN; $NO_2$; $N_3$; $CH_2OH$; $CONH_2$; $CONR^{24}R^{25}$; $CO_2R^{24}$; $CH_2OR^{24}$; $NHCO_2R^{24}$; $NHCO_2R^{24}$; $C_{1-3}$ alkylthio; sulfate; sulfonic acid; sulfonate esters; phosphonic acid; phosphate; phosphonate; mono-, di-, or triphosphate esters: trityl; monomethoxytrityl; $R^{24}SO$; $R^{24}SO_2$; $CF_3S$; $CF_3SO_2$; and trialkylsilyl; wherein $R^{24}$ and $R^{25}$ are each independently selected from H or $C_{1-10}$ alkyl.

17. The compound of claim 2, wherein any optional substituent is independently selected from the group consisting of $C_{1-10}$ alkyl; $C_{3-6}$ cycloalkyl; hydroxylalkyl; $C_{1-10}$ alkoxy; $C_{2-10}$ alkenyl; $C_{2-10}$ alkynyl; $C_{6-12}$ aryl; aryloxy; heteroaryl; heterocyclyl; halo; hydroxyl; halogenated alkyl; amino; alkylamino; arylamino; acyl; amido; CN; $NO_2$; $N_3$; $CH_2OH$; $CONH_2$; $CONR^{24}R^{25}$; $CO_2R^{24}$; $CH_2OR^{24}$; $NHCOR^{24}$; $NHCO_2R^{24}$; $C_{1-3}$ alkylthio; sulfate; sulfonic acid; sulfonate esters; phosphonic acid; phosphate; phosphonate; mono-, di-, or triphosphate esters; trityl; monomethoxytrityl; $R^{24}SO$; $R^{24}SO_2$; $CF_3S$; $CF_3SO_2$; and trialkylsilyl; wherein $R^{24}$ and $R^{25}$ are each independently selected from H or $C_{1-10}$ alkyl.

18. The compound of claim 3, wherein any optional substituent is independently selected from the group consisting of $C_{1-10}$ alkyl; $C_{3-6}$ cycloalkyl; hydroxylalkyl; $C_{1-10}$ alkoxy; $C_{2-10}$ alkenyl; $C_{2-10}$ alkynyl; $C_{6-12}$ aryl; aryloxy; heteroaryl; heterocyclyl; halo; hydroxyl; halogenated alkyl; amino; alkylamino; arylamino; acyl; amido; CN; $NO_2$; $N_3$; $CH_2OH$; $CONH_2$; $CONR^{24}R^{25}$; $CO_2R^{24}$; $CH_2OR^{24}$; $NHCOR^{24}$; $NHCO_2R^{24}$; $C_{1-3}$ alkylthio; sulfate; sulfonic acid; sulfonate esters; phosphonic acid; phosphate; phosphonate; mono-, di-, or triphosphate esters; trityl; monomethoxytrityl; $R^{24}SO$; $R^{24}SO_2$; $CF_3S$; $CF_3SO_2$; and trialkylsilyl; wherein $R^{24}$ and $R^{25}$ are each independently selected from H or $C_{1-10}$ alkyl.

19. A pharmaceutical composition comprising the compound of claim 2, or the pharmaceutically acceptable salt or solvate thereof, and a pharmaceutically acceptable carrier, diluent and/or excipient.

20. A method of treating or preventing a disease, disorder or condition in a subject including the step of administering an effective amount of the compound of claim 2, or the pharmaceutically acceptable salt or solvate thereof, to the subject thereby treating or preventing the disease, disorder or condition, wherein the disease, disorder or condition is responsive to inhibition of activation of the NLRP3 inflammasome.

21. The method of claim 20, wherein the disease, disorder or condition is:
(i) a disease, disorder or condition of the immune system; and/or
(ii) an inflammatory disease, disorder or condition or an autoimmune disease, disorder or condition; and/or
(iii) a disease, disorder or condition of the skin; and/or (iv) a disease, disorder or condition of the cardiovascular system; and/or
(v) a cancer, tumour or other malignancy; and/or
(vi) a disease, disorder or condition of the renal system; and/or
(vii) a disease, disorder or condition of the gastro-intestinal tract; and/or
(viii) a disease, disorder or condition of the respiratory system; and/or
(ix) a disease, disorder or condition of the endocrine system; and/or
(x) a disease, disorder or condition of the central nervous system (CNS); and/or
(xi) selected from the group consisting of constitutive inflammation, autoinflammatory disease, autoimmune diseases, respiratory diseases, central nervous system diseases, metabolic disease, ocular diseases, kidney disease, liver disease, inflammatory reactions in skin, inflammatory reactions in the joints, viral infections, and cancers; and/or
(xii) selected from the group consisting of cryopyrin-associated periodic syndromes (CAPS); Muckle-Wells syndrome (MWS); familial cold autoinflammatory syndrome (FCAS); neonatal-onset multisystem inflammatory disease (NOMID); familial Mediterranean fever (FMF); TNF receptor associated periodic syndrome (TRAPS); mevalonate kinase deficiency (MKD); hyperimmunoglobulinemia D and periodic fever syndrome (HIDS); deficiency of interleukin 1 receptor antagonist (DIRA); Majeed syndrome; pyogenic arthritis, pyoderma gangrenosum and acne syndrome (PAPA); haploinsufficiency of A20 (HA20); pediatric granulomatous arthritis (PGA); PLCG2-associated antibody deficiency and immune dysregulation (PLAID); autoinflammation, PLCG2-associated antibody deficiency and immune dysregulation (APLAID); and sideroblastic anemia with B-cell immunodeficiency, periodic fevers, and developmental delay (SIFD); multiple sclerosis (MS); type-1 diabetes; psoriasis; rheumatoid arthritis; Behcet's disease; Sjogren's syndrome; Schnitzler syndrome; chronic obstructive pulmonary disorder (COPD); steroid-resistant asthma; asbestosis; silicosis; cystic fibrosis; Parkinson's disease; Alzheimer's disease; motor neuron disease; Huntington's disease; cerebral malaria; brain injury from pneumococcal meningitis; Type 2 diabetes; atherosclerosis; obesity; gout; pseudo-gout; ocular diseases of the ocular epithelium; age-related macular degeneration (AMD); corneal infection; dry eye; chronic kidney disease; oxalate nephropathy; diabetic nephropathy; non-alcoholic steatohepatitis (NASH); alcoholic liver disease; contact hypersensitivity; and sunburn; osteoarthritis; systemic juvenile idiopathic arthritis; adult-onset Still's disease; relapsing polychondritis; infections, with alpha virus (Chikungunya, Ross River); infection with flavivirus (Dengue, Zika); flu; HIV; hidradenitis suppurativa (HS); cyst-causing skin diseases; lung cancer metastasis; pancreatic cancers; gastric cancers; myelodysplastic syndrome; leukemia; polymyositis; stroke; myocardial infarction; Graft versus Host Disease; hypertension; colitis; helminth infection; bacterial infection; abdominal aortic aneurysm; wound healing; depression; psychological stress; ischaemia reperfusion injury; and diseases where an individual has been determined to carry a germline or somatic non-silent mutation in NLRP3.

22. The method of claim 20, wherein the subject is a mammal, such as a human subject.

23. A method of diagnosing a disease, disorder or condition in a mammal including the step of administering the compound of claim 2, or the pharmaceutically acceptable salt or solvate thereof, which compound, pharmaceutically acceptable salt or solvate is labelled, to the mammal or to a biological sample obtained from the mammal to facilitate diagnosis of the disease, disorder or condition in the mammal, wherein the disease, disorder or condition is responsive to inhibition of activation of the NLRP3 inflammasome.

24. A method of modulating the activity of a biological target comprising the step of exposing the biological target to the compound of claim 2, or the pharmaceutically acceptable salt or solvate thereof, wherein the biological target is selected from the group consisting of the NLRP3 inflammasome, IL-1β and IL-18.

25. A pharmaceutical composition comprising the compound of claim 3, or the pharmaceutically acceptable salt or solvate thereof, and a pharmaceutically acceptable carrier, diluent and/or excipient.

26. A method of treating or preventing a disease, disorder or condition in a subject including the step of administering an effective amount of the compound of claim 3, or the pharmaceutically acceptable salt or solvate thereof, to the subject thereby treating or preventing the disease, disorder or condition, wherein the disease, disorder or condition is responsive to inhibition of activation of the NLRP3 inflammasome.

27. The method of claim 26, wherein the disease, disorder or condition is:
(i) a disease, disorder or condition of the immune system; and/or
(ii) an inflammatory disease, disorder or condition or an autoimmune disease, disorder or condition; and/or
(iii) a disease, disorder or condition of the skin; and/or
(iv) a disease, disorder or condition of the cardiovascular system; and/or
(v) a cancer, tumour or other malignancy; and/or
(vi) a disease, disorder or condition of the renal system; and/or
(vii) a disease, disorder or condition of the gastro-intestinal tract; and/or
(viii) a disease, disorder or condition of the respiratory system; and/or
(ix) a disease, disorder or condition of the endocrine system; and/or
(xi) a disease, disorder or condition of the central nervous system (CNS); and/or
(xii) selected from the group consisting of constitutive inflammation, autoinflammatory diseases, autoimmune diseases, respiratory diseases, central nervous system diseases, metabolic diseases, ocular diseases, kidney disease, liver disease, inflammatory reactions in skin, inflammatory reactions in the joints, viral infections, and cancers; and/or
(xii) selected from the group consisting of cryopyrin-associated periodic syndromes (CAPS); Muckle-Wells syndrome (MWS); familial cold autoinflammatory syndrome (FCAS); neonatal-onset multisystem inflammatory disease (NOMID); familial Mediterranean fever (FMF); TNF receptor associated periodic syndrome (TRAPS); mevalonate kinase deficiency (MKD); hyperimmunoglobulinemia D and periodic fever syndrome (HIDS); deficiency of interleukin 1 receptor antagonist (DIRA); Majeed syndrome; pyogenic arthritis, pyoderma gangrenosum and acne syndrome (PAPA); haploinsufficiency of A20 (HA20); pediatric granulomatous arthritis (PGA); PLCG2-associated antibody deficiency and immune dysregulation (PLAID); autoinflammation, PLCG2-associated antibody deficiency and immune dysregulation (APLAID); sideroblastic anemia with B-cell immunodeficiency, periodic fevers, and developmental delay (SIFD); multiple sclerosis (MS); type-1 diabetes; psoriasis; rheumatoid arthritis; Behcet's disease; Sjogren's syndrome; Schnitzler syndrome; chronic obstructive pulmonary disorder (COPD); steroid-resistant asthma; asbestosis; silicosis; cystic fibrosis; Parkinson's disease; Alzheimer's disease; motor neuron disease; Huntington's disease; cerebral malaria; brain injury from pneumococcal meningitis; Type 2 diabetes; atherosclerosis; obesity; gout; pseudo-gout; ocular diseases of the ocular epithelium; age-related macular degeneration (AMD); corneal infection; dry eye; chronic kidney disease; oxalate nephropathy; diabetic nephropathy; non-alcoholic steatohepatitis (NASH); alcoholic liver disease; contact hypersensitivity; sunburn; osteoarthritis; systemic juvenile idiopathic arthritis; adult-onset Still's disease; relapsing polychondritis; infections with alpha virus (Chikungunya, Ross River); infection with flavivirus (Dengue, Zika); flu; HIV; hidradenitis suppurativa (HS); cyst-causing skin diseases; lung cancer metastasis; pancreatic cancers; gastric cancers; myelodysplastic syndrome; leukemia; polymyositis; stroke; myocardial infarction; Graft versus Host Disease; hypertension; colitis; helminth infection; bacterial infection; abdominal aortic aneurism; wound healing; depression; psychological stress; ischaemia reperfusion injury; and diseases where an individual has been determined to carry a germline or somatic non-silent mutation in NLRP3.

28. The method of claim 26, wherein the subject is a mammal, such as a human subject.

29. A method of diagnosing a disease, disorder or condition in a mammal including the step of administering the compound of claim 3, or the pharmaceutically acceptable salt or solvate thereof, which compound, pharmaceutically acceptable salt or solvate is labelled, to the mammal or to a biological sample obtained from the mammal to facilitate diagnosis of the disease, disorder or condition in the mammal, wherein the disease, disorder or condition is responsive to inhibition of activation of the NLRP3 inflammasome.

30. A method of modulating the activity of a biological target comprising the step of exposing the biological target to the compound of claim 3, or the pharmaceutically acceptable salt or solvate thereof, wherein the biological target is selected from the group consisting of the NLRP3 inflammasome, IL-1β and IL-18.

31. A prodrug of a compound, or a pharmaceutically acceptable salt or solvate thereof, wherein the compound is a compound of formula (II) or (III), or a pharmaceutically acceptable salt or solvate thereof:

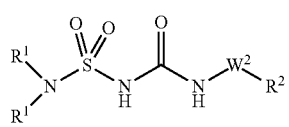

Formula II

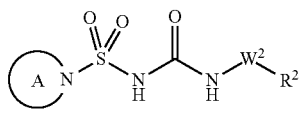

Formula III wherein:
R$^1$ is independently selected from the group consisting of hydrogen, $C_1$-$C_{12}$ alkyl, $C_2$-$C_{12}$ alkenyl, $C_2$-$C_{12}$ alkynyl, aryl, heterocyclyl, heteroaryl, cycloalkyl, cycloalkenyl, amino, amido, alkylthio, acyl, arylalkyl and acylamido, all of which may be optionally substituted; and
A is heteroaryl or heterocyclyl, each of which is optionally substituted and linked to the sulfonyl sulphur through a ring nitrogen; and
W$^2$ and R$^2$ form an indacene group or a substituted or hydrogenated variant thereof.

32. A prodrug of a compound, or a pharmaceutically acceptable salt or solvate thereof, wherein the compound is a compound of formula (II) or (III), or a pharmaceutically acceptable salt or solvate thereof:

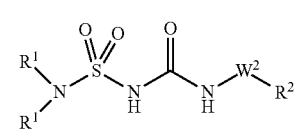

Formula II

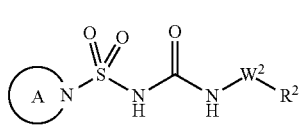

Formula III wherein:
W$^2$ and R$^2$ form an indacene group or a substituted or hydrogenated variant thereof; and
(R$^1$)$_2$N— in formula (II) or A in formula (III) is selected from the group consisting of:

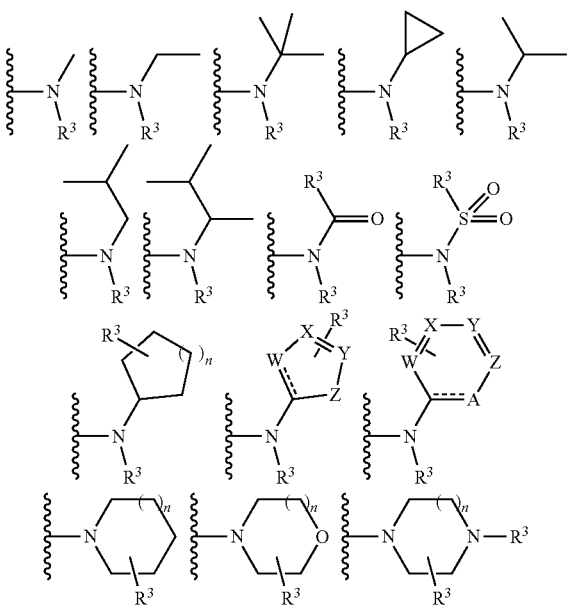

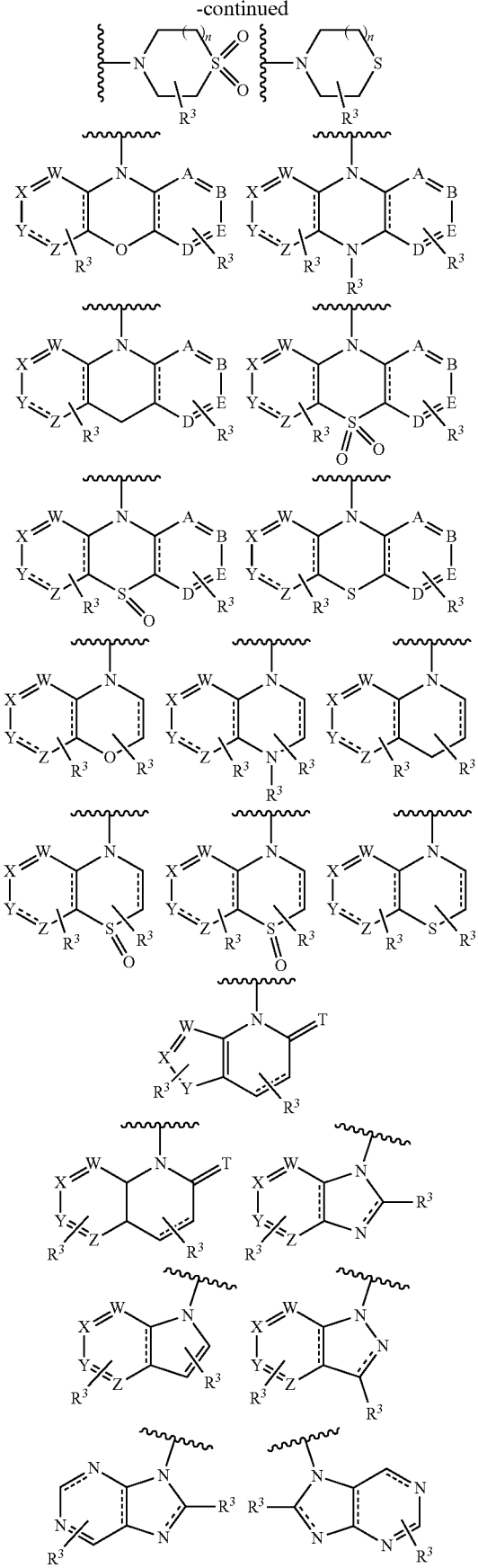

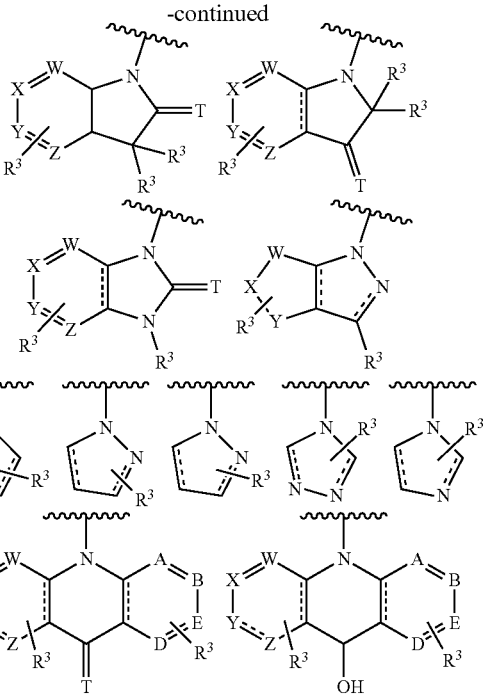

wherein:
 each dashed line may independently be a bond;
 T is O or S;
 A, B, D, E, W, X, Y and Z, when present, are each independently selected from O, $C(R^3)$, $C(R^3)_2$, N, $N(R^3)$ and S;
 each incidence of $R^3$ is independently selected from the group consisting of hydrogen, halide, cyano, $C_1$-$C_6$ alkyl, $C_1$-$C_6$ trifluoroalkyl, $C_1$-$C_6$ alkoxy, C=O, $SO_2$, acyl, amino, hydroxyl, $C_5$-$C_6$ heteroaryl, $C_5$-$C_6$ heterocyclyl and $C_3$-$C_6$ cycloalkyl, each of which may be optionally substituted; and
 n is 0, 1, 2 or 3.

33. A prodrug of a compound, or a pharmaceutically acceptable salt or solvate thereof, wherein the compound is a compound of formula (II) or (III), or a pharmaceutically acceptable salt or solvate thereof:

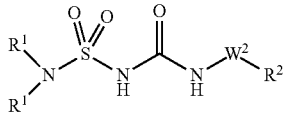

Formula II

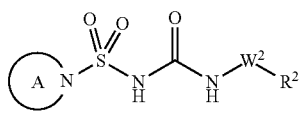

Formula III wherein:
 each $R^1$ is independently selected from a hydrogen atom and pyrazole, imidazole, triazole, tetrazole, pyrrole, morpholine, piperazine, 4-methyl piperazine, and fused bicyclics or tricyclics comprising a benzene ring fused with at least one 5-membered heterocycle, each of which groups may be optionally substituted at a ring atom with a group selected from halo, isopropyl, morpholinyl, piperidinyl, and piperazinyl, each of which groups may themselves be optionally substituted with $C_1$-$C_6$ alkyl;

A is selected from pyrazole, imidazole, triazole, tetrazole, pyrrole, morpholine, piperazine, 4-methyl piperazine, and fused bicyclics or tricyclics comprising a benzene ring fused with at least one 5-membered heterocycle, each of which groups may be optionally substituted at a ring atom with a group selected from halo, isopropyl, morpholinyl, piperidinyl, and piperazinyl, each of which groups may themselves be optionally substituted with $C_1$-$C_6$ alkyl; and $W^2$ and $R^2$ form an indacene group or a substituted or hydrogenated variant thereof.

34. A method of treating or preventing a disease, disorder or condition in a subject including the step of administering an effective amount of the prodrug or the pharmaceutically acceptable salt or solvate thereof, as claimed in claim 31, to the subject thereby treating or preventing the disease, disorder or condition, wherein the disease, disorder or condition is responsive to inhibition of activation of the NLRP3 inflammasome.

35. A method of treating or preventing a disease, disorder or condition in a subject including the step of administering an effective amount of the prodrug or the pharmaceutically acceptable salt or solvate thereof, as claimed in claim 32, to the subject thereby treating or preventing the disease, disorder or condition, wherein the disease, disorder or condition is responsive to inhibition of activation of the NLRP3 inflammasome.

36. A method of treating or preventing a disease, disorder or condition in a subject including the step of administering an effective amount of the prodrug or the pharmaceutically acceptable salt or solvate thereof, as claimed in claim 33, to the subject thereby treating or preventing the disease, disorder or condition, wherein the disease, disorder or condition is responsive to inhibition of activation of the NLRP3 inflammasome.

* * * * *